United States Patent
Tusche et al.

(10) Patent No.: US 10,533,015 B1
(45) Date of Patent: Jan. 14, 2020

(54) OPIOID RECEPTOR ANTAGONIST PRODRUGS

(71) Applicant: Nirsum Laboratories, Inc., New York, NY (US)

(72) Inventors: Michael W. Tusche, New York, NY (US); Nikej Shah, New York, NY (US)

(73) Assignee: Nirsum Laboratories, Inc., New York, NY (US)

( * ) Notice: Subject to any disclaimer, the term of this patent is extended or adjusted under 35 U.S.C. 154(b) by 0 days.

(21) Appl. No.: 16/440,989

(22) Filed: Jun. 14, 2019

Related U.S. Application Data

(63) Continuation-in-part of application No. PCT/CN2019/085813, filed on May 7, 2019.

(51) Int. Cl.
| | |
|---|---|
| *C07D 489/08* | (2006.01) |
| *A61K 31/485* | (2006.01) |
| *A61K 47/44* | (2017.01) |

(52) U.S. Cl.
CPC ............ *C07D 489/08* (2013.01); *A61K 47/44* (2013.01)

(58) Field of Classification Search
CPC .. A61K 31/485; C07D 489/02; C07D 489/04; C07D 489/08
See application file for complete search history.

(56) References Cited

U.S. PATENT DOCUMENTS

| | | |
|---|---|---|
| 4,673,679 A | 6/1987 | Aungst et al. |
| 8,440,686 B2 | 5/2013 | Guillaume et al. |
| 2004/0033253 A1 | 2/2004 | Shevchuk et al. |
| 2009/0246265 A1 | 10/2009 | Stinchcomb et al. |
| 2011/0053971 A1 | 3/2011 | Guillaume et al. |

FOREIGN PATENT DOCUMENTS

| | | |
|---|---|---|
| CN | 101570539 A | 11/2009 |
| DE | 2323192 A1 | 12/1973 |
| EP | 0250796 A2 | 1/1988 |
| EP | 1476141 A2 | 11/2004 |
| EP | 2254561 A2 | 12/2010 |
| EP | 2291380 A1 | 3/2011 |
| EP | 2307420 A1 | 4/2011 |
| FR | 2184065 A1 | 12/1973 |
| RU | 2215741 C1 | 11/2003 |
| RU | 2215742 C1 | 11/2003 |
| RU | 2221566 C1 | 1/2004 |
| WO | 2003/070191 A2 | 8/2003 |
| WO | 2009/120889 A2 | 10/2009 |
| WO | 2019/018638 A1 | 1/2019 |
| WO | 2019/086017 A1 | 5/2019 |

OTHER PUBLICATIONS

Gaekens et al., Lipophilic nalmefene prodrugs to achieve a one-month sustained release. J Control Release. Jun. 28, 2016;232:196-202.
Pillai et al., Physicochemical evaluation, in vitro human skin diffusion, and concurrent biotransformation of 3-O-alkyl carbonate prodrugs of naltrexone. Pharm Res. Jul. 2004;21(7):1146-52.
U.S. Appl. No. 16/440,985, filed Jun. 14, 2019, Pending.
U.S. Appl. No. 16/440,986, filed Jun. 14, 2019, Pending.
U.S. Appl. No. 16/440,988, filed Jun. 14, 2019, Pending.
Hahan et al., Narcotic Antagonists. 4. Carbon-6 Derivatives of N-Substituted Noroxymorphones as Narcotic Antagonists, Journal of Medical Chemistry, 1975, vol. 18, No. 3, pp. 259-262.

*Primary Examiner* — Noble E Jarrell
(74) *Attorney, Agent, or Firm* — McCarter & English, LLP; Steven G. Davis; Wei Song

(57) ABSTRACT

Provided herein are prodrugs of opioid receptor antagonists such as nalmefene and naltrexone, pharmaceutical compositions comprising said compounds, and methods for using said compounds for the treatment of behavioral disorders.

4 Claims, 49 Drawing Sheets

OPIOID RECEPTOR ANTAGONIST PRODRUGS

CROSS-REFERENCE TO RELATED APPLICATIONS

This application is a continuation-in-part application of International Application No. PCT/CN2019/085813, filed on May 7, 2019. The entire contents of the aforementioned application are incorporated herein by reference.

BACKGROUND

A need exists in the medicinal arts for compositions and methods for the modulation of opioid receptor activity in the course of treating behavioral disorders.

BRIEF SUMMARY OF THE INVENTION

Provided herein are prodrugs of opioid receptor antagonists such as nalmefene and naltrexone, pharmaceutical compositions comprising said compounds, and methods for using said compounds for the treatment of behavioral disorders.

Some compounds of the invention have superior properties. For example, some compounds of the invention have superior stabilities in oil based pharmaceutical compositions such as sesame oil or cottonseed oil.

Some compounds of the invention have better pharmacokinetic activities in vivo (for example, rat or dog), e.g., extended half-life.

Some compounds of the invention have better safety in vivo (for example, rat or dog), e.g., diminished injection site reactions.

Some compounds of the invention have superior stability either neat or in oil based pharmaceutical compositions.

In one aspect, provided herein is a compound, or pharmaceutically acceptable salt thereof, having a structure provided in Formula (II),

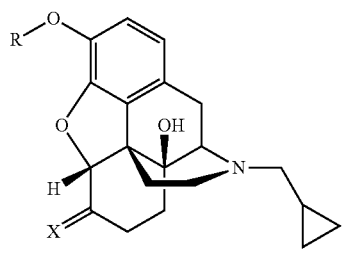

(II)

wherein,
X is O or $CH_2$;

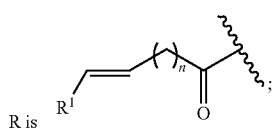

R is wherein $R^1$ is a $C_4$-$C_{10}$ alkyl or a $C_4$-$C_{10}$ alkenyl; and n is 7-15; provided if X is O, then n is not 7.

In some embodiments, X is O. In some embodiments, X is $CH_2$.

In another aspect, also provided herein is a compound, or pharmaceutically acceptable salt thereof, having a structure provided in Formula (IIa),

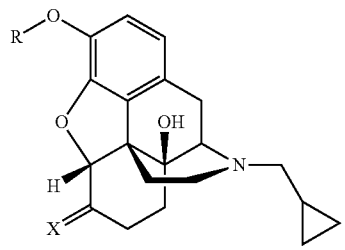

(IIa)

wherein,
X is O or $CH_2$;
R is:

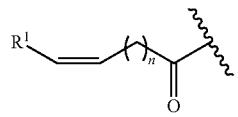

wherein $R^1$ is a $C_4$-$C_{10}$ alkyl or a $C_4$-$C_{10}$ alkenyl; and n is 9-15.

In some embodiments, X is O. In some embodiments, X is $CH_2$.

In another aspect, also provided herein is a compound, or pharmaceutically acceptable salt thereof, having a structure provided in Formula (III),

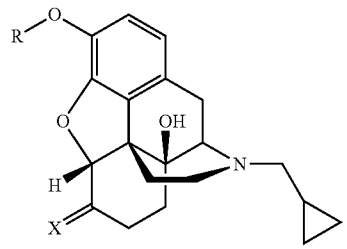

(III)

wherein,
X is O or $CH_2$;
R is selected from:
—[CH($R^3$)O]z-$R^4$;
—[CH($R^3$)O]z-C(=O)O$R^4$;
—[CH($R^3$)O]z-C(=O)N$R^4$$R^5$; and
—[CH($R^3$)O]z-P(=O)(O$R^4$)(O$R^5$);
wherein z is 1, 2, 3, 4, 5, 6, or 7;
$R^3$ is hydrogen, halogen, alkyl, alkenyl, cycloalkylalkyl, or aryl;
each $R^4$ and $R^5$ is independently selected from hydrogen, alkyl, alkenyl, cycloalkylalkyl, or aryl.

In some embodiments, X is O. In some embodiments, X is $CH_2$.

One embodiment provides a pharmaceutical composition comprising a pharmaceutically acceptable excipient and a compound of any one of Formula (II), (IIa), or (III), or a compound disclosed in Table 1, or a pharmaceutically acceptable salt thereof.

Provided herein is a method of treating opioid dependence in a patient in need thereof comprising administering a pharmaceutical composition comprising a compound of Formula (II), (IIa), or (III), or a compound disclosed in Table 1, or pharmaceutically acceptable salt thereof, and a pharmaceutically acceptable excipient.

One embodiment provides a method of treating a patient wherein the therapeutic effect of a long acting opioid antagonist depot can be overcome in a patient by administering an opioid based analgesic.

One embodiment provides a method of treating opioid dependence in a patient in need thereof, wherein the patient receives a first injection of an injectable formulation comprising a compound of any one of Formula (II), (IIa), or (III), or a compound disclosed in Table 1, or a pharmaceutically acceptable salt thereof, wherein said first injection provides a therapeutically relevant plasma concentration for about 1 week, about 2 weeks, about 3 weeks or about 4 weeks, at least about 2 months, at least about 3 months, at least about 4 months, at least about 5 months or at least about 6 months, followed by a second injection of an injectable formulation comprising a compound of any one of Formula (II), (IIa), or (III), or a compound disclosed in Table 1, or a pharmaceutically acceptable salt thereof, wherein said second injection provides a therapeutically relevant plasma concentration for at least about 2 months, at least about 3 months, at least about 4 months, at least about 5 months or at least about 6 months.

One embodiment provides a method of treating opioid dependence in a patient in need thereof, wherein the patient receives a first injection of an injectable formulation of naltrexone loaded PLGA microspheres that provides a therapeutically relevant plasma concentration for about 4 weeks, followed by one or more injections of an injectable formulation comprising a compound of any one of Formula (II), (IIa), or (III), or a compound disclosed in Table 1, or a pharmaceutically acceptable salt thereof, that provides a therapeutically relevant plasma concentration for about 2 months, about 3 months, about 4 months, or about 5 months or more.

One embodiment provides a method of treating opioid dependence in a patient in need thereof, wherein the patient receives one or more injections of an injectable formulation comprising at least one compound of any one of Formula (II), (IIa), or (III), or a compound disclosed in Table 1, or a pharmaceutically acceptable salt thereof, wherein the patient has been previously treated with opioid agonists or partial agonists, such as buprenorphine or methadone, and the patients are now transitioning to discontinuation from such agonist or partial agonist treatment.

One embodiment provides a method of treating opioid dependence in a patient in need thereof, wherein the patient receives one or more injections of an injectable formulation comprising at least one compound of any one of Formula (II), (IIa), or (III), or a compound disclosed in Table 1, or a pharmaceutically acceptable salt thereof, wherein the patient is recently addicted and naïve to prior medication assisted treatment, or wherein the patient has recently discontinued opioid pain medication, are at risk of future opioid drug abuse, and are in need of prevention of future opioid drug abuse via antagonist treatment.

INCORPORATION BY REFERENCE

All publications, patents, and patent applications mentioned in this specification are herein incorporated by reference for the specific purposes identified herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below. The patent application file contains at least one drawing executed in color. Copies of this patent application publication with color drawing(s) will be provided by the Office upon request and payment of the necessary fee.

DETAILED DESCRIPTION OF THE INVENTION

Figure 1:
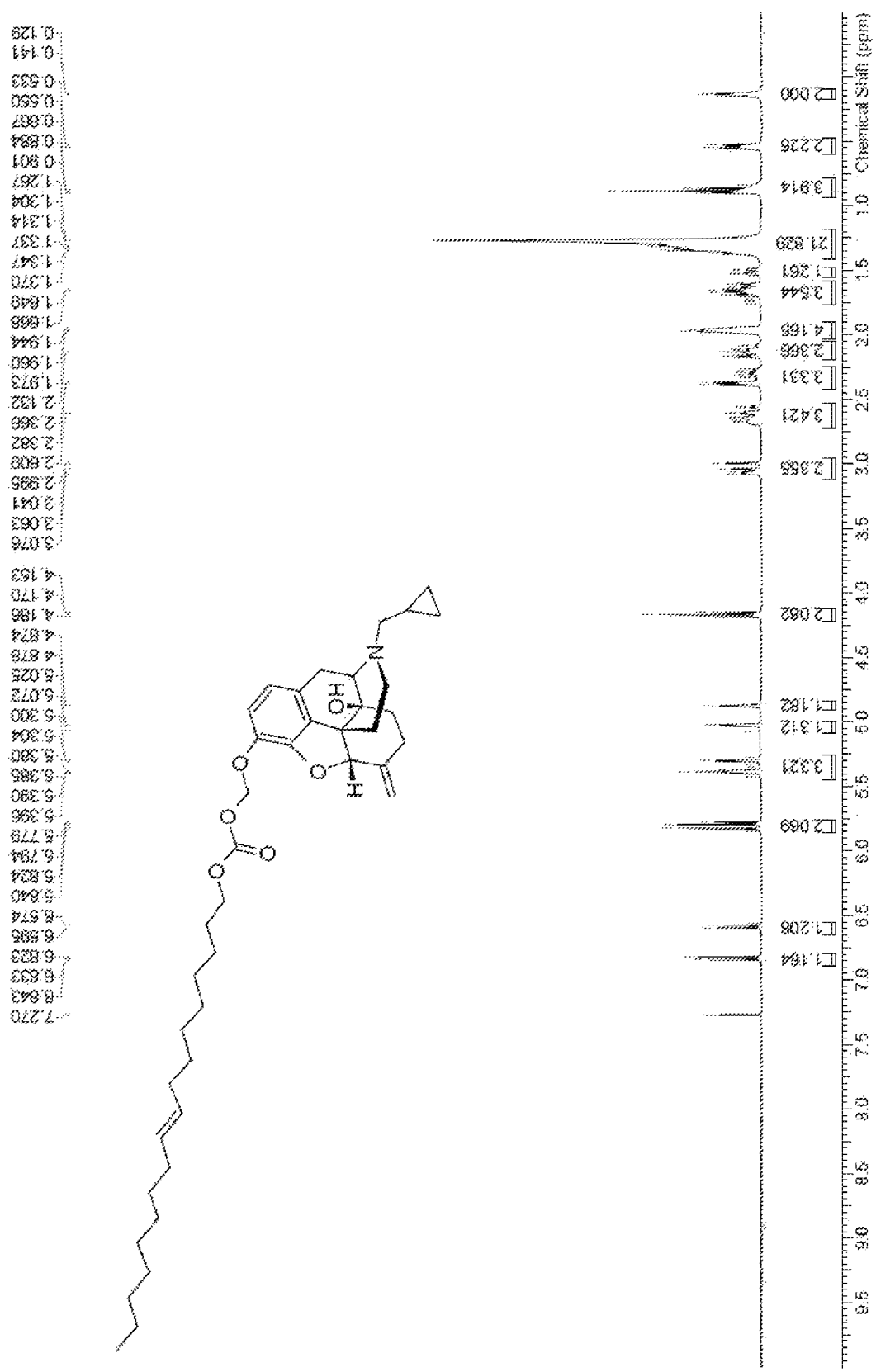
FIG. 1 provides the nuclear magnetic resonance spectrum of Example 1 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl ((E)-octadec-9-en-1-yl) carbonate.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —OC(O)—N($R^a)_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —OC(O)—N($R^a)_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond.

The points of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —OC(O)—N($R^a)_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hickel theory. The ring system from which aryl groups are derived include, but are not limited to, groups such as benzene, fluorene, indane, indene, tetralin and naphthalene.

Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —Re-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—Re-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

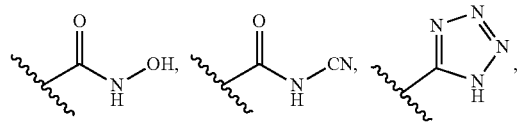

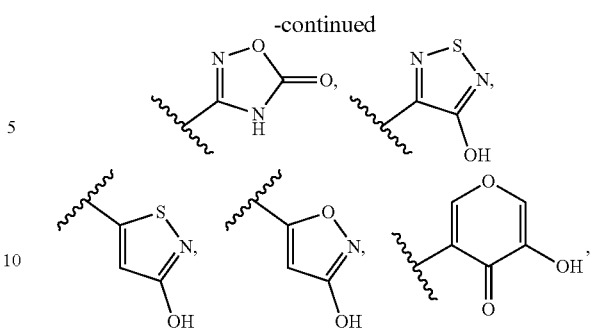

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized.

One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) i-electron system in accordance with the Hickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

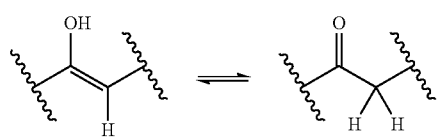

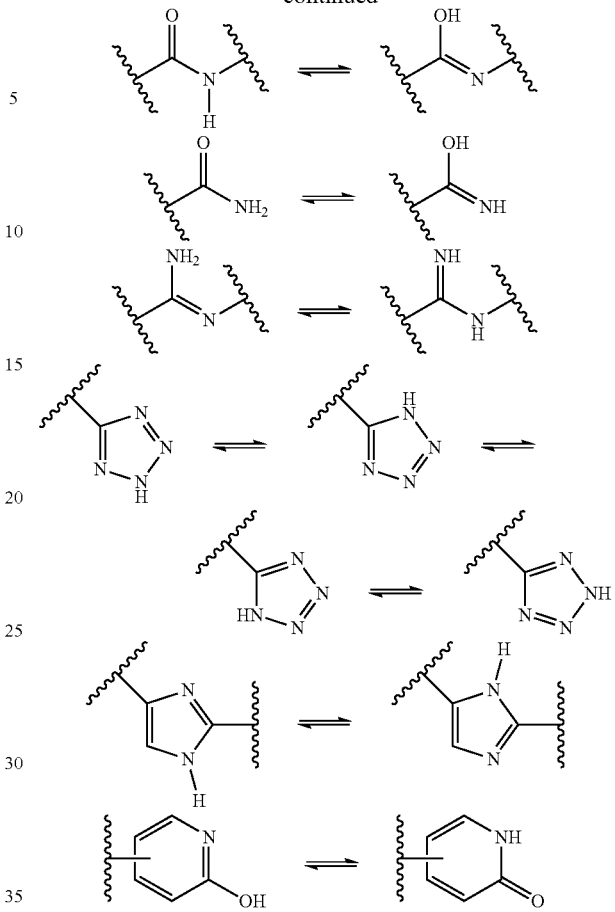

The compounds disclosed herein, in some embodiments, are used in different enriched isotopic forms, e.g., enriched in the content of $^2H$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

In another embodiment, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d₃ (CD₃I), are readily available and may be employed to transfer a deuterium-substituted carbon atom under nucleophilic substitution reaction conditions to the reaction substrate. The use of CD₃I is illustrated, by way of example only, in the reaction schemes below.

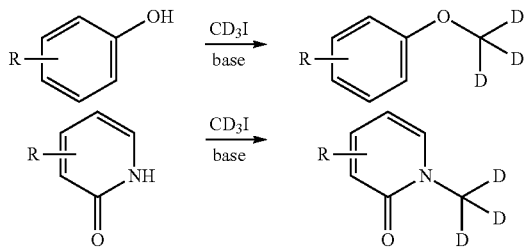

Deuterium-transfer reagents, such as lithium aluminum deuteride (LiAlD₄), are employed to transfer deuterium under reducing conditions to the reaction substrate. The use of LiAlD₄ is illustrated, by way of example only, in the reaction schemes below.

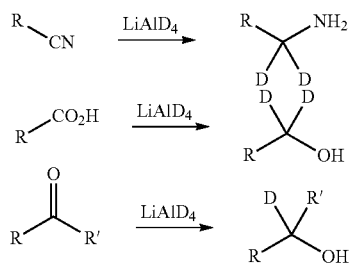

Deuterium gas and palladium catalyst are employed to reduce unsaturated carbon-carbon linkages and to perform a reductive substitution of aryl carbon-halogen bonds as illustrated, by way of example only, in the reaction schemes below.

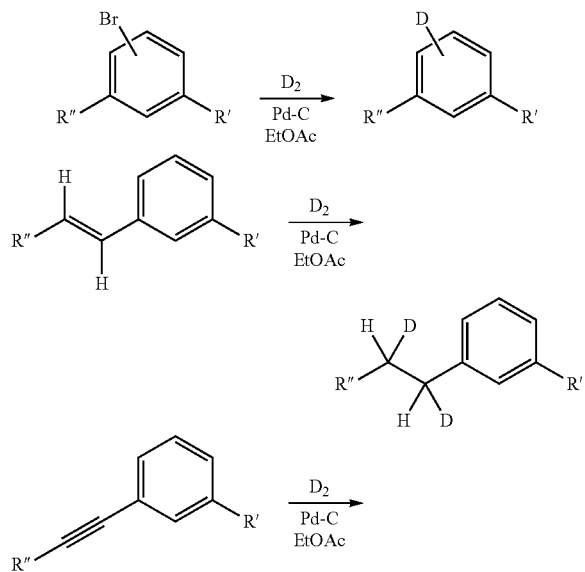

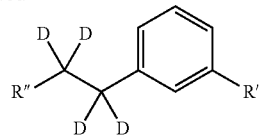

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the opioid receptor antagonist prodrug compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Opioid Receptor Pharmacology

The opioid receptors, $\mu$, $\delta$, $\kappa$, and the opioid-like receptor ORL-1 belong to the super family of G-protein coupled receptors (GPCRs) that possess seven helical trans-membrane spanning domains in their architecture. The majority of research efforts focused upon this group of proteins has been directed toward the receptor since it mediates the actions of both the opiate and opioid analgesics such as morphine and fentanyl, respectively. However, over the years it has become increasingly clear that the entire family of proteins is actively involved in a host of biological processes. Furthermore, the advent of selective antagonists has demonstrated that pharmacotherapeutic opportunities exist via both negative and positive modulation of this receptor family.

The $\mu$ (mu, $OP_3$ or MOP) receptor was originally defined and characterized pharmacologically by Martin, Kosterlitz and their colleagues on the basis of its high affinity for, and sensitivity to, morphine (Martin et al. The effects of morphine- and nalorphine-like drugs in the nondependent and morphine-dependent chronic spinal dog *J. Pharmacol. Exp. Ther.* (1976), 197: 517-532; Kosterlitz, et al. Endogenous opioid peptides: multiple agonists and receptors, *Nature* (1977) 267: 495-499). The endogenous opioids, [Met$^5$]-enkephalin, [Leu$^5$]-enkephalin, extended forms of [Met$^5$]-enkephalin including metorphamide and BAM-18, β-endorphin, and truncated forms of dynorphin (e.g. dynorphin-(1-9) and shorter dynorphin peptides), also have affinities for μ receptors that are consistent with a possible role for each of these peptides as natural ligands for this receptor type, although these endogenous peptides are not selective for μ receptors. Two putative natural ligands, endomorphin-1 and -2, that appear to mediate their effects exclusively through the μ opioid receptor, also have been reported to be present in brain although no gene, precursor protein, or other mechanism for their endogenous synthesis has been identified.

The μ receptors are distributed throughout the neuraxis. The highest receptor densities are found in the thalamus, caudate putamen, neocortex, nucleus accumbens, amygdala, interpeduncular complex, and inferior and superior colliculi (Watson et al. Autoradiographic differentiation of mu, delta and kappa receptors in the rat forebrain and midbrain, *J. Neurosci.* (1987), 7: 2445-2464). The μ receptors, as well as δ and κ receptors, are also present in the superficial layers of the dorsal horn of spinal cord. A moderate density of receptors is found in periaqueductal gray and raphé nuclei. These brain regions have a well-established role in pain and analgesia. Other physiological functions regulated by receptors include respiratory and cardiovascular functions, intestinal transit, feeding, mood, thermoregulation, hormone secretion and immune functions.

The δ (delta, $OP_1$ or DOP) opioid receptor was defined using the mouse vas deferens preparation and the enkephalins are generally considered the preferred endogenous ligands. The δ receptors are discretely distributed in the central nervous system (CNS), with a prominent gradient of receptor density from high levels in forebrain structures to relatively low levels in most hindbrain regions. The highest densities are found in olfactory bulb, neocortex, caudate putamen, nucleus accumbens, and amygdala (Watson et al. Autoradiographic differentiation of mu, delta and kappa receptors in the rat forebrain and midbrain, *J. Neurosci.* (1987), 7: 2445-2464). The thalamus and hypothalamus have a moderate density of δ receptors; in more caudal regions the interpeduncular nucleus and pontine nuclei show high binding in rat, but much lower levels in mouse (Kitchen et al. Quantitative autoradiographic mapping of mu, delta and kappa-opioid receptors in knockout mice lacking the mu-opioid receptor gene, *Brain Res.* (1997), 778: 73-88). In the spinal cord, δ receptors are present in dorsal horn where they play a role in mediating the analgesic effects of δ agonists.

The κ (kappa, $OP_2$ or KOP) opioid receptor was first proposed on the basis of in vivo studies in dogs with ketocyclazocine and related drugs (Martin et al. The effects of morphine- and nalorphine-like drugs in the nondependent and morphine-dependent chronic spinal dog *J. Pharmacol. Exp. Ther.* (1976), 197: 517-532). Subsequent studies have confirmed the presence of this receptor type in other species including guinea pig, a species that was preferred for many of the early studies on kappa opioid receptors. Dynorphins A and B and α-neoendorphin appear to be the endogenous ligands for opioid κ receptors, although shorter peptides derived from prodynorphin have comparable affinities at μ and κ receptors. The κ receptors are located predominantly in the cerebral cortex, nucleus accumbens, claustrum and hypothalamus of rat and mouse (Kitchen et al. Quantitative autoradiographic mapping of mu, delta and kappa-opioid receptors in knockout mice lacking the mu-opioid receptor gene, *Brain Res.* (1997), 778: 73-88; Watson et al. Autoradiographic differentiation of mu, delta and kappa receptors in the rat forebrain and midbrain, *J. Neurosci.* (1987), 7: 2445-2464), and have been implicated in the regulation of nociception, diuresis, feeding, neuroendocrine and immune system functions (Dhawan et al. International Union of Pharmacology. XII. Classification for opioid receptors, *Pharmacol. Rev.* (1996), 48: 567-592).

ORL1 receptors (also called nociceptin, or orphaninFQ receptors) are the youngest members of the opioid receptor family. Agonist-induced internalization of ORL1 is rapid and concentration dependent. Agonist challenge also reduces the ability of ORL1 to couple to inhibition of forskolin-stimulated cAMP production, suggesting that ORL1 undergoes similar desensitization mechanisms as compared with the other three opioid receptors subtypes.

The structure of the ORL1 receptor indicates that it has evolved as part of the opioid receptor family. Sequence comparisons with μ, κ, and δ receptors, and with other similar G protein-coupled receptors (e.g. of the SOM receptor family), indicate that the ORL1 receptor is more closely related to opioid receptors than to other types of G protein-coupled receptors (Birgul, et al. Reverse Physiology in *drosophila*: identification of a novel allatostatin-like neuropeptide and its cognate receptor structurally related to the mammalian somatostatin/galanin/opioid receptor family. *EMBO J.* (1999), 18: 5892-5900). Additionally, agonists at ORL1 receptors induce activation of the same set of transduction pathways activated by μ, κ, and δ receptors, and the endogenous ligand, ORL1, shares considerable sequence homology with dynorphin A and, to a lesser extent, with the enkephalins. Thus, the ORL1 receptor and its endogenous ligand are closely related in an evolutionary sense to the μ, κ, and δ receptors.

Despite the evidence of evolutionary and functional homology, the ORL1 receptor is not an opioid receptor from a pharmacological perspective. The effects of activation of this receptor are not obviously 'opiate-like' with respect to pain perception. The ORL1 receptor has negligible affinity for naloxone and for most other antagonists at μ, κ or δ receptors. The ORL1 receptor is, however, expressed in many functional systems in which endogenous opioids play a regulatory role. Although the functions of ORL1 are not yet fully understood, regulatory functions for ORL1 parallel to but not identical to those of the endogenous opioid peptides seem very probable. Despite these functional differences, the subcommittee finds the structural relationship between the ORL1 receptor and μ, δ and κ receptors compelling.

ORL1 receptor regulation, while increasingly studied, is still in the infant stages of understanding when compared to the other three opioid receptor subtypes. To date few site-directed mutagenesis studies have been conducted, and receptor regulation in primary neurons, dorsal root ganglion, or dorsal horn neurons remains unknown.

An integral part of the effort to characterize the opioid receptor system has been the discovery of potent, pure antagonists of opioid receptors. Nalmefene (1a) and naltrexone (1b), both competitive antagonists at μ, δ, and κ opioid receptors, were used as pharmacological tools to identify and characterize opioid systems.

Nalmefene is an opioid receptor antagonist that has been available for several years as Revex® injection for use in reversing opioid effects and for opioid overdose. Nalmefene is also described in literature for the treatment of substance abuse disorders such as alcohol dependence and abuse, and impulse control disorders such as pathological gambling and addiction to shopping. It is marketed as Selincro in Europe as an on demand oral pill for alcohol abuse. It has the IUPAC name 17-cyclopropylmethyl-4,5α-epoxy-6-methylenemorphinan-3,14-diol and has the structure provided in Formula (1A).

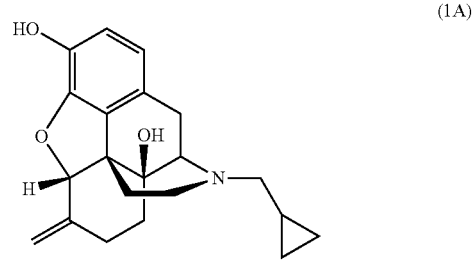

(1A)

Naltrexone is an opioid receptor antagonist used primarily in the management of alcohol dependence and opioid dependence. It is marketed in the generic form as its hydrochloride salt, naltrexone hydrochloride under the trade names Revia® and Depade® in the form of 50 mg film coated tablets. Once monthly extended release naltrexone, marketed in the United States as Vivitrol, has gained wide acceptance in opioid use disorder due to increased patient adherence. Naltrexone has the IUPAC name 17-(cyclopropylmethyl)-4,5α-epoxy-3,14-dihydroxymorphinan-6-one and has the structure provided in Formula (1B)

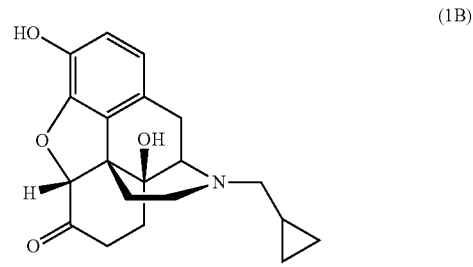

(1B)

Low doses of naltrexone have also been investigated in patients with multiple sclerosis, autism, active Crohn's disease, AIDS, rheumatoid arthritis, celiac disease, certain forms of cancer, and autoimmune diseases. Opioids act as cytokines, the principal communication signallers of the immune system, creating immunomodulatory effects through opioid receptors on immune cells. Very low doses of naltrexone were shown to boost the immune system and helps to fight against diseases characterized by inadequate immune function.

In terms of pharmacology, naltrexone blocks the effects of opioids by its highly competitive binding at the μ-opioid receptors. Being a competitive antagonist, the suppression of an opiate's agonistic, euphorigenic effect can be overcome. However, clinical studies have indicated that naltrexone in an oral dosage of approximately 50 mg is able to block the pharmacological effects of up to 25 mg of intravenously administered heroin for periods as long as twenty four hours.

The mechanism of action of naltrexone in the treatment of alcoholism is not understood although involvement of the endogenous opioid system is suggested by preclinical data. Opioid antagonists have been shown to reduce alcohol consumption by animals, and naltrexone has shown efficacy in maintaining abstinence in clinical studies in humans.

Opioid Receptor Antagonists Prodrugs

Although using nalmefene and naltrexone in the treatment of alcohol dependence and opioid dependence provides a great benefit to the society, the problem with these drugs is that they have very short period of action. Thus, for example, well absorbed orally (approximately 96% of an oral dose is absorbed from the gastrointestinal tract), naltrexone is subject to significant first pass metabolism with oral bioavailability estimates ranging from 5% to 40%. The activity of naltrexone is believed to be as a result of both naltrexone and its 6-β-naltrexol metabolite. Two other minor metabolites are 2-hydroxy-3-methoxy-6-β-naltrexol and 2-hydroxy-3-methyl-naltrexone. Peak plasma levels of both naltrexone and 6-β-naltrexol occur within one hour after oral dosing; mean elimination half-life values for naltrexone and 6-β-naltrexol are four and thirteen hours respectively. Even for long acting naltrexone injections, clinicians indicate that patients discontinue treatment too early. Therefore, a need exists for ultra-long acting opioid antagonists in the treatment of substance abuse disorder.

One of the solutions to overcome the problem of short period of action of nalmefene and naltrexone is to use prodrugs which provide a long, sustained, and controlled release of nalmefene and naltrexone opioid receptor antagonists upon administration into the body.

As used in this disclosure, the term "prodrug" is meant to indicate a compound that is converted under physiological conditions to nalmefene or naltrexone. A prodrug, in some embodiments, is inactive when administered to a subject, but is converted in vivo to an active compound, for example, by hydrolysis. Thus, the term "prodrug" refers to a precursor compound that is pharmaceutically acceptable, and in some embodiments, is devoid of the pharmacological properties of nalmefene or naltrexone. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of nalmefene or naltrexone, as described herein, are prepared by modifying functional groups present in the active compound in such a way that the modifications are cleaved to the parent active compound. Prodrugs include compounds wherein a hydroxy group is bonded to any group that, when the prodrug of the active compound is administered to a mammalian subject, cleaves to form a free hydroxy group.

Provided herein are prodrugs of opioid receptor antagonists nalmefene and naltrexone.

In another aspect, also provided herein is a compound, or pharmaceutically acceptable salt thereof, having a structure provided in Formula (II),

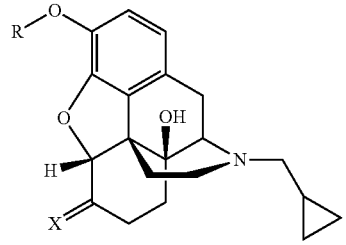

(II)

wherein,

X is O or CH$_2$;

R is 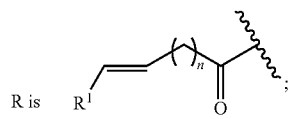;

wherein R$^1$ is a C$_4$-C$_{10}$ alkyl or a C$_4$-C$_{10}$ alkenyl; and n is 7-15; provided if X is O, then n is not 7.

In some embodiments, X is O. In some embodiments, X is CH$_2$.

In some embodiments, R$^1$ is a C$_4$-C$_{10}$ alkyl or a C$_4$-C$_{10}$ alkenyl.

In some embodiments, R$^1$ is a C$_4$-C$_{10}$ alkyl. In some embodiments, R$^1$ is a C$_4$-C$_5$ alkyl. In some embodiments, R$^1$ is a C$_4$-C$_6$ alkyl. In some embodiments, R$^1$ is a C$_4$-C$_7$ alkyl. In some embodiments, R$^1$ is a C$_4$-C$_8$ alkyl. In some embodiments, R$^1$ is a C$_4$-C$_9$ alkyl. In some embodiments, R$^1$ is a C$_5$-C$_6$ alkyl. In some embodiments, R$^1$ is a C$_5$-C$_7$ alkyl. In some embodiments, R$^1$ is a C$_5$-C$_8$ alkyl. In some embodiments, R$^1$ is a C$_5$-C$_9$ alkyl. In some embodiments, R$^1$ is a C$_5$-C$_{10}$ alkyl. In some embodiments, R$^1$ is a C$_6$-C$_7$ alkyl. In some embodiments, R$^1$ is a C$_6$-C$_8$ alkyl. In some embodiments, R$^1$ is a C$_6$-C$_9$ alkyl. In some embodiments, R$^1$ is a C$_6$-C$_{10}$ alkyl. In some embodiments, R$^1$ is a C$_7$—C alkyl. In some embodiments, R$^1$ is a C$_7$-C$_9$ alkyl. In some embodiments, R$^1$ is a C$_7$-C$_{10}$ alkyl. In some embodiments, R$^1$ is a C$_8$-C$_9$ alkyl. In some embodiments, R$^1$ is a C$_8$-C$_{10}$ alkyl. In some embodiments, R$^1$ is a C$_9$-C$_{10}$ alkyl. In some embodiments, R$^1$ is a C$_4$ alkyl. In some embodiments, R$^1$ is a C$_5$ alkyl. In some embodiments, R$^1$ is a C$_6$ alkyl. In some embodiments, R$^1$ is a C$_7$ alkyl. In some embodiments, R$^1$ is a C$_8$ alkyl. In some embodiments, R$^1$ is a C$_9$ alkyl. In some embodiments, R$^1$ is a C$_{10}$ alkyl.

In some embodiments, R$^1$ is a C$_4$-C$_{10}$ alkenyl. In some embodiments, R$^1$ is a C$_4$-C$_5$ alkenyl. In some embodiments, R$^1$ is a C$_4$-C$_6$ alkenyl. In some embodiments, R$^1$ is a C$_4$-C$_7$ alkenyl. In some embodiments, R$^1$ is a C$_4$-C$_8$ alkenyl. In some embodiments, R$^1$ is a C$_4$-C$_9$ alkenyl. In some embodiments, R$^1$ is a C$_5$-C$_6$ alkenyl. In some embodiments, R$^1$ is a C$_5$-C$_7$ alkenyl. In some embodiments, R$^1$ is a C$_5$-C$_8$ alkenyl. In some embodiments, R$^1$ is a C$_5$-C$_9$ alkenyl. In some embodiments, R$^1$ is a C$_5$-C$_{10}$ alkenyl. In some embodiments, R$^1$ is a C$_6$-C$_7$ alkenyl. In some embodiments, R$^1$ is a C$_6$-C$_8$ alkenyl. In some embodiments, R$^1$ is a C$_6$-C$_9$ alkenyl. In some embodiments, R$^1$ is a C$_6$-C$_{10}$ alkenyl. In some embodiments, R$^1$ is a C$_7$-C$_8$ alkenyl. In some embodiments, R$^1$ is a C$_7$-C$_9$ alkenyl. In some embodiments, R$^1$ is a C$_7$-C$_{10}$ alkenyl. In some embodiments, R$^1$ is a C$_8$-C$_9$ alkenyl. In some embodiments, R$^1$ is a C$_8$-C$_{10}$ alkenyl. In some embodiments, R$^1$ is a C$_9$-C$_{10}$ alkenyl. In some embodiments, R$^1$ is a $C_4$ alkenyl. In some embodiments, $R^1$ is a $C_5$ alkenyl. In some embodiments, $R^1$ is a $C_6$ alkenyl. In some embodiments, $R^1$ is a $C_7$ alkenyl. In some embodiments, $R^1$ is a $C_8$ alkenyl. In some embodiments, $R^1$ is a $C_9$ alkenyl. In some embodiments, $R^1$ is a $C_{10}$ alkenyl.

In some embodiments, n is 7-15. In some embodiments, n is 7-8. In some embodiments, n is 7-9. In some embodiments, n is 7-10. In some embodiments, n is 7-11. In some embodiments, n is 7-12. In some embodiments, n is 7-13. In some embodiments, n is 7-14. In some embodiments, n is 8-9. In some embodiments, n is 8-10. In some embodiments, n is 8-11. In some embodiments, n is 8-12. In some embodiments, n is 8-13. In some embodiments, n is 8-14. In some embodiments, n is 8-15. In some embodiments, n is 9-10. In some embodiments, n is 9-11. In some embodiments, n is 9-12. In some embodiments, n is 9-13. In some embodiments, n is 9-14. In some embodiments, n is 9-15. In some embodiments, n is 10-11. In some embodiments, n is 10-12. In some embodiments, n is 10-13. In some embodiments, n is 10-14. In some embodiments, n is 10-15. In some embodiments, n is 11-12. In some embodiments, n is 11-13. In some embodiments, n is 11-14. In some embodiments, n is 11-15. In some embodiments, n is 12-13. In some embodiments, n is 12-14. In some embodiments, n is 12-15. In some embodiments, n is 13-14. In some embodiments, n is 13-15. In some embodiments, n is 14-15. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15.

In another aspect, also provided herein is a compound, or pharmaceutically acceptable salt thereof, having a structure provided in Formula (IIa),

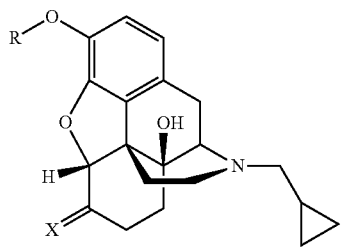

(IIa)

wherein,
X is O or $CH_2$;
R is:

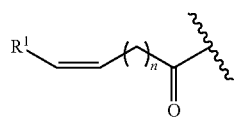

wherein $R^1$ is a $C_4$-$C_{10}$ alkyl or a $C_4$-$C_{10}$ alkenyl; and n is 9-15.

In some embodiments, X is O. In some embodiments, X is $CH_2$.

In some embodiments, $R^1$ is a $C_4$-$C_{10}$ alkyl or a $C_4$-$C_{10}$ alkenyl.

In some embodiments, $R^1$ is a $C_4$-$C_{10}$ alkyl. In some embodiments, $R^1$ is a $C_4$-$C_5$ alkyl. In some embodiments, $R^1$ is a $C_4$-$C_6$ alkyl. In some embodiments, $R^1$ is a $C_4$-$C_7$ alkyl. In some embodiments, $R^1$ is a $C_4$—C alkyl. In some embodiments, $R^1$ is a $C_4$-$C_9$ alkyl. In some embodiments, $R^1$ is a $C_5$-$C_6$ alkyl. In some embodiments, $R^1$ is a $C_5$-$C_7$ alkyl. In some embodiments, $R^1$ is a $C_5$-$C_8$ alkyl. In some embodiments, $R^1$ is a $C_5$-$C_9$ alkyl. In some embodiments, $R^1$ is a $C_5$-$C_{10}$ alkyl. In some embodiments, $R^1$ is a $C_6$-$C_7$ alkyl. In some embodiments, $R^1$ is a $C_6$-$C_8$ alkyl. In some embodiments, $R^1$ is a $C_6$-$C_9$ alkyl. In some embodiments, $R^1$ is a $C_6$-$C_{10}$ alkyl. In some embodiments, $R^1$ is a $C_7$-$C_8$ alkyl. In some embodiments, $R^1$ is a $C_7$-$C_9$ alkyl. In some embodiments, $R^1$ is a $C_7$-$C_{10}$ alkyl. In some embodiments, $R^1$ is a $C_8$-$C_9$ alkyl. In some embodiments, $R^1$ is a $C_8$-$C_{10}$ alkyl. In some embodiments, $R^1$ is a $C_9$-$C_{10}$ alkyl. In some embodiments, $R^1$ is a $C_4$ alkyl. In some embodiments, $R^1$ is a $C_5$ alkyl. In some embodiments, $R^1$ is a $C_6$ alkyl. In some embodiments, $R^1$ is a $C_7$ alkyl. In some embodiments, $R^1$ is a $C_8$ alkyl. In some embodiments, $R^1$ is a $C_9$ alkyl. In some embodiments, $R^1$ is a $C_{10}$ alkyl.

In some embodiments, $R^1$ is a $C_4$-$C_{10}$ alkenyl. In some embodiments, $R^1$ is a $C_4$-$C_5$ alkenyl. In some embodiments, $R^1$ is a $C_4$-$C_6$ alkenyl. In some embodiments, $R^1$ is a $C_4$-$C_7$ alkenyl. In some embodiments, $R^1$ is a $C_4$-$C_8$ alkenyl. In some embodiments, $R^1$ is a $C_4$-$C_9$ alkenyl. In some embodiments, $R^1$ is a $C_5$-$C_6$ alkenyl. In some embodiments, $R^1$ is a $C_5$-$C_7$ alkenyl. In some embodiments, $R^1$ is a $C_5$-$C_8$ alkenyl. In some embodiments, $R^1$ is a $C_5$-$C_9$ alkenyl. In some embodiments, $R^1$ is a $C_5$-$C_{10}$ alkenyl. In some embodiments, $R^1$ is a $C_6$-$C_7$ alkenyl. In some embodiments, $R^1$ is a $C_6$-$C_8$ alkenyl. In some embodiments, $R^1$ is a $C_6$-$C_9$ alkenyl. In some embodiments, $R^1$ is a $C_6$-$C_{10}$ alkenyl. In some embodiments, $R^1$ is a $C_7$-$C_8$ alkenyl. In some embodiments, $R^1$ is a $C_7$-$C_9$ alkenyl. In some embodiments, $R^1$ is a $C_7$-$C_{10}$ alkenyl. In some embodiments, $R^1$ is a $C_8$-$C_9$ alkenyl. In some embodiments, $R^1$ is a $C_8$-$C_{10}$ alkenyl. In some embodiments, $R^1$ is a $C_9$-$C_{10}$ alkenyl. In some embodiments, $R^1$ is a $C_4$ alkenyl. In some embodiments, $R^1$ is a $C_5$ alkenyl. In some embodiments, $R^1$ is a $C_6$ alkenyl. In some embodiments, $R^1$ is a $C_7$ alkenyl. In some embodiments, $R^1$ is a $C_8$ alkenyl. In some embodiments, $R^1$ is a $C_9$ alkenyl. In some embodiments, $R^1$ is a $C_{10}$ alkenyl.

In some embodiments, n is 9-15. In some embodiments, n is 9-10. In some embodiments, n is 9-11. In some embodiments, n is 9-12. In some embodiments, n is 9-13. In some embodiments, n is 9-14. In some embodiments, n is 10-11. In some embodiments, n is 10-12. In some embodiments, n is 10-13. In some embodiments, n is 10-14. In some embodiments, n is 10-15. In some embodiments, n is 11-12. In some embodiments, n is 11-13. In some embodiments, n is 11-14. In some embodiments, n is 11-15. In some embodiments, n is 12-13. In some embodiments, n is 12-14. In some embodiments, n is 12-15. In some embodiments, n is 13-14. In some embodiments, n is 13-15. In some embodiments, n is 14-15. In some embodiments, n is 9. In some embodiments, n is 10. In some embodiments, n is 11. In some embodiments, n is 12. In some embodiments, n is 13. In some embodiments, n is 14. In some embodiments, n is 15.

In another aspect, also provided herein is a compound, or pharmaceutically acceptable salt thereof, having a structure provided in Formula (III),

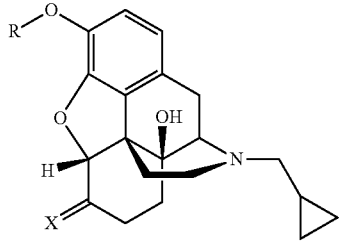

(III)

wherein,
X is O or $CH_2$;
R is selected from:
—[CH($R^3$)O]z-$R^4$;
—[CH($R^3$)O]z-C(=O)O$R^4$;
—[CH($R^3$)O]z-C(=O)N$R^4R^5$; and
—[CH($R^3$)O]z-P(=O)(O$R^4$)(O$R^5$);
wherein z is 1, 2, 3, 4, 5, 6, or 7;
$R^3$ is hydrogen, halogen, alkyl, alkenyl, cycloalkylalkyl, or aryl;
each $R^4$ and $R^5$ is independently selected from hydrogen, alkyl, alkenyl, cycloalkylalkyl, or aryl.

In some embodiments, X is O. In some embodiments, X is $CH_2$.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 1 or 2. In some embodiments, z is 2 or 3. In some embodiments, z is 1, 2, or 3.

In some embodiments, $R^3$ is hydrogen, halogen or alkyl. In some embodiments, $R^3$ is alkyl. In some embodiments, $R^3$ is hydrogen. In some embodiments, $R^3$ is hydrogen, halogen, alkyl, cycloalkylalkyl, or aryl. In some embodiments, $R^3$ is hydrogen, halogen, cycloalkylalkyl, or aryl. In some embodiments, $R^3$ is halogen. In some embodiments, the halogen is fluorine.

In some embodiments, each $R^4$ and $R^5$ is independently selected from alkyl, or aryl. In some embodiments, each $R^4$ and $R^5$ is independently selected from alkyl. In some embodiments, each $R^4$ and $R^5$ is independently selected from hydrogen or alkyl. In some embodiments, the alkyl is $C_{10}$-$C_{18}$ alkyl. In some embodiments, the alkyl is $C_5$-$C_9$ alkyl. In some embodiments, the alkyl is $C_1$-$C_4$ alkyl. In some embodiments, the alkyl is $C_9$-$C_{13}$ alkyl. In some embodiments, the alkyl is $C_{10}$-$C_{12}$ alkyl. In some embodiments, the alkyl is $C_{10}$ alkyl. In some embodiments, the alkyl is $C_{11}$ alkyl. In some embodiments, the alkyl is $C_{12}$ alkyl.

In some embodiments, R is: —[CH($R^3$)O]z-$R^4$. In some embodiments, R is: —[CH($R^3$)O]z-C(=O)O$R^4$. In some embodiments, R is: —[CH($R^3$)O]z-C(=O)N$R^4R^5$. In some embodiments, R is: —[CH($R^3$)O]z-P(=O)(O$R^4$)(O$R^5$). In some embodiments, R is: —[CH($R^3$)O]z-C(=O)O$R^4$, wherein $R^3$ is hydrogen, and $R^4$ is $C_9$-$C_{13}$ alkyl. In some embodiments, R is: —[CH($R^3$)O]z-C(=O)O$R^4$, wherein $R^3$ is hydrogen, and $R^4$ is $C_{10}$-$C_{12}$ alkyl. In some embodiments, R is: —[CH($R^3$)O]z-C(=O)O$R^4$, wherein $R^3$ is hydrogen, and $R^4$ is $C_{10}$ alkyl. In some embodiments, R is: —[CH($R^3$)O]z-C(=O)O$R^4$, wherein $R^3$ is hydrogen, and $R^4$ is $C_{11}$ alkyl. In some embodiments, R is: —[CH($R^3$)O]z-C(=O)O$R^4$, wherein $R^3$ is hydrogen, and $R^4$ is $C_{12}$ alkyl.

In some embodiments, the opioid receptor antagonist prodrug compound described herein has a structure provided in Table 1.

TABLE 1

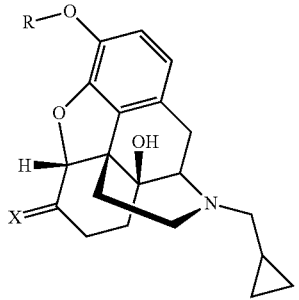

| Chemical Synthesis Example | R | X | Chemical Name |
|---|---|---|---|
| 1 | 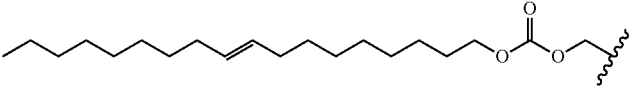 [SMILES: *COC(=O)OCCCCCCCC/C=C/CCCCCCCC] | $CH_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl ((E)-octadec-9-en-1-yl) carbonate |

TABLE 1-continued

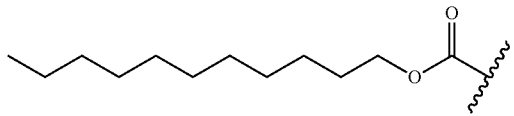 [SMILES: *C(=O)OCCCCCCCCCCC]

| Chemical Synthesis Example | R | X | Chemical Name |
|---|---|---|---|
| 2 | 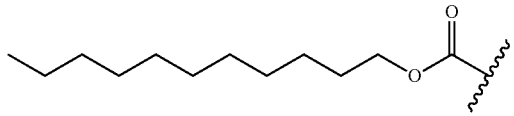 [SMILES: *C(=O)OCCCCCCCCCCC] | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl undecyl carbonate |
| 3 | 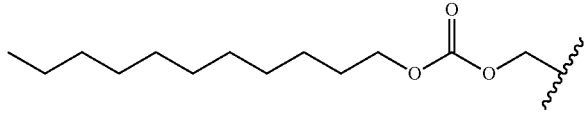 [SMILES: *COC(=O)OCCCCCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl undecyl carbonate |
| 4 | 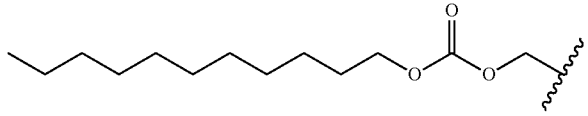 [SMILES: *COC(=O)OCCCCCCCCCCC] | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl yl)oxy)methyl undecyl carbonate |
| 5 | 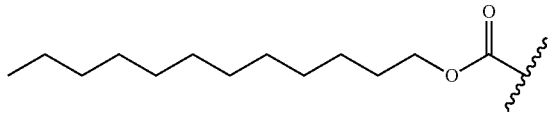 [SMILES: *C(=O)OCCCCCCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl undecyl carbonate |
| 6 | 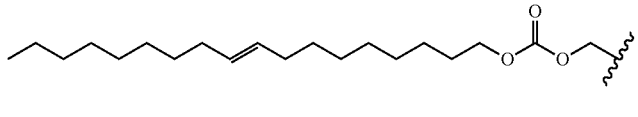 [SMILES: *COC(=O)OCCCCCCCC/C=C/CCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl dodecyl carbonate |
| 7 |  | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl ((E)-octadec-9-en-1-yl) carbonate |

TABLE 1-continued

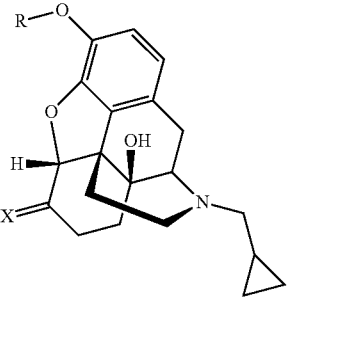

| Chemical Synthesis Example | R | X | Chemical Name |
|---|---|---|---|
| 8 | 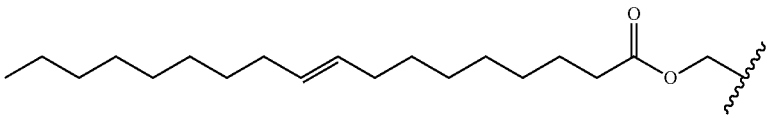 [SMILES: *COC(=O)CCCCCCC/C=C/CCCCCCCC] | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (E)-octadec-9-enoate |
| 9 | 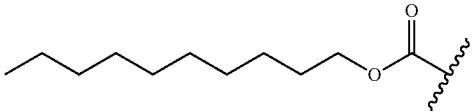 [SMILES: *C(=O)OCCCCCCCCCC] | $CH_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl (E)-octadec-9-enoate |
| 10 | 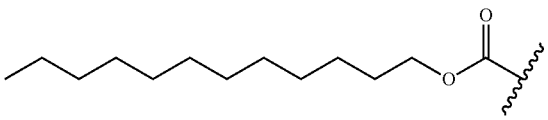 [SMILES: *C(=O)OCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl decyl carbonate |
| 11 | 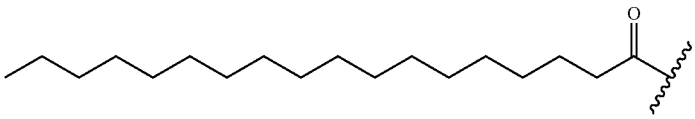 [SMILES: *C(=O)CCCCCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl dodecyl carbonate |
| 12 |  | $CH_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl stearate |

TABLE 1-continued

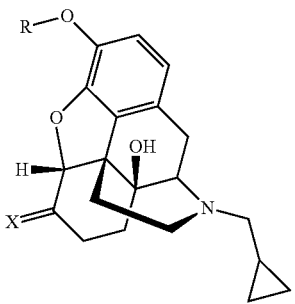

| Chemical Synthesis Example | R | X | Chemical Name |
|---|---|---|---|
| 13 | (Z)-docos-13-enyl chain with C(=O) attachment | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (Z)-docos-13-enoate |
| 14 | docosanoyl chain | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl docosanoate |
| 15 | (E)-octadec-9-enoyl chain | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (E)-octadec-9-enoate |
| 16 | icosanoyl chain | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosanoate |
| 17 | octyl carbonate group | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octyl carbonate |
| 18 | decyl carbonate group | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl decyl carbonate |

TABLE 1-continued

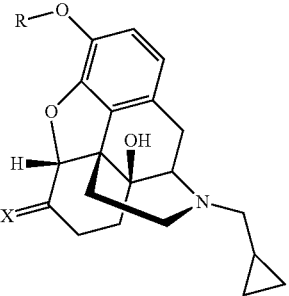

| Chemical Synthesis Example | R | X | Chemical Name |
|---|---|---|---|
| 19 | 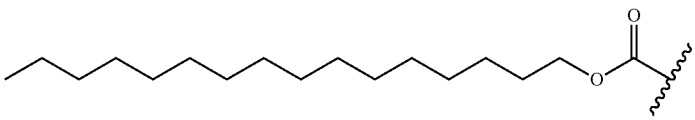 [SMILES: *C(=O)OCCCCCCCCCCCCCCCC] | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl hexadecyl carbonate |
| 20 | 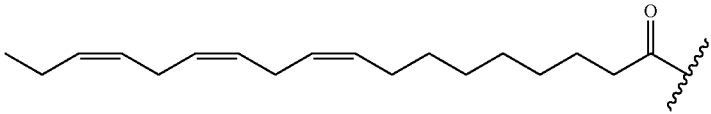 [SMILES: *C(=O)CCCCCCC/C=C\C/C=C\C/C=C\CC] | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z,15Z)-octadeca-9,12,15-trienoate |
| 21 | 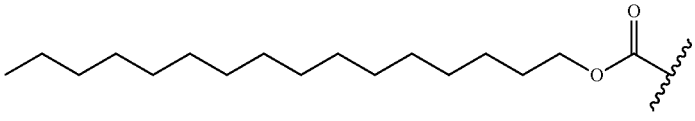 [SMILES: *C(=O)OCCCCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl hexadecyl carbonate |
| 22 | 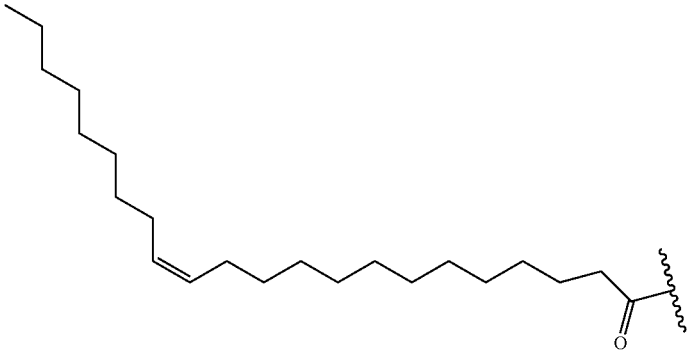 [SMILES: *C(=O)CCCCCCCCCCC/C=C\CCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (Z)-docos-13-enoate |
| 23 | 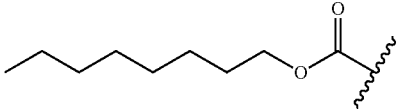 [SMILES: *C(=O)OCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl octyl carbonate |
| 24 | 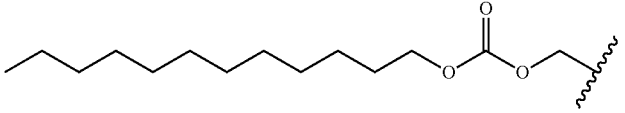 [SMILES: *COC(=O)OCCCCCCCCCCCC] | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2- |

TABLE 1-continued

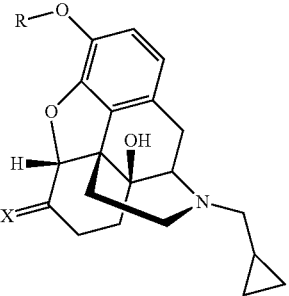

| Chemical Synthesis Example | R | X | Chemical Name |
|---|---|---|---|
| | | | e]isoquinolin-9-yl)oxy)methyl dodecyl carbonate |
| 25 | 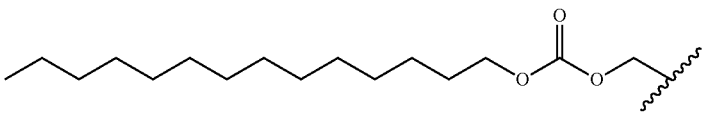 [SMILES: *COC(=O)OCCCCCCCCCCCCCC] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecyl carbonate |
| 26 | 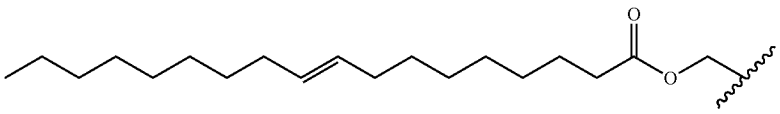 [SMILES: *COC(=O)CCCCCCC/C=C/CCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl (E)-octadec-9-enoate |
| 27 | 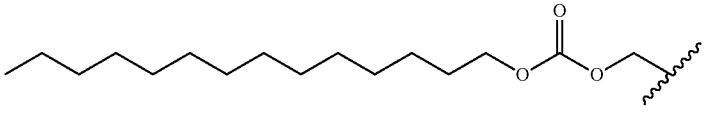 [SMILES: *COC(=O)OCCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl tetradecyl carbonate |
| 28 | 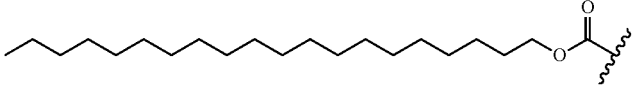 [SMILES: *C(=O)OCCCCCCCCCCCCCCCCCCCC] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosyl carbonate |
| 29 | 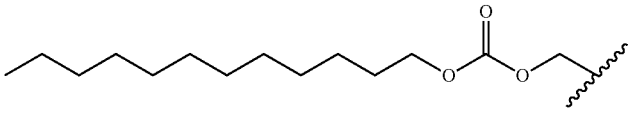 [SMILES: *COC(=O)OCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)ocy)methyl dodecyl carbonate |
| 30 | 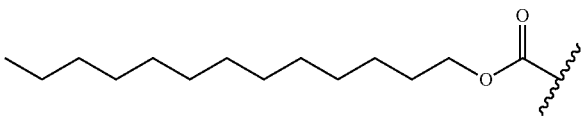 [SMILES: *C(=O)OCCCCCCCCCCCCC] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinilin-9-yl tridecyl carbonate |

TABLE 1-continued

| Chemical Synthesis Example | R | X | Chemical Name |
|---|---|---|---|
| 31 | CH₃(CH₂)₁₂CH₂-O-C(=O)- | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tetradecyl carbonate |
| 32 | CH₃(CH₂)₁₃CH₂-O-C(=O)- | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl pentadecyl carbonate |
| 33 | CH₃(CH₂)₁₆CH₂-O-C(=O)- | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octadecyl carbonate |
| 34 | CH₃(CH₂)₁₄CH₂-O-C(=O)-O-CH₂- | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecyl carbonate |
| 35 | CH₃(CH₂)₈CH₂-O-C(=O)-O-CH₂- | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl decyl carbonate |
| 36 | oleoyl group (CH₃(CH₂)₇CH=CH(CH₂)₇C(=O)-) | CH₂ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl oleate |

TABLE 1-continued

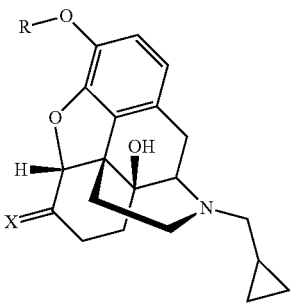

| Chemical Synthesis Example | R | X | Chemical Name |
|---|---|---|---|
| 37 | 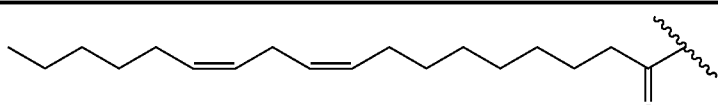 | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z)-octadeca-9,12-dienoate |
| 38 | 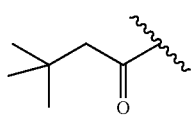 [SMILES: *C(=O)CC(C)(C)C] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl 3,3-dimethylbutanoate |
| 39 | 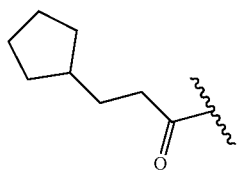 [SMILES: *C(=O)CCC1CCCC1] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl 3-cyclopentylpropanoate |
| 40 | 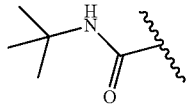 [SMILES: *C(=O)NC(C)(C)C] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tert-butylcarbamate |
| 41 | 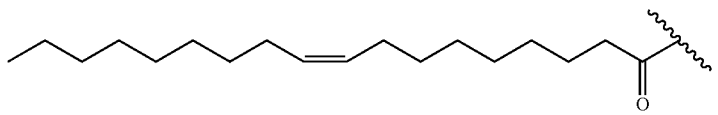 [SMILES: *C(=O)CCCCCCC/C=C\CCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl oleate |
| 42 | 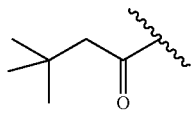 [SMILES: *C(=O)CC(C)(C)C] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3,3-dimethylbutyanoate |
| 43 | 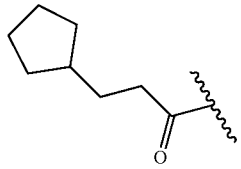 [SMILES: *C(=O)CCC1CCCC1] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3-cyclopentylpropanoate |

TABLE 1-continued

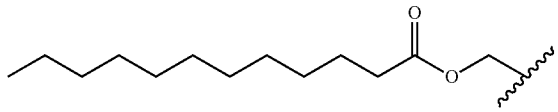 [SMILES: *COC(=O)CCCCCCCCCCC]

| Chemical Synthesis Example | R | X | Chemical Name |
|---|---|---|---|
| 44 | 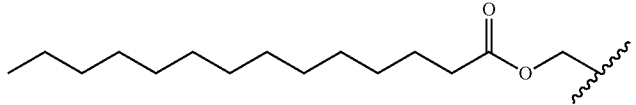 [SMILES: *COC(=O)CCCCCCCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)ocy)methyl dodecanoate |
| 45 | 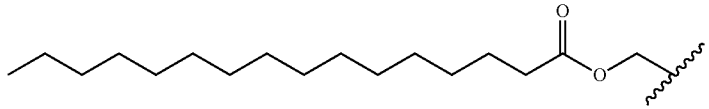 [SMILES: *COC(=O)CCCCCCCCCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)ocy)methyl tetradecanoate |
| 46 | 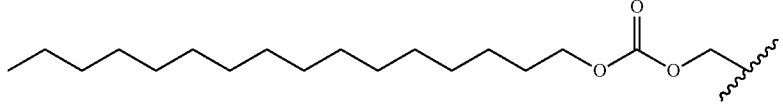 [SMILES: *COC(=O)OCCCCCCCCCCCCCCCC] | CH$_2$ | (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecanoate |
| 47 | 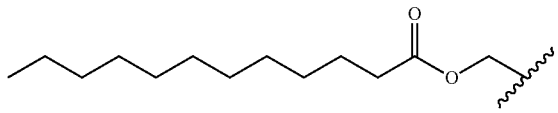 [SMILES: *COC(=O)CCCCCCCCCCC] | CH$_2$ | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecyl carbonate |
| 48 | 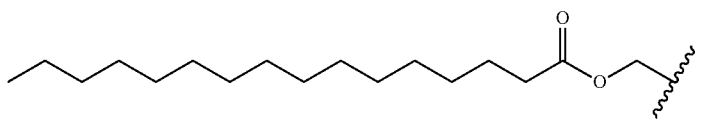 [SMILES: *COC(=O)CCCCCCCCCCCCCCC] | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl dodecanoate |
| 49 |  | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecanoate |

In some embodiments, the opioid receptor antagonist prodrug compound described herein has a structure provided in Table 2.

TABLE 2

| Example | R | X | Chemical Name |
|---|---|---|---|
| 50 | CH3-(CH2)18-C(=O)- | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl iconsanoate |
| 51 | CH3-(CH2)20-C(=O)- | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl docosanoate |
| 52 | (9Z,12Z,15Z)-octadeca-9,12,15-trienoyl | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (9Z,12Z)-octadeca-9,12,15-trienoate |
| 53 | (9Z,12Z)-octadeca-9,12-dienoyl | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (9Z,12Z)-octadeca-9,12-dienoate |
| 54 | stearoyl | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl stearate |
| 55 | palmitoyl | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl palmitate |

TABLE 2-continued

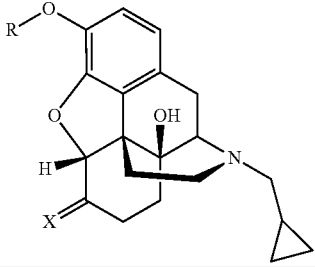

| Example | R | X | Chemical Name |
|---|---|---|---|
| 56 | 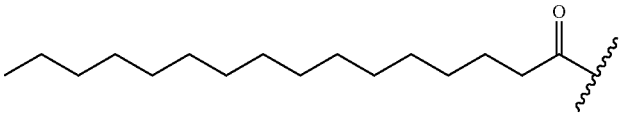 [SMILES: *C(=O)CCCCCCCCCCCCCCC] | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl palmitate |
| 57 | 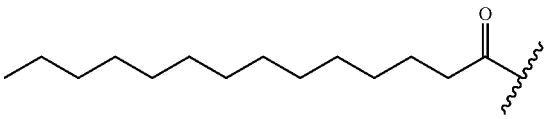 [SMILES: *C(=O)CCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl tetradecanoate |
| 58 | 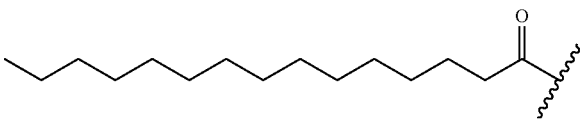 [SMILES: *C(=O)CCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]-isoquinolin-9-yl pentadecanoate |
| 59 | 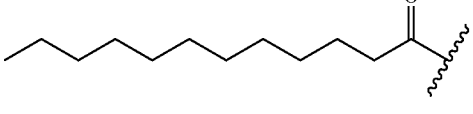 | CH$_2$ | (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl dodecanoate |
| 60 | 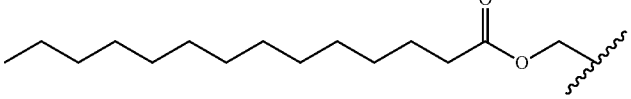 | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl tetradecanoate |
| 61 | H | CH$_2$ | Nalmefene |
| 62 | H | O | Naltrexone |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the opioid receptor antagonist prodrug compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the opioid receptor antagonist prodrug compound as described herein is administered as a pure chemical. In other embodiments, the opioid receptor antagonist prodrug compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one opioid receptor antagonist prodrug compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of any one of Formula (II), (IIa), or (III), or a compound disclosed in Table 1, or a pharmaceutically acceptable salt thereof.

In certain embodiments, the opioid receptor antagonist prodrug compound as described by any one of Formula (II), (IIa), or (III), or a compound disclosed in Table 1, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

In some embodiments, the opioid receptor antagonist prodrug compound as described by any one of Formula (II), (IIa), or (III), or a compound disclosed in Table 1, is formulated for administration by injection. In some instances, the injection formulation is an aqueous formulation. In some instances, the injection formulation is a non-aqueous formulation. In some instances, the injection formulation is an oil-based formulation, such as sesame oil, cottonseed oil, or the like.

The dose of the composition comprising at least one opioid receptor antagonist prodrug compound as described herein differ, depending upon the patient's (e.g., human) condition, that is, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Dosing and Therapeutic Regimens

In some embodiments, the pharmaceutical compositions described herein are administered for therapeutic applications. In some embodiments, the pharmaceutical composition is administered once per day, twice per day, three times per day, four times per day or more. The pharmaceutical composition is administered daily, every day, every alternate day, two days a week, three days a week, four days a week, five days a week, once a week, every other week, two weeks per month, three weeks per month, once a month, twice a month, three times per month, or other greater or lesser intervening frequency; also, it could be dosed once every 2 months, once every 3 months, once every 4 months, once every 5 months, once every 6 months, once yearly, or with greater or lesser than aforementioned interval frequency. The pharmaceutical composition is administered for at least 1 week, 2 weeks, 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does not improve, upon the physician's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, 365 days, or 366 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be adjusted, as a function of the symptoms, to a level at which the improved disease, disorder or condition is retained.

In some embodiments, the amount of given opioid receptor antagonist prodrug compound varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

In some embodiments, the amount of given opioid receptor antagonist prodrug compound will typically be in the range of about 0.02 mg to about 5000 mg per dose. (Note: all prodrug mass quantities are expressed in base moiety equivalents). In some embodiments, the amount of given opioid receptor antagonist prodrug compound is in the range of about 1 mg to about 5000 mg per dose. In some embodiments, the amount of given opioid receptor antagonist prodrug compound is in the range of about 10 mg to about 1600 mg per dose. The desired dose may conveniently be presented in a single dose or as divided doses administered simultaneously (or over a short period of time) or at appropriate intervals, for example as two, three, four or more sub-doses per day.

In some embodiments, the daily dosages appropriate for the opioid receptor antagonist prodrug compound described herein are from about 0.01 mg/kg to about 30 mg/kg. In one embodiment, the daily dosages are from about 0.1 mg/kg to about 165 mg/kg. An indicated daily dosage in the larger mammal, including, but not limited to, humans, is in the range from about 0.5 mg to about 1000 mg, conveniently administered in a single dose or in divided doses. Suitable unit dosage forms for intramuscular administration include from about 1 to about 5000 mg active ingredient. In one embodiment, the unit dosage is about 10 mg, about 50 mg, about, 100 mg, about 200 mg, about 500 mg, about 1000 mg, about 2000 mg, about 2500 mg, about 4000 mg, or about 5000 mg.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Treatment of Behavioral Disorders

In some embodiments, described herein is a method of treating one or more medical conditions in a subject in need thereof, comprising administering to the subject in need thereof an opioid receptor antagonist compound described herein.

In some embodiments, the medical condition is selected from the group comprising opioid dependence, alcohol dependence, drug addiction, polydrug addiction and pain.

In some embodiments, described herein is an opioid receptor antagonist compound for use in reduction of opioid consumption in a patient with opioid dependence.

In some embodiments, described herein is an opioid receptor antagonist compound for use in reduction of alcohol consumption in a patient with alcohol dependence, pathological gambling shopping addiction or other diseases of compulsive behavior.

Provided herein is a method of treating opioid dependence in a patient in need thereof comprising administering a pharmaceutical composition comprising a compound of Formula (II), (IIa), or (III), or a compound disclosed in Table 1, or pharmaceutically acceptable salt thereof, and a pharmaceutically acceptable excipient. Provided herein is the method wherein the pharmaceutical composition is administered orally. Provided herein is the method wherein the pharmaceutical composition is administered by injection. Provided herein is the method wherein the pharmaceutical composition is administered by intramuscular injection. Provided herein is the method wherein the intramuscular injection is a depot injection. Provided herein is the method wherein the depot injection provides a therapeutically effective concentration for a period of 2 days to 3 months. Provided herein is the method wherein the depot injection provides a therapeutically effective concentration for a period of about 2 days. Provided herein is the method wherein the depot injection provides a therapeutically effective concentration for a period of about 4 days. Provided herein is the method wherein the depot injection provides a therapeutically effective concentration for a period of about 7 days. Provided herein is the method wherein the depot injection provides a therapeutically effective concentration for a period of about 10 days. Provided herein is the method wherein the depot injection provides a therapeutically effective concentration for a period of about 1 week. Provided herein is the method wherein the depot injection provides a therapeutically effective concentration for a period of about 2 weeks. Provided herein is the method wherein the depot injection provides a therapeutically effective concentration for a period of about 3 weeks. Provided herein is the method wherein the depot injection provides a therapeutically effective concentration for a period of about 4 weeks. Provided herein is the method wherein the depot injection provides a therapeutically effective concentration for a period of about 5 weeks. Provided herein is the method wherein the depot injection provides a therapeutically effective concentration for a period of about 6 weeks. Provided herein is the method wherein the depot injection provides a therapeutically effective concentration for a period of about 1 month. Provided herein is the method wherein the depot injection provides a therapeutically effective concentration for a period of about 2 months. Provided herein is the method wherein the depot injection provides a therapeutically effective concentration for a period of about 3 months. Provided herein is the method wherein the depot injection provides a therapeutically effective concentration for a period of about 4 months. Provided herein is the method wherein the depot injection provides a therapeutically effective concentration for a period of about 5 months. Provided herein is the method wherein the depot injection provides a therapeutically effective concentration for a period of about 6 months or greater.

Provided herein is a method of treating opioid dependence in a patient in need thereof comprising administering a pharmaceutical composition comprising a compound disclosed in Table 3, or pharmaceutically acceptable salt thereof, and a pharmaceutically acceptable excipient.

TABLE 3

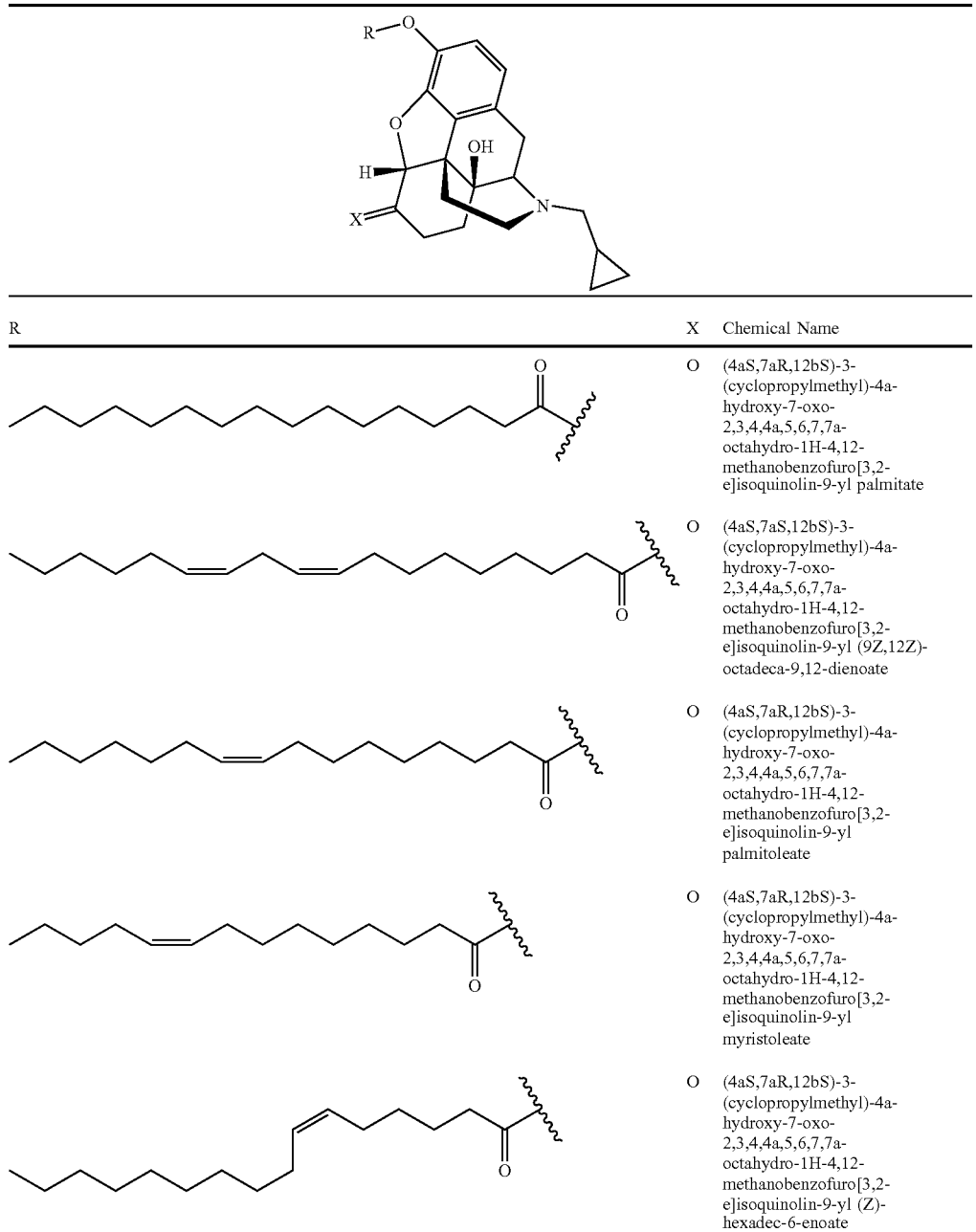

TABLE 3-continued

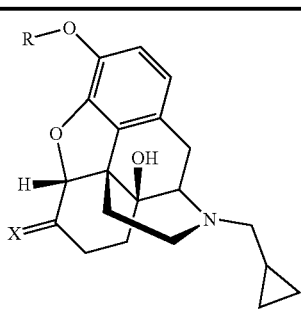

| R | X | Chemical Name |
|---|---|---|
| 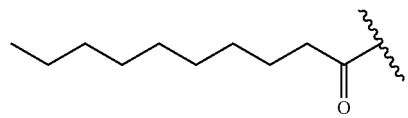 [SMILES: *C(=O)CCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl decanoate |
| 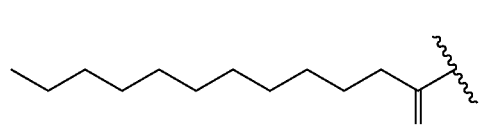 | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl undecanoate |
| 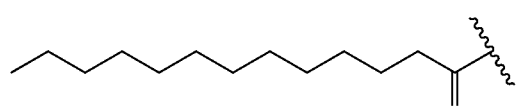 | O | (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl dodecanoate |
| 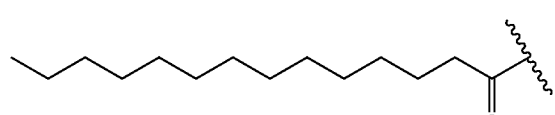 | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl tridecanoate |
| 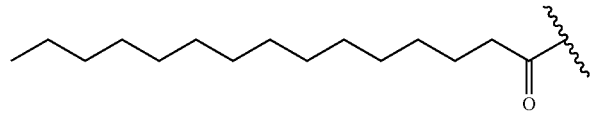 [SMILES: *C(=O)CCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl tetradecanoate |
| 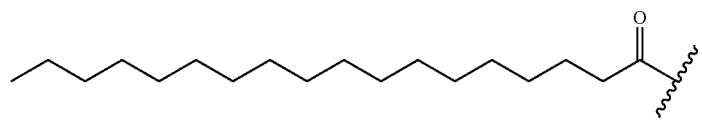 [SMILES: *C(=O)CCCCCCCCCCCCCCCCC] | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl pentadecanoate |
|  | O | (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl stearate |

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

In some embodiments, opioid receptor antagonists prodrug compounds disclosed herein are synthesized according to the following examples.

General Scheme 1 for the Synthesis of Nalmefene Prodrugs.

General Scheme 2 for the Synthesis of Naltrexone Prodrugs.

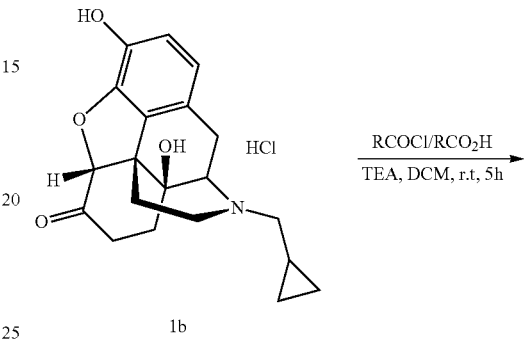

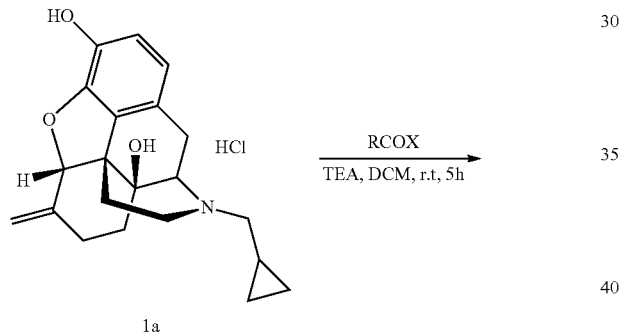

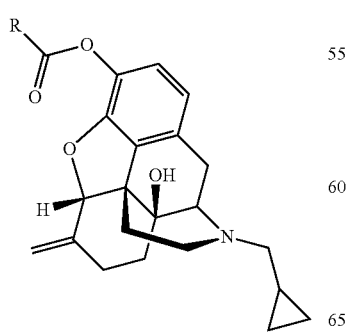

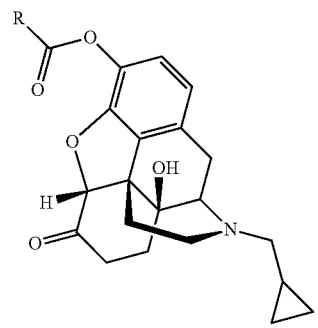

Example 1: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl ((E)-octadec-9-en-1-yl) carbonate

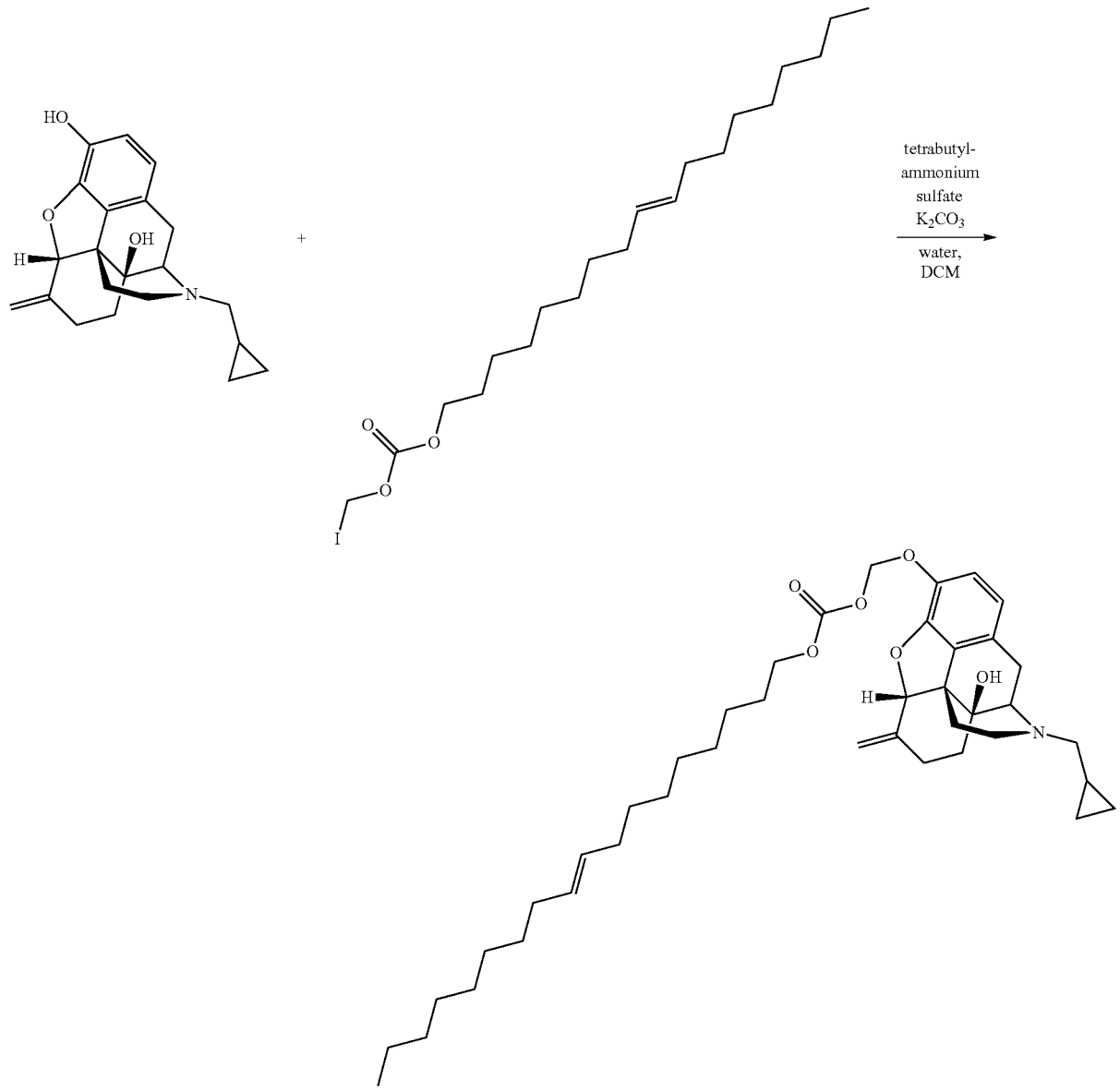

To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (8 g, 21.28 mmol, 1 eq, HCl) in $H_2O$ (100 mL) was added $K_2CO_3$ (8.82 g, 63.85 mmol, 3 eq) in one portion at 25° C. under $N_2$. The mixture was stirred at 25° C. for 30 min. To a mixture of tetrabutylammonium sulfate (24.73 g, 21.28 mmol, 24.49 mL, 50% solution, 1 eq) in DCM (100 mL) then the later mixture was added to the former mixture. Iodomethyl (E)-octadec-9-en-1-yl carbonate (14.44 g, 31.92 mmol, 1.5 eq), obtained according to procedure described in Example 42B, was added and the mixture was stirred for 12 hours. The residue was concentrated in vacuum to remove the DCM then was dissolved by saturated solution of $NaHCO_3$ (100 mL). The aqueous phase was extracted with ethyl acetate 600 mL (200 mL*3). The combined organic phase was dried with anhydrous $Na_2SO_4$, filtered and concentrated in vacuum. The residue was purified by silica gel chromatography (Petroleum ether/Ethyl acetate=20/1 to 1/1). The residue was further purified by prep-HPLC, MeOH as solvent, select conventional reverse phase separation as method, separation system is TFA. $NaHCO_3$ was added to adjust pH to about 8, the aqueous phase was extracted with ethyl acetate 900 mL (300 mL*3).The combined organic phase was washed with brine (200 mL), dried with anhydrous $Na_2SO_4$, filtered and concentrated in vacuum. The compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl[(E)-octadec-9-enyl] carbonate (5 g, 7.46 mmol, 35.03% yield) was obtained as a yellow oil. M+H⁺=665.5 (LCMS). ¹H NMR (400 MHz, CDCl₃): see FIG. 1.

Example 2: Step 2A: Synthesis of (4-nitrophenyl) undecyl carbonate

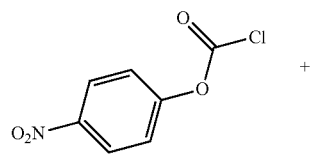

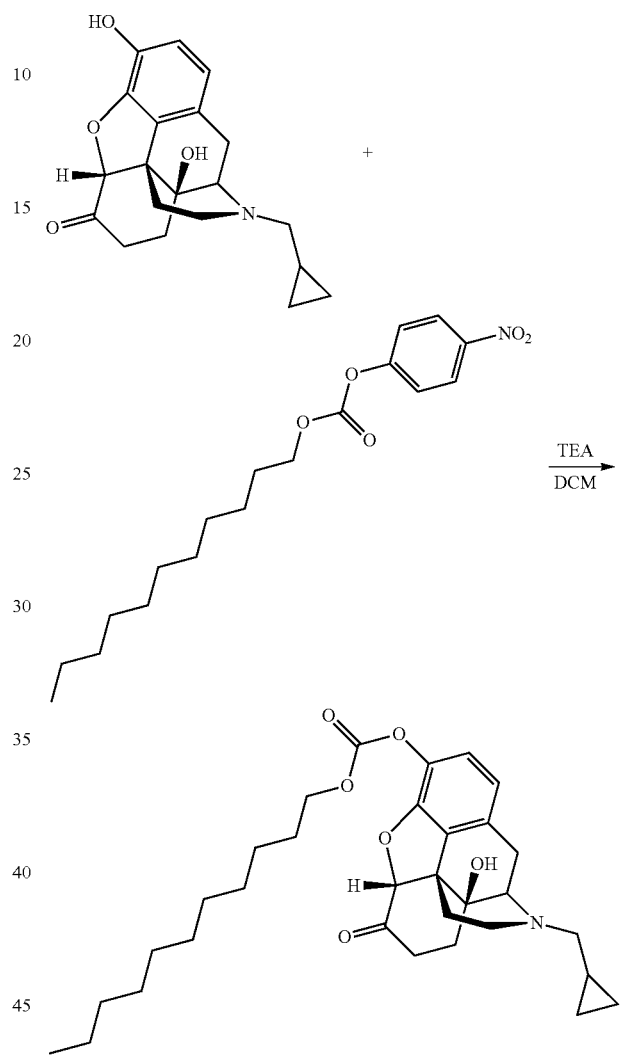

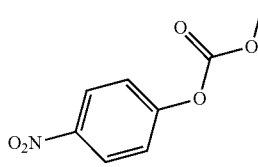

To a mixture of undecan-1-ol (40 g, 232.14 mmol, 1 eq) in DCM (600 mL) was added TEA (46.98 g, 464.29 mmol, 64.62 mL, 2 eq) (4-nitrophenyl) carbonochloridate (70.19 g, 348.22 mmol, 1.5 eq) was added to the former mixture portionwise under N₂. The mixture was stirred at 25° C. for 12 hr. The reaction mixture was concentrated under reduced pressure to remove solvent. The residue was purified by column chromatography. Compound (4-nitrophenyl) undecyl carbonate (33.95 g, 100.62 mmol, 43.34% yield) was obtained as a yellow solid.

Figure 2:
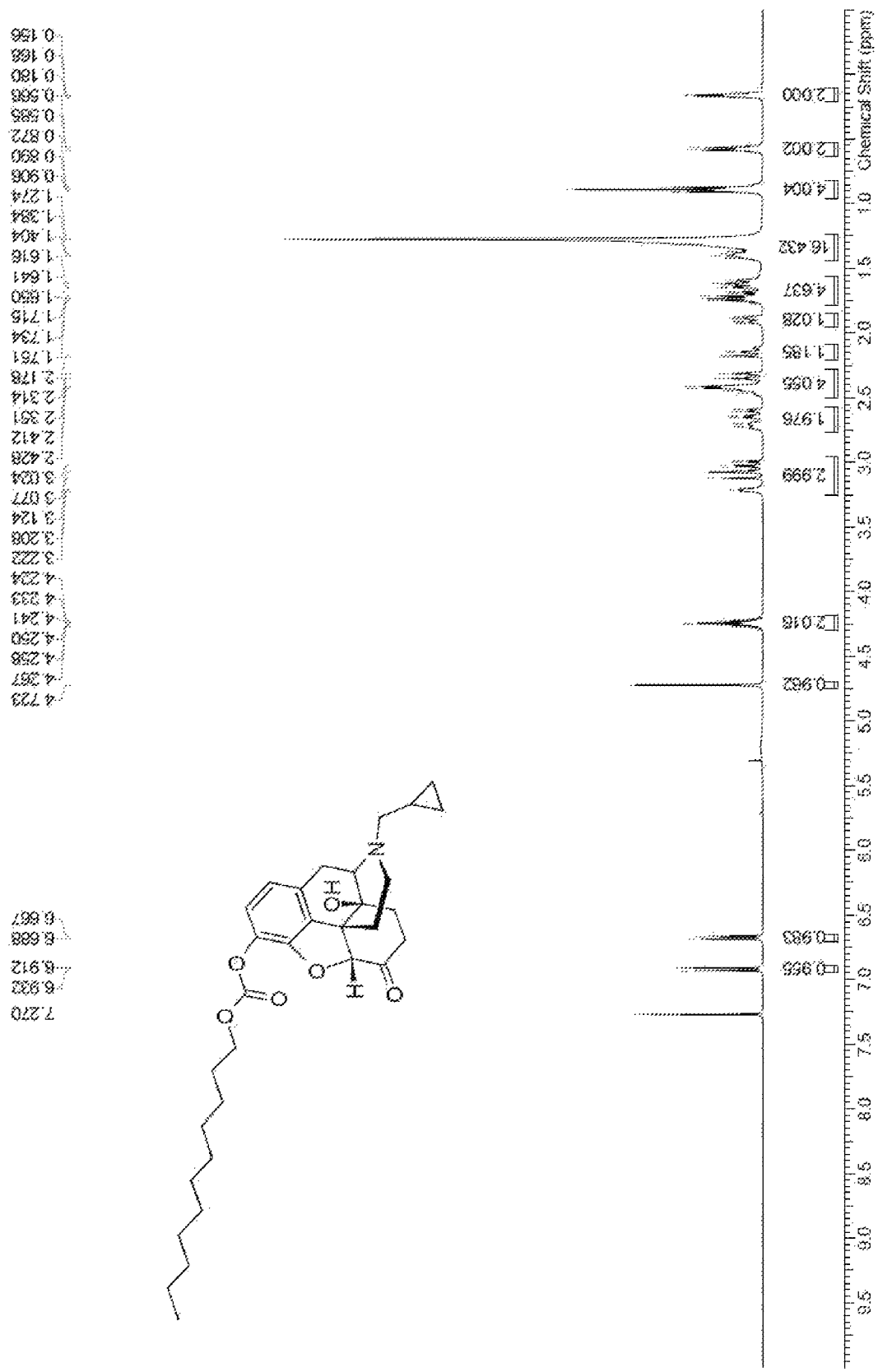
FIG. 2 provides the nuclear magnetic resonance spectrum of Example 2 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl undecyl carbonate.

Step 2B: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl undecyl carbonate To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (15 g, 39.70 mmol, 1 eq, HCl) in DCM (150 mL) was added TEA (12.05 g, 119.09 mmol, 16.58 mL, 3 eq) in one portion at 25° C. under N₂. The mixture was stirred at 25° C. for 30 min, To a mixture of (4-nitrophenyl) undecyl carbonate (26.79 g, 79.39 mmol, 2 eq) in DCM (150 mL), then add to the former mixture, the mixture was stirred at 25° C. for 12 h. The residue was concentrated in vacuum to remove the DCM then was dissolved by saturated solution of NaHCO₃. The aqueous phase was extracted with ethyl acetate (200 mL*3). The combined organic phase was dried with anhydrous Na₂SO₄, filtered and concentrated in vacuum. The residue was purified by column chromatography (SiO₂, Petroleum ether/Ethyl acetate=40:1 to 1:1). The residue was further purified by prep-HPLC, MeOH as solvent, select conventional reverse phase separation as method, separation system is TFA. NaHCO₃ was added to adjust pH to about 8, the aqueous phase was extracted with ethyl acetate (200 mL*3). The combined organic phase was washed with brine (500 mL), dried with anhydrous Na₂SO₄, filtered and concentrated in vacuum. Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl] undecyl carbonate (7.91 g, 14.63 mmol, 36.85% yield) was obtained as a yellow oil. M+H⁺=540.3 (LCMS). ¹H NMR (400 MHz, CDCl₃): see FIG. 2.

Example 3: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl undecyl carbonate

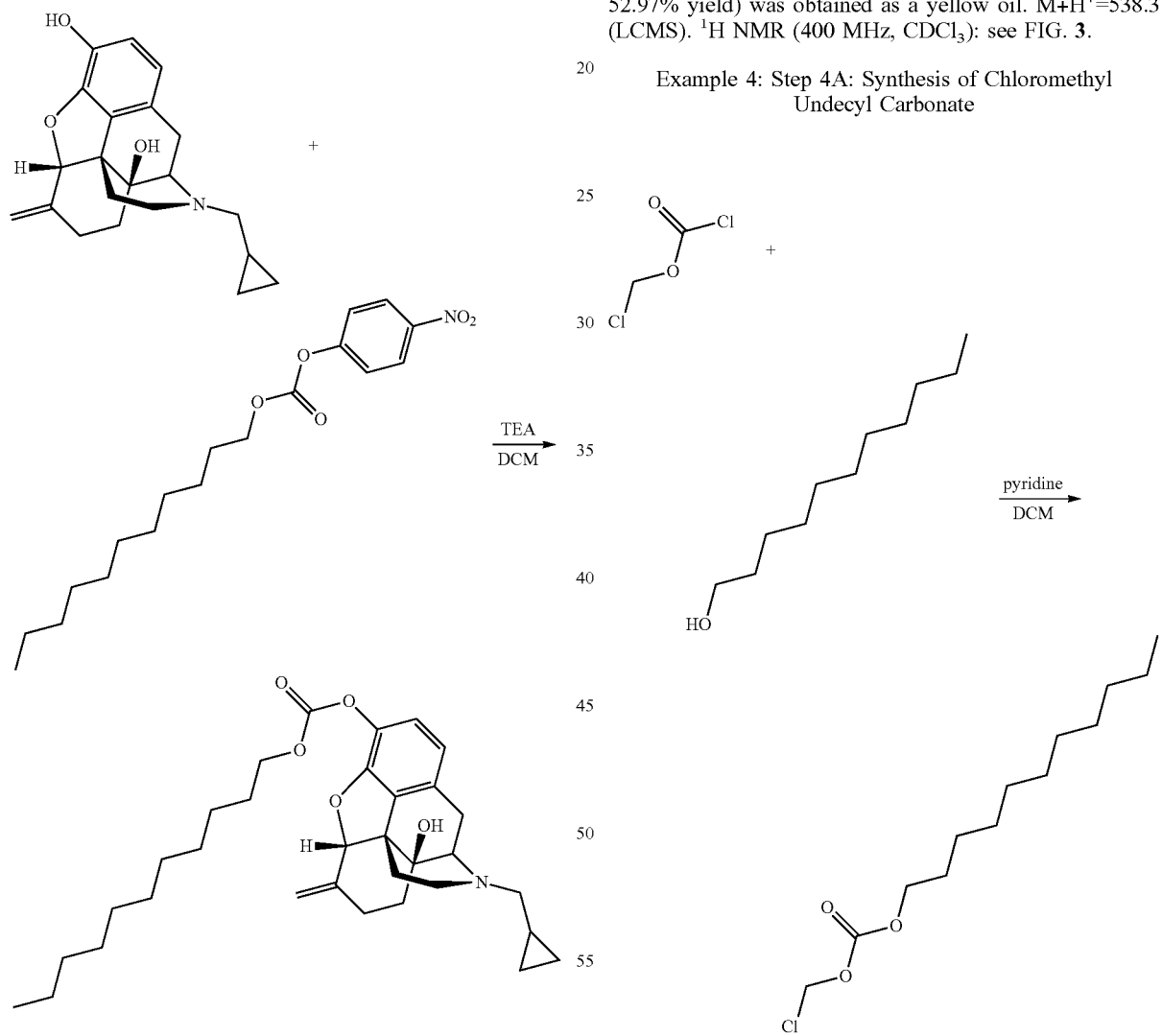

Figure 3:
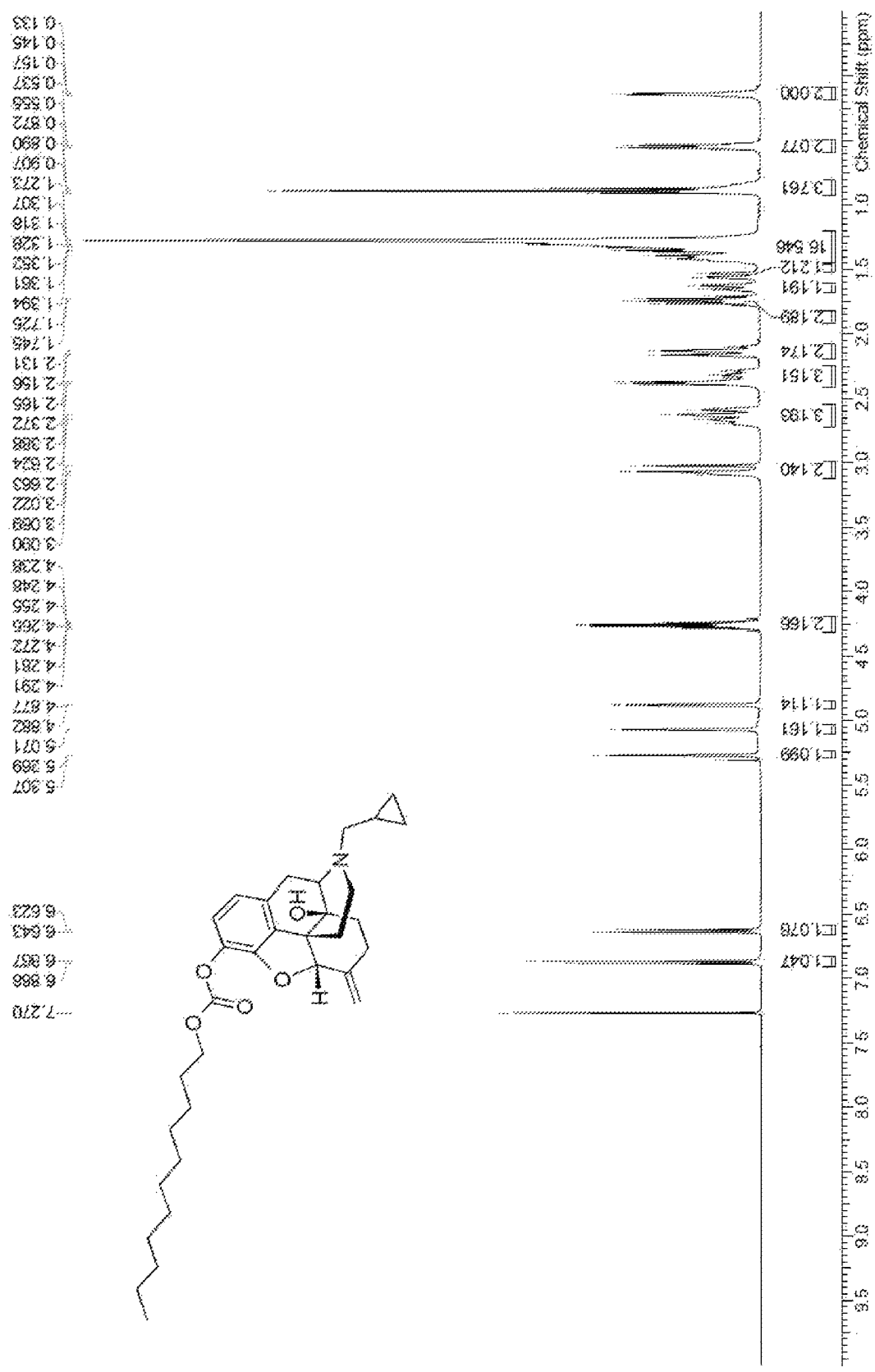
FIG. 3 provides the nuclear magnetic resonance spectrum of Example 3 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl undecyl carbonate.

To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (15 g, 39.91 mmol, 1 eq, HCl) in DCM (150 mL) was added TEA (12.11 g, 119.72 mmol, 16.66 mL, 3 eq) in one portion at 25° C. under N₂. The mixture was stirred at 25° C. for 30 min, To a mixture of (4-nitrophenyl) undecyl carbonate (26.93 g, 79.81 mmol, 2 eq) in DCM (150 mL), then add to the former mixture, the mixture was stirred at 25° C. for 12 h. The mixture was diluted with H₂O (800 mL), extracted with DCM (300 mL*3). The organic phase was washed with brine (300 mL), dried over Na₂SO₄, filtered and the filtrate was concentrated under reduced pressure. The residue was purified by silica gel chromatography (Petroleum ether/Ethyl acetate=40/1 to 1/1). The residue was further purified by prep-HPLC, MeOH as solvent, select conventional reverse phase separation as method, separation system is TFA. NaHCO₃ was added to adjust pH to about 8, the aqueous phase was extracted with ethyl acetate (200 mL*3). The combined organic phase was washed with brine (500 mL), dried with anhydrous Na₂SO₄, filtered and concentrated in vacuum. The compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl] undecyl carbonate (11.40 g, 21.14 mmol, 52.97% yield) was obtained as a yellow oil. M+H⁺=538.3 (LCMS). ¹H NMR (400 MHz, CDCl₃): see FIG. 3.

Example 4: Step 4A: Synthesis of Chloromethyl Undecyl Carbonate

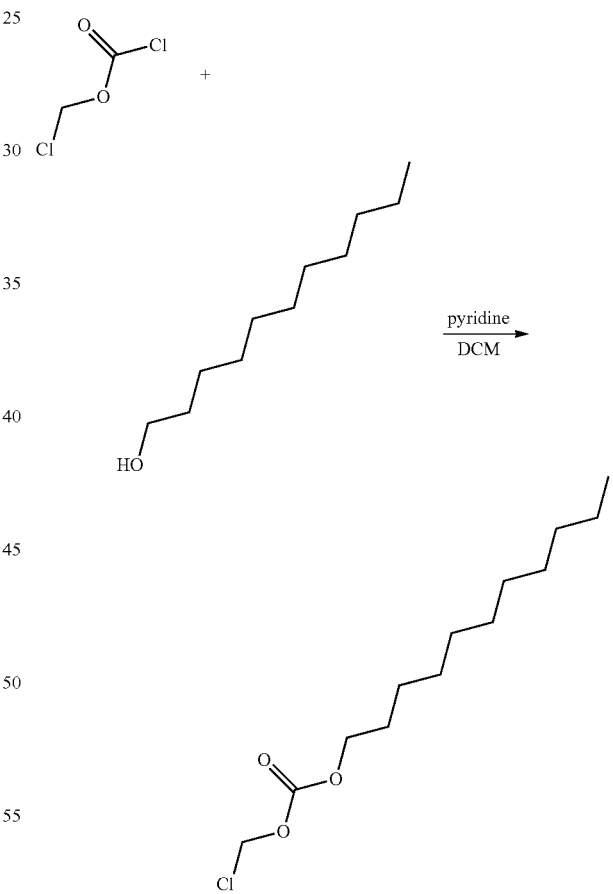

To a mixture of undecan-1-ol (80 g, 464.29 mmol, 1 eq) and pyridine (73.45 g, 928.58 mmol, 74.95 mL, 2 eq) in DCM (600 mL) was added chloromethyl carbonochloridate (119.73 g, 928.58 mmol, 82.57 mL, 2 eq) dropwise at 0° C. under N₂. The mixture was stirred at 25° C. for 12 h. The reaction mixture was extracted by DCM 1500 mL (500 mL*3). The organic phase was separated, washed with brine 30 mL (150 mL*2), dried over Na₂SO₄, filtered and con-

67 centrated under reduced pressure to give a residue. The residue was purified by column chromatography (SiO$_2$, Petroleum ether/Ethyl acetate=50/1 to 1:1). Compound chloromethyl undecyl carbonate (80 g, 302.13 mmol, 65.07% yield) was obtained as a yellow oil.

Step 4B: Synthesis of Iodomethyl Undecyl Carbonate

68

Step 4C: Synthesis of (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl undecyl carbonate

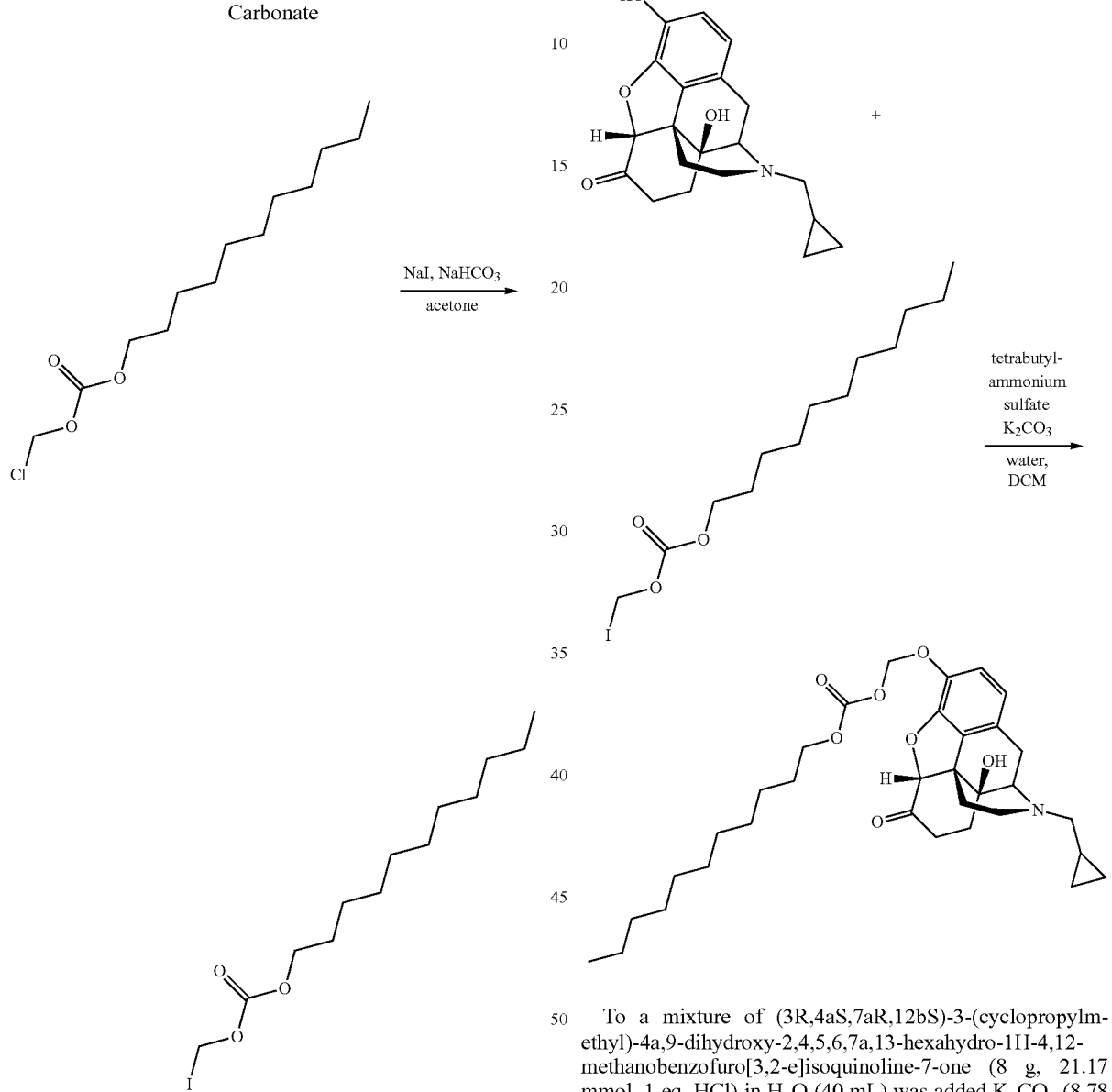

To a mixture of chloromethyl undecyl carbonate (30 g, 113.30 mmol, 1 eq) in acetone (400 mL) was added NaHCO$_3$ (11.42 g, 135.96 mmol, 5.29 mL, 1.2 eq) and NaI (20.38 g, 135.96 mmol, 1.2 eq) in one portion at 25° C. under N$_2$. The mixture was stirred at 25° C. for 12 h in dark. The reaction mixture was partitioned between EtOAc (400 mL) and H$_2$O (400 mL). The organic phase was separated, washed with brine (80 mL), dried with anhydrous Na$_2$SO$_4$, filtered and concentrated in vacuum. The residue was purified by column chromatography (SiO$_2$, Petroleum ether/Ethyl acetate=1/0). Compound iodomethyl undecyl carbonate (60 g, 74.33% yield) was obtained as a yellow oil.

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (8 g, 21.17 mmol, 1 eq, HCl) in H$_2$O (40 mL) was added K$_2$CO$_3$ (8.78 g, 63.52 mmol, 3 eq) in one portion at 25° C. under N$_2$. The mixture was stirred at 25° C. for 30 min. Then was added tetrabutylammonium sulfate (24.60 g, 21.17 mmol, 24.36 mL, 50% solution, 1 eq) in DCM (40 mL) in one portion at 25° C. Then the mixture was added iodomethyl undecyl carbonate (15.08 g, 42.34 mmol, 2 eq) the mixture was stirred at 25° C. for 11.5 h. The reaction mixture was partitioned between DCM 200 mL (100 mL*2) and H$_2$O 100 mL. The organic phase was separated, washed with brine 40 mL, dried with anhydrous Na$_2$SO$_4$, filtered and concentrated in vacuum. The residue was purified by column chromatography (SiO$_2$, Petroleum ether/Ethyl acetate=50/1 to 1:1).

Figure 4:
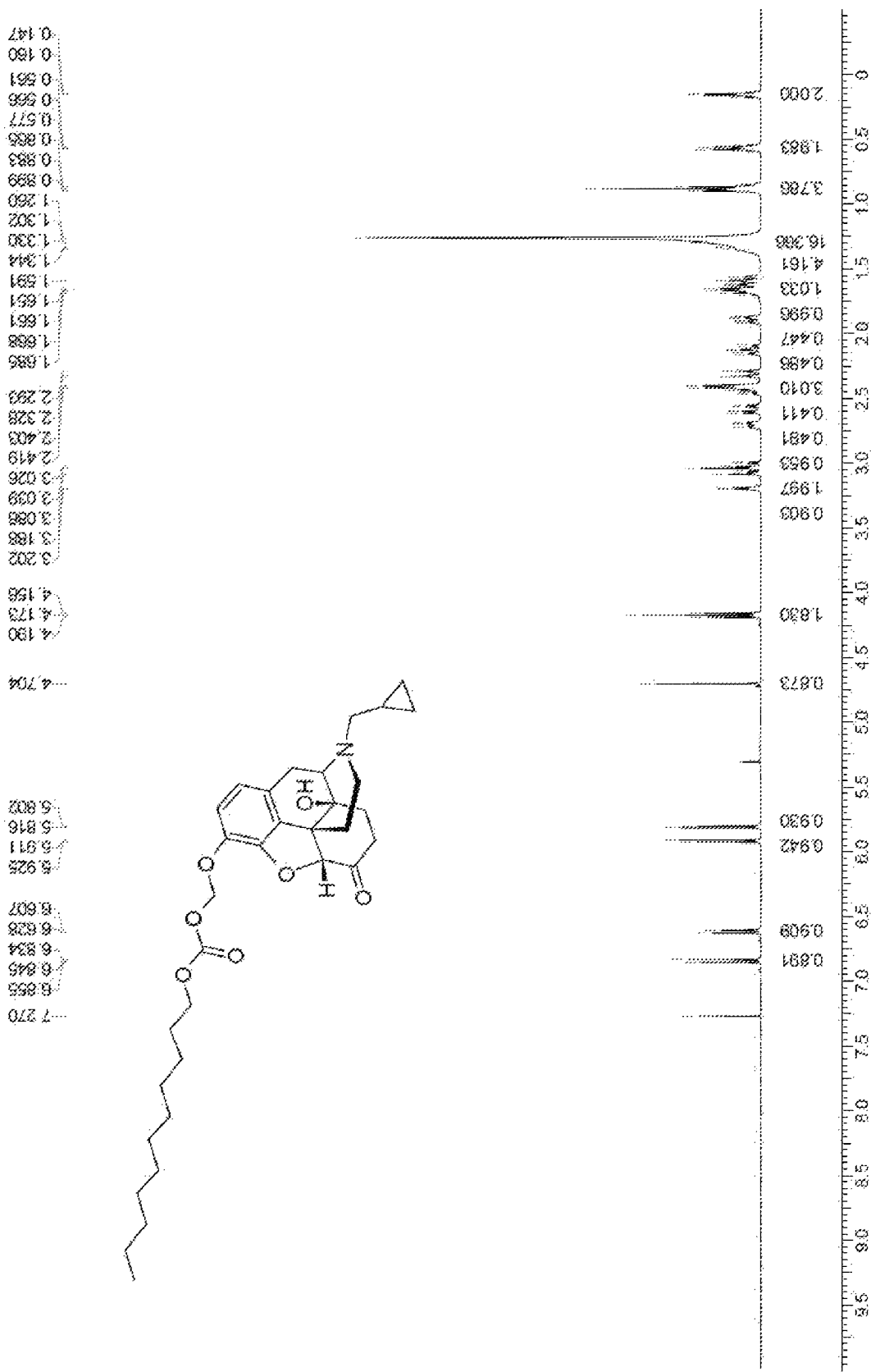
FIG. 4 provides the nuclear magnetic resonance spectrum of Example 4 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl undecyl carbonate.

Then was further purified by prep-HPLC, MeOH as solvent, select conventional reverse phase separation as method, separation system is TFA. NaHCO$_3$ was added to adjust pH to about 8, the aqueous phase was extracted with ethyl acetate (400 mL*3).washed with brine 300 mL, dried with anhydrous Na$_2$SO$_4$, filtered and concentrated in vacuum. Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl undecyl carbonate (6.9 g) was obtained as a yellow oil. M+H$^+$=570.3 (LCMS). $^1$H NMR (400 MHz, CDCl$_3$): see FIG. 4.

Example 5: Synthesis of Example 5: (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl undecyl carbonate

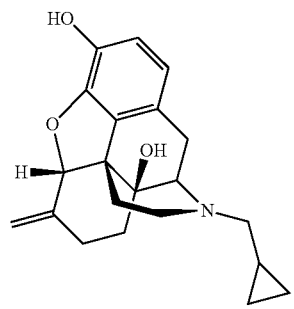

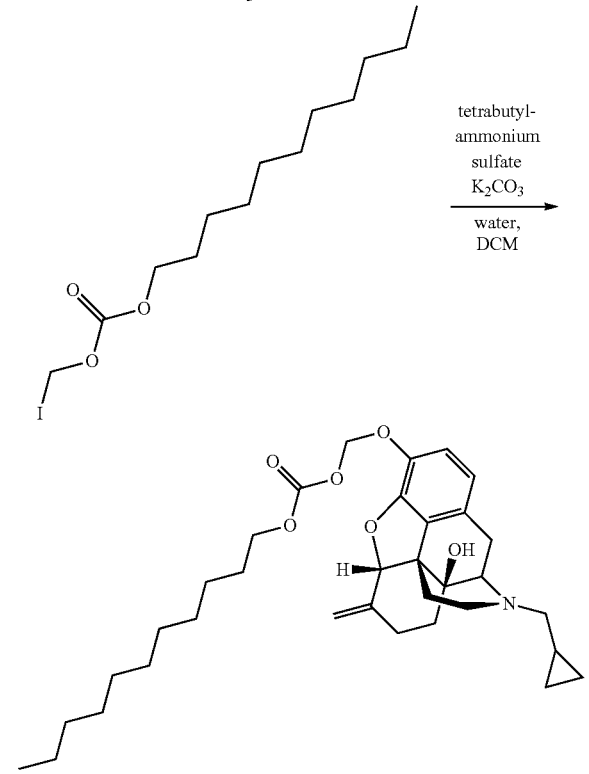

tetrabutylammonium sulfate
K$_2$CO$_3$ water, DCM

Figure 5:
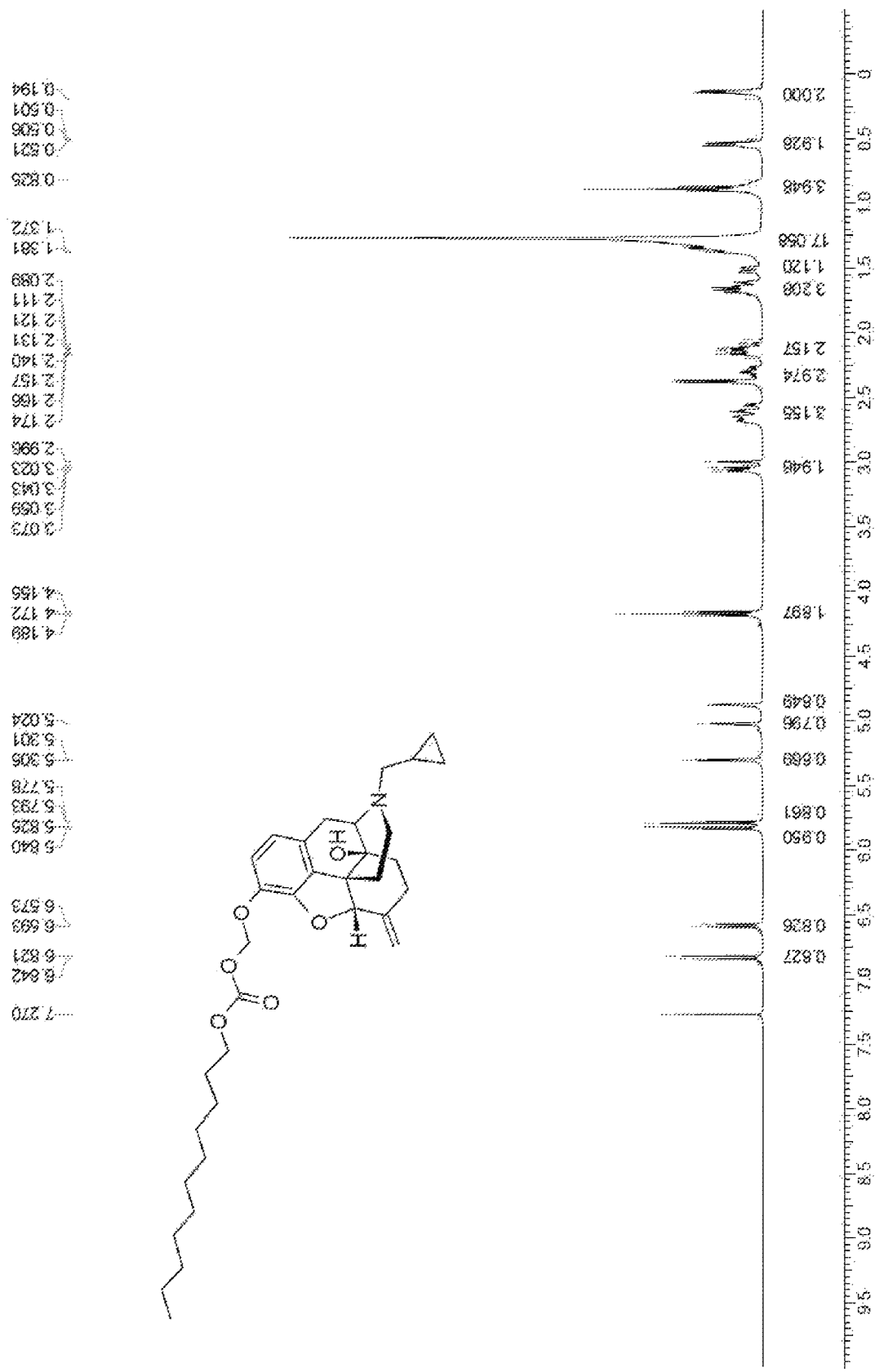
FIG. 5 provides the nuclear magnetic resonance spectrum of Example 5 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl undecyl carbonate.

To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (8 g, 21.28 mmol, 1 eq, HCl) in H$_2$O (40 mL) was added K$_2$CO$_3$ (8.82 g, 63.85 mmol, 3 eq) in one portion at 25° C. under N$_2$. The mixture was stirred at 25° C. for 30 min. Then was added tetrabutylammonium sulfate (24.73 g, 21.28 mmol, 24.49 mL, 50% solution, 1 eq) in DCM (40 mL) in one portion at 25° C. Then the mixture was added iodomethyl undecyl carbonate (15.16 g, 42.57 mmol, 2 eq), the mixture was stirred at 25° C. for 11.5 h. The reaction mixture was partitioned between DCM 200 mL (100 mL*2) and H$_2$O 100 mL. The organic phase was separated, washed with brine 50 mL, dried with anhydrous Na$_2$SO$_4$, filtered and concentrated in vacuum. The residue was purified by column chromatography (SiO$_2$, Petroleum ether/Ethyl acetate=50/1 to 1:1). Then was further purified by prep-HPLC, MeOH as solvent, select conventional reverse phase separation as method, separation system is TFA. NaHCO$_3$ was added to adjust pH to about 8, the aqueous phase was extracted with ethyl acetate (400 mL*3), washed with brine 300 mL, dried with anhydrous Na$_2$SO$_4$, filtered and concentrated in vacuum. Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl undecyl carbonate (5.9 g) was obtained as a yellow oil. M+H$^+$=568.3 (LCMS). $^1$H NMR (400 MHz, CDCl$_3$): see FIG. 5.

Example 6: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl dodecyl carbonate

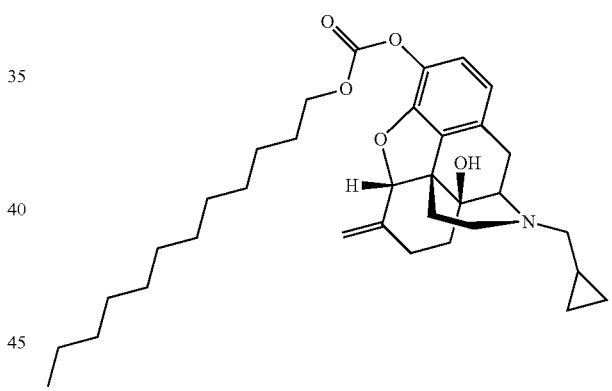

Figure 6:
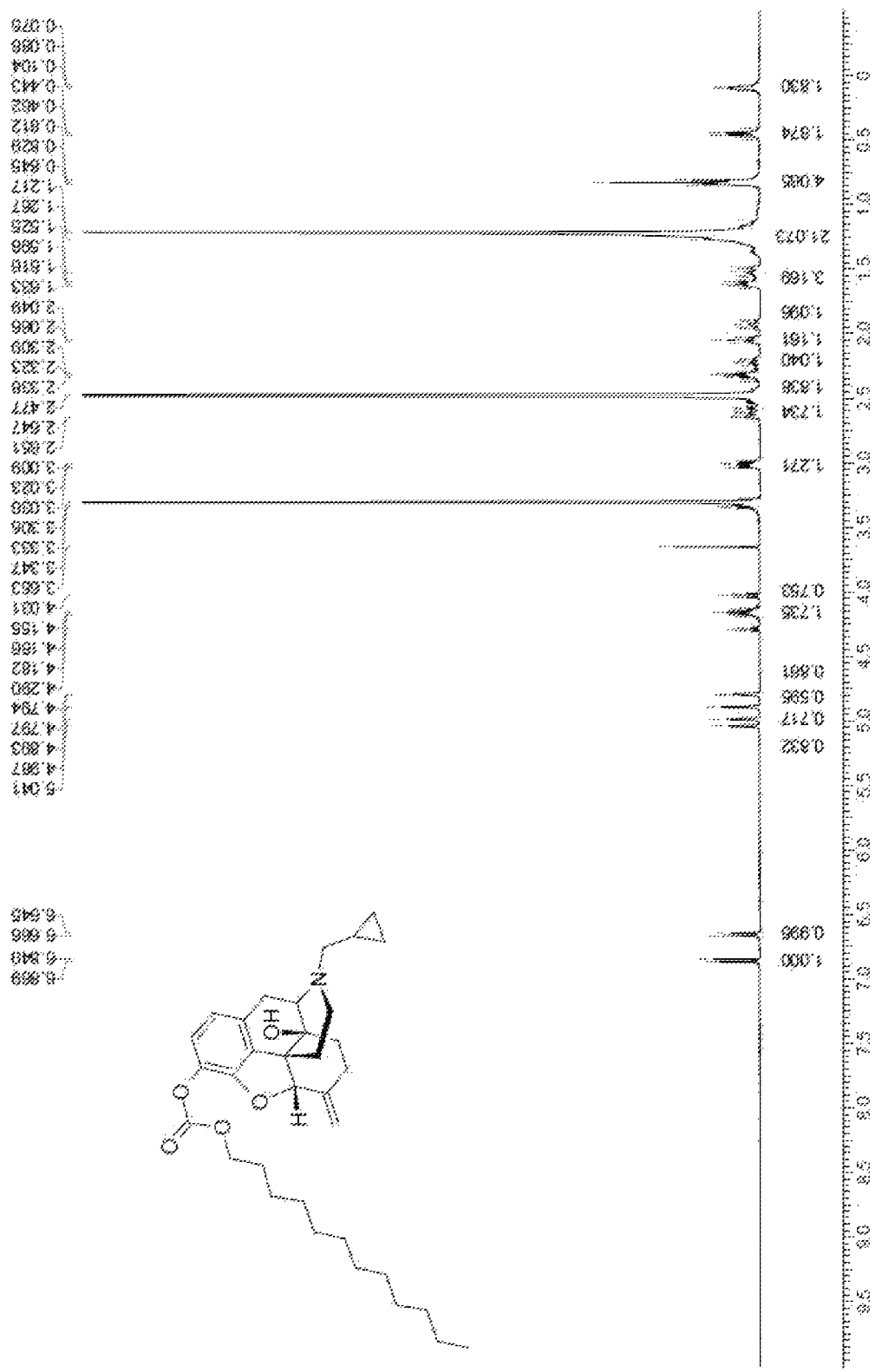
FIG. 6 provides the nuclear magnetic resonance spectrum of Example 6 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl dodecyl carbonate.

The title compound was synthesized according to the general Scheme 1 for the synthesis of nalmefene prodrugs. 1.5 g; $^1$H NMR (400 MHz, CDCl$_3$): see FIG. 6. Briefly, to a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (2.5 g, 6.65 mmol, 1 eq, HCl) in DCM (10 mL) was added TEA (2.02 g, 19.95 mmol, 2.78 mL, 3 eq) and dodecyl carbonochloridate (2.48 g, 9.98 mmol, 1.5 eq). The mixture was stirred at −10° C. for 1 hour and then warmed to 25° C. for 4 hours under N$_2$. The reaction mixture was concentrated under reduced pressure to give a residue. The residue was purified by column chromatography (SiO2, petroleum ether/ethyl acetate=5/1 to 1:1. The compound [(4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl dodecyl carbonate] was 98.570% pure and obtained as a yellow oil (1.5 g, 40.56% yield).

Example 7: Step 7A: Synthesis of chloromethyl (E)-octadec-9-en-1-yl carbonate

Step 7B: Synthesis of iodomethyl (E)-octadec-9-en-1-yl carbonate

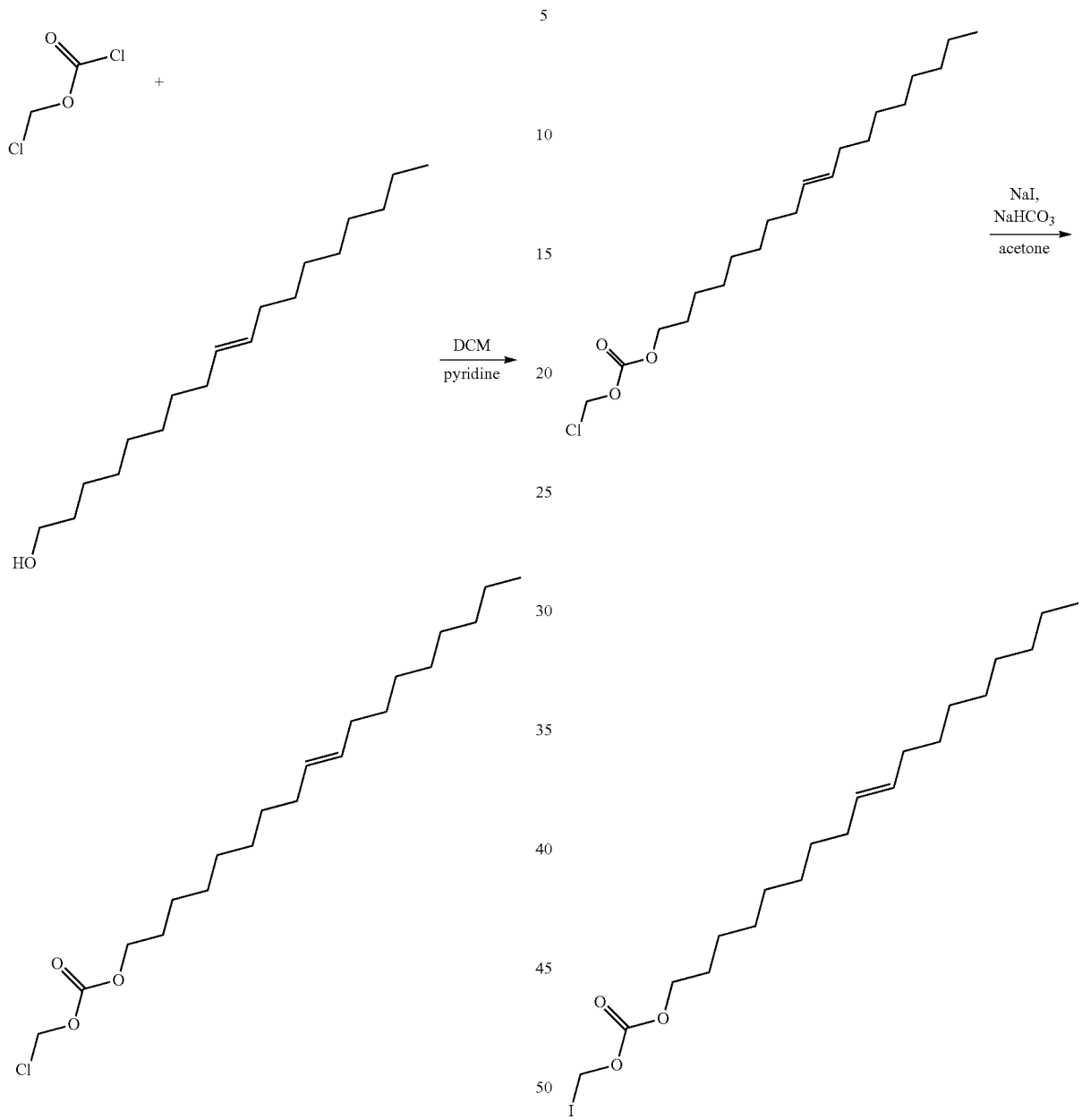

To a mixture of (E)-octadec-9-en-1-ol (22 g, 81.94 mmol, 1 eq) and chloromethyl carbonochloridate (21.13 g, 163.89 mmol, 14.57 mL, 2 eq) in DCM (200 mL) was added pyridine (16.20 g, 204.86 mmol, 16.54 mL, 2.5 eq) dropwise at 0° C. under $N_2$. The reaction was stirred at 25° C. for 12 hr under $N_2$. The reaction mixture was quenched by addition $H_2O$ 400 mL, and extracted with DCM 400 mL*1. The combined organic layers were washed with brine 300 mL, dried over $Na_2SO_4$, filtered and concentrated under reduced pressure to give a oil. The residue was purified by column chromatography ($SiO_2$, Petroleum ether/Ethyl acetate=1/0) to give product. Compound chloromethyl (E)-octadec-9-en-1-yl carbonate (50 g, 138.52 mmol, 84.52% yield) was obtained as a colorless oil.

To a mixture of chloromethyl (E)-octadec-9-en-1-yl carbonate (30 g, 83.11 mmol, 1 eq) and NaI (18.69 g, 124.67 mmol, 1.5 eq) in acetone (300 mL) was added $NaHCO_3$ (8.38 g, 99.73 mmol, 3.88 mL, 1.2 eq) in one portion at 25° C. under $N_2$. The mixture was stirred at 25° C. for 12 hr. The reaction mixture was concentrated under reduced pressure to remove solvent. The residue was diluted with $H_2O$ 500 mL and extracted with EtOAc 800 mL (400 mL*2). The combined organic layers were washed with NaCl aq. 400 mL, dried over, filtered and concentrated under reduced pressure to give target product. Compound iodomethyl (E)-octadec-9-en-1-yl carbonate (29 g, 64.10 mmol, 77.13% yield) was obtained as light yellow oil and was used into the next step without further purification.

Step 7C: Synthesis of (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl ((E)-octadec-9-en-1-yl) carbonate

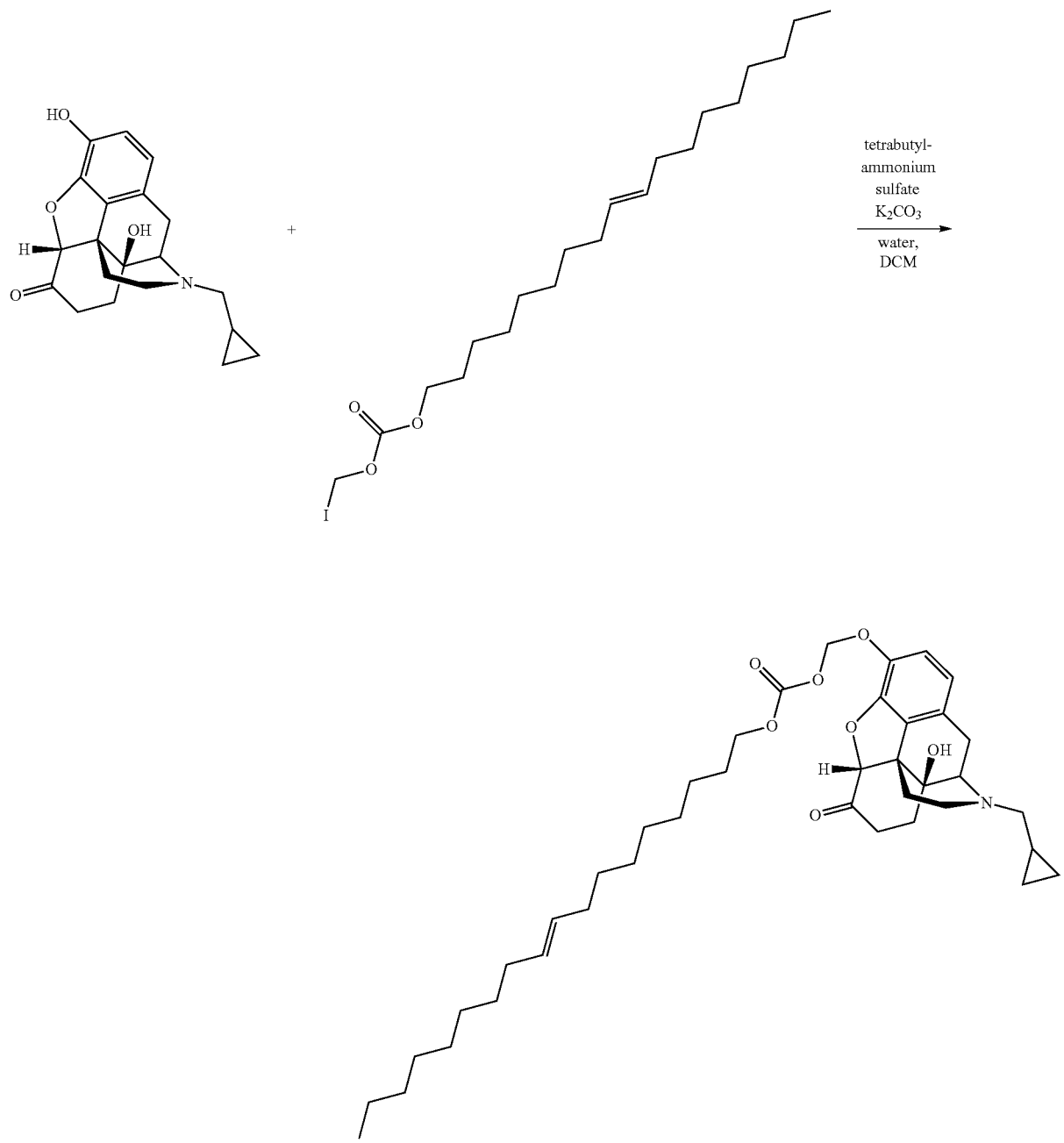

Figure 7:
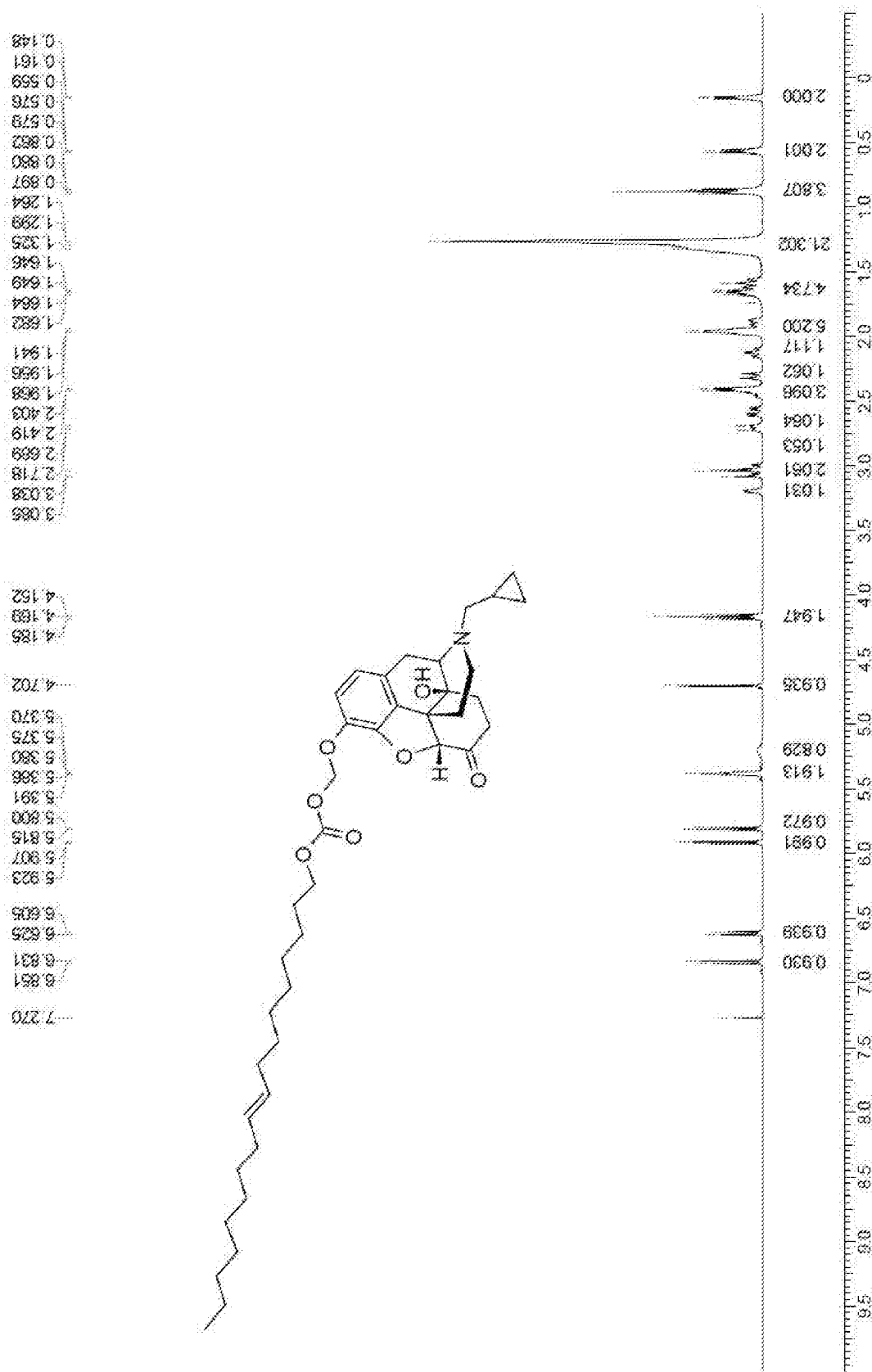
FIG. 7 provides the nuclear magnetic resonance spectrum of Example 7 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl ((E)-octadec-9-en-1-yl) carbonate.

To a mixture of (4R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one; hydrochloride (8 g, 21.17 mmol, 1 eq) and K$_2$CO$_3$ (8.78 g, 63.52 mmol, 3 eq) in H$_2$O (200 mL) was stirred at 25° C. for 0.5 hr. Tetrabutylammonium sulfate (12.30 g, 21.17 mmol, 12.18 mL, 1 eq) in DCM (200 mL) was added the mixture and stirred for 0.5 hr at 25° C. Iodomethyl (E)-octadec-9-en-1-yl carbonate (14.37 g, 31.76 mmol, 1.5 eq) was added to the mixture and stirred for 11 hours. The reaction mixture was concentrated under reduced pressure to remove DCM. The residue was diluted with H$_2$O (300 mL) and extracted with EtOAc (300 mL*3). The combined organic layers were washed with NaCl aq. (300 mL), dried over Na$_2$SO$_4$, filtered and concentrated under reduced pressure to give a residue. The crude was purified by column chromatography (SiO$_2$, Petroleum ether/Ethyl acetate=10/1 to 3:1) to give target product. Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl [(E)-octadec-9-enyl] carbonate (8.08 g, 12.09 mmol, 57.12% yield,) was obtained as a colorless oil. M+H$^+$=666.5 (LCMS). $^1$H NMR (400 MHz, CDCl$_3$): see FIG. 7.

Example 8: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (E)-octadec-9-enoate

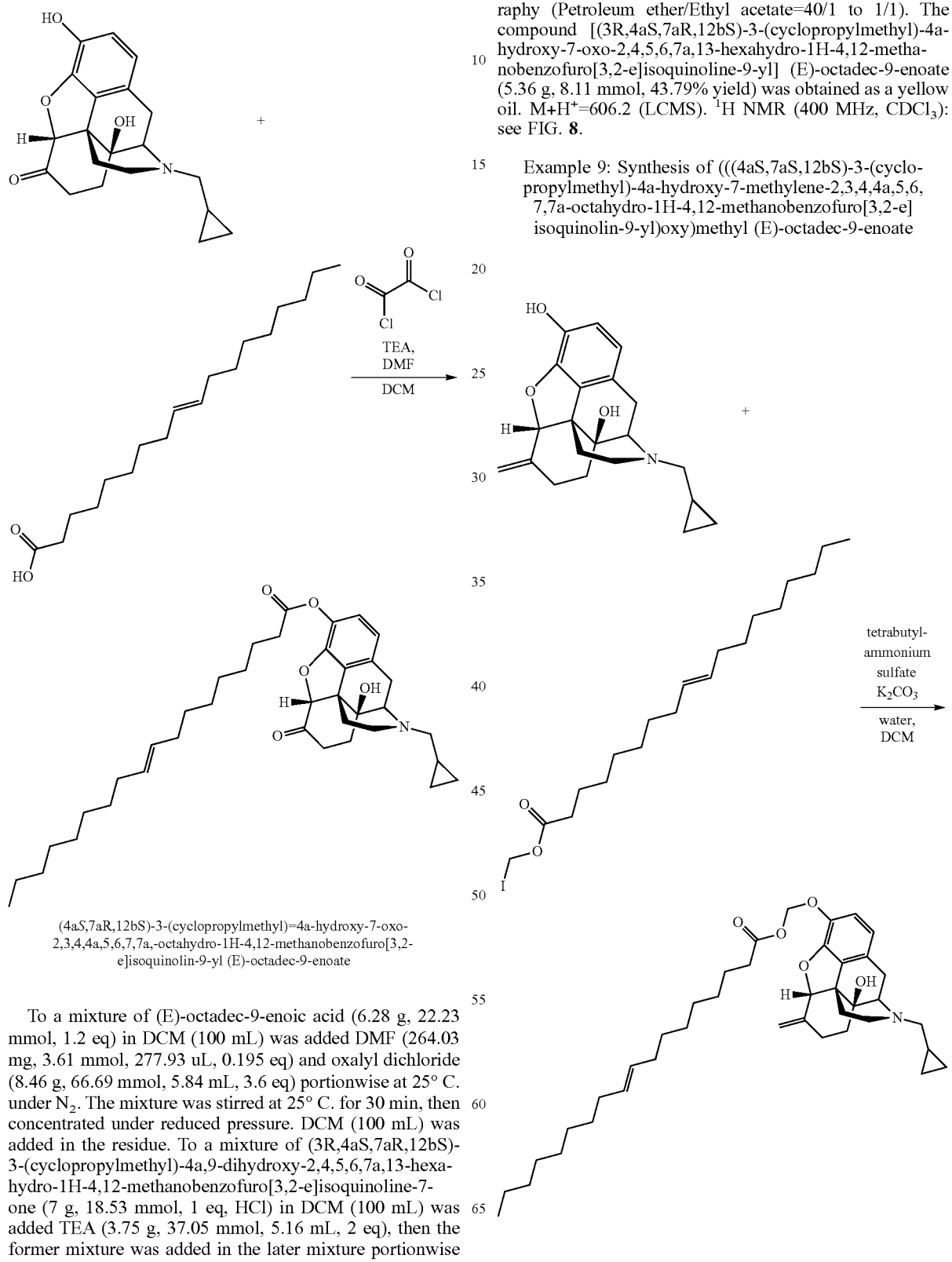

Figure 8:
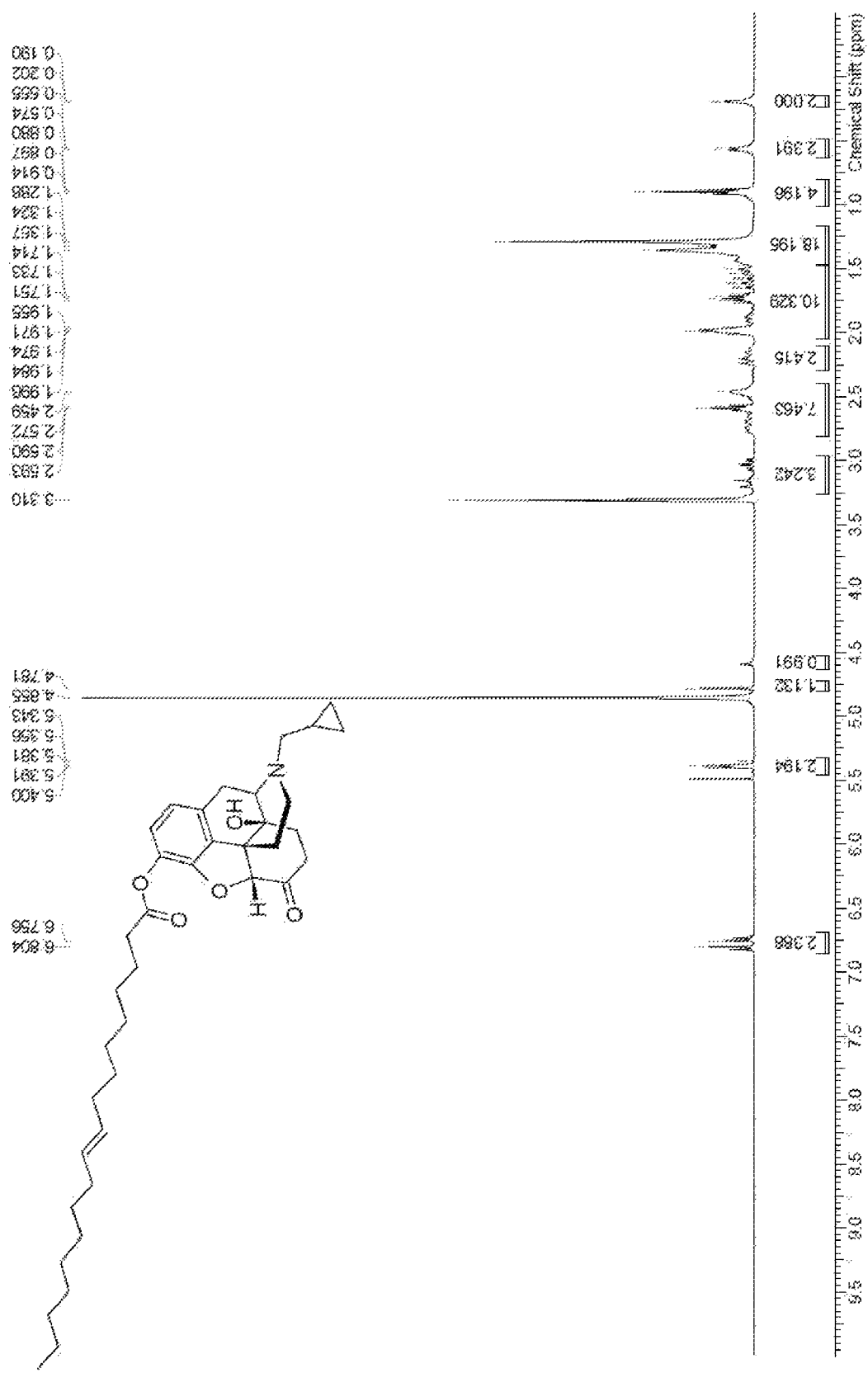
FIG. 8 provides the nuclear magnetic resonance spectrum of Example 8 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (E)-octadec-9-enoate.

(4aS,7aR,12bS)-3-(cyclopropylmethyl)=4a-hydroxy-7-oxo-2,3,4,4a,5,6,7,7a,-octahydro-1H-4,12-methanobenzofuro[3,2-e]isoquinolin-9-yl (E)-octadec-9-enoate To a mixture of (E)-octadec-9-enoic acid (6.28 g, 22.23 mmol, 1.2 eq) in DCM (100 mL) was added DMF (264.03 mg, 3.61 mmol, 277.93 uL, 0.195 eq) and oxalyl dichloride (8.46 g, 66.69 mmol, 5.84 mL, 3.6 eq) portionwise at 25° C. under N₂. The mixture was stirred at 25° C. for 30 min, then concentrated under reduced pressure. DCM (100 mL) was added in the residue. To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (7 g, 18.53 mmol, 1 eq, HCl) in DCM (100 mL) was added TEA (3.75 g, 37.05 mmol, 5.16 mL, 2 eq), then the former mixture was added in the later mixture portionwise at 25° C. under N₂. The mixture was stirred at 25° C. for 12 hr. The residue was concentrated in vacuum to remove the DCM then was dissolved by saturated solution of NaHCO₃ (200 mL), The aqueous phase was extracted with ethyl acetate (100 mL*2). The combined organic phase was dried with anhydrous Na₂SO₄, filtered and concentrated in vacuum. The residue was purified by silica gel chromatography (Petroleum ether/Ethyl acetate=40/1 to 1/1). The compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl] (E)-octadec-9-enoate (5.36 g, 8.11 mmol, 43.79% yield) was obtained as a yellow oil. M+H⁺=606.2 (LCMS). ¹H NMR (400 MHz, CDCl₃): see FIG. 8.

Figure 9:
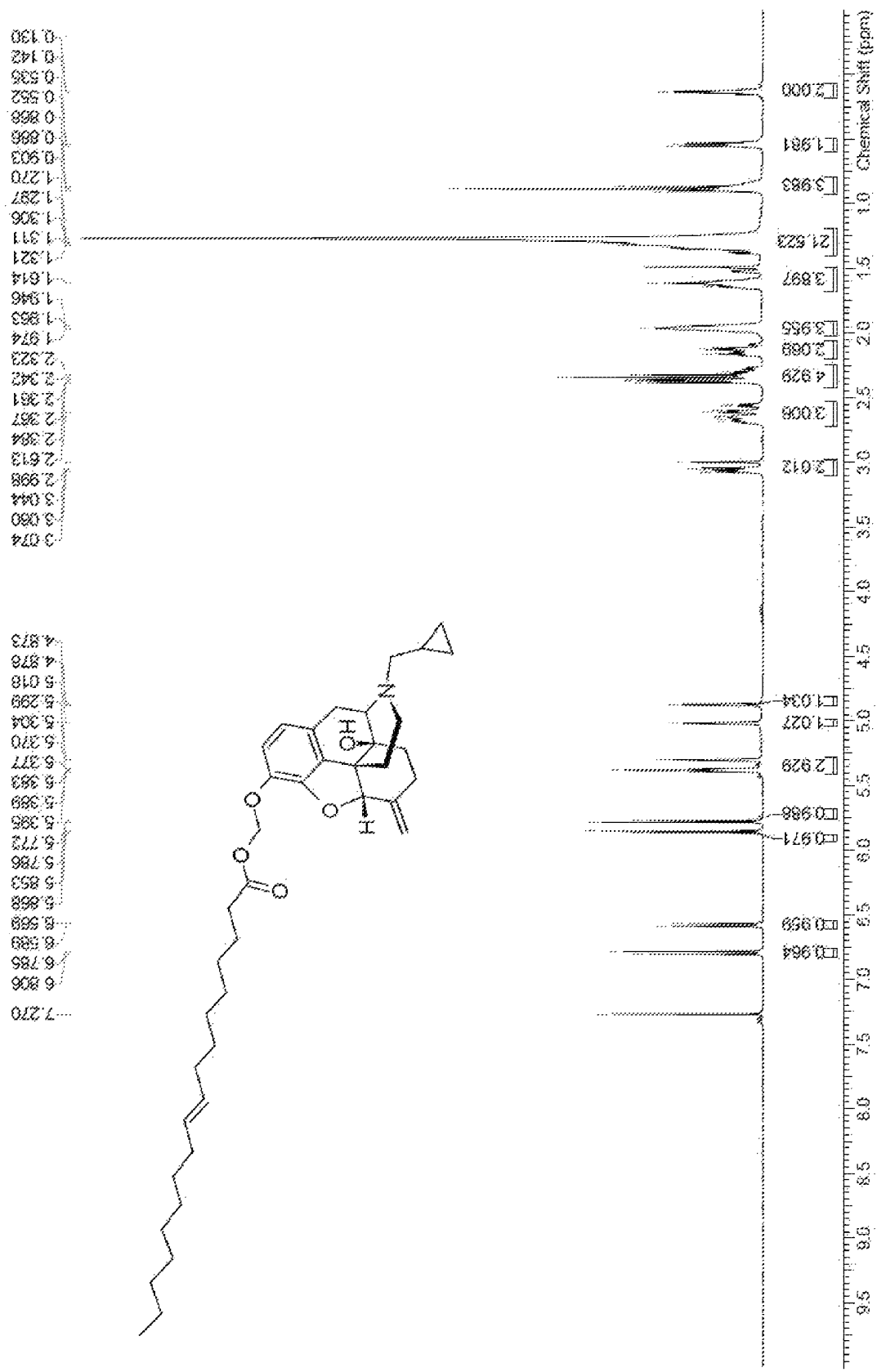
FIG. 9 provides the nuclear magnetic resonance spectrum of Example 9 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl (E)-octadec-9-enoate.

Example 9: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl (E)-octadec-9-enoate To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (10 g, 26.60 mmol, 1 eq, HCl) in H$_2$O (100 mL) was added K$_2$CO$_3$ (11.03 g, 79.81 mmol, 3 eq) in one portion at 25° C. under N$_2$. The mixture was stirred at 25° C. for 30 min. To a mixture of tetrabutylammonium sulfate (30.91 g, 26.60 mmol, 30.61 mL, 50% solution, 1 eq) in DCM (100 mL) then the later mixture was added to the former mixture. Iodomethyl (E)-octadec-9-enoate (16.86 g, 39.91 mmol, 1.5 eq), obtained according to procedure described in Example 41B, was added and the mixture was stirred for 12 hours. The mixture was diluted with H$_2$O (100 mL), collect the organic phase, then the aqueous phase was extracted with Ethyl Acetate (300 mL*3), the organic phase was washed with brine (300 mL), dried over Na$_2$SO$_4$, filtered and concentrated under reduced pressure. The residue was purified by silica gel chromatography (Petroleum ether/Ethyl acetate=20/1 to 1/1). Then was further purified by prep-HPLC, MeOH as solvent, select conventional reverse phase separation as method, separation system is TFA. NaHCO$_3$ was added to adjust pH to about 8, the aqueous phase was extracted with ethyl acetate (400 mL*3). The combined organic phase was washed with brine (500 mL), dried with anhydrous Na$_2$SO$_4$, filtered and concentrated in vacuum. The compound[(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl (E)-octadec-9-enoate (7.16 g, 11.15 mmol, 41.91% yield) was obtained as a yellow oil. M+H$^+$=634.4 (LCMS). $^1$H NMR (400 MHz, CDCl$_3$): see FIG. 9.

Example 10: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl decyl carbonate

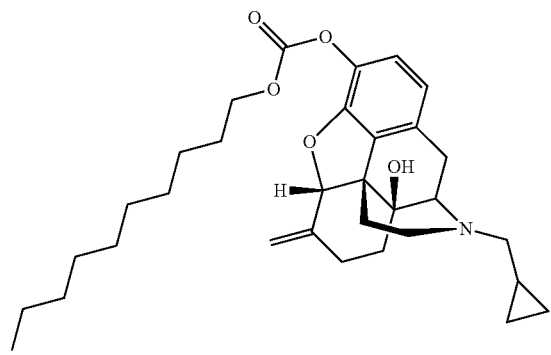

Figure 10:
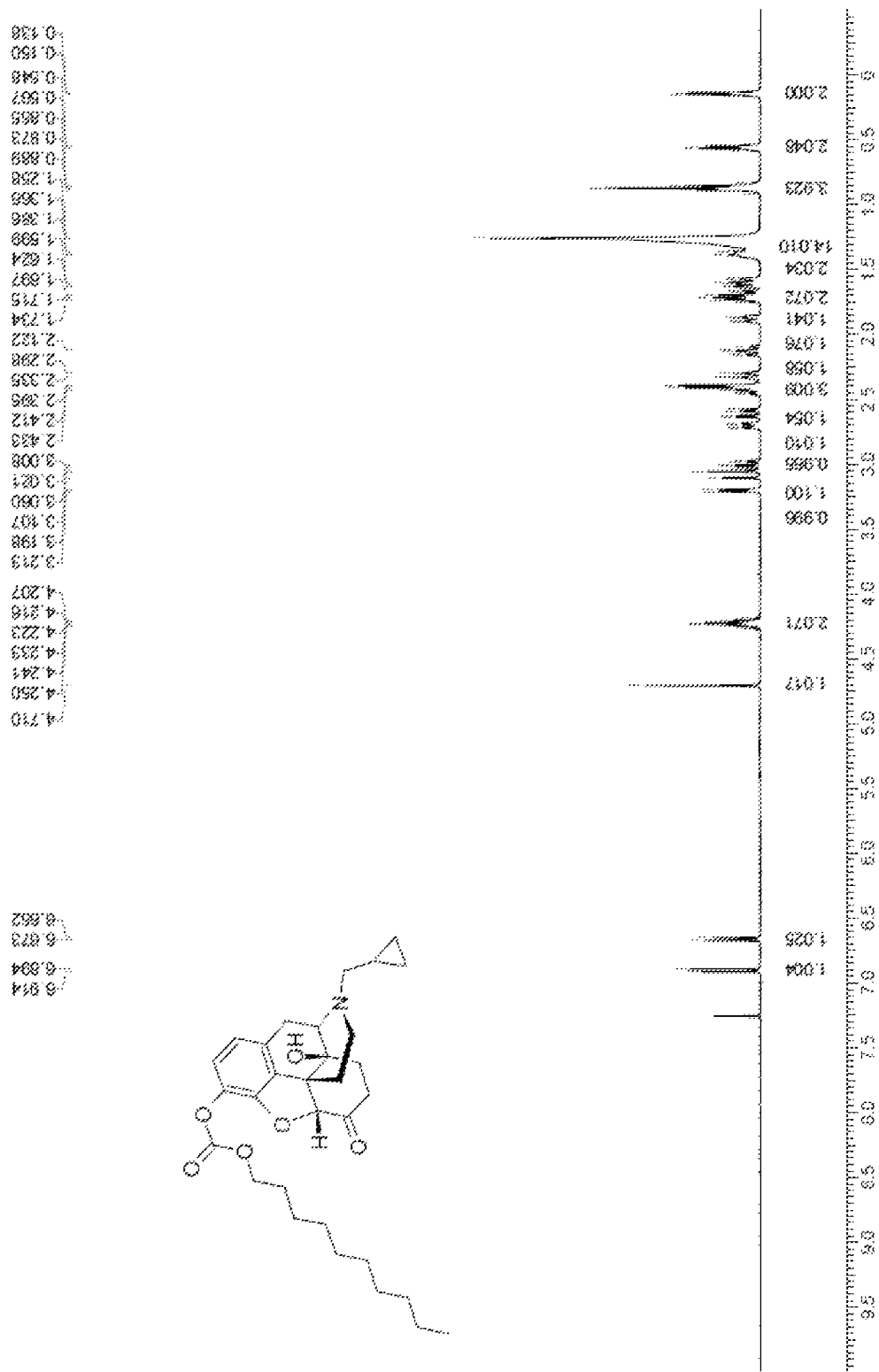
FIG. 10 provides the nuclear magnetic resonance spectrum of Example 10 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl decyl carbonate.

The title compound was synthesized according to the general Scheme 2 for the synthesis of naltrexone prodrugs. 1.31 g; $^1$H NMR (400 MHz, CDCl$_3$): see FIG. 10. Briefly, to a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (1.9 g, 5.57 mmol, 1 eq) in DCM (15 mL), cooled to −10° C. was added TEA (1.69 g, 16.70 mmol, 2.32 mL, 2 eq) and decyl carbonochloridate (2.46 g, 11.13 mmol, 2 eq). The mixture was stirred at 25° C. for 5 hr. The reaction mixture was concentrated under reduced pressure to give a residue. The crude product was purified by column chromatography (SiO$_2$, petroleum ether/ethyl acetate=7/3 to 0:1) The compound [(4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl decyl carbonate] was 97.43% pure and obtained as a yellow oil with a 43.63% yield.

Example 11: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl dodecyl carbonate

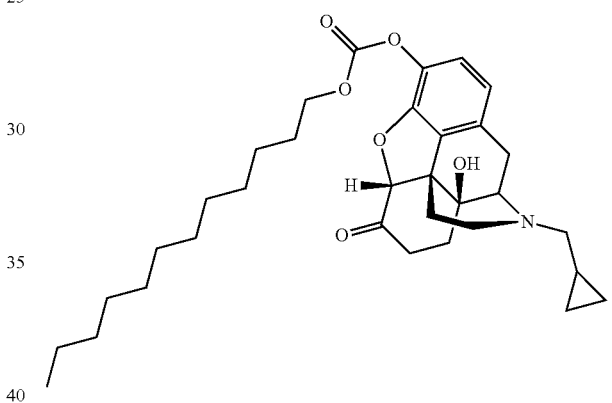

Figure 11:
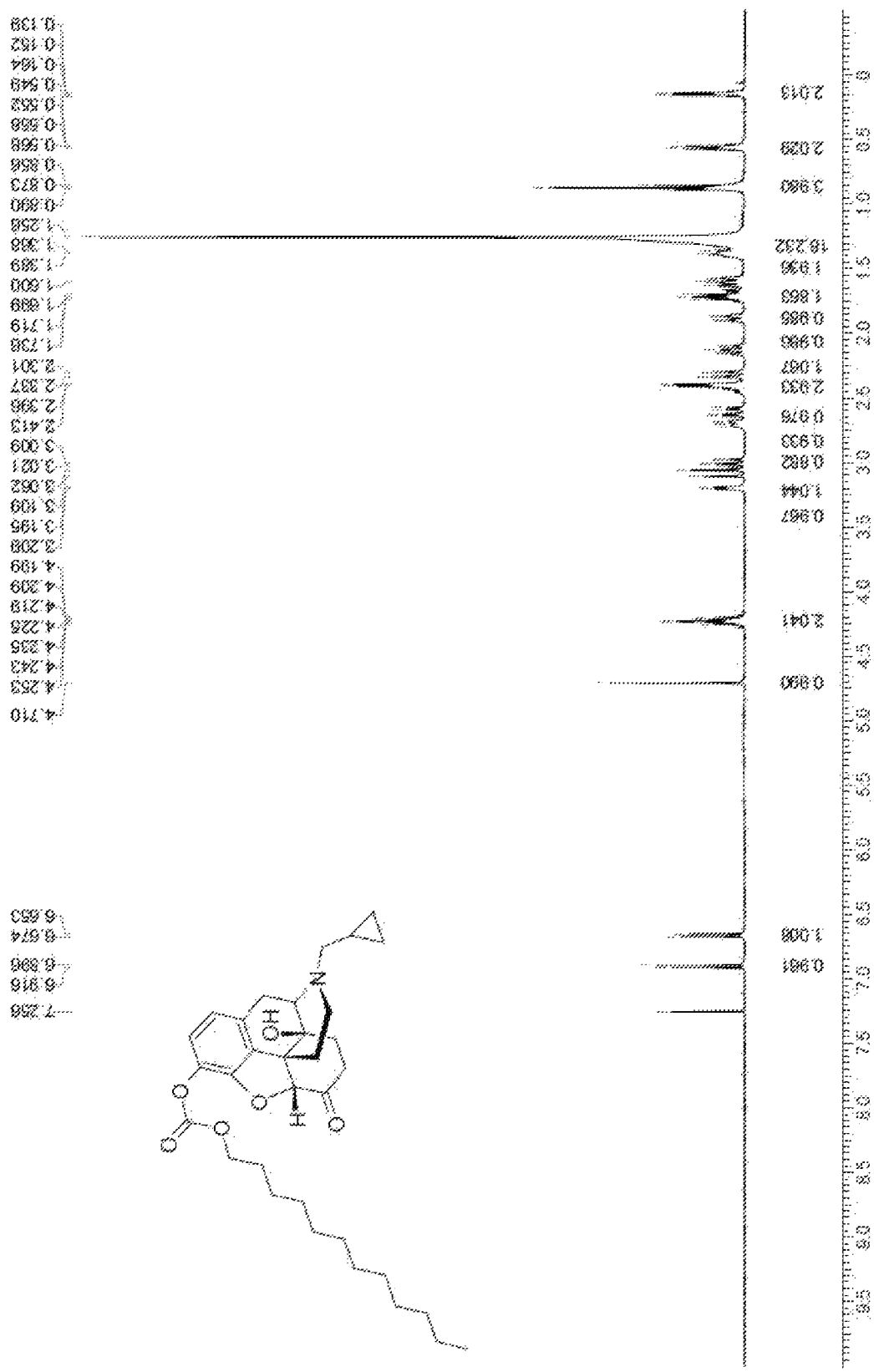
FIG. 11 provides the nuclear magnetic resonance spectrum of Example 11 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl dodecyl carbonate.

The title compound was synthesized according to the general Scheme 2 for the synthesis of naltrexone prodrugs. 1.5 g; $^1$H NMR (400 MHz, CDCl$_3$): see FIG. 11. Briefly, to a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (2.5 g, 6.62 mmol, 1 eq, HCl) and TEA (1.34 g, 13.23 mmol, 1.84 mL, 2 eq) in DCM (15 mL) was added dodecyl carbonochloridate (1.56 g, 6.29 mmol, 0.95 eq). The mixture was stirred at −10° C. for 1 hr, then warmed to 25° C. and stirred for 4 hr. The reaction mixture was concentrated under reduced pressure to give a residue. The residue product was purified by column chromatography (SiO2, petroleum ether/ethyl acetate=7/3 to 0:1). The crude product was purified by prep-HPLC (column: Gemini 200*30 10p; mobile phase—[water(10 mM NH$_4$HCO$_3$)—CAN]; B %70-100%, 12 minutes) The compound [(4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl dodecyl carbonate] was 99.497% pure and obtained as a white solid (1.5 g, 40.74% yield).

Example 12: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl stearate

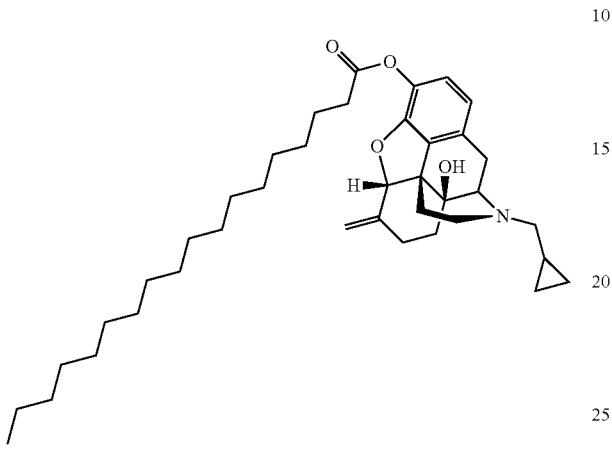

Figure 12:
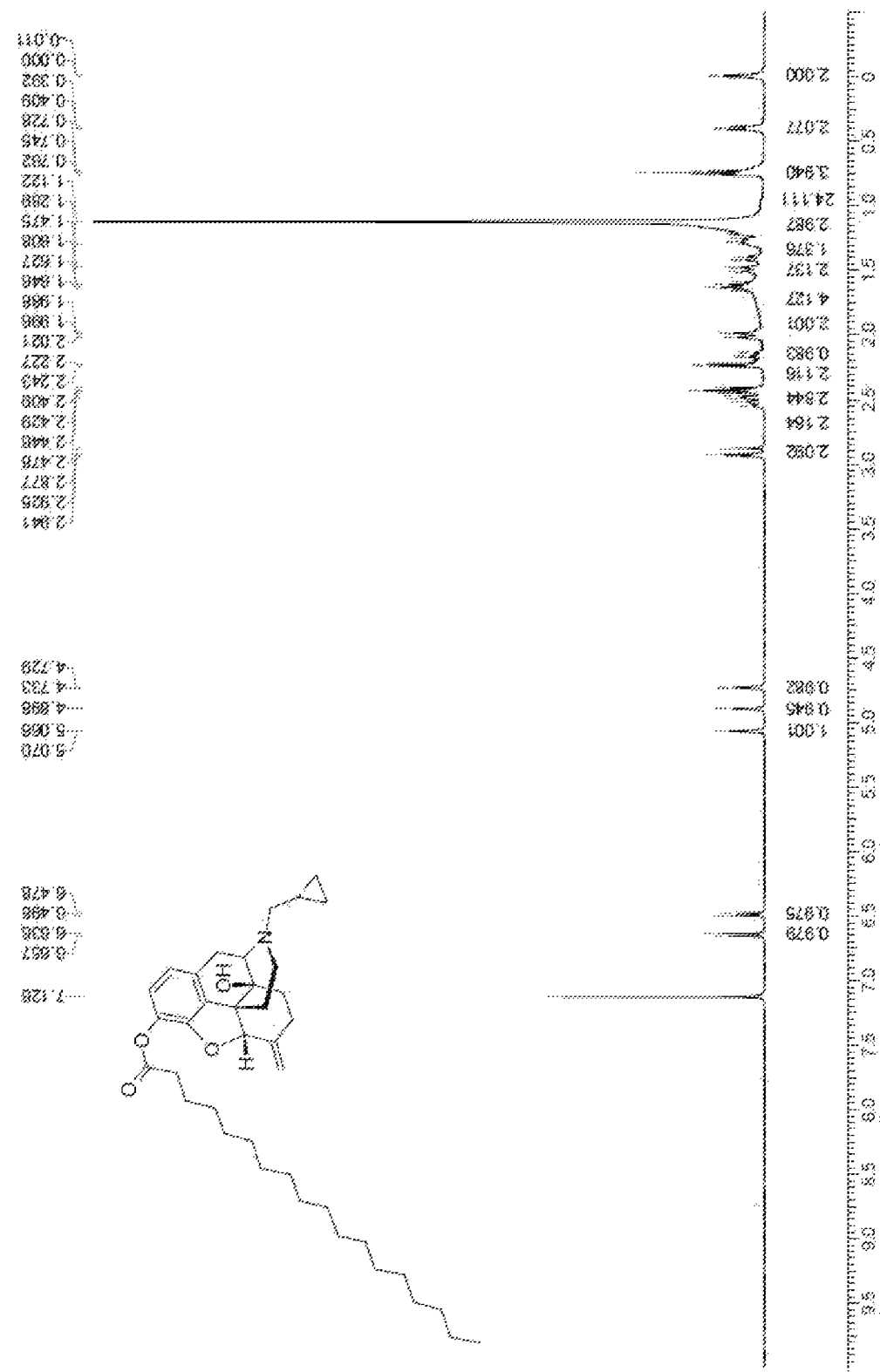
FIG. 12 provides the nuclear magnetic resonance spectrum of Example 12 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl stearate.

The title compound was synthesized according to the general Scheme 1 for the synthesis of nalmefene prodrugs. 1.2 g; $^1$H NMR (400 MHz, CDCl$_3$): see FIG. 12.

Example 13: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (Z)-docos-13-enoate

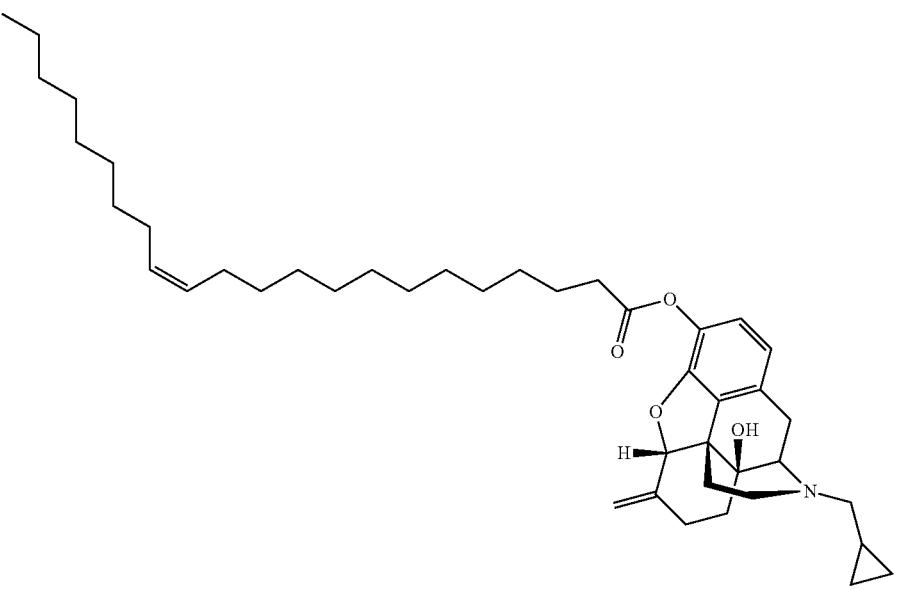

Figure 13:
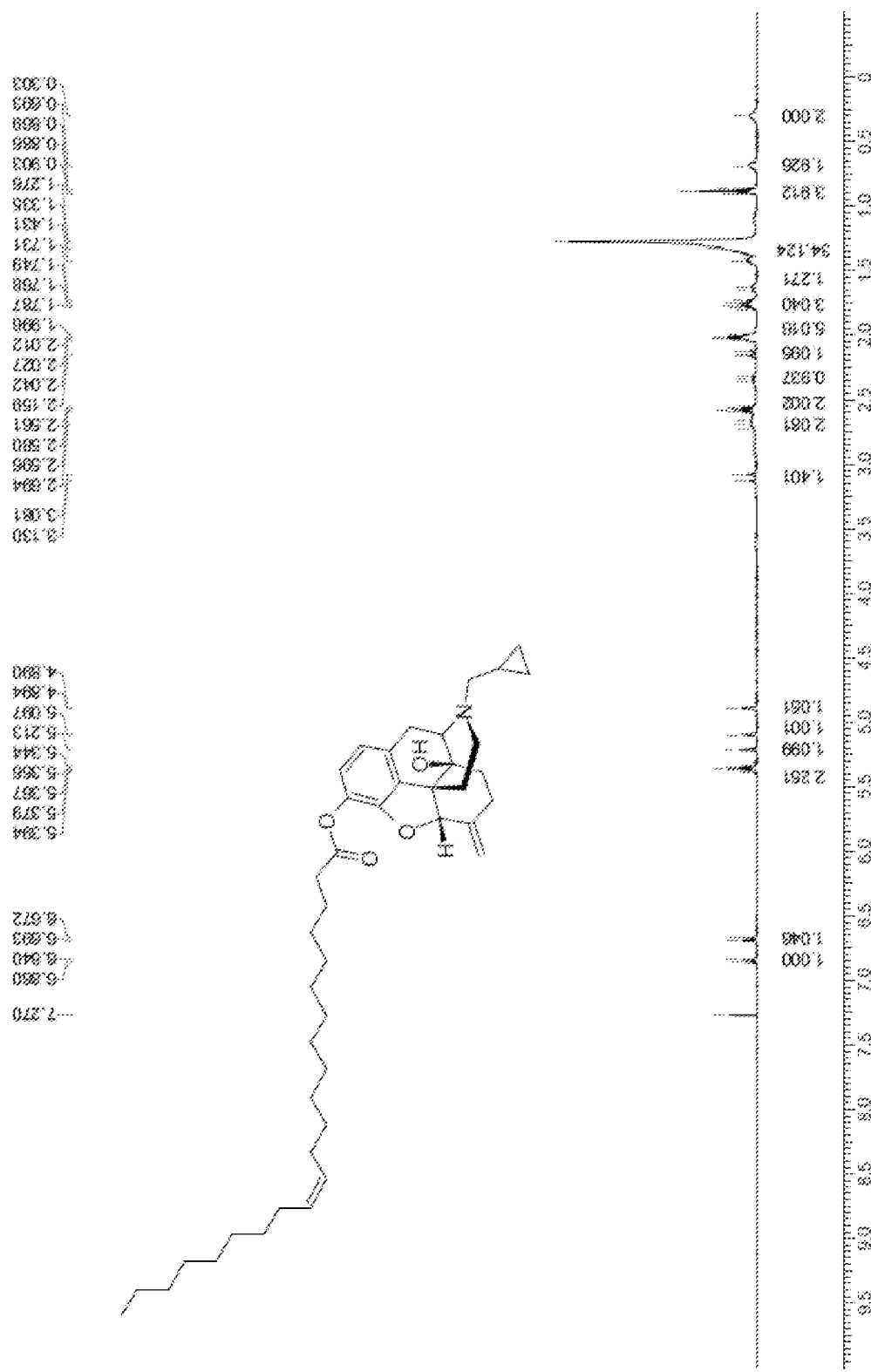
FIG. 13 provides the nuclear magnetic resonance spectrum of Example 13 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (Z)-docos-13-enoate.

The title compound was synthesized according to the general Scheme 1 for the synthesis of nalmefene prodrugs. 1.3 g; $^1$H NMR (400 MHz, CDCl$_3$): see FIG. 13.

Example 14: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl docosanoate

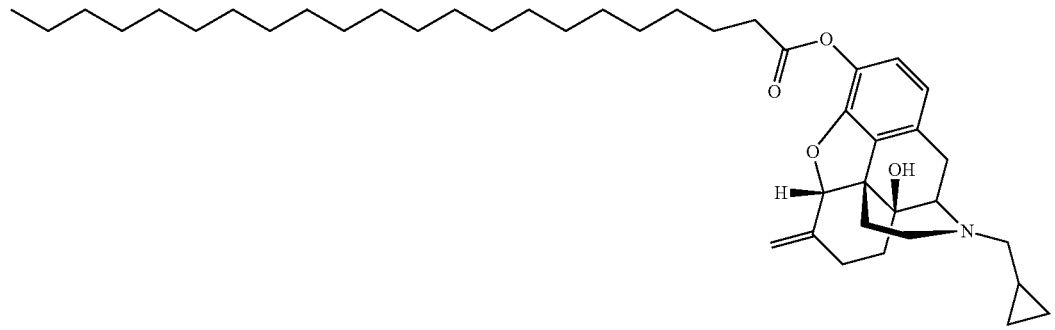

Figure 14:
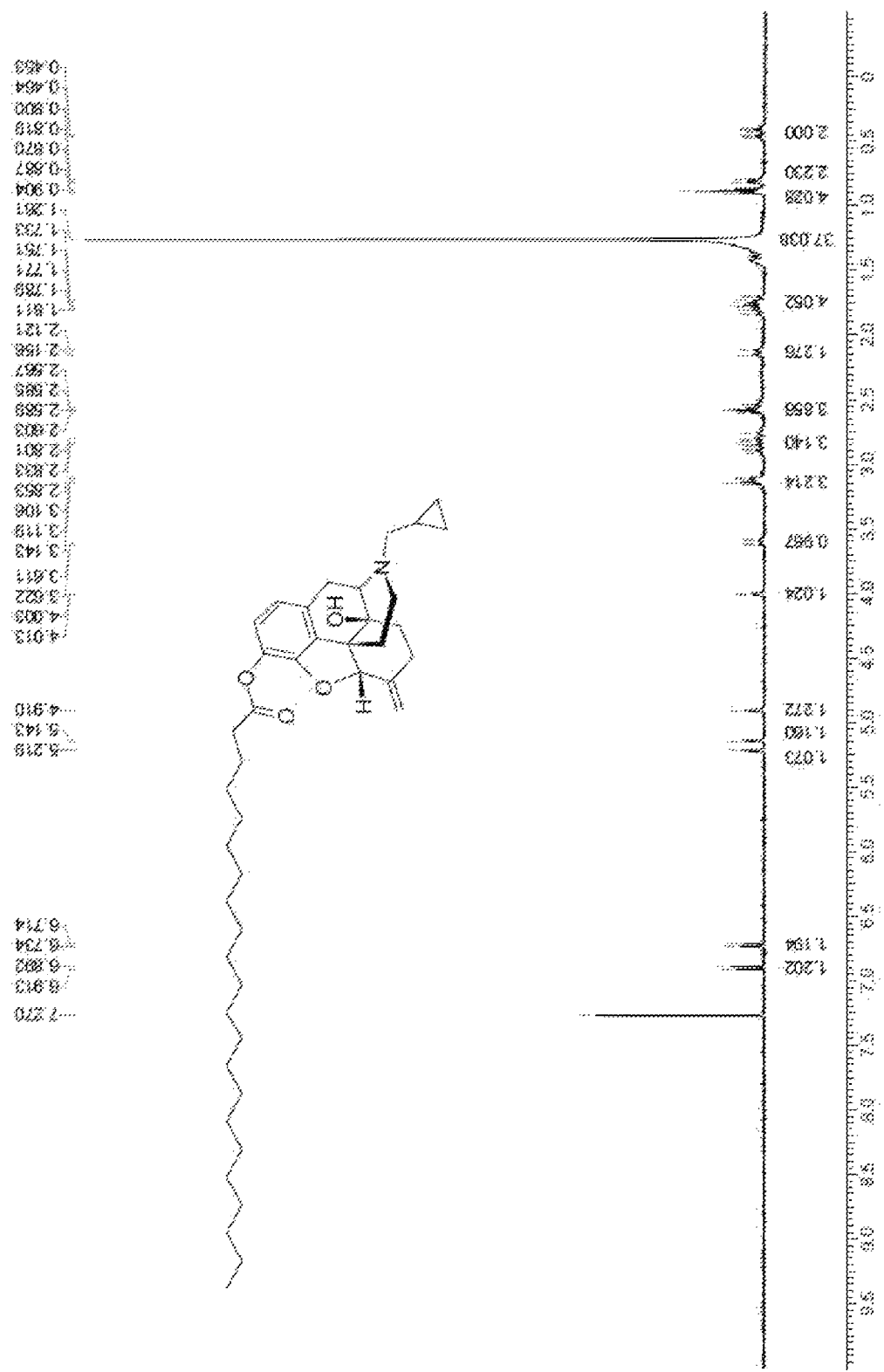
FIG. 14 provides the nuclear magnetic resonance spectrum of Example 14 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl docosanoate.

The title compound was synthesized according to the general Scheme 1 for the synthesis of nalmefene prodrugs. 1.5 g; ¹H NMR (400 MHz, CDCl₃): see FIG. 14. Briefly, to a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (2 g, 5.32 mmol, 1 eq, HCl) in DCM (10 mL) was added TEA (1.62 g, 15.96 mmol, 2.22 mL, 3 eq) and docosanoyl chloride (3.82 g, 10.64 mmol, 2 eq) one portion at 25° C. under N₂. The mixture was stirred at 25° C. for 12 hr. The reaction mixture was concentrated under reduced pressure to give a residue. The residue was purified by column chromatography (SiO₂, Petroleum ether/Ethyl acetate=5/1 to 1:1) The residue was purified using prep-HPLC (TFA condition: column: Phenomenx luna (2) C18 250*50 10 u; mobile phase: [water (0.1% TFA)-CAN]; B %: 65-95%, 20 minutes]). The compound [(4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl docosanoate] was 97.01% pure and obtained as a white solid (1.5 g, 41.31% yield).

Figure 15:
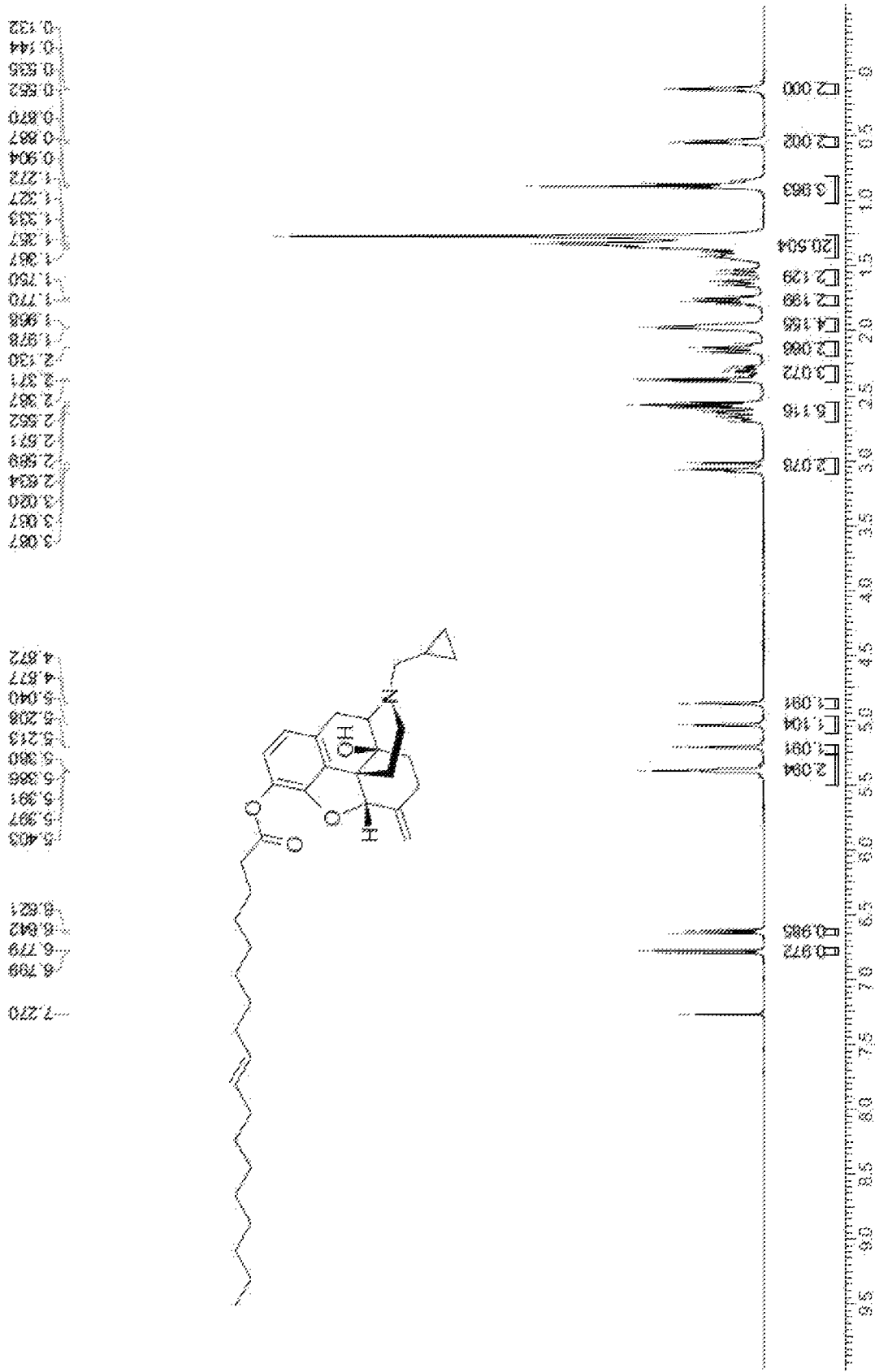
FIG. 15 provides the nuclear magnetic resonance spectrum of Example 15 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (E)-octadec-9-enoate.

Example 15: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (E)-octadec-9-enoate The title compound was synthesized according to the general Scheme 1 for the synthesis of nalmefene prodrugs. 1.8 g; ¹H NMR (400 MHz, CDCl₃): see FIG. 15. Briefly, to a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (2 g, 5.32 mmol, 1 eq, HCl) in DCM (30 mL) was added TEA (1.08 g, 10.64 mmol, 1.48 mL, 2 eq) and (E)-octadec-9-enoyl chloride (1.92, 6.38 mmol, 1.2 eq). The mixture was stirred at 15° C. for 12 hr. The reaction mixture was mixed with H₂O (80 mL) and extracted with DCM (80 mL×3). The combined organic phase was washed with saturated NaHCO₃ solution (60 mL×2) and brine (60 mL×3), dried with anhydrous Na₂SO₄, filtered, and concentrated in vacuum. The residue was purified by column chromatography (SiO₂, Petroleum ether/Ethyl acetate=10/1 to 1:1). The compound was purified again using a pre-HPLC column Phenomenex luna C18, 250×50 mm×10 μm; mobile phase: [water(0.1% TFA)-CAN]; B: 60-90%, 20 minutes). After pre-HPLC, the mixture was concentrated under reduced pressure. The aqueous phase was combined with NaHCO₃ to adjust the pH to 8, then the aqueous phase was extracted with ethyl acetate (30 mL×4). The combined organic phase was washed with brine (20 mL×1), dried with anhydrous Na₂SO₄, filtered and concentrated in a vacuum The compound [(4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (E)-octadec-9-enoate] was 95% pure and obtained as a yellow oil (1.8 g, 29.57% yield).

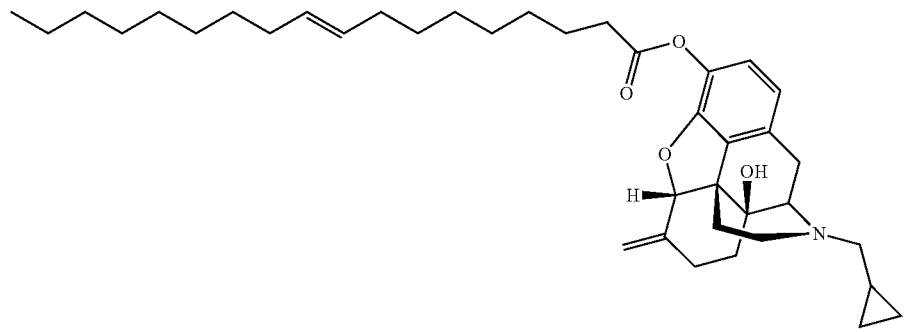

Example 16: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosanoate

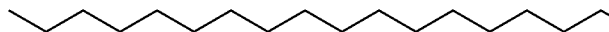
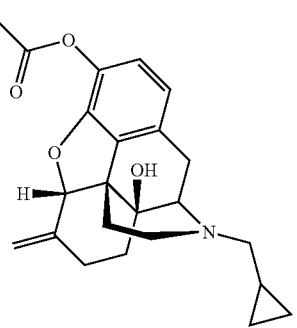

Figure 16:
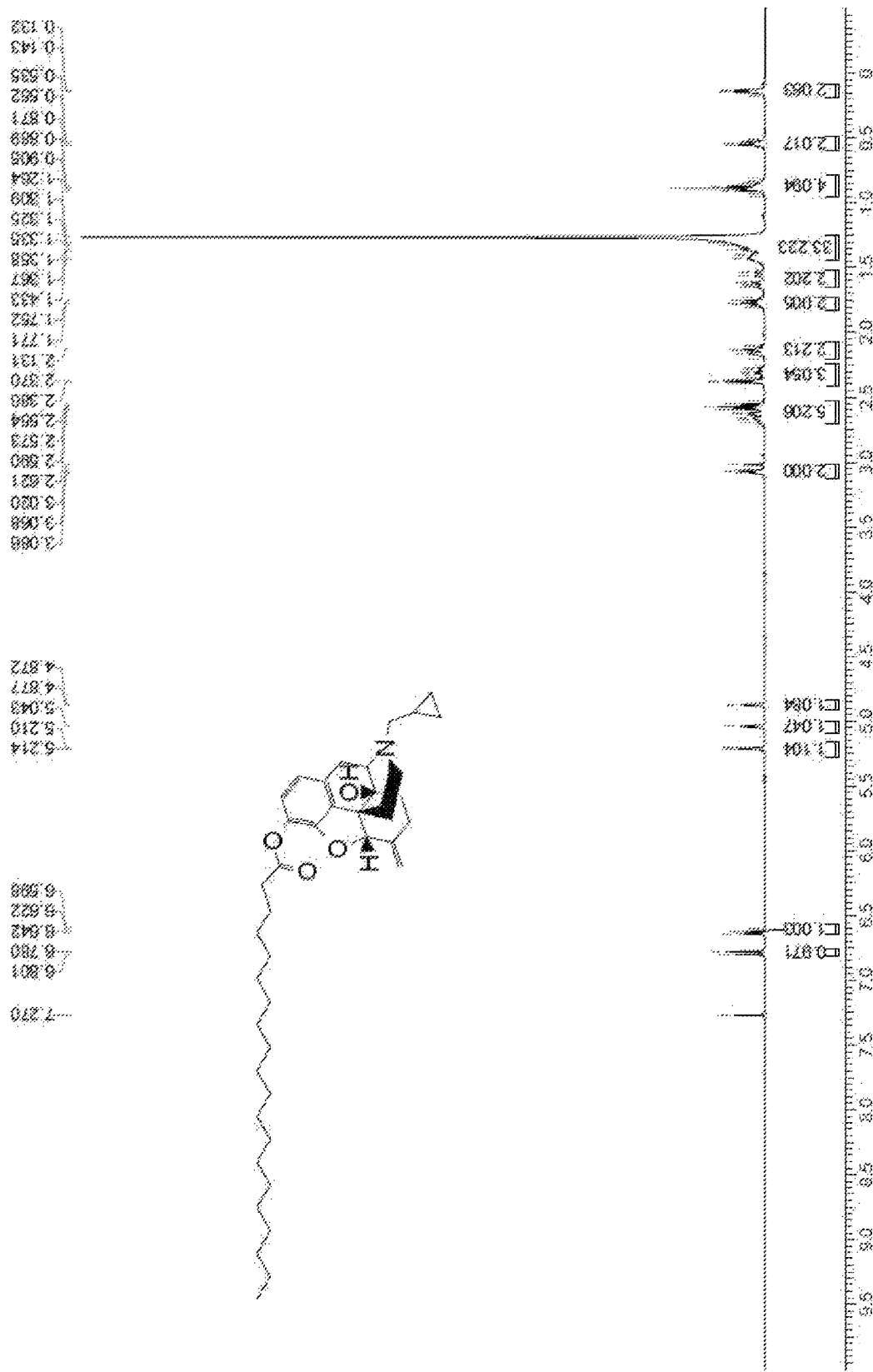
FIG. 16 provides the nuclear magnetic resonance spectrum of Example 16 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosanoate.

The title compound was synthesized according to the general Scheme 1 for the synthesis of nalmefene prodrugs. 1.1 g; $^1$H NMR (400 MHz, CDCl$_3$): see FIG. 16. Briefly, to a solution of icosanoic acid (5 g, 16.00 mmol, 5.92 mL, 1 eq) in DCM (50 mL) was added DMF (116.93 mg, 1.6 mmol, 123.09 μL, 0.1 eq), cooled to 0° C., was add (COCl)$_2$ (2.34 g, 18.40 mmol, 1.61 mL, 1.15 eq). TEA (4.86 g, 48.80 mmol, 6.68 mL, 3 eq) and (3R,4aS,7aS,12bS)-3-(cyclopropylmethyl)-7-methylene-2,4,56,7a,13-hexahydro-1H-4,12-methanobenzofuro[3,2-e]isoquinoline-4a,9-diol (3.01 g, 8.00 mmol, 0.5 eq, HCl). The mixture was stirred at 25° C. for 12 hours. The reaction mixture was extracted with H2O (80 mL×1) and DCM (80 mL×2). The combined organic phase was washed with brine (60 mL×3), dried with anhydrous Na$_2$SO$_4$, filtered and concentrated in vacuum. The compound was purified by column chormoatrography (SiO$_2$, petroleum ether/ethyl acetate=10/1 to 1:1. The compound [4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosanoate] was 100% pure and obtained as a white solid (1.1 g, 10.84% yield).

Example 17: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octyl carbonate

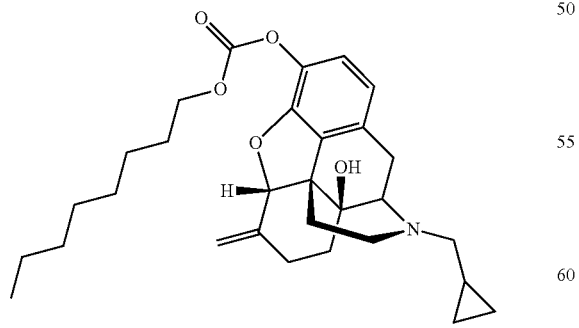

Figure 17:
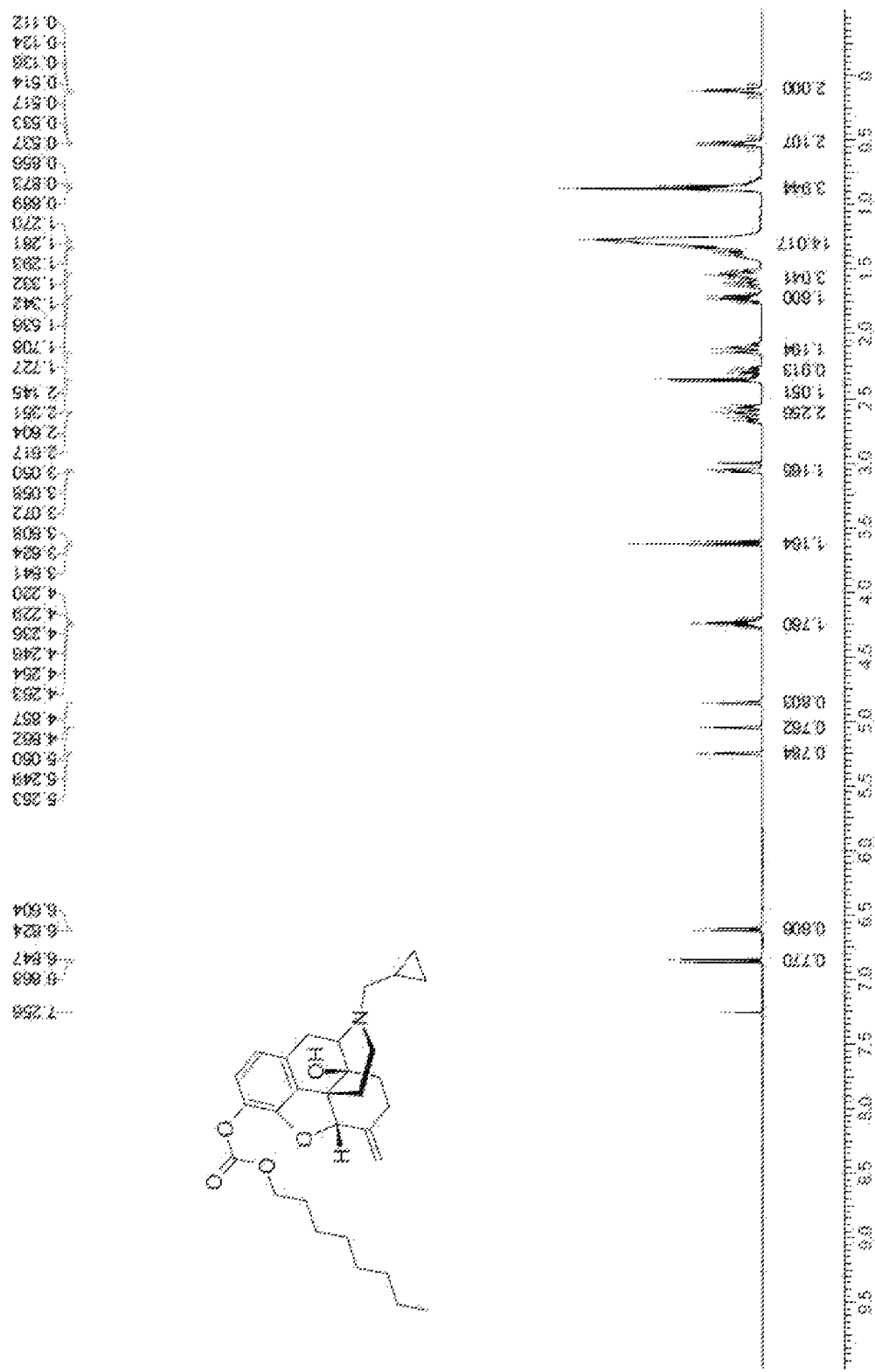
FIG. 17 provides the nuclear magnetic resonance spectrum of Example 17 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octyl carbonate.

The title compound was synthesized according to the general Scheme 1 for the synthesis of nalmefene prodrugs and was obtained as an oil. 1.5 g; $^1$H NMR (400 MHz, CDCl$_3$): see FIG. 17.

Example 18: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl decyl carbonate

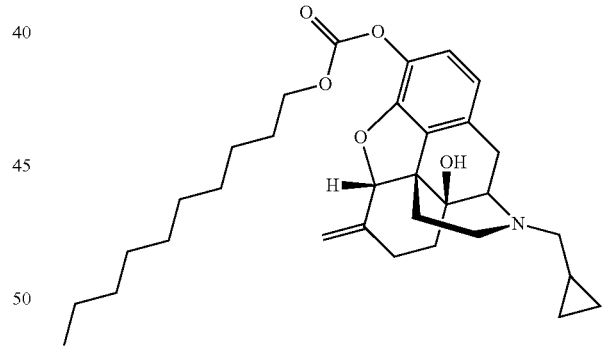

Figure 18:
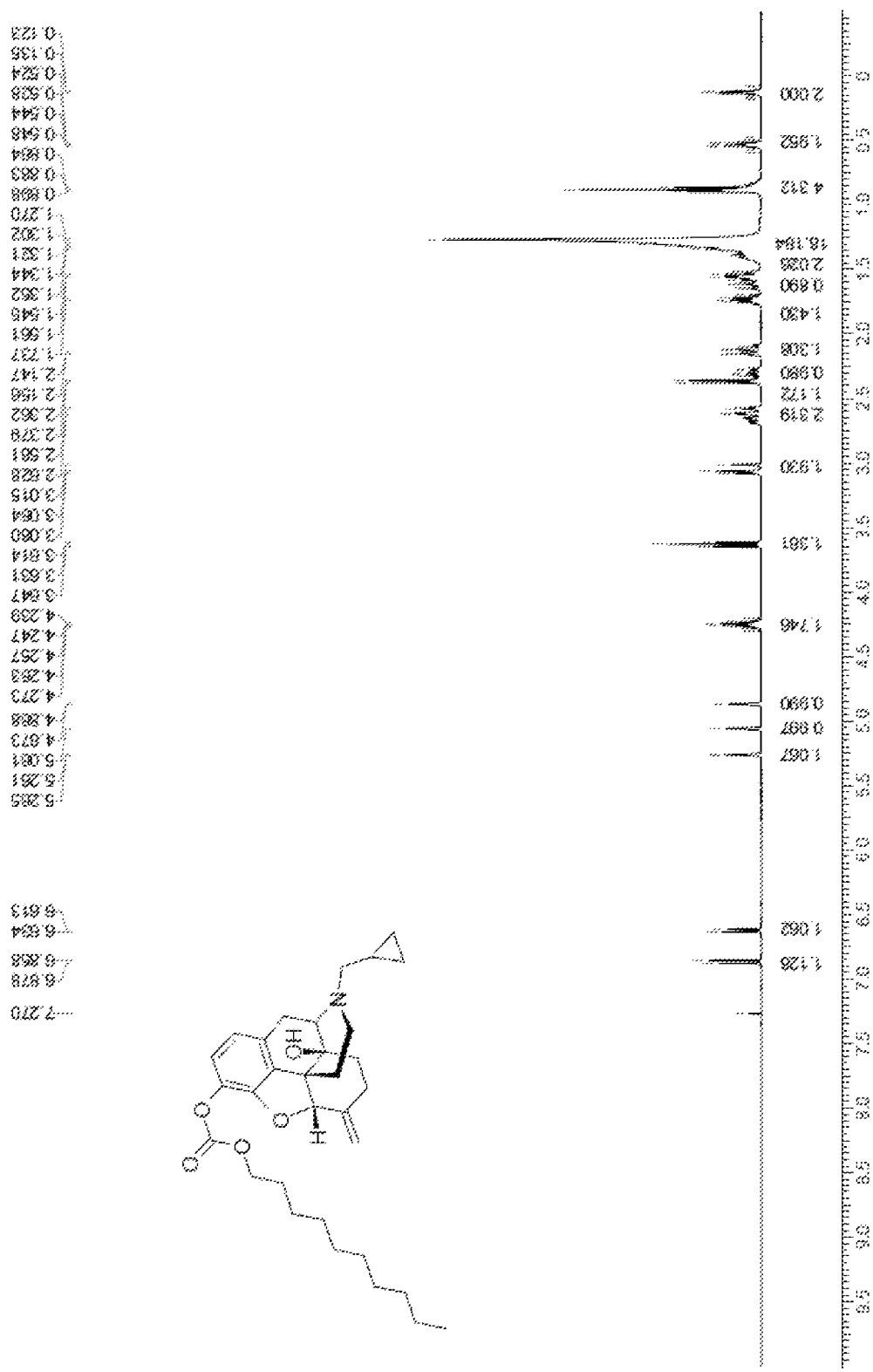
FIG. 18 provides the nuclear magnetic resonance spectrum of Example 18 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl decyl carbonate.

The title compound was synthesized according to the general Scheme 1 for the synthesis of nalmefene prodrugs and was obtained as an oil. 1.5 g; $^1$H NMR (400 MHz, CDCl$_3$): see FIG. 18.

Example 19: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl hexadecyl carbonate

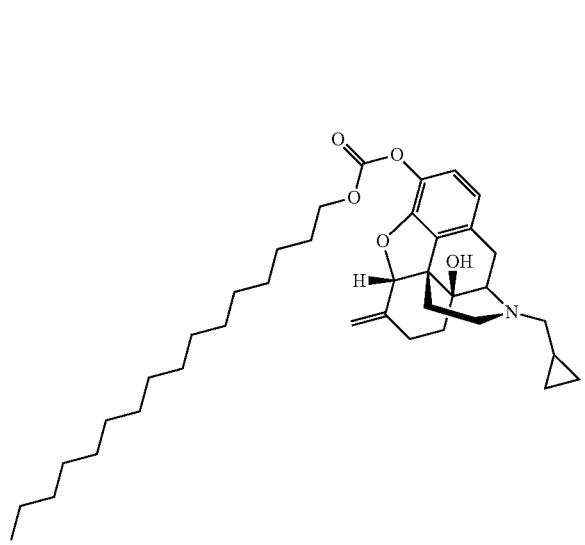

Figure 19:
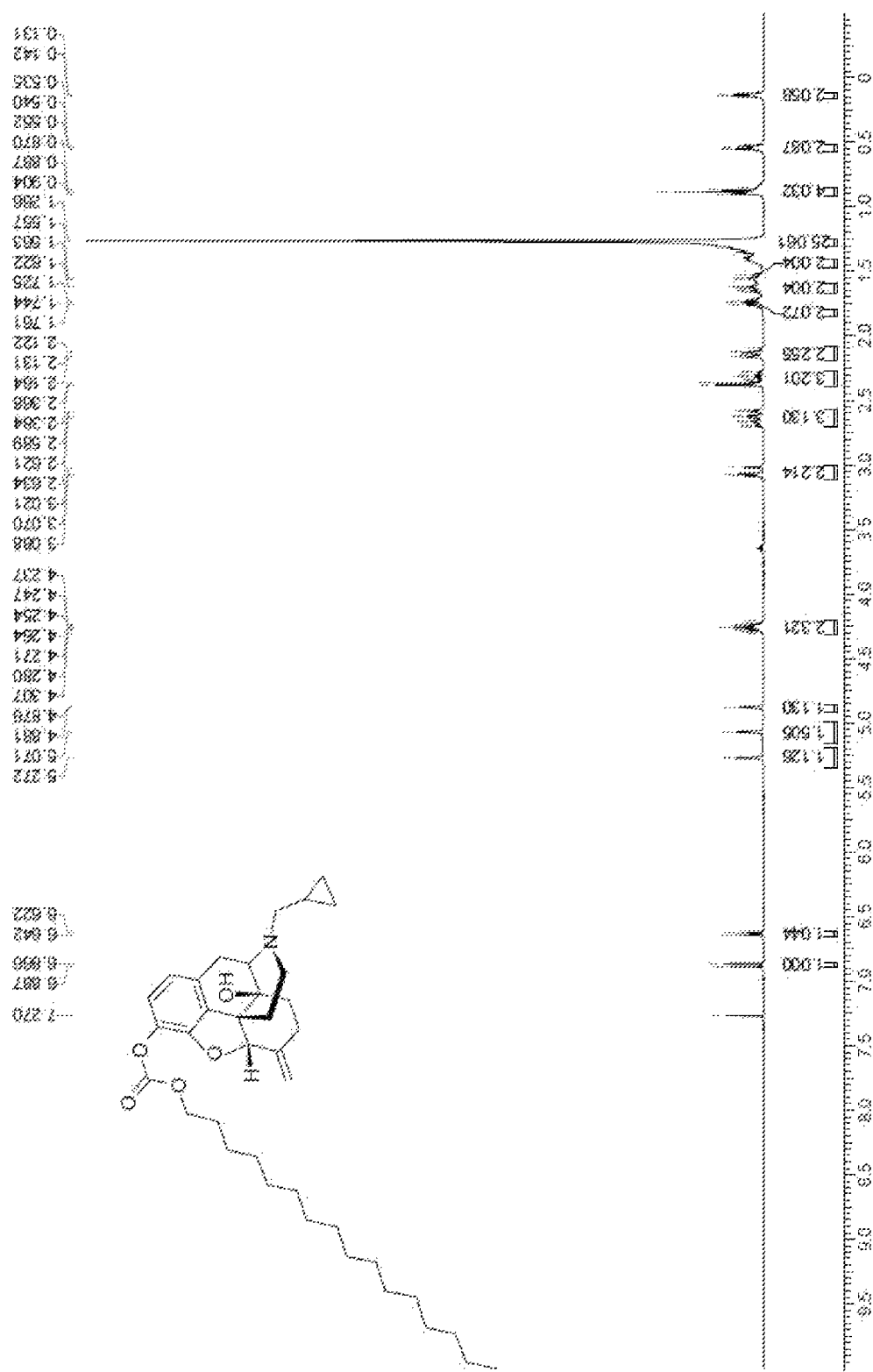
FIG. 19 provides the nuclear magnetic resonance spectrum of Example 19 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl hexadecyl carbonate.

The title compound was synthesized according to the general Scheme 1 for the synthesis of nalmefene prodrugs. 1.8 g; $^1$H NMR (400 MHz, CDCl$_3$): see FIG. 19. Briefly, to a solution of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (5 g, 13.30 mmol, 1 eq) in DCM (50 mL), cooled to −10° C., TEA (4.04 g, 39.91 mmol, 5.55 mL, 3 eq) and hexadecyl carbonochloridate (8.11 g, 26.60 mmol, 2 eq) was added. Then, the mixture was stirred at 25° C. for 5 hours under N$_2$ atmosphere. The reaction mixture was extracted with H$_2$O (80 mL×1) and DCM (80 mL×2). The combined organic phase was washed with brine (60 mL×3), dried with anhydrous Na$_2$SO$_4$, filtered and concentration in vacuum. The reside and compound was purified by column chromatography (SiO2, petroleum ether/ethyl acetate=10/1 to 1:1) The residue was purified by prep-HPLC (TFA condition: column—Phenomenex lune C18 250×50 mm×10 μm; mobile phase—[water (0.1% TFA)-CAN]; B % 65-95%, 20 minutes). NaHCO$_3$ was added to adjust pH to 8, and then extracted with EtOAc (20 mL×3). The organic layer was evaporated under reduced pressure to get the final product. The compound [4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl hexadecyl carbonate] was 99.723% pure and was obtained as a white solid (1.8 g, 12.33% yield).

Example 20: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z,15Z)-octadeca-9,12,15-trienoate

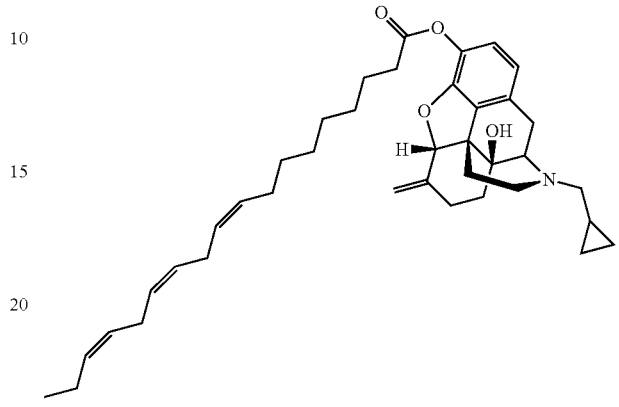

Figure 20:
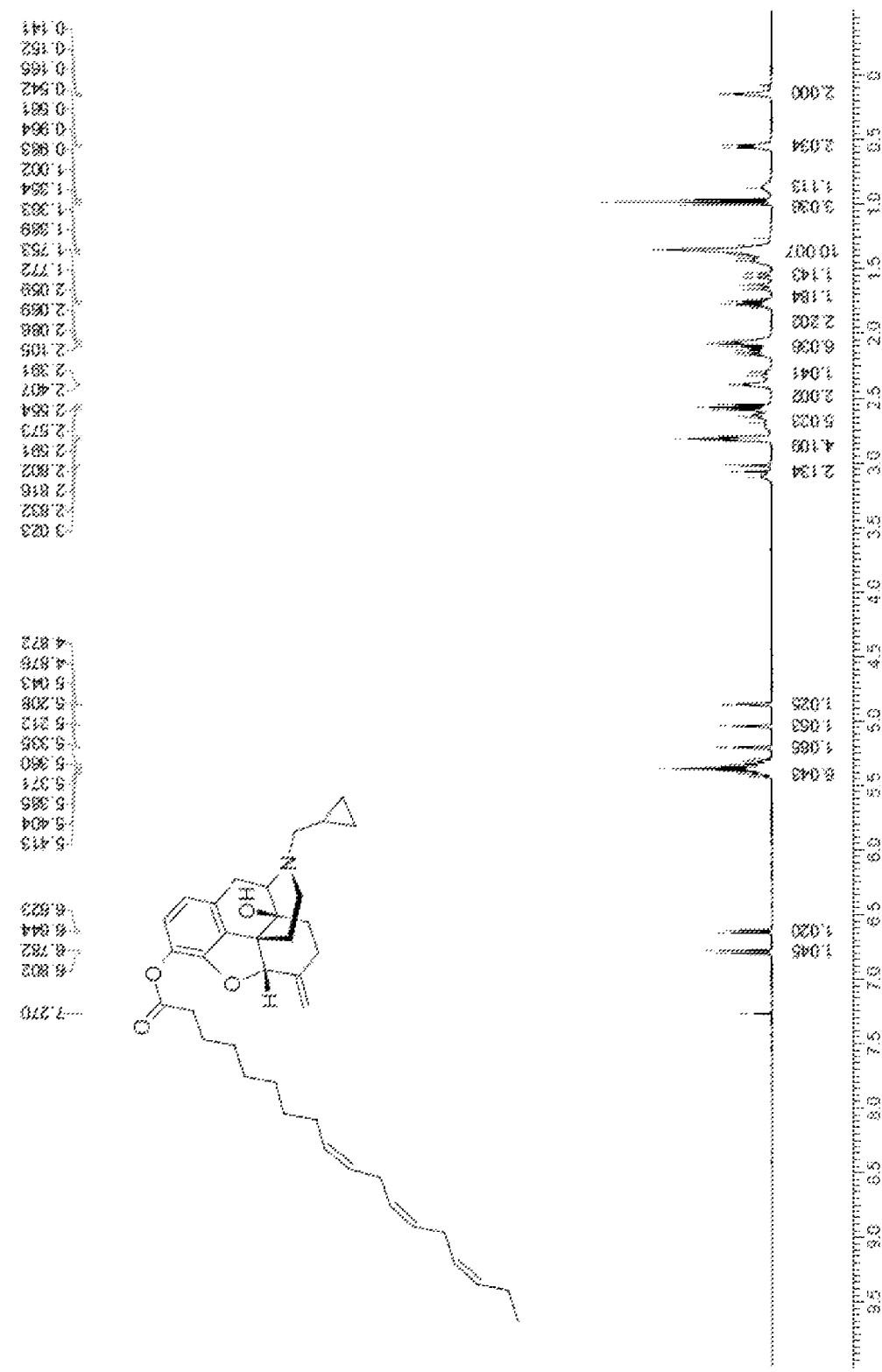
FIG. 20 provides the nuclear magnetic resonance spectrum of Example 20 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z,15Z)-octadeca-9,12,15-trienoate.

The title compound was synthesized according to the general Scheme 1 for the synthesis of nalmefene prodrugs. 1.4 g; $^1$H NMR (400 MHz, CDCl$_3$): see FIG. 20.

Example 21: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl hexadecyl carbonate

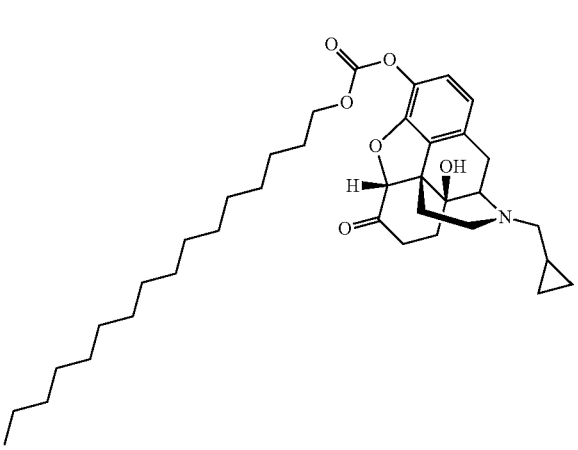

Figure 21:
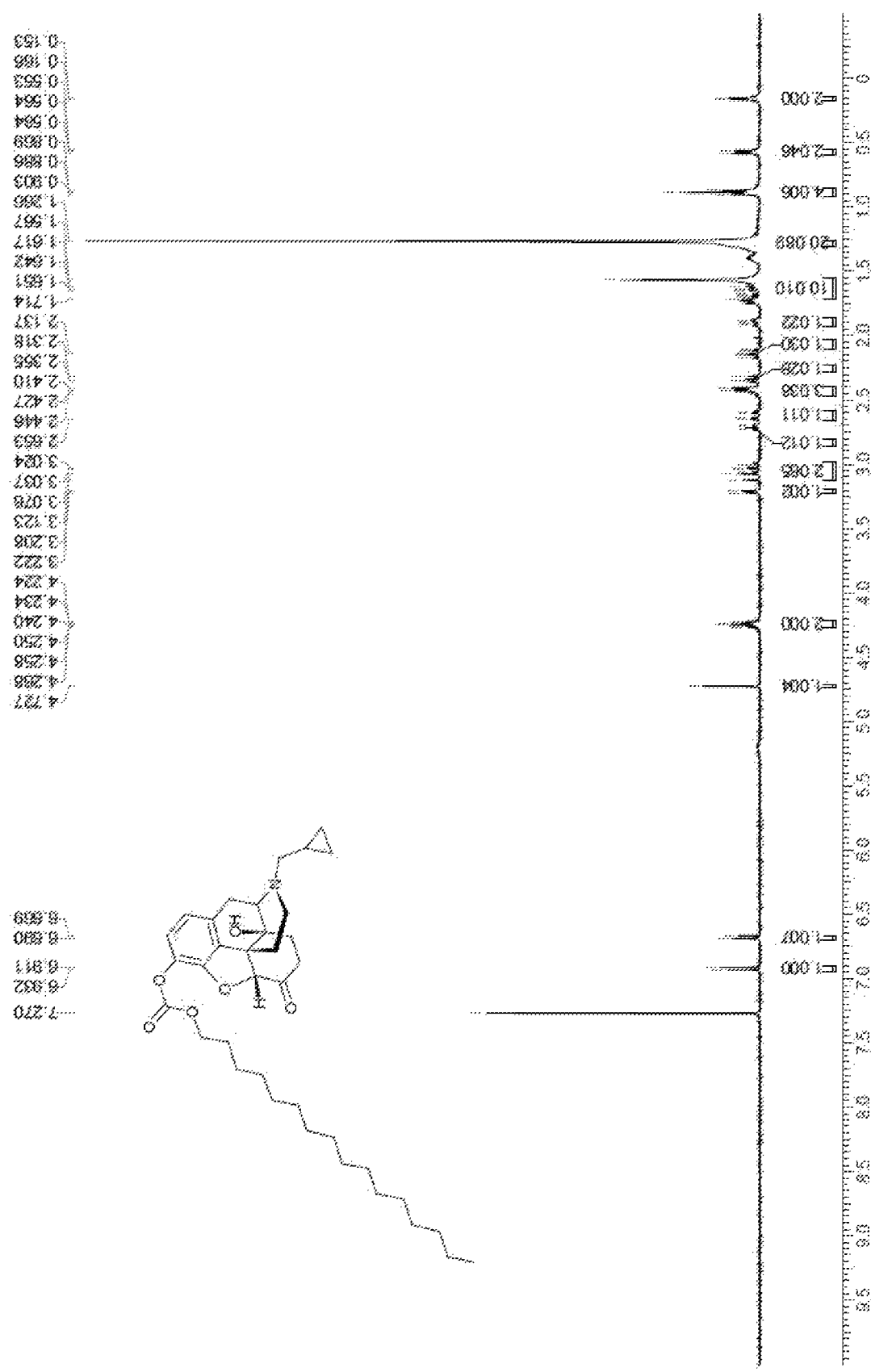
FIG. 21 provides the nuclear magnetic resonance spectrum of Example 21 of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl hexadecyl carbonate.

The title compound was synthesized according to the general Scheme 2 for the synthesis of naltrexone prodrugs. 2.15 g; $^1$H NMR (400 MHz, CDCl$_3$): see FIG. 21. Briefly, to a mixture of (3R, 4aS, 7aR, 12bS)-3-(cyclopropylmethyl)-4a,9-dihydroxy-2,4,5,6,7a,13-hexahydro-1H-4,12-methanobenzofuro[3,2-e]isoquinoline-7-one (2 g, 5.29 mmol, 1 eq, HCl0 in DCM (20 mL), cooled to −10° C., was added TEA (1.61 g, 15.88 mmol, 2.21 mL, 3 eq) and hexadecyl carbonochloridate (3.23 g, 10.59 mmol, 2 eq). Then, the mixture was stirred at 25° C. for 5 hours under N$_2$ atmosphere. The reaction mixture was extracted with H20 (80 mL×1) and DCM (80 mL×2). The residue was purified by prep-HPLC (TFA condition: column—Phenomenex luna (2) C18 250×50 mm×10 μm; mobile phase—[water(0.1% TFA)-CAN]; B % 60-90%, 20 minutes). NaHCO₃ was added to adjust pH to 8, and then extracted with EtOAc (20 mL×3). The organic layer was evaporated under reduced pressure to get the final product. The compound [(4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl hexadecyl carbonate] was 97.669% pure and obtained as a white solid (2.15 g, 65.06% yield)

Example 22: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (Z)-docos-13-enoate

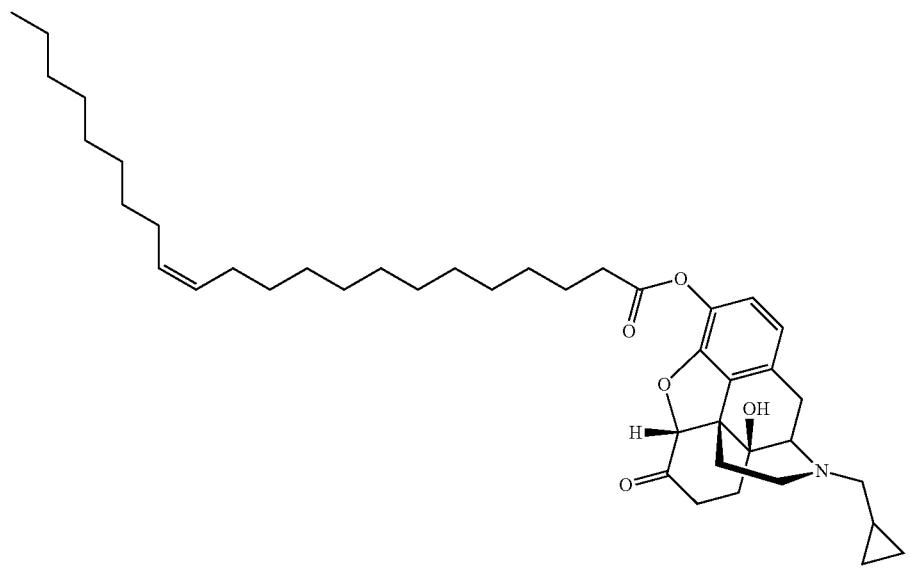

Figure 22:
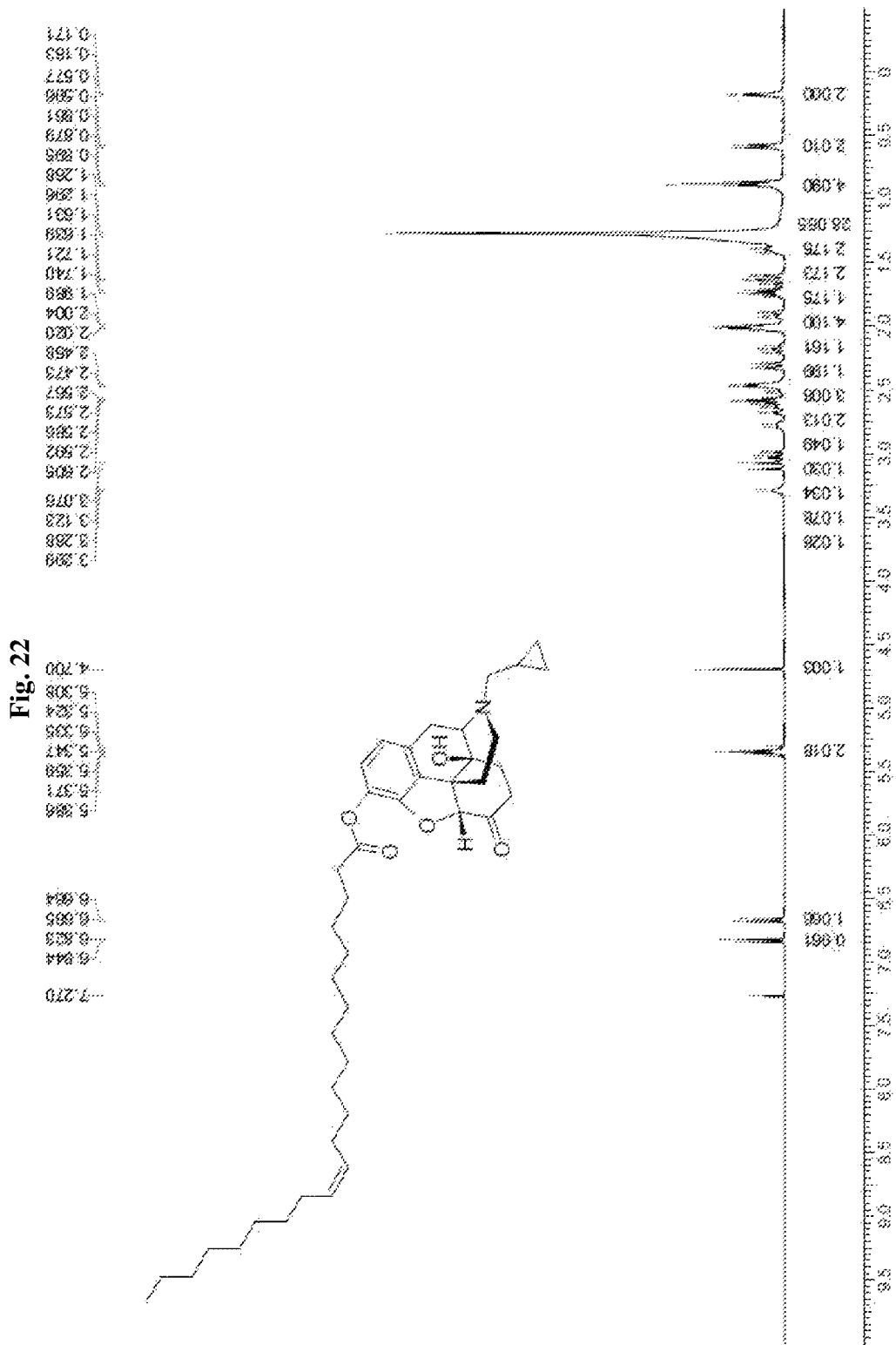
FIG. 22 provides the nuclear magnetic resonance spectrum of Example 22 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl (Z)-docos-13-enoate.

The title compound was synthesized according to the general Scheme 2 for the synthesis of naltrexone prodrugs. 2.17 g; ¹H NMR (400 MHz, CDCl₃): see FIG. 22.

Figure 23:
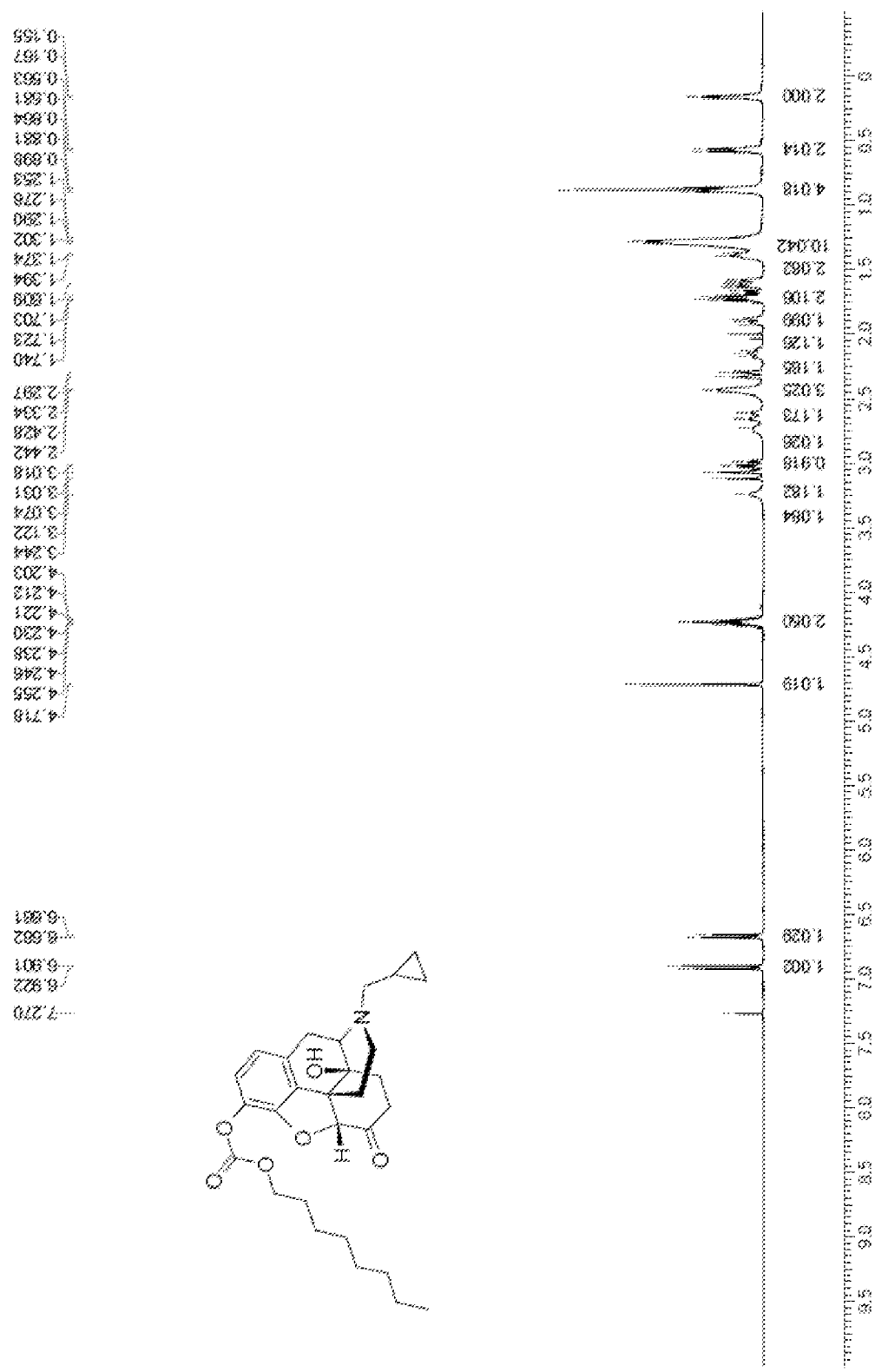
FIG. 23 provides the nuclear magnetic resonance spectrum of Example 23 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl octyl carbonate.

Example 23: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl octyl carbonate The title compound was synthesized according to the general Scheme 2 for the synthesis of naltrexone prodrugs. 1.33 g; ¹H NMR (400 MHz, CDCl₃): see FIG. 23.

Example 24: Step 24A: Synthesis of Chloromethyl Dodecyl Carbonate

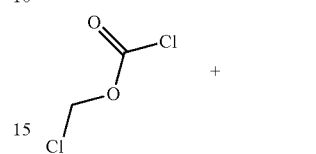

-continued

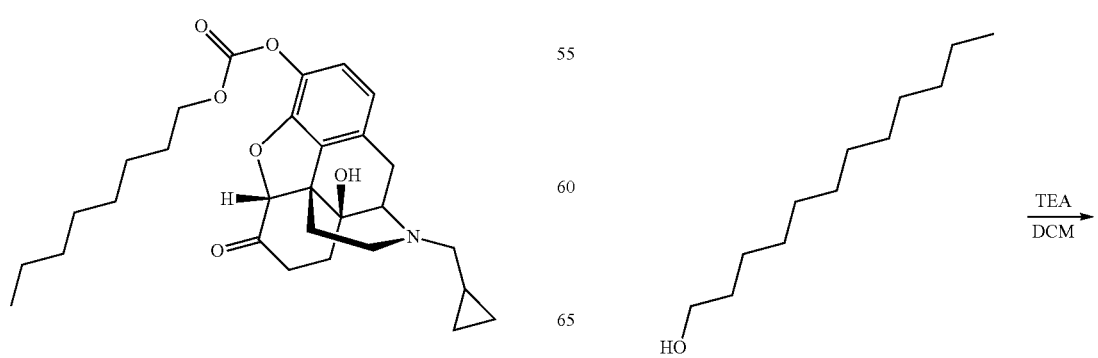

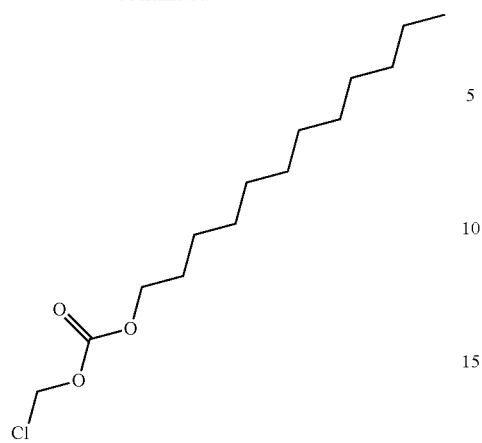

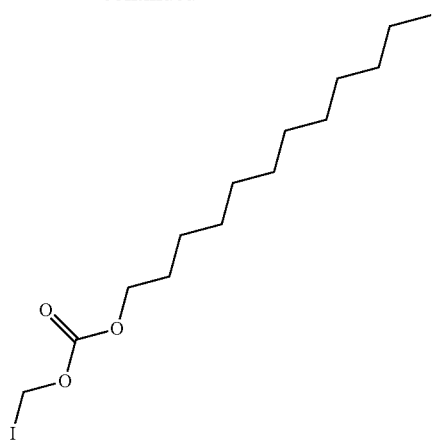

To a mixture of dodecan-1-ol (30 g, 161.00 mmol, 1 eq) in DCM (300 mL) was added TEA (32.58 g, 322.00 mmol, 44.82 mL, 2 eq) and chloromethyl carbonochloridate (41.52 g, 322.00 mmol, 28.63 mL, 2 eq) in one portion at 0° C. under $N_2$. The mixture was heated to 25° C. and stirred for 12 hr. The reaction mixture was quenched by addition water 200 mL at 25° C., and then extracted with DCM 100 mL (50 mL*2). The combined organic layers were dried over $Na_2SO_4$, filtered and concentrated under reduced pressure to give a residue. The residue was purified by column chromatography ($SiO_2$, Petroleum ether/Ethyl acetate=1/0 to 80:1). Compound chloromethyl dodecyl carbonate (10.3 g, 36.94 mmol, 22.95% yield) was obtained as a colorless oil.

To a mixture of chloromethyl dodecyl carbonate (10 g, 35.87 mmol, 1 eq) in acetone (100 mL) was added $NaHCO_3$ (3.62 g, 43.04 mmol, 1.67 mL, 1.2 eq) and NaI (6.45 g, 43.04 mmol, 1.2 eq) in one portion at 25° C. under $N_2$. The mixture was stirred at 25° C. for 12 hours in dark. The reaction mixture was filtered to remove the insoluble and concentrated under reduced pressure to give a residue. The residue was dissolved in ethyl acetate 50 mL and the organic layer was washed with water 60 mL (30 mL*2), dried over $Na_2SO_4$, filtered and concentrated under reduced pressure to give a residue. Compound dodecyl iodomethyl carbonate (12.6 g, crude) was obtained as a light red oil. The crude product dodecyl iodomethyl carbonate was used into the next step without further purification.

Step 24B: Synthesis of Iodomethyl Dodecyl Carbonate

Step 24C: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl dodecyl carbonate

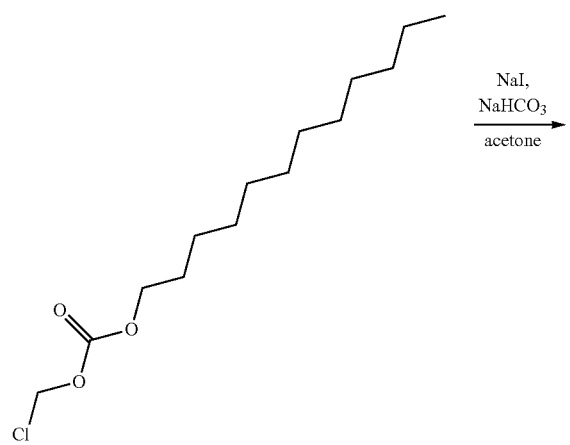

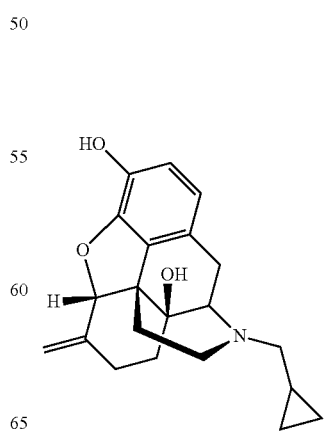

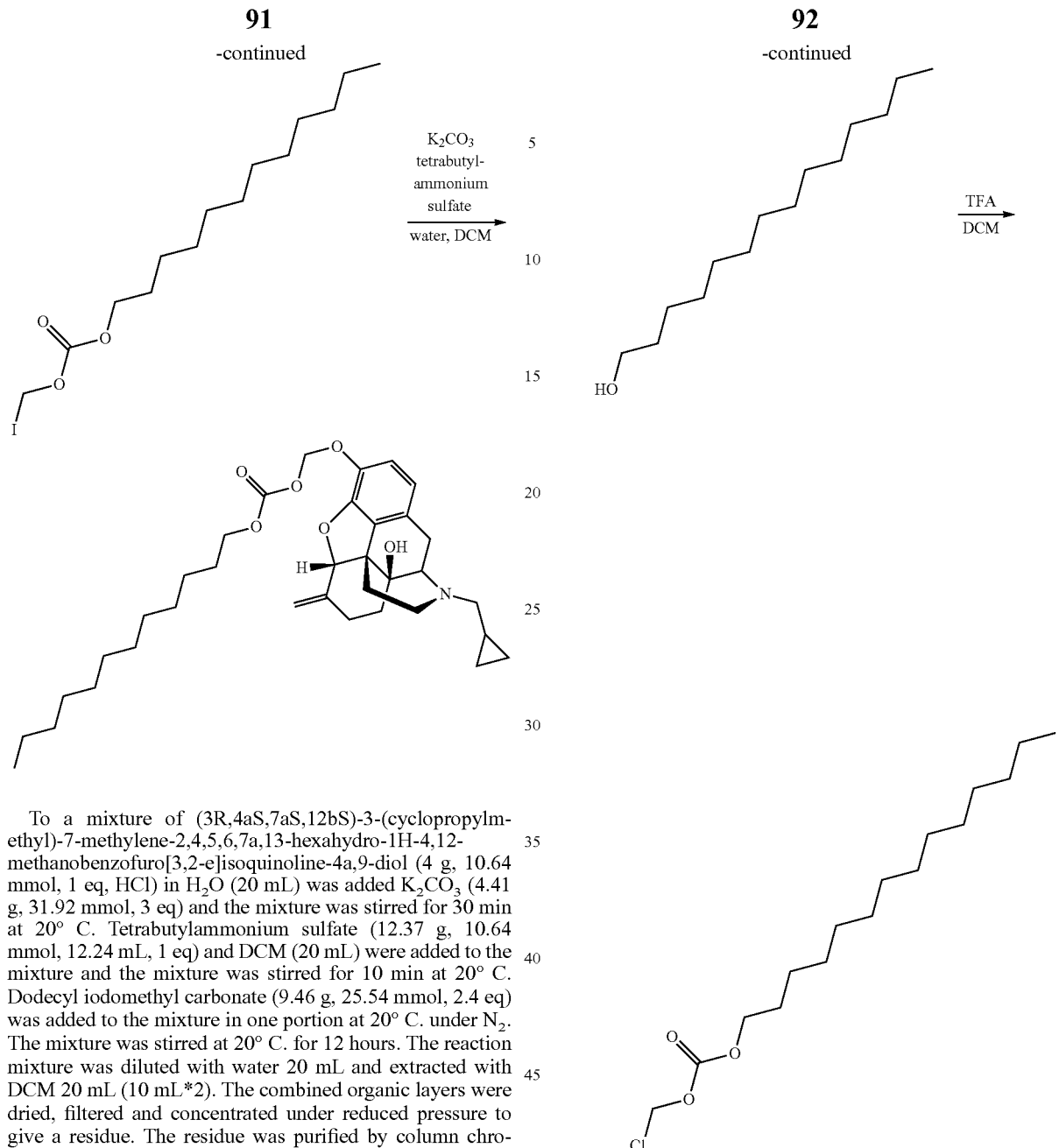

Figure 24:
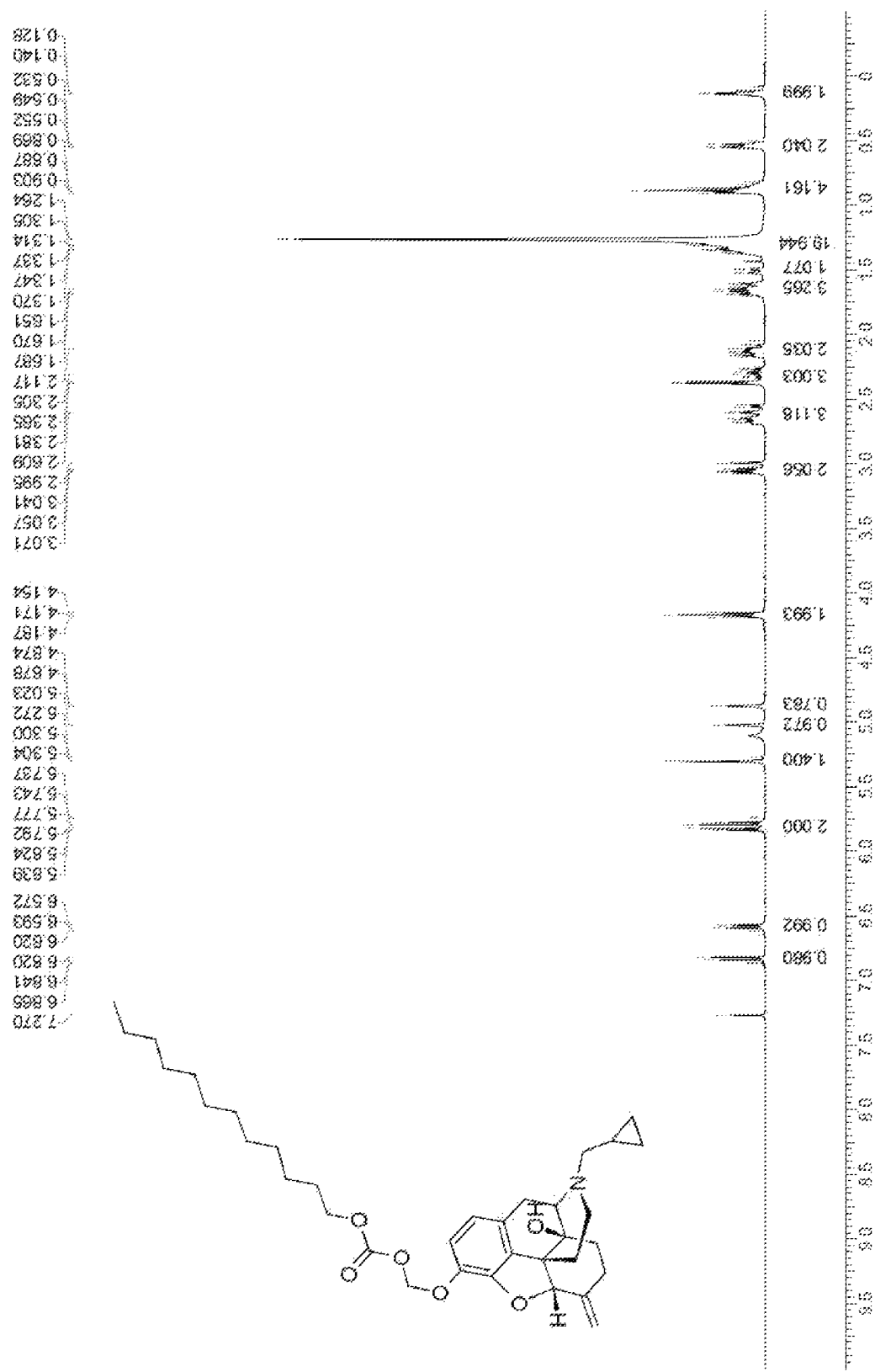
FIG. 24 provides the nuclear magnetic resonance spectrum of Example 24 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl dodecyl carbonate.

To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (4 g, 10.64 mmol, 1 eq, HCl) in H$_2$O (20 mL) was added K$_2$CO$_3$ (4.41 g, 31.92 mmol, 3 eq) and the mixture was stirred for 30 min at 20° C. Tetrabutylammonium sulfate (12.37 g, 10.64 mmol, 12.24 mL, 1 eq) and DCM (20 mL) were added to the mixture and the mixture was stirred for 10 min at 20° C. Dodecyl iodomethyl carbonate (9.46 g, 25.54 mmol, 2.4 eq) was added to the mixture in one portion at 20° C. under N$_2$. The mixture was stirred at 20° C. for 12 hours. The reaction mixture was diluted with water 20 mL and extracted with DCM 20 mL (10 mL*2). The combined organic layers were dried, filtered and concentrated under reduced pressure to give a residue. The residue was purified by column chromatography (SiO$_2$, Petroleum ether/Ethyl acetate=1:0 to 10:1). Compound [(3R,4aS,7aS,12bS)-3-(cyclopropylmethyl)-4a-hydroxy-7-methylene-2,4,5,6,7a,13-hexahydro-1H-4,12-methanobenzofuro[32-e]isoquinoline-9-yl]oxymethyl dodecyl carbonate (2.92 g, 5.00 mmol, 47.02% yield) was obtained as a colorless oil. M+H$^+$=582.3 (LCMS). $^1$H NMR (400 MHz, CDCl$_3$): see FIG. 24.

Example 25: Step 25A: Synthesis of Chloromethyl Tetradecyl Carbonate

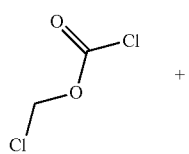

To a mixture of tetradecan-1-ol (30 g, 139.93 mmol, 1 eq) in DCM (300 mL) was added TEA (28.32 g, 279.87 mmol, 38.95 mL, 2 eq) and chloromethyl carbonochloridate (36.09 g, 279.87 mmol, 24.89 mL, 2 eq) in one portion at 0° C. under N$_2$, then heated to 25° C. for 12 hr. The reaction mixture was quenched by addition water 200 mL at 25° C., and then extracted with DCM 100 mL (50 mL*2). The combined organic layers were dried over Na$_2$SO$_4$, filtered and concentrated under reduced pressure to give a residue. The residue was purified by column chromatography (SiO$_2$, Petroleum ether/Ethyl acetate=1/0 to 80:1). Compound chloromethyl tetradecyl carbonate (11 g, 35.85 mmol, 25.62% yield) was obtained as a colorless oil.

Example 25B: Synthesis of Iodomethyl Tetradecyl Carbonate

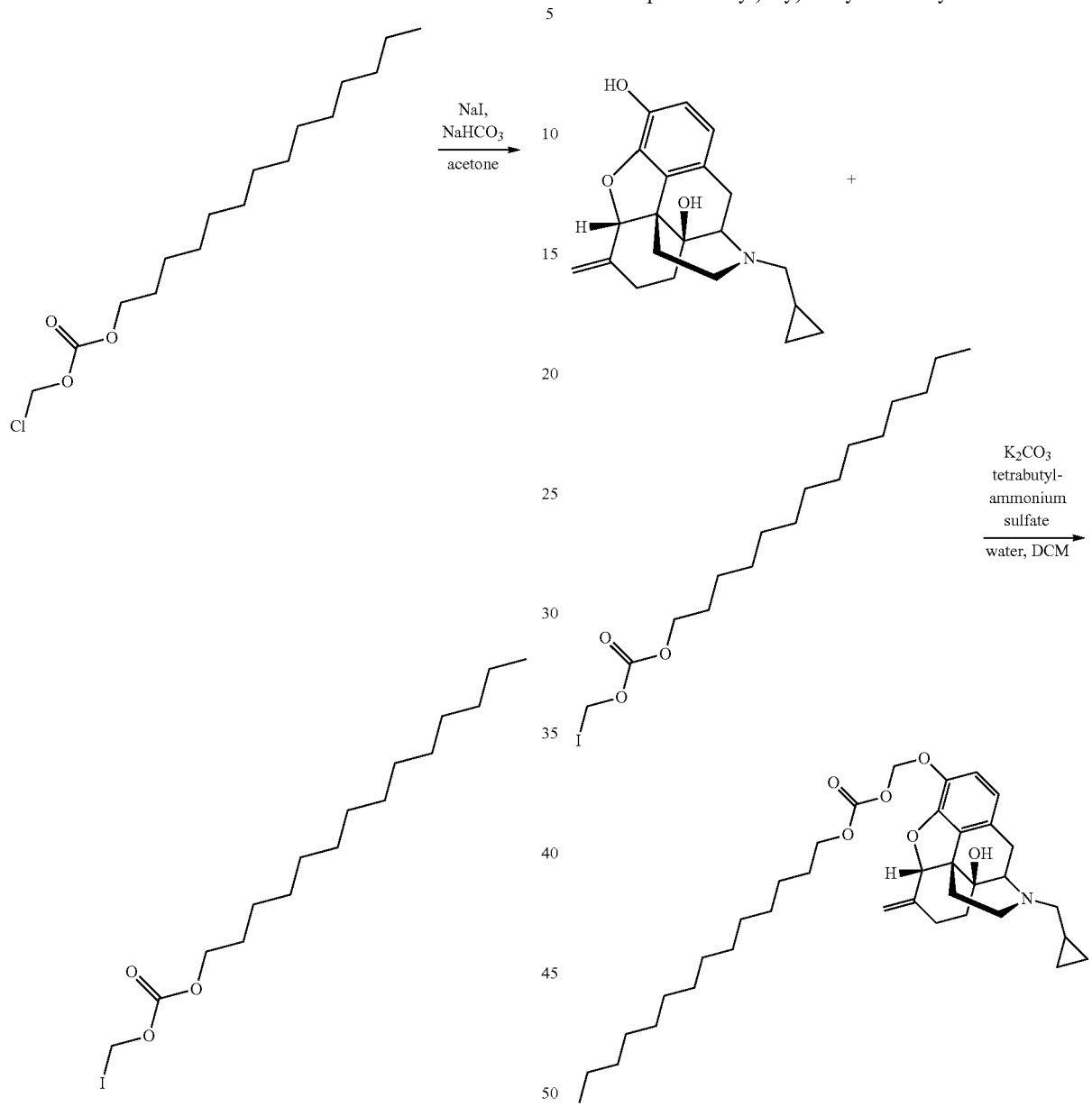

Step 25C: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecyl carbonate To a mixture of chloromethyl tetradecyl carbonate (11.1 g, 36.17 mmol, 1 eq) in acetone (100 mL) was added NaHCO$_3$ (3.04 g, 36.17 mmol, 1.41 mL, 1 eq) and NaI (5.42 g, 36.17 mmol, 1 eq) in one portion at 15° C. under N$_2$. The mixture was stirred at 15° C. for 12 h. The reaction mixture was concentrated under reduced pressure to remove solvent. The residue was diluted with ethyl acetate 40 mL and washed with water 40 mL (20 mL*2). The organic layers were dried, filtered and concentrated under reduced pressure to give a residue. The crude product iodomethyl tetradecyl carbonate (13.1 g, 32.89 mmol, 90.92% yield) was obtained as light red oil and used into the next step without further purification.

Figure 25:
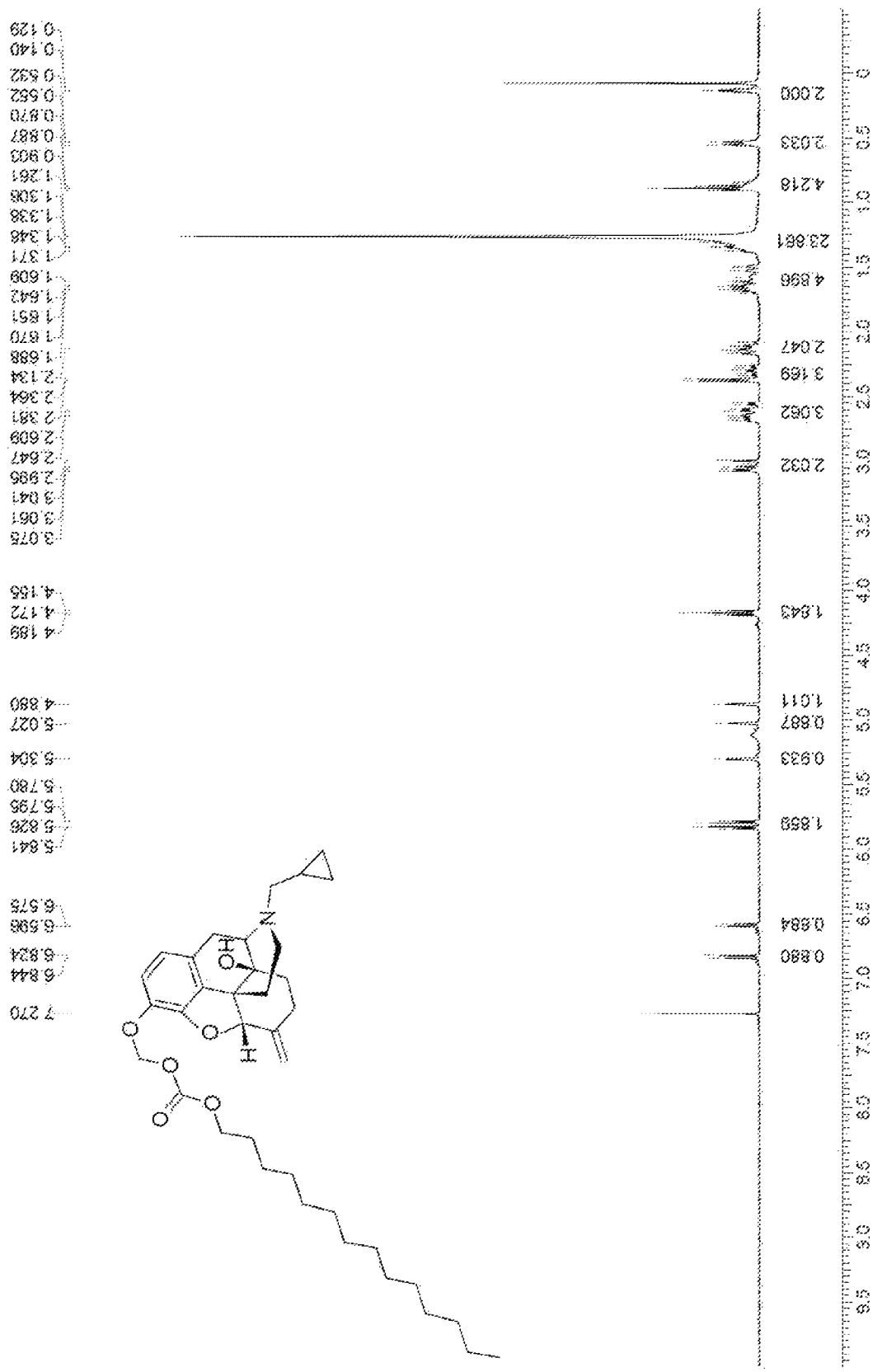
FIG. 25 provides the nuclear magnetic resonance spectrum of Example 25 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecyl carbonate.

To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (3 g, 7.98 mmol, 1 eq, HCl) and iodomethyl tetradecyl carbonate (7.63 g, 19.15 mmol, 2.4 eq) in H$_2$O (30 mL) was added K$_2$CO$_3$ (3.31 g, 23.94 mmol, 3 eq) and the mixture was stirred for 0.5 h at 15° C. After 0.5 h, tetrabutylammonium sulfate (4.64 g, 7.98 mmol, 4.59 mL, 1 eq) and DCM (30 mL) were added to the mixture and the mixture was stirred for 10 min at 15° C. After 10 min, iodomethyl tetradecyl carbonate (7.63 g, 19.15 mmol, 2.4 eq) was added to the mixture in one portion at 15° C. under N$_2$. The mixture was stirred at 15° C. for 12 h. The residue was diluted with water 10 mL and extracted with DCM 20 mL (10 mL*2). The combined organic layers were dried, filtered, and concentrated under reduced pressure to give a residue. The residue was purified by column chromatography (SiO$_2$, Petroleum ether/Ethyl acetate=1:0 to 10:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl tetradecyl carbonate (2.0 g, 3.25 mmol, 40.76% yield) was obtained as a colorless oil. M+H$^+$=610.5 (LCMS). $^1$H NMR (400 MHz, CDCl$_3$): see FIG. 25.

Example 26: Step 26A: Synthesis of chloromethyl (E)-octadec-9-enoate

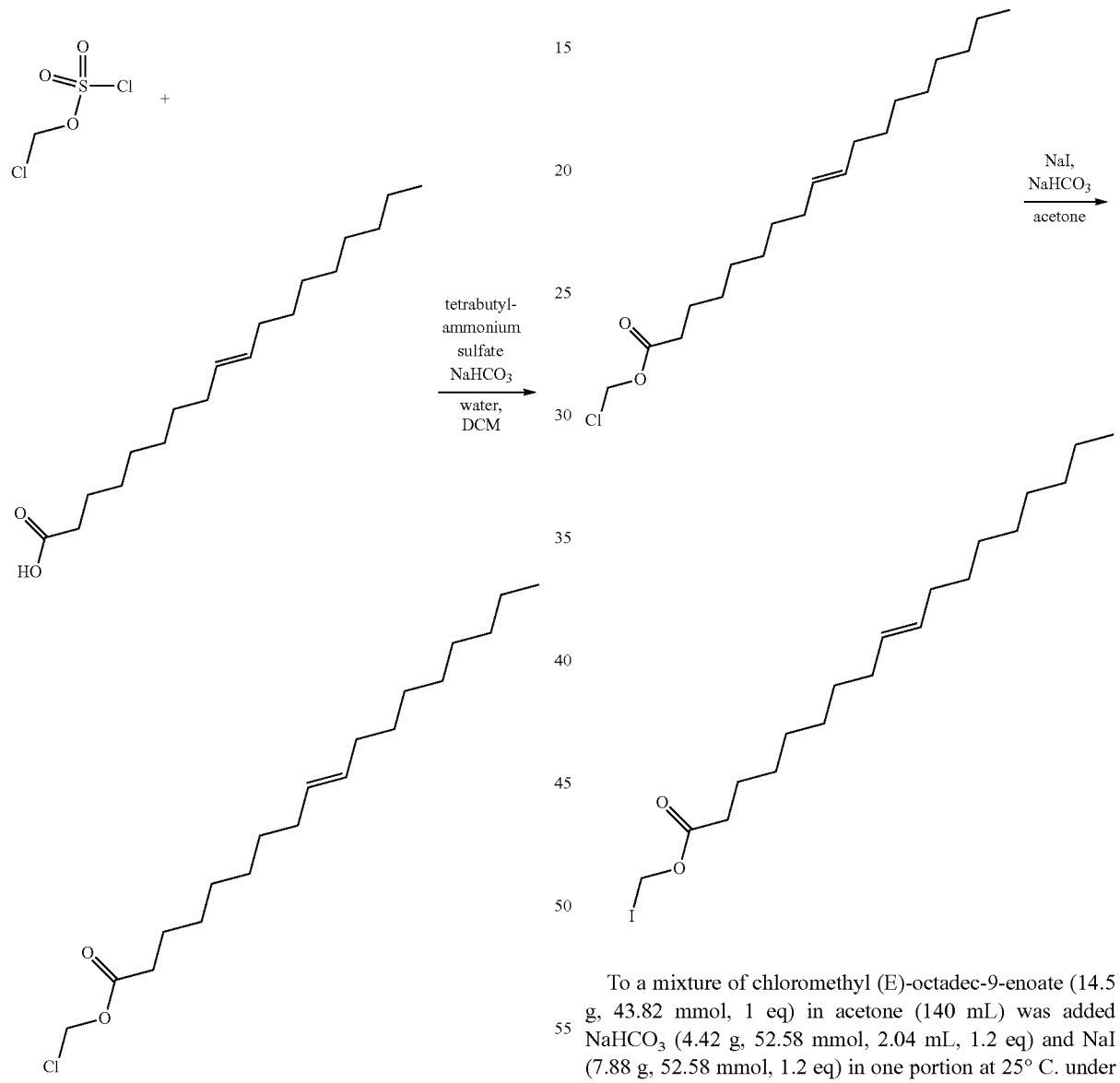

To a mixture of (E)-octadec-9-enoic acid (2 g, 7.08 mmol, 1 eq) in DCM (15 mL) and H$_2$O (8 mL) was added NaHCO$_3$ (2.38 g, 28.32 mmol, 1.10 mL, 4 eq) and tetrabutylammonium sulfate (822.29 mg, 708.06 umol, 50% solution, 0.1 eq) in one portion at 25° C. under N$_2$, then the mixture was cooled to 0° C. Chloro(chlorosulfonyloxy)methane (1.17 g, 7.08 mmol, 1 eq) in DCM (10 mL) was added to the mixture at 0° C. The mixture was heated to 25° C. and stirred for 18 hours. The reaction mixture was extracted with DCM 30 mL (15 mL*2). The combined organic layers were dried over Na$_2$SO$_4$, filtered and concentrated under reduced pressure to give a residue. Compound chloromethyl (E)-octadec-9-enoate (1.97 g, 5.95 mmol, 84.07% yield) was obtained as a white solid and was used into the next step without purification.

Step 26B: Synthesis of iodomethyl (E)-octadec-9-enoate

To a mixture of chloromethyl (E)-octadec-9-enoate (14.5 g, 43.82 mmol, 1 eq) in acetone (140 mL) was added NaHCO$_3$ (4.42 g, 52.58 mmol, 2.04 mL, 1.2 eq) and NaI (7.88 g, 52.58 mmol, 1.2 eq) in one portion at 25° C. under N$_2$. The mixture was stirred at 25° C. for 12 hours in dark. The reaction mixture was filtered to remove the insoluble and concentrated under reduced pressure to give a residue. The residue was dissolved in ethyl acetate (100 mL) and the organic layer was washed with brine 100 mL, dried over Na$_2$SO$_4$, filtered and concentrated under reduced pressure to give a residue. Compound iodomethyl (E)-octadec-9-enoate (18.6 g, crude) was obtained as a brown oil and was used into the next step without purification.

Step 26C: Synthesis of (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl (E)-octadec-9-enoate

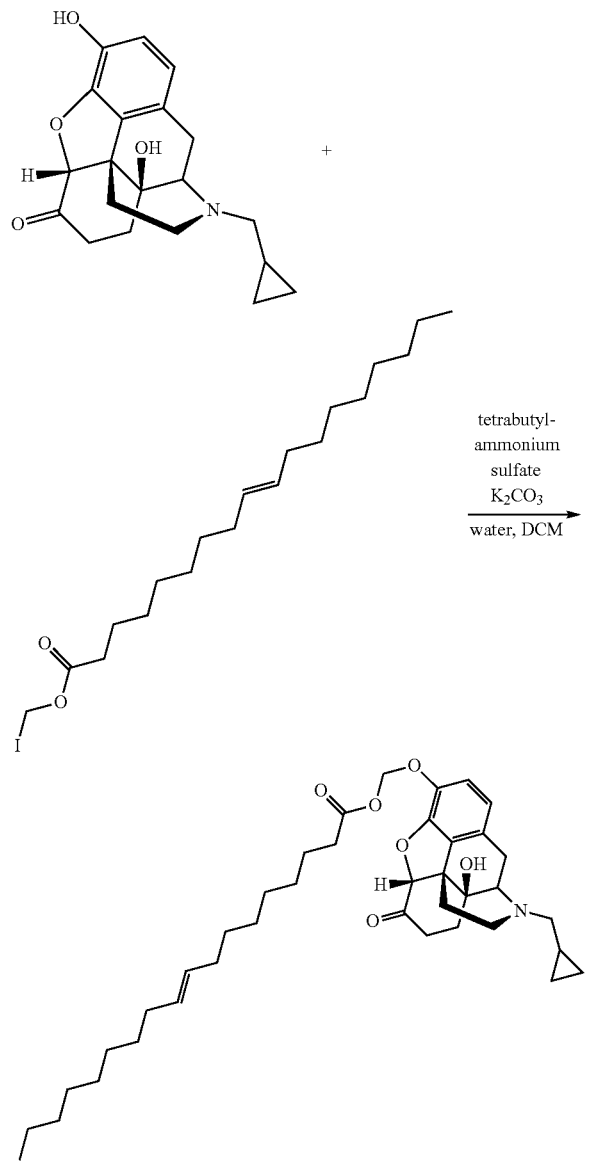

Figure 26:
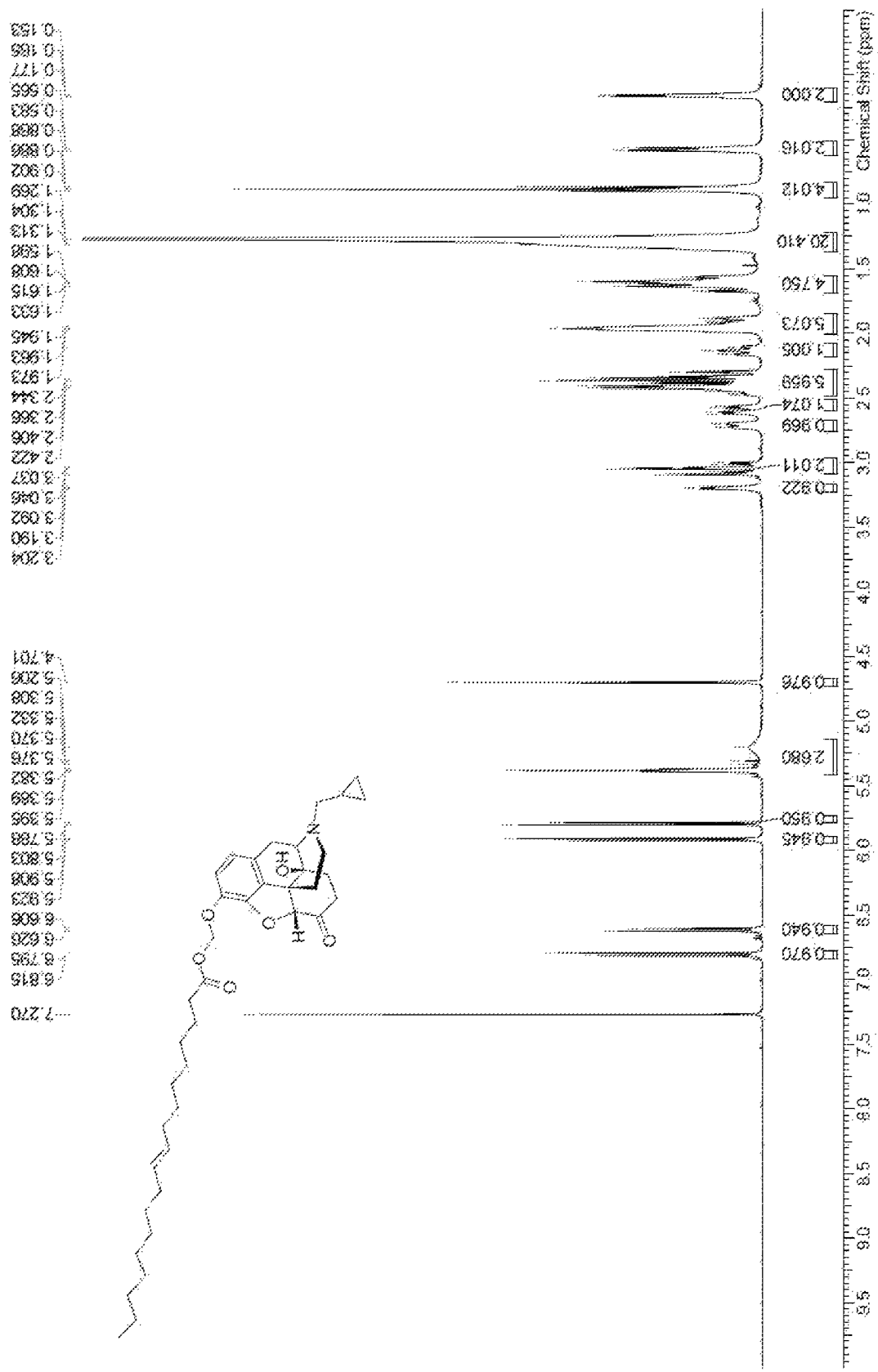
FIG. 26 provides the nuclear magnetic resonance spectrum of Example 26 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl (E)-octadec-9-enoate.

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (10.09 g, 26.71 mmol, 1 eq, HCl) in H₂O (100 mL) was added K₂CO₃ (11.07 g, 80.12 mmol, 3 eq) in one portion at 25° C. under N₂. The mixture was stirred at 25° C. for 30 min. A mixture of tetrabutylammonium sulfate (15.01 g, 12.92 mmol, 50% solution, 4.84e-1 eq) in DCM (100 mL) then the later mixture was added to the former mixture. Iodomethyl (E)-octadec-9-enoate (16.92 g, 40.06 mmol, 1.5 eq) was added and the mixture was stirred for 12 hours. The mixture was diluted with H₂O (800 mL), collect the organic layer, then was extracted with Ethyl Acetate (300 mL*3). All the organic phase was washed with brine (300 mL), dried over Na₂SO₄, filtered and the filtrate was concentrated under reduced pressure. The residue was purified by silica gel chromatography (Petroleum ether/Ethyl acetate=20/1 to 1/1). The residue was further purified by prep-HPLC, MeOH as solvent, select conventional reverse phase separation as method, separation system is TFA. NaHCO₃ was added to adjust pH to about 8, the aqueous phase was extracted with ethyl acetate (400 mL*3). The combined organic phase was washed with brine (500 mL), dried with anhydrous Na₂SO₄, filtered and concentrated in vacuum. The compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl (E)-octadec-9-enoate (10.20 g, 15.85 mmol, 59.35% yield) was obtained as a yellow oil. M+H⁺=636.4 (LCMS). ¹H NMR (400 MHz, CDCl₃): see FIG. 26.

Example 27: Synthesis of (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl tetradecyl carbonate

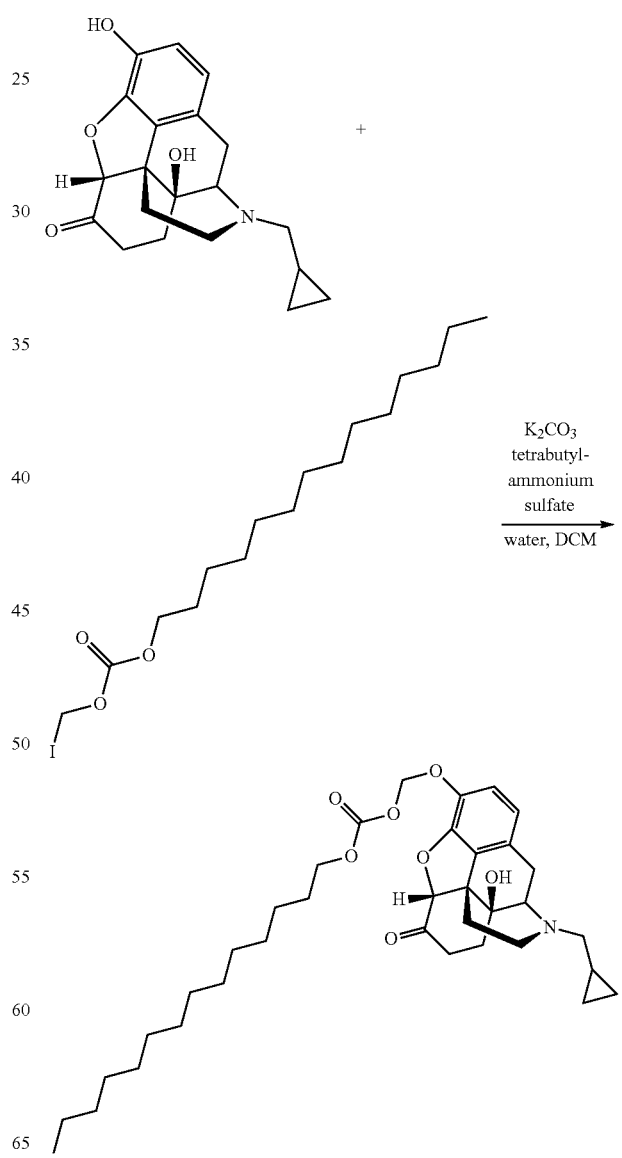

Figure 27:
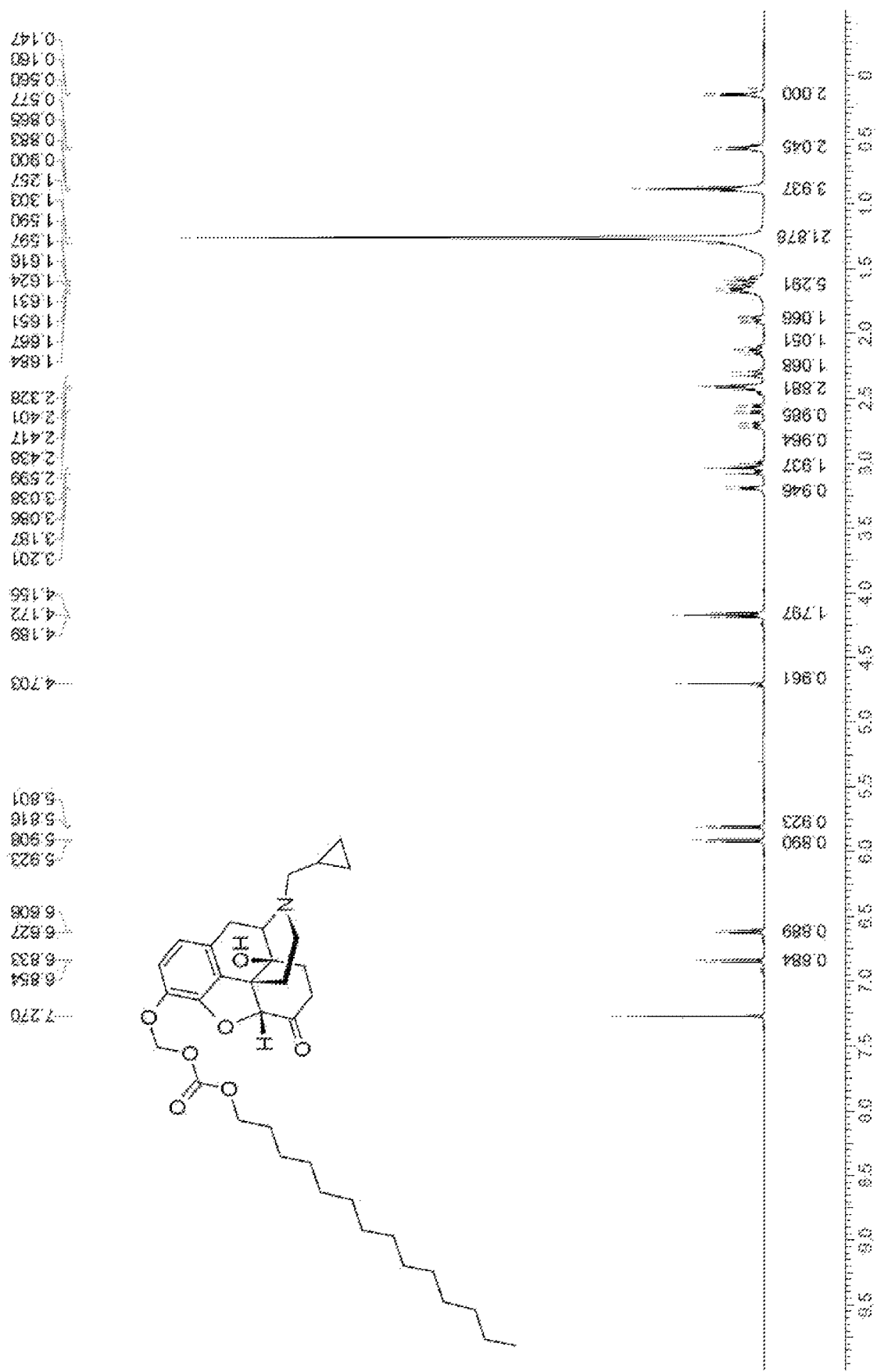
FIG. 27 provides the nuclear magnetic resonance spectrum of Example 27 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl tetradecyl carbonate.

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (4.5 g, 11.91 mmol, 1 eq, HCl) in H$_2$O (30 mL) was added K$_2$CO$_3$ (4.94 g, 35.73 mmol, 3 eq) in one portion at 25° C. under N$_2$. The mixture was stirred at 25° C. for 30 min. tetrabutylammonium sulfate (13.84 g, 11.91 mmol, 13.70 mL, 50% solution, 1 eq) and DCM (30 mL) were added to the mixture in one portion at 25° C. under N$_2$. The mixture was stirred at 25° C. for 10 min. Iodomethyl tetradecyl carbonate (11.38 g, 28.58 mmol, 2.4 eq) was added to the mixture in one portion at 25° C. under N$_2$. The mixture was stirred at 25° C. for 12 hours. The reaction mixture was extracted with DCM 30 mL (15 mL*2). The combined organic layers were dried over Na$_2$SO$_4$, filtered and concentrated under reduced pressure to give a residue. The residue was purified by column chromatography (SiO$_2$, Petroleum ether/Ethyl acetate=1/0 to 5:1). Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl tetradecyl carbonate (2.8 g, 4.53 mmol, 38.05% yield, 99% purity) was obtained as a colorless oil. $^1$H NMR (400 MHz, CDCl$_3$): see FIG. 27.

Example 28: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosyl carbonate

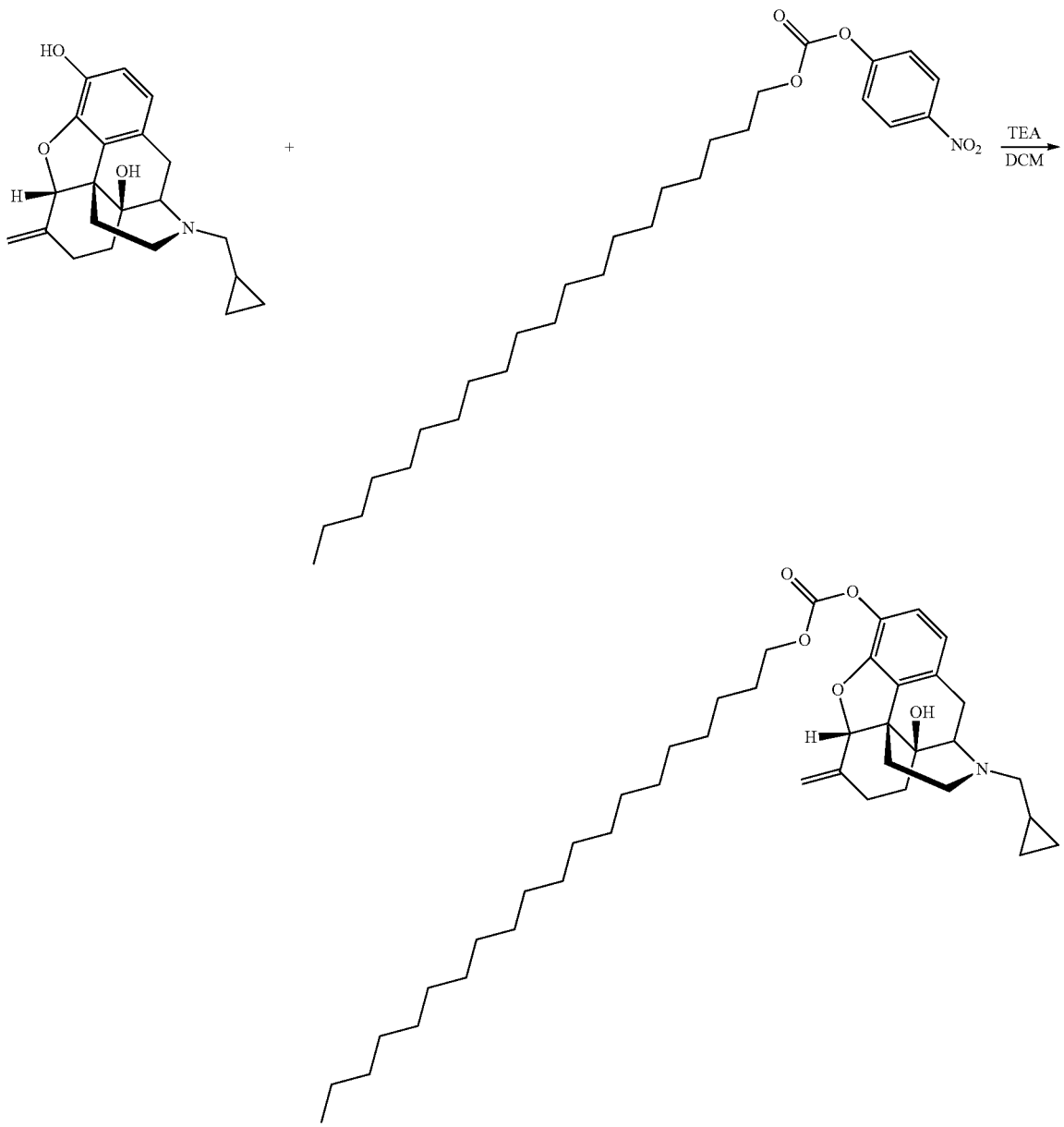

Figure 28:
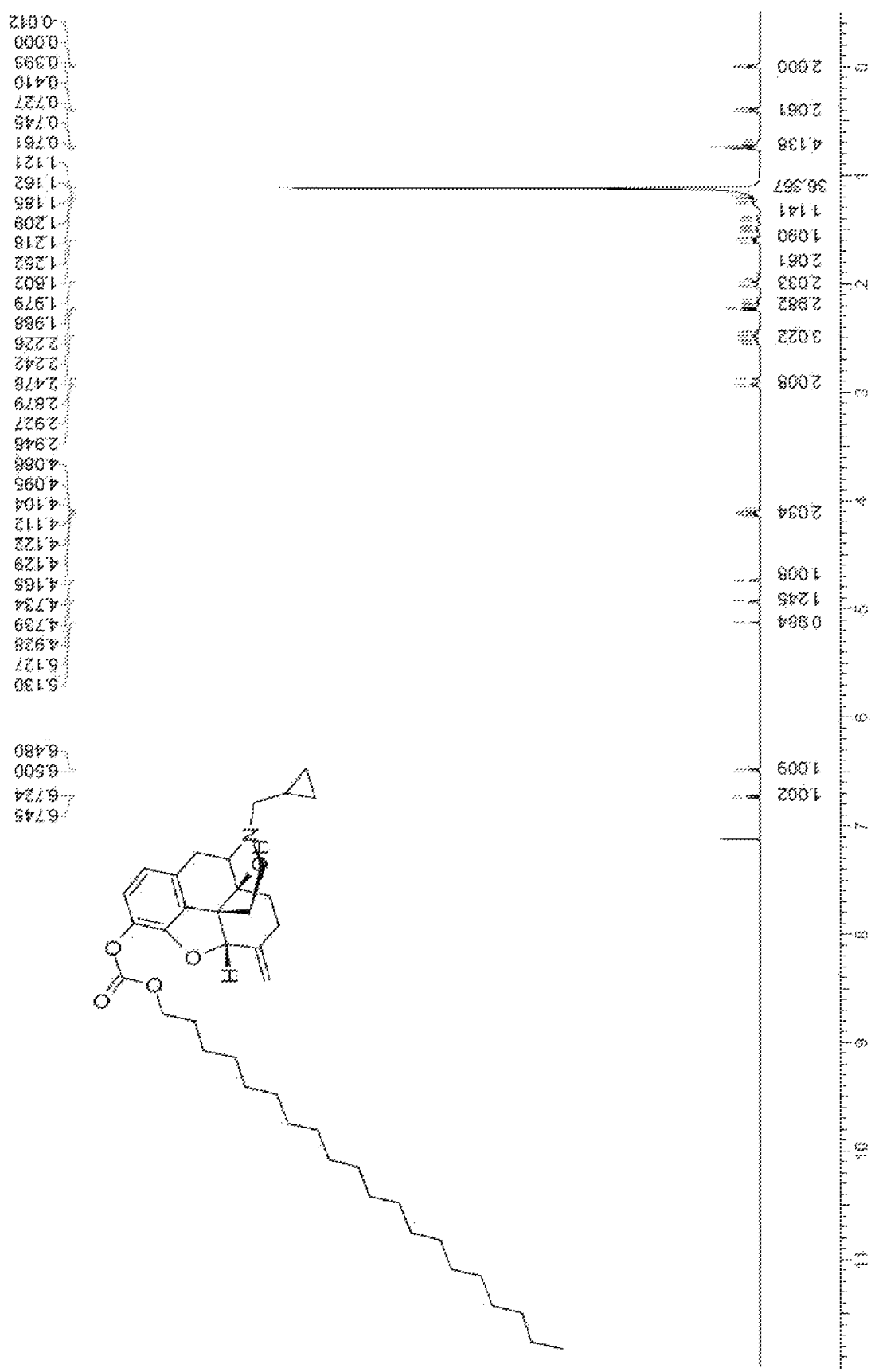
FIG. 28 provides the nuclear magnetic resonance spectrum of Example 28 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl icosyl carbonate.

To a mixture of icosyl (4-nitrophenyl) carbonate (9.87 g, 21.28 mmol, 4 eq) in DCM (40 mL) was added TEA (538.40 mg, 5.32 mmol, 740.58 uL, 1 eq) and (3R,4aS,7aS,12bS)-3-(cyclopropylmethyl)-7-methylene-2,4,56,7a,13-hexahydro-1H-4,12-methanobenzofuro[3,2-e]isoquinoline-4a,9-diol (2 g, 5.32 mmol, 1 eq, HCl) in one portion at 15° C. under N₂. The mixture was stirred at 15° C. for 12 hr. The reaction mixture was extracted with H₂O mL (20 mL*2). The combined organic layers were dried over Na₂SO₄, filtered and concentrated under reduced pressure to give a residue. The residue was purified by prep-HPLC. Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl] icosyl carbonate (1.6 g, 2.35 mmol, 44.25% yield) was obtained as a white solid. ¹H NMR (400 MHz, CDCl₃): see FIG. 28.

Figure 29:
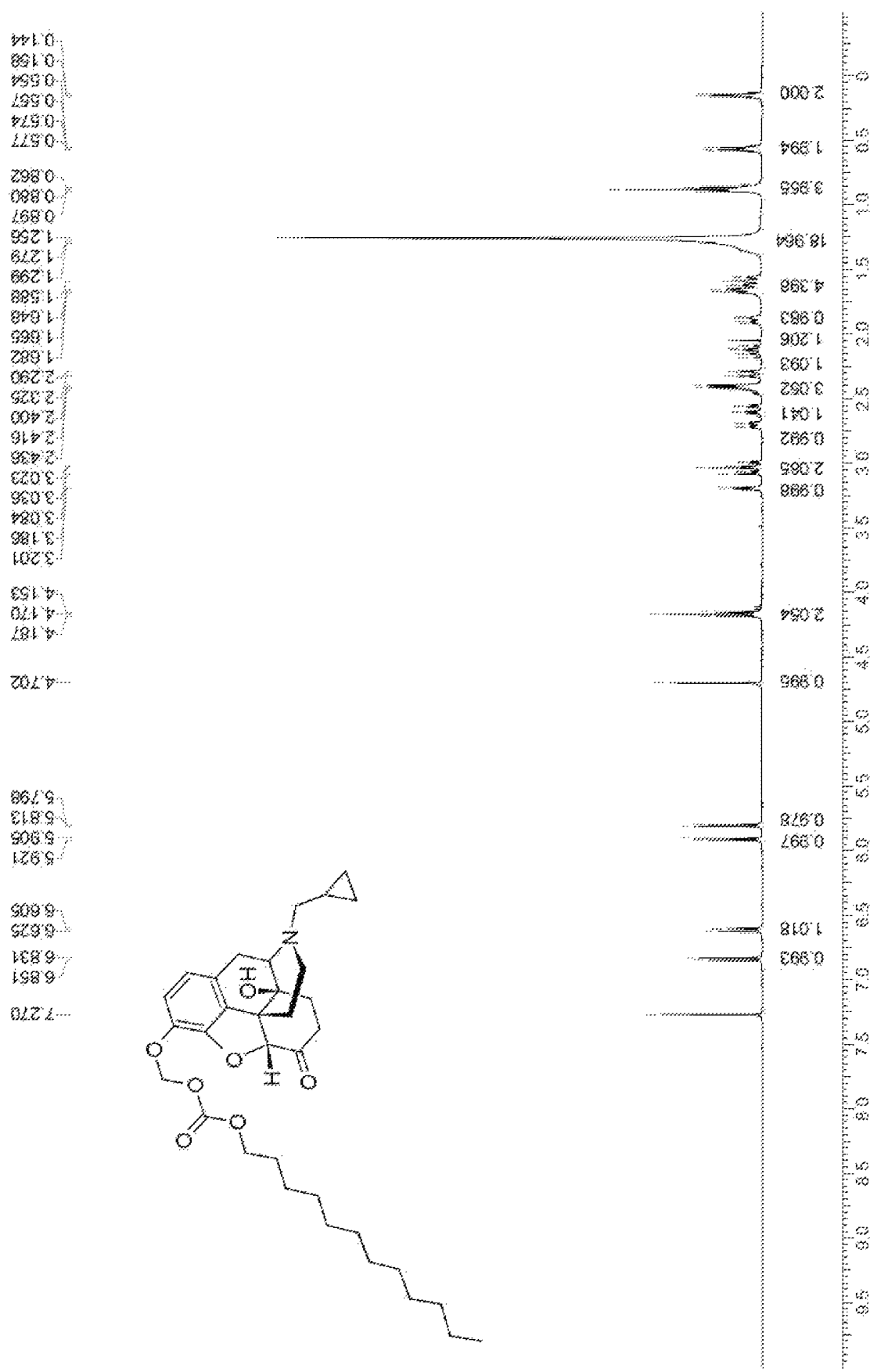
FIG. 29 provides the nuclear magnetic resonance spectrum of Example 29 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl dodecyl carbonate.

Example 29: Synthesis of ((((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl dodecyl carbonate mmol, 1 eq, HCl) in H₂O (30 mL) was added K₂CO₃ (4.94 g, 35.73 mmol, 3 eq) in one portion at 25° C. under N₂. The mixture was stirred at 25° C. for 30 min. tetrabutylammonium sulfate (13.84 g, 11.91 mmol, 13.70 mL, 50% solution, 1 eq) and DCM (30 mL) were added to the mixture in one portion at 25° C. under N₂. The mixture was stirred at 25° C. for 10 min. Dodecyl iodomethyl carbonate (10.58 g, 28.58 mmol, 2.4 eq) was added to the mixture in one portion at 25° C. under N2. The mixture was stirred at 25° C. for 12 hours. The reaction mixture was extracted with DCM 30 mL (15 mL*2). The combined organic layers were dried over Na₂SO₄, filtered and concentrated under reduced pressure to give a residue. The residue was purified by column chromatography (SiO₂, Petroleum ether/Ethyl acetate=1/0 to 5:1). Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl dodecyl carbonate (3.1 g, 5.26 mmol, 44.19% yield, 99.1% purity) was obtained as a colorless oil. ¹H NMR (400 MHz, CDCl₃): see FIG. 29.

Example 30: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tridecyl carbonate

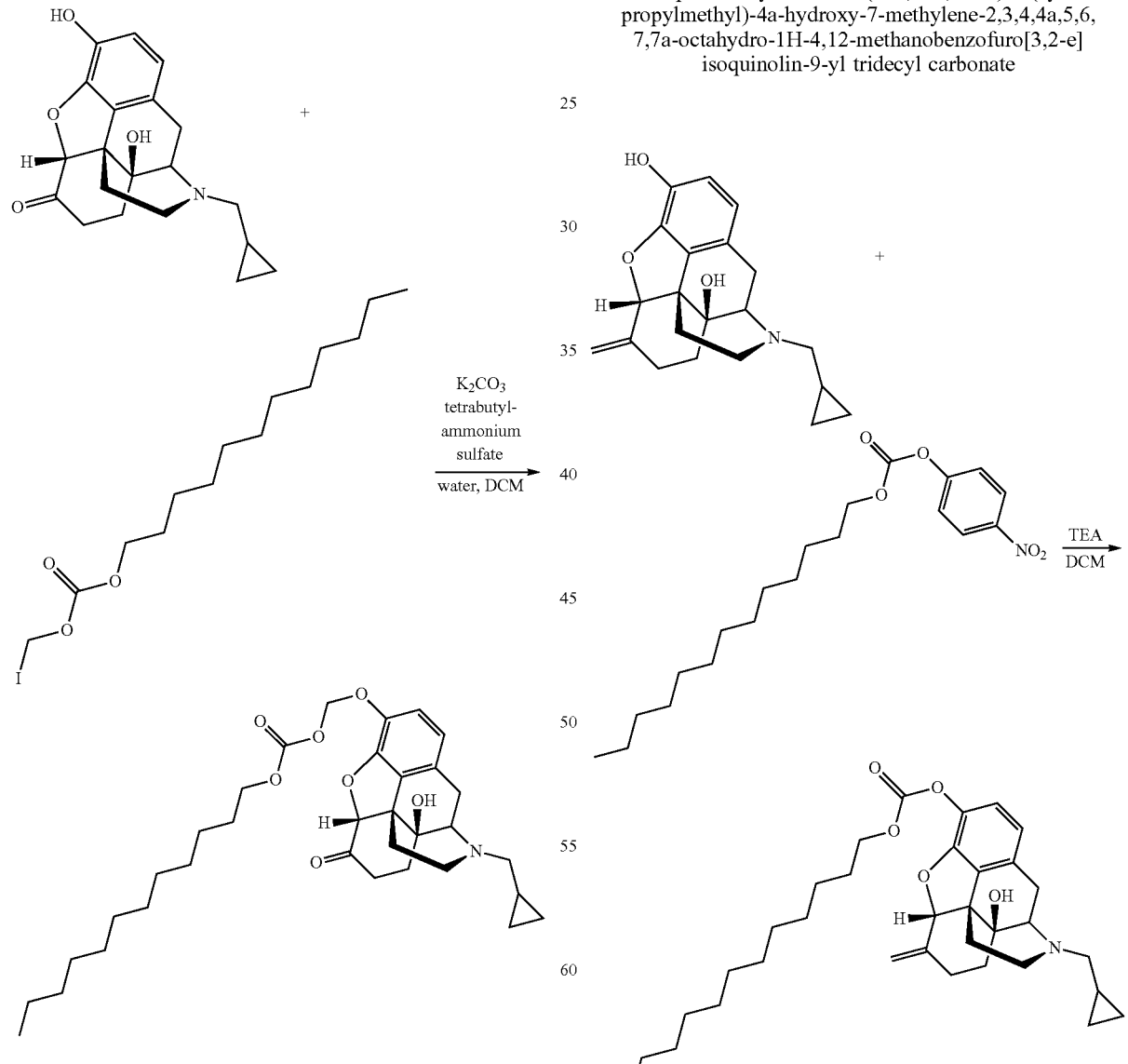

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (4.5 g, 11.91

Figure 30:
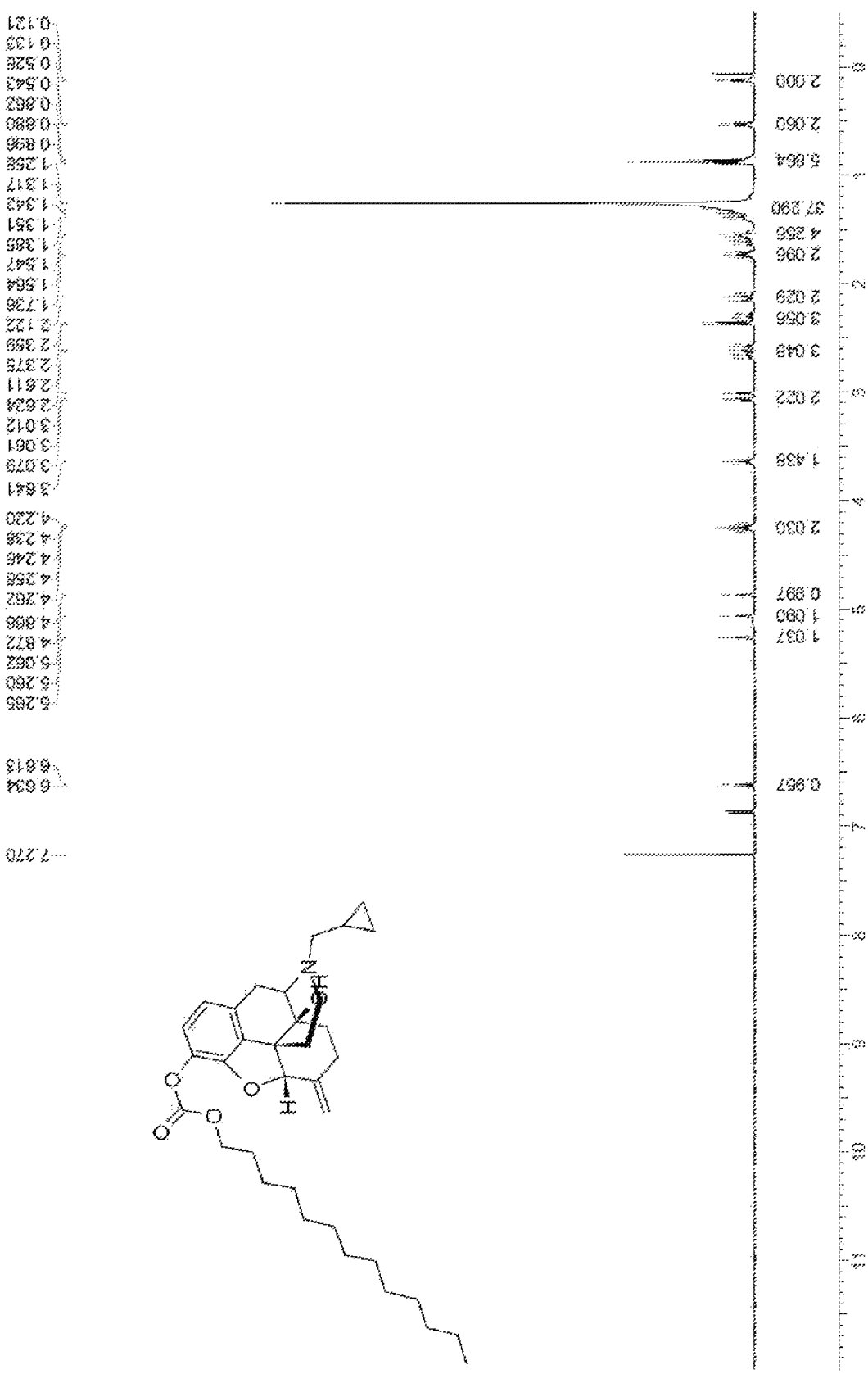
FIG. 30 provides the nuclear magnetic resonance spectrum of Example 30 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tridecyl carbonate.

To a mixture of (4-nitrophenyl) tridecyl carbonate (5.83 g, 15.96 mmol, 2 eq) in DCM (50 mL) was added TEA (2.42 g, 23.94 mmol, 3.33 mL, 3 eq) and (3R,4aS,7aS,12bS)-3-(cyclopropylmethyl)-7-methylene-2,4,56,7a,13-hexahydro-1H-4,12-methanobenzofuro[3,2-e]isoquinoline-4a,9-diol (3 g, 7.98 mmol, 1 eq, HCl) in one portion at 15° C. under N2. The mixture was stirred at 15° C. for 12 hr. The reaction mixture was concentrated under reduced pressure to remove solvent. The residue was purified by column chromatography (SiO2, Petroleum ether/Ethyl acetate=1/0 to 3:1). [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl] tridecyl carbonate (2.3 g, 4.07 mmol, 50.94% yield) was obtained as a colorless oil. $^1$H NMR (400 MHz, CDCl$_3$): see FIG. 30.

Figure 31:
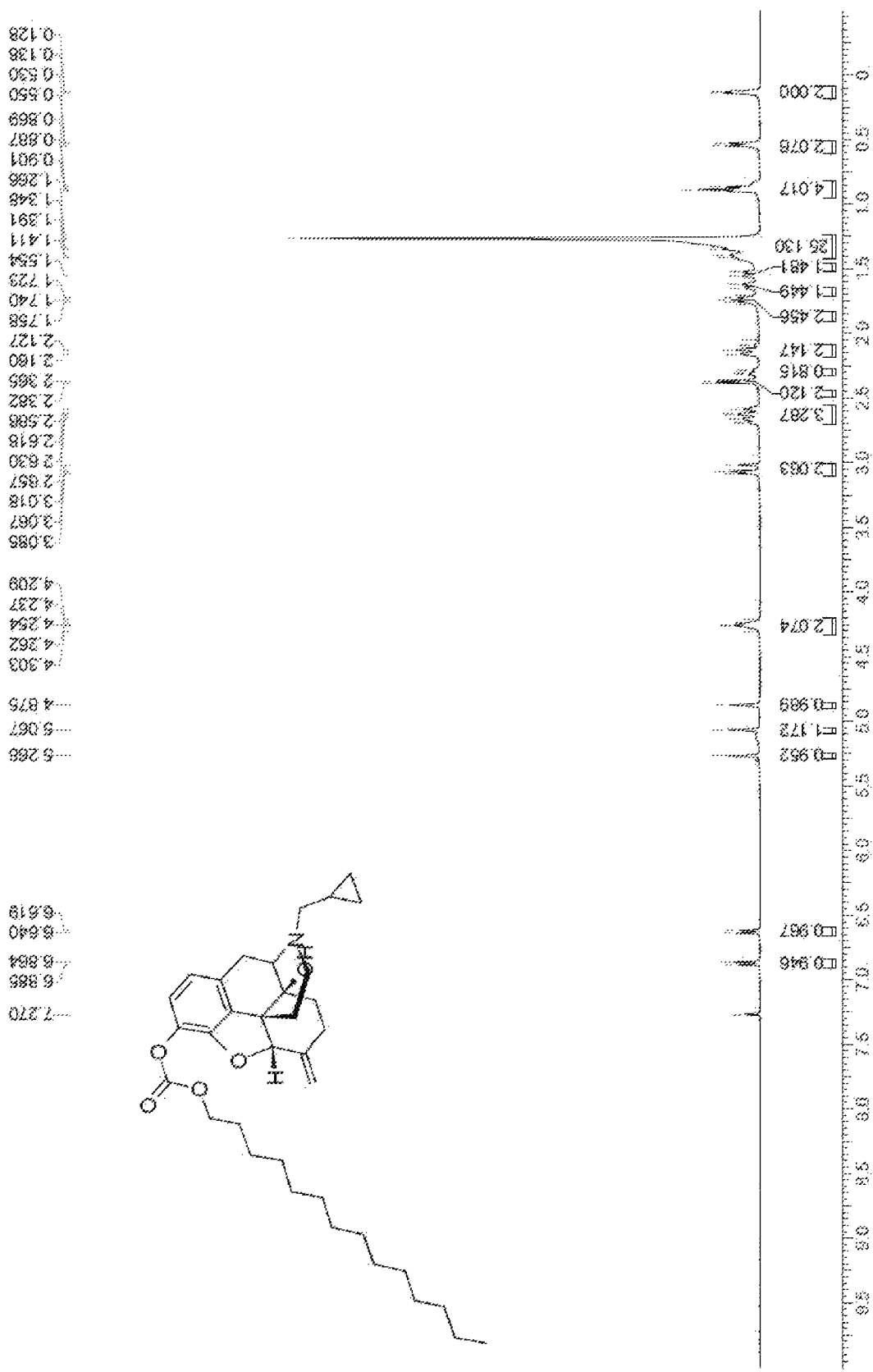
FIG. 31 provides the nuclear magnetic resonance spectrum of Example 31 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tetradecyl carbonate.

Example 31: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tetradecyl carbonate To a solution of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (3 g, 7.98 mmol, 1 eq, HCl) in DCM (20 mL) was added TEA (1.62 g, 15.96 mmol, 2.22 mL, 2 eq) and tetradecyl carbonochloridate (2.21 g, 7.98 mmol, 1 eq). The mixture was stirred at 15° C. for 12 hr. The mixture was concentrated under reduced pressure. The residue was mixed with H$_2$O (80 mL) and extracted with DCM (80 mL*3). The combined organic phase was washed with saturated NaHCO$_3$ solution (60 mL*2) and brine (60 mL*3), dried with anhydrous Na$_2$SO$_4$, filtered and concentrated in vacuum. The residue was purified by column chromatography (SiO$_2$, Petroleum ether/Ethyl acetate=4/1 to 0:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl] tetradecyl carbonate (2 g, 3.41 mmol, 42.79% yield) was obtained as a colorless oil. M+H$^+$=580.4 (LCMS). $^1$H NMR (400 MHz, CDCl$_3$): see FIG. 31.

Example 32: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl pentadecyl carbonate

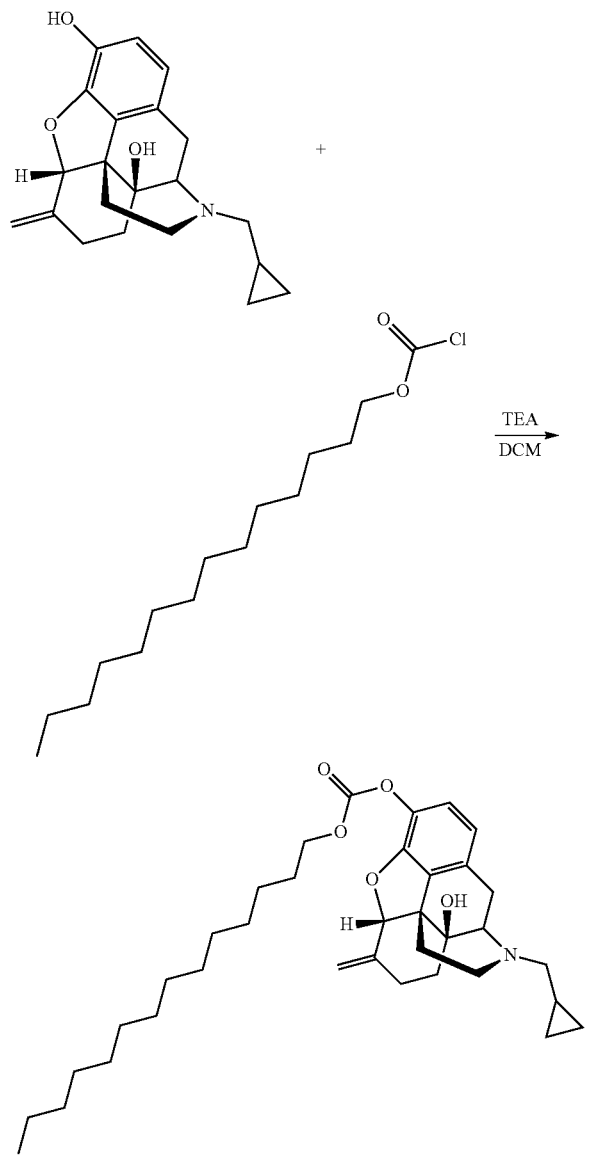

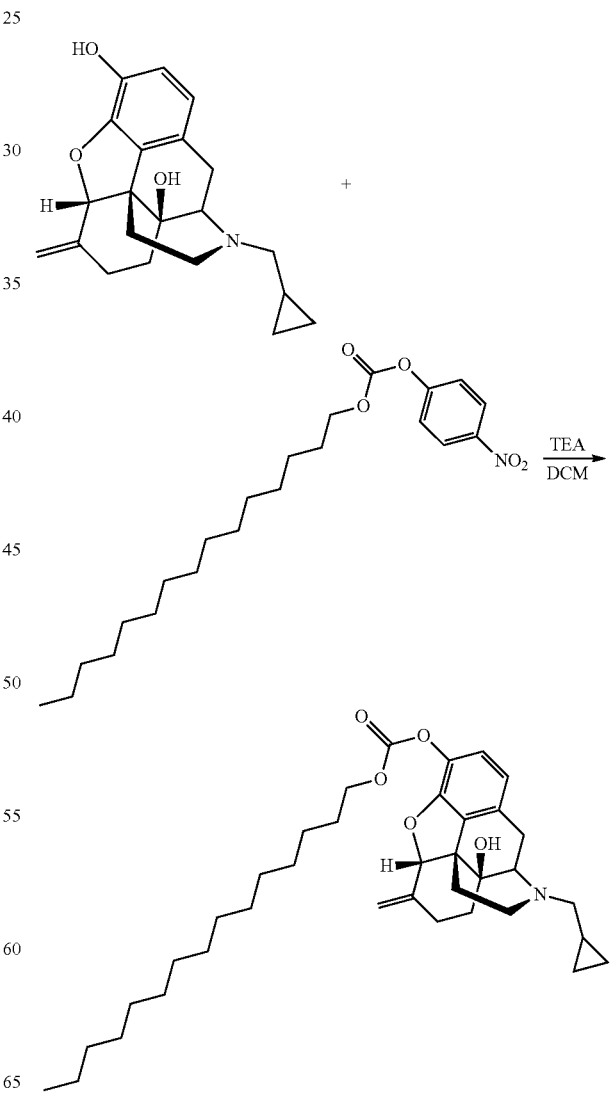

Figure 32:
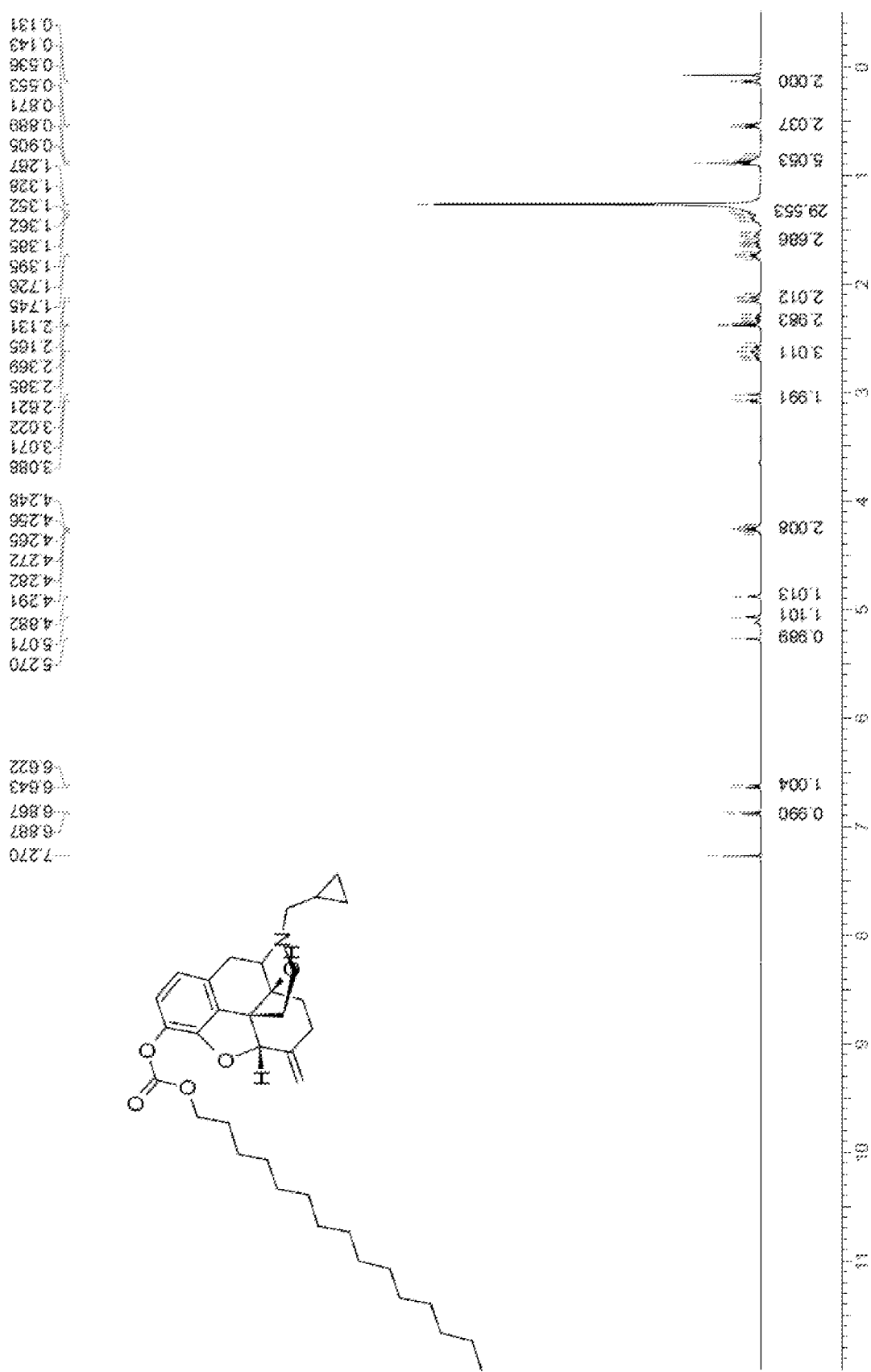
FIG. 32 provides the nuclear magnetic resonance spectrum of Example 32 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl pentadecyl carbonate.

To a mixture of (4-nitrophenyl) pentadecyl carbonate (6.28 g, 15.96 mmol, 2 eq) in DCM (30 mL) was added TEA (2.42 g, 23.94 mmol, 3.33 mL, 3 eq) and [(3R,4aS,7aS,12bS)-3-(cyclopropylmethyl)-7-methylene-2,4,56,7a,13-hexahydro-1H-4,12-methanobenzofuro[3,2-e]isoquinoline-4a,9-diol (3 g, 7.98 mmol, 1 eq, HCl) in one portion at 15° C. under N$_2$. The mixture was stirred at 15° C. for 12 hr. The residue was purified by column chromatography (SiO$_2$, Petroleum ether/Ethyl acetate=1/0 to 2:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl] pentadecyl carbonate (2.6 g, 1.80 mmol, 22.49% yield) was obtained as a white solid. M+H$^+$=594.3 (LCMS). $^1$H NMR (400 MHz, CDCl$_3$): see FIG. 32.

Figure 33:
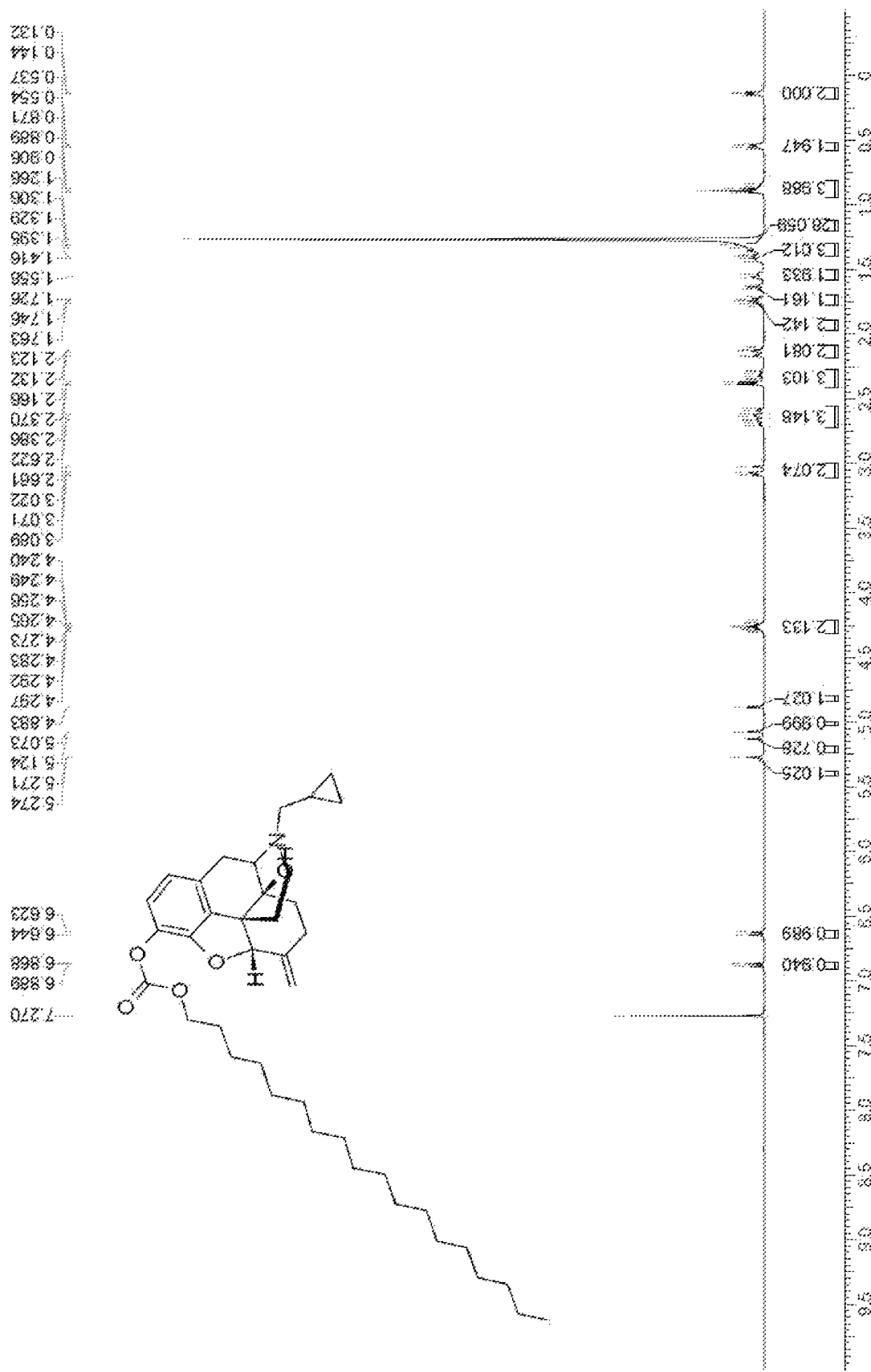
FIG. 33 provides the nuclear magnetic resonance spectrum of Example 33 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octadecyl carbonate.

Example 33: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl octadecyl carbonate To a solution of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (2 g, 5.32 mmol, 1 eq, HCl) in DCM (30 mL) was added TEA (1.62 g, 15.96 mmol, 2.22 mL, 3 eq) and (4-nitrophenyl) octadecyl carbonate (3.48 g, 7.98 mmol, 1.5 eq). The mixture was stirred at 15° C. for 12 hr. The reaction mixture was concentrated under reduced pressure. The residue was purified by column chromatography (SiO$_2$, Petroleum ether/Ethyl acetate=10/1 to 1:1) and then by pre-HPLC. Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]octadecyl carbonate (0.8 g, 1.22 mmol, 22.93% yield) was obtained as a yellow oil. M+H$^+$=636.5 (LCMS). $^1$H NMR (400 MHz, CDCl$_3$): see FIG. 33.

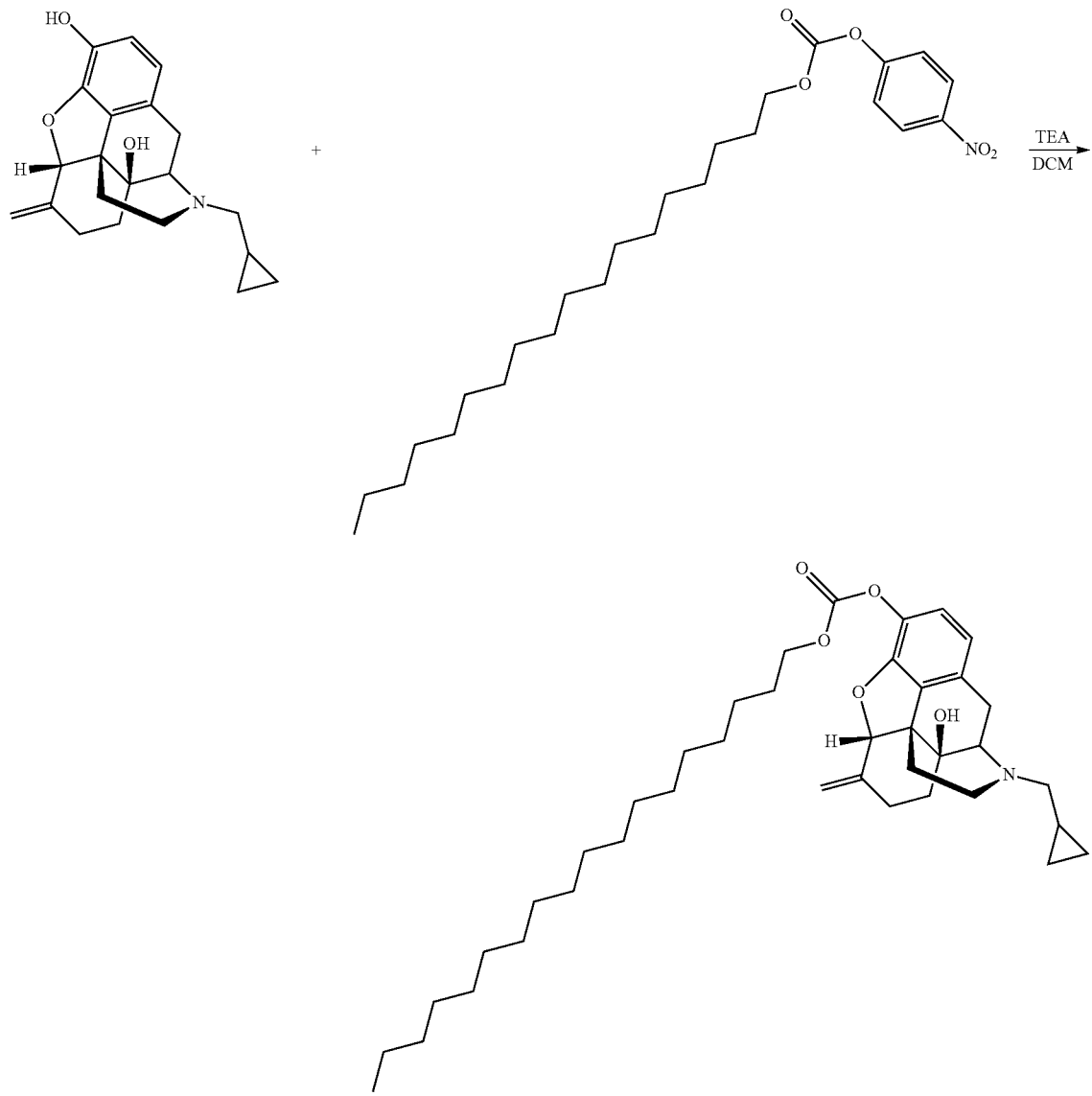

Example 34: Step 34A: Synthesis of Chloromethyl Hexadecyl Carbonate

Step 34B: Synthesis of Iodomethyl Hexadecyl Carbonate

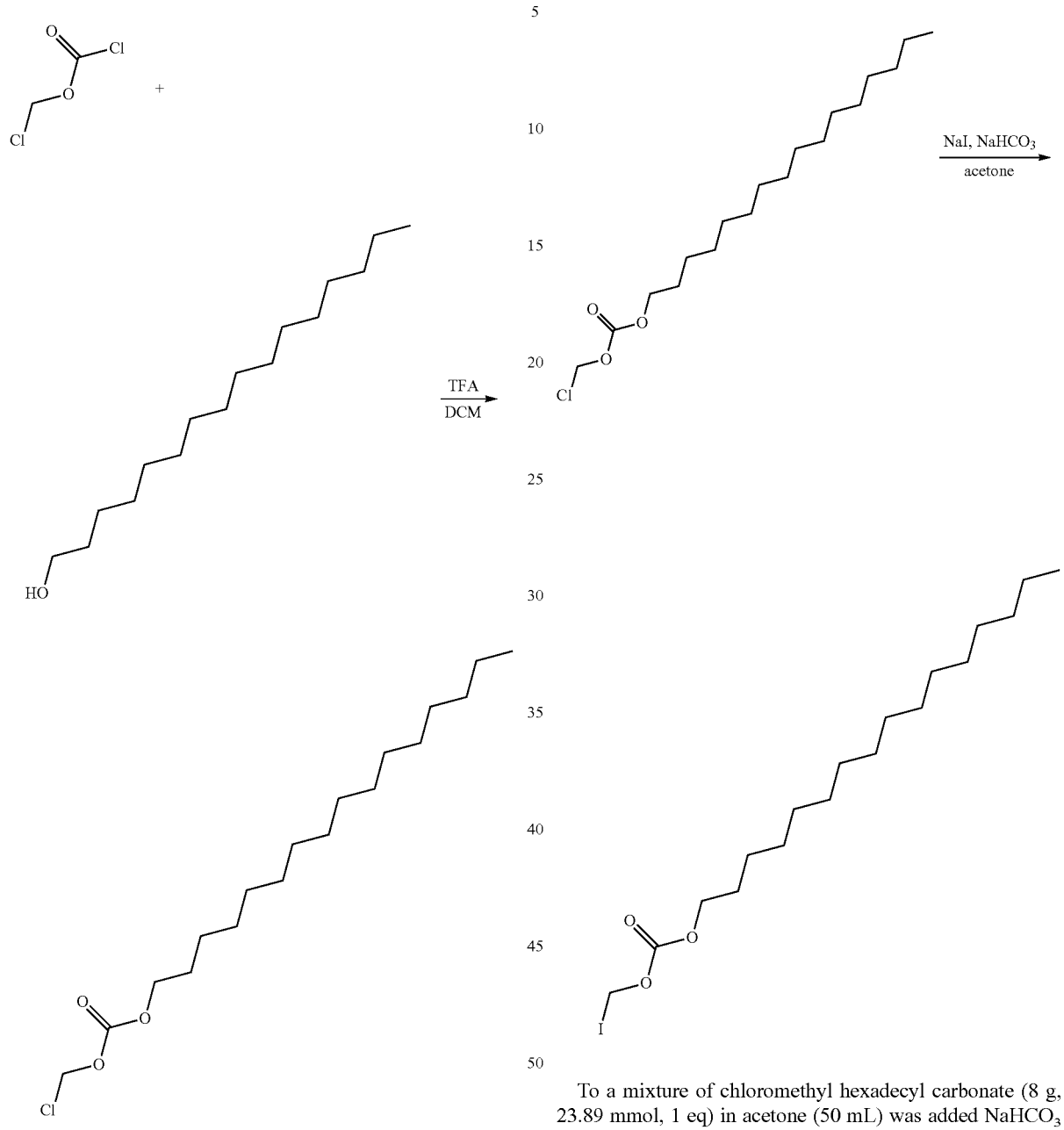

To a mixture of hexadecan-1-ol (30 g, 123.74 mmol, 1 eq) in DCM (200 mL) was added TEA (25.04 g, 247.48 mmol, 34.45 mL, 2 eq) and chloromethyl carbonochloridate (31.91 g, 247.48 mmol, 22.01 mL, 2 eq) in one portion at 0° C. under $N_2$. The mixture was heated to 20° C. and stirred for 12 hours. The reaction mixture was quenched by addition water 50 mL at 20° C., and then extracted with DCM 100 mL (50 mL*2). The combined organic layers were dried over $Na_2SO_4$, filtered and concentrated under reduced pressure to give a residue. The residue was purified by column chromatography ($SiO_2$, Petroleum ether/Ethyl acetate=1/0 to 80:1). Compound chloromethyl hexadecyl carbonate (18 g, 53.74 mmol, 43.43% yield) was obtained as a white solid.

To a mixture of chloromethyl hexadecyl carbonate (8 g, 23.89 mmol, 1 eq) in acetone (50 mL) was added $NaHCO_3$ (2.41 g, 28.66 mmol, 1.11 mL, 1.2 eq) and NaI (4.30 g, 28.66 mmol, 1.2 eq) in one portion at 15° C. under $N_2$. The mixture was stirred at 15° C. for 12 h. The reaction mixture was concentrated under reduced pressure to remove solvent. The residue was diluted with ethyl acetate 20 mL and washed with water 20 mL (10 mL*2). The organic layers were dried, filtered and concentrated under reduced pressure to give a residue. The crude product hexadecyl iodomethyl carbonate (9 g, crude) was obtained as a light red solid and used into the next step without further purification. Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecyl carbonate

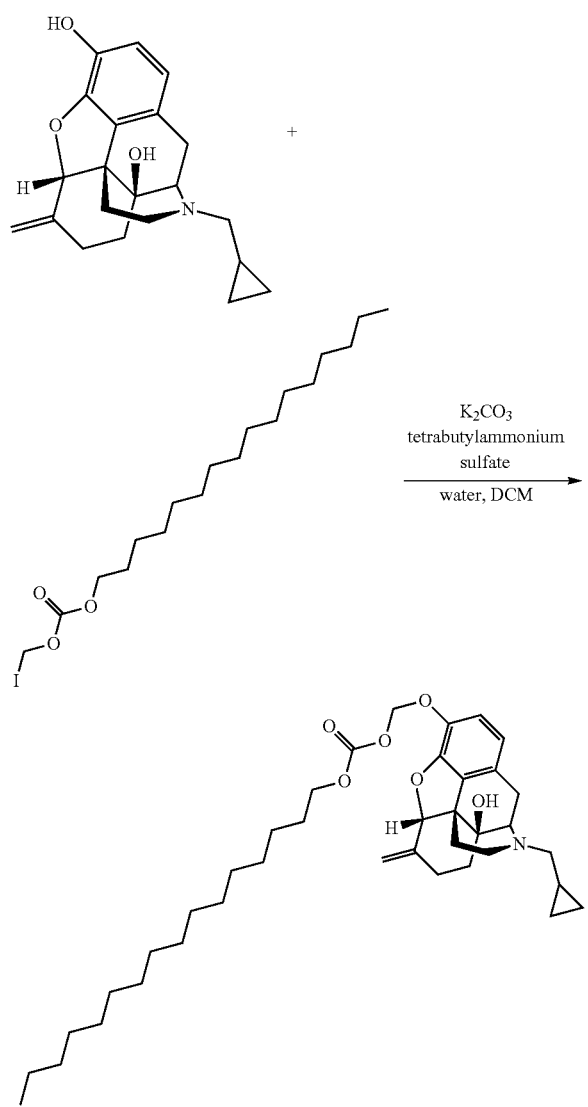

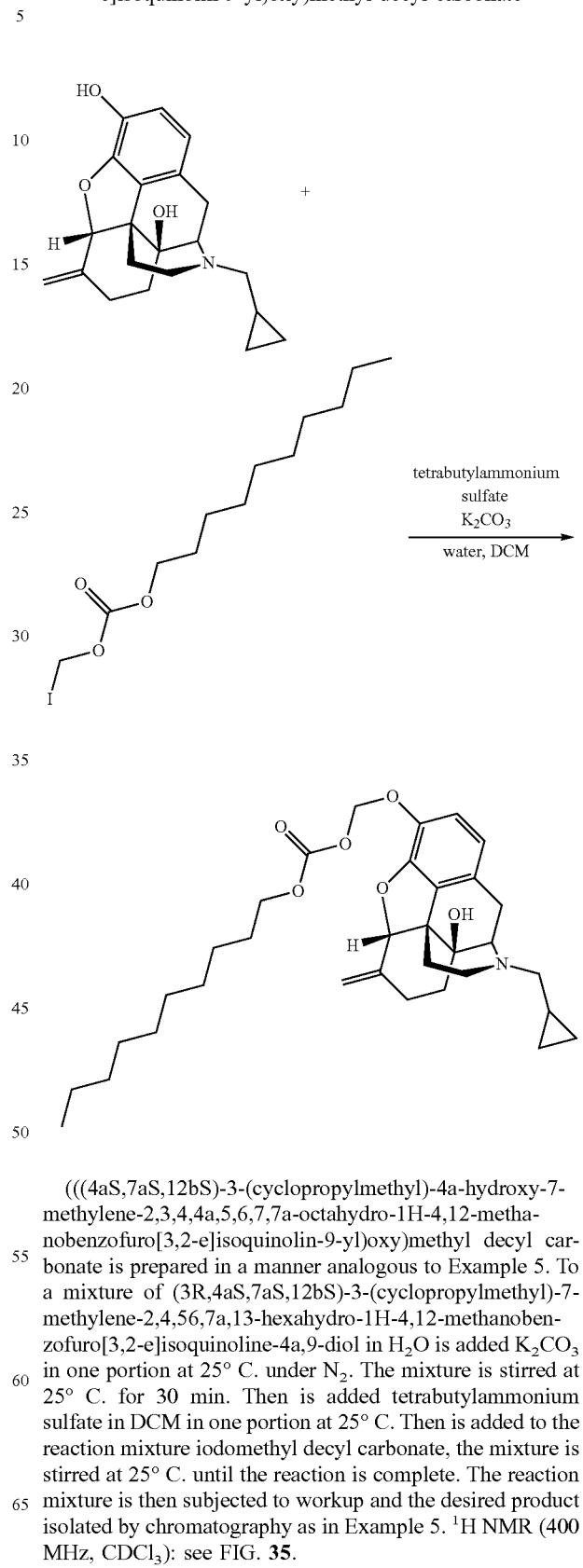

Figure 34:
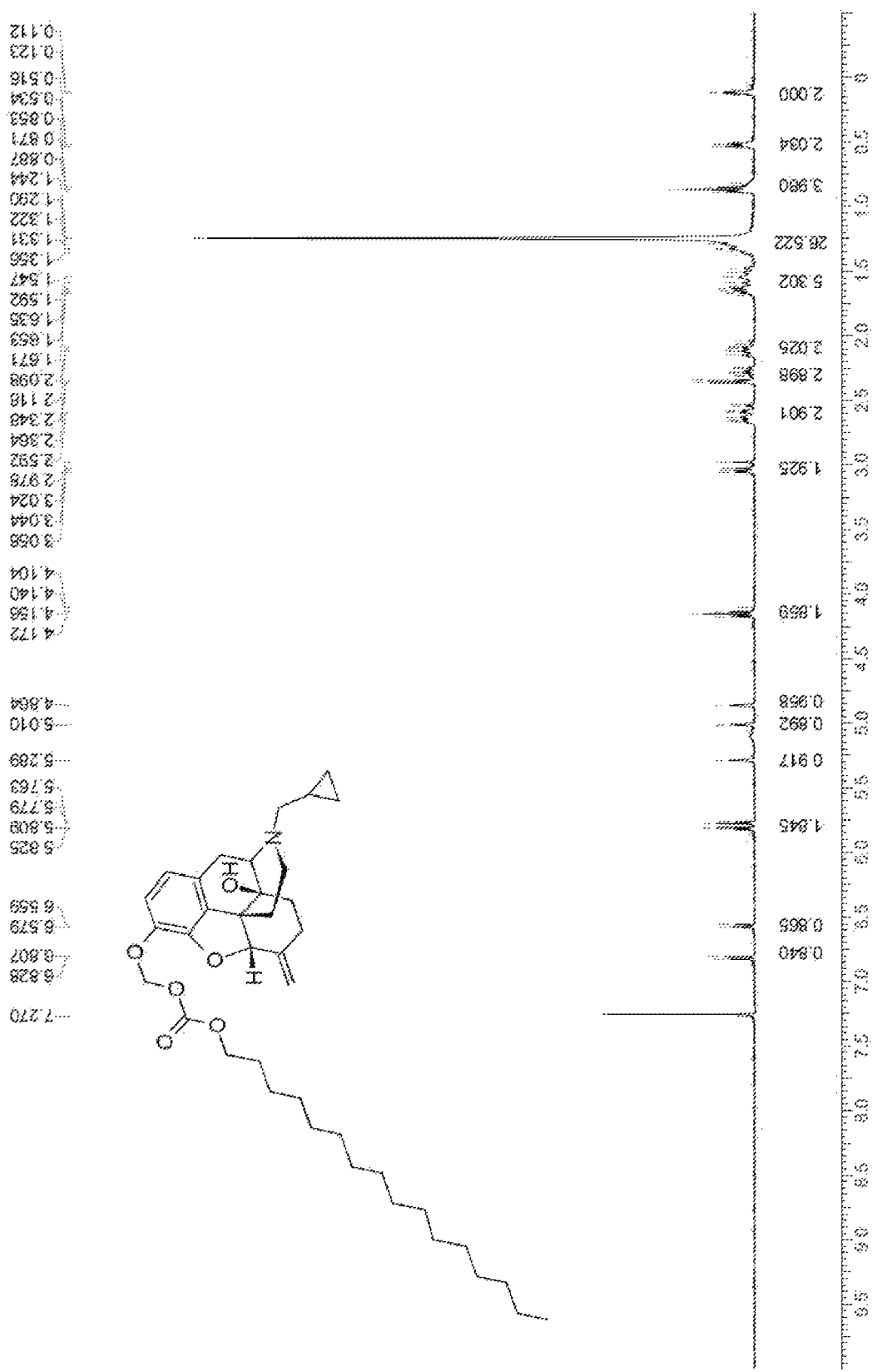
FIG. 34 provides the nuclear magnetic resonance spectrum of Example 34 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecyl carbonate.

Example 35: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl decyl carbonate To a mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (2.75 g, 7.32 mmol, 1 eq, HCl) and hexadecyl iodomethyl carbonate (7.49 g, 17.56 mmol, 2.4 eq) in H₂O (25 mL) was added K₂CO₃ (3.03 g, 21.95 mmol, 3 eq) and stirred for 0.5 h at 15° C. After 30 min, tetrabutylammonium sulfate (4.25 g, 7.32 mmol, 4.21 mL, 1 eq) and DCM (25 mL) were added to the mixture and the mixture was stirred for more 10 min. After 10 min, hexadecyl iodomethyl carbonate (7.49 g, 17.56 mmol, 2.4 eq) was added to the mixture in one portion at 15° C. under N₂. The mixture was stirred at 15° C. for 12 hours. The residue was diluted with water 10 mL and extracted with DCM 20 mL (10 mL*2). The combined organic layers were dried, filtered, and concentrated under reduced pressure to give a residue. The residue was purified by column chromatography (SiO₂, Petroleum ether/Ethyl acetate=1:0 to 10:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl hexadecyl carbonate (2.0 g, 3.10 mmol, 42.38% yield) was obtained as a colorless oil. M+H⁺=638.3 (LCMS). ¹H NMR (400 MHz, CDCl₃): see FIG. 34.

Figure 35:
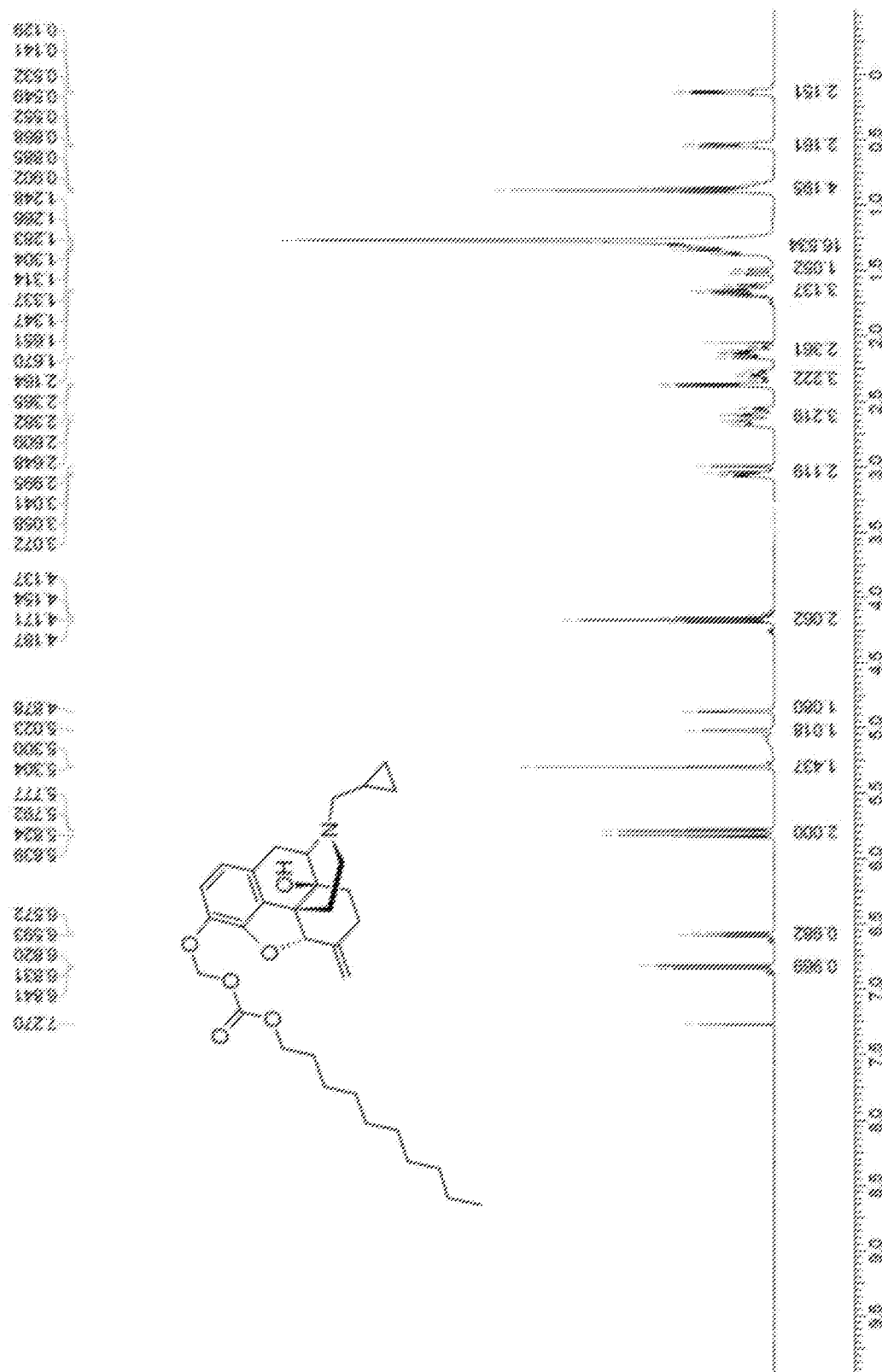
FIG. 35 provides the nuclear magnetic resonance spectrum of Example 35 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl decyl carbonate.

(((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl decyl carbonate is prepared in a manner analogous to Example 5. To a mixture of (3R,4aS,7aS,12bS)-3-(cyclopropylmethyl)-7-methylene-2,4,56,7a,13-hexahydro-1H-4,12-methanobenzofuro[3,2-e]isoquinoline-4a,9-diol in H₂O is added K₂CO₃ in one portion at 25° C. under N₂. The mixture is stirred at 25° C. for 30 min. Then is added tetrabutylammonium sulfate in DCM in one portion at 25° C. Then is added to the reaction mixture iodomethyl decyl carbonate, the mixture is stirred at 25° C. until the reaction is complete. The reaction mixture is then subjected to workup and the desired product isolated by chromatography as in Example 5. ¹H NMR (400 MHz, CDCl₃): see FIG. 35.

Example 36: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl oleate

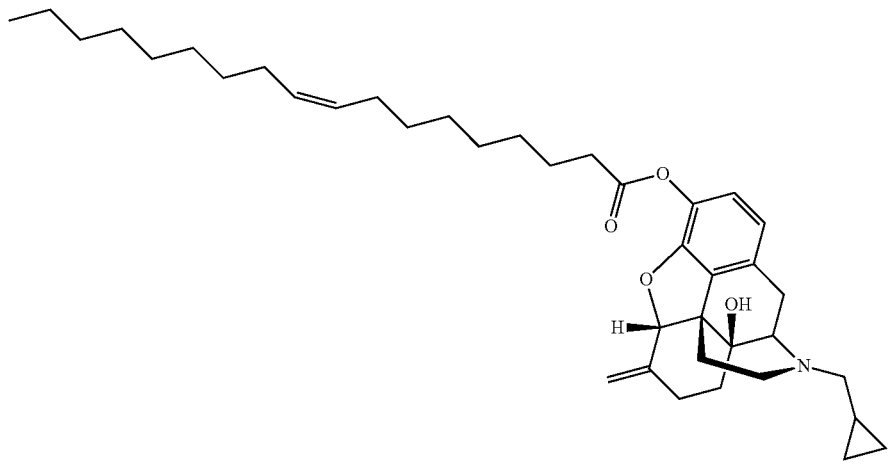

Figure 36:
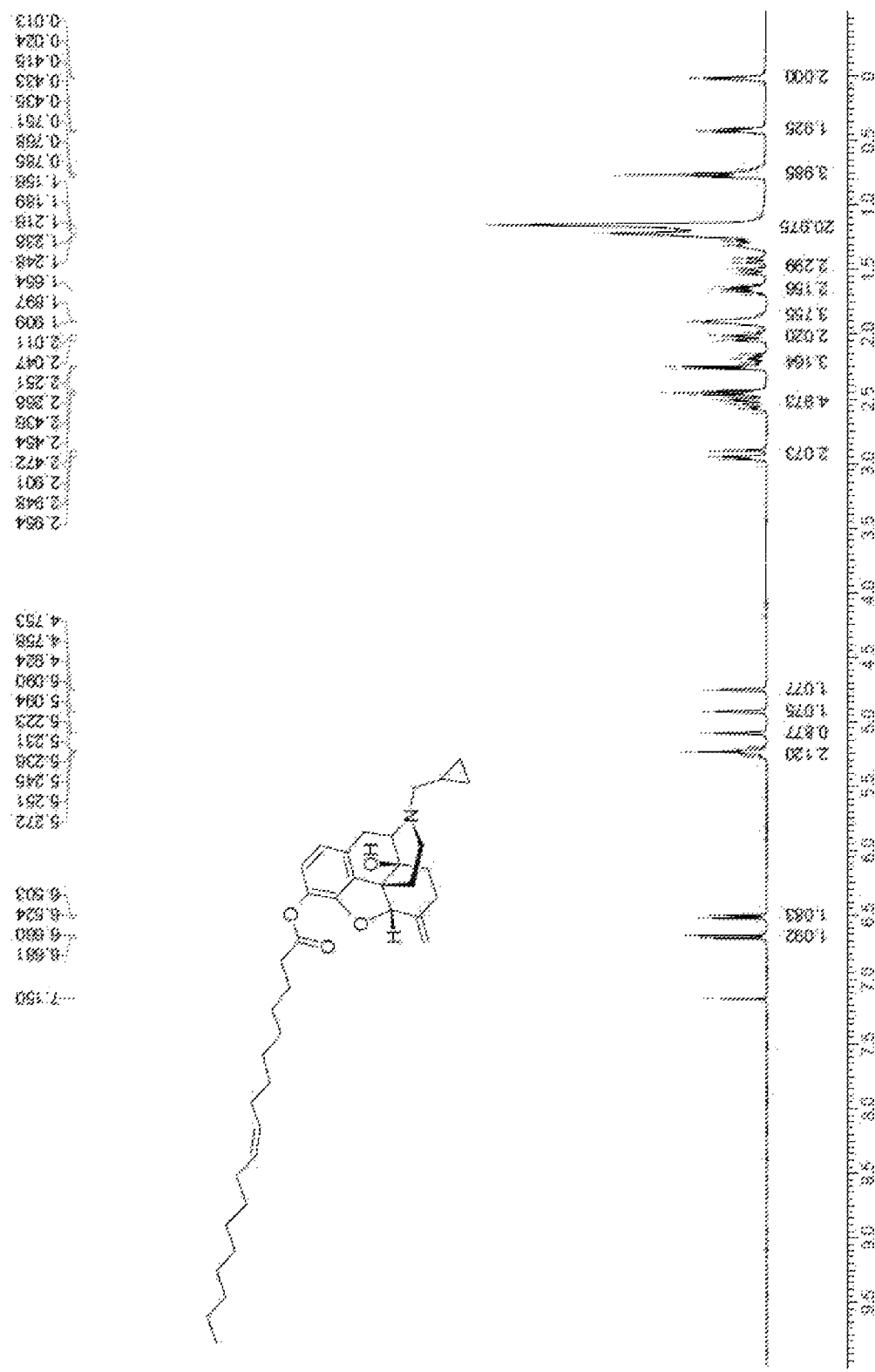
FIG. 36 provides the nuclear magnetic resonance spectrum of Example 36 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl oleate.

The title compound was synthesized according to the general Scheme 1 for the synthesis of nalmefene prodrugs. 1.5 g; $^1$H NMR (400 MHz, CDCl$_3$): see FIG. 36.

Example 37: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z)-octadeca-9,12-dienoate

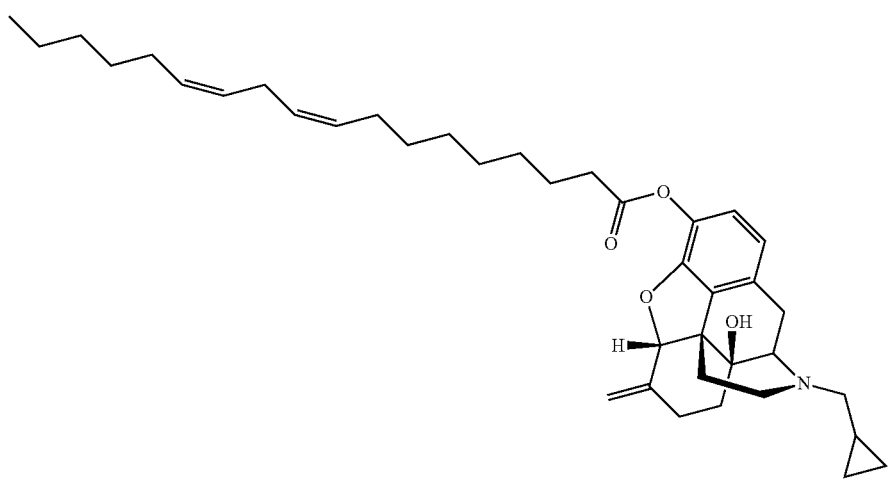

Figure 37:
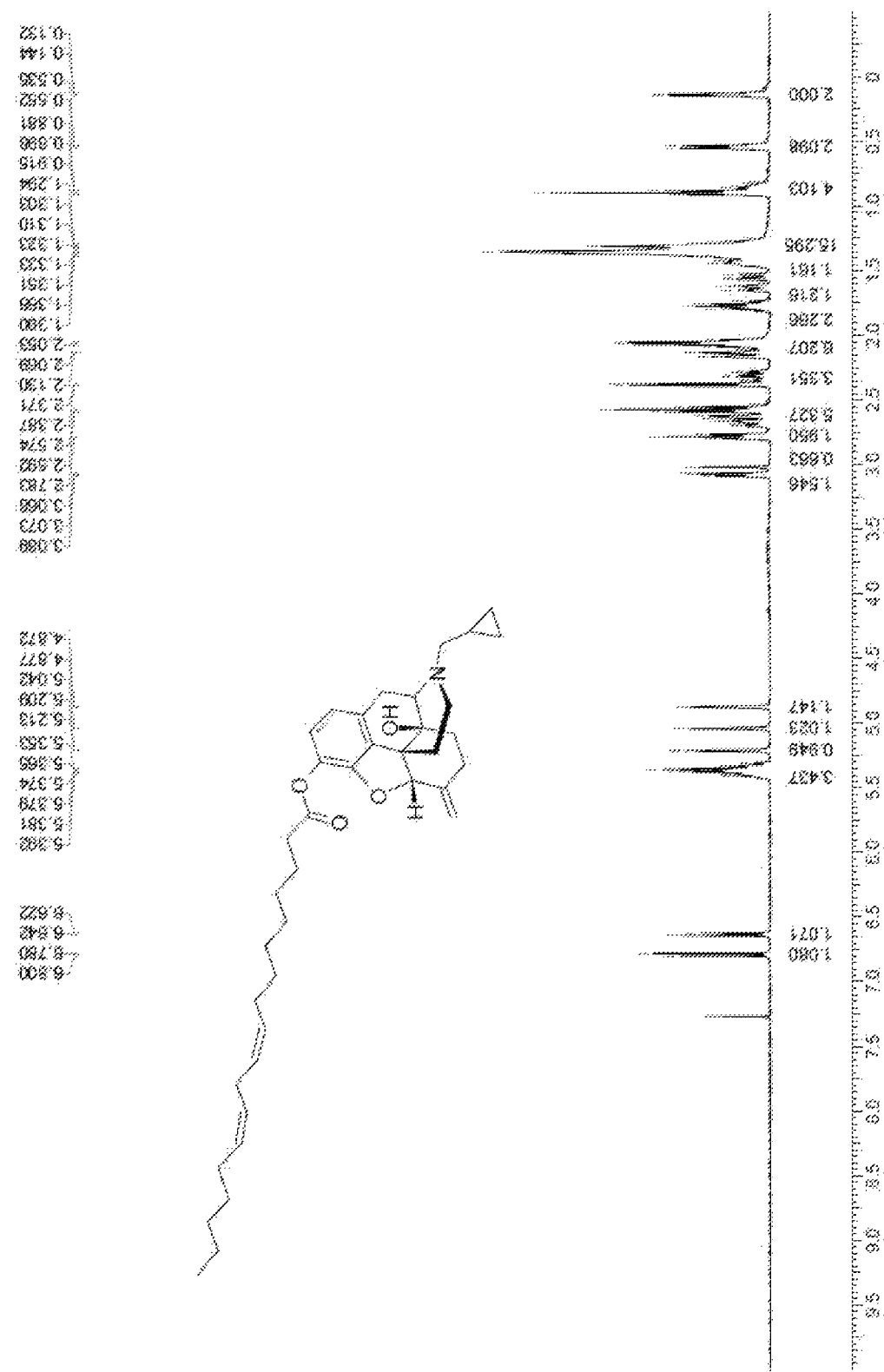
FIG. 37 provides the nuclear magnetic resonance spectrum of Example 37 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl (9Z,12Z)-octadeca-9,12-dienoate.

The title compound was synthesized according to the general Scheme 1 for the synthesis of nalmefene prodrugs. 1.3 g; $^1$H NMR (400 MHz, CDCl$_3$): see FIG. 37.

Example 38: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl 3,3-dimethylbutanoate

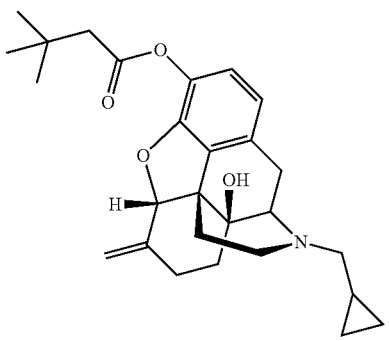

Figure 38:
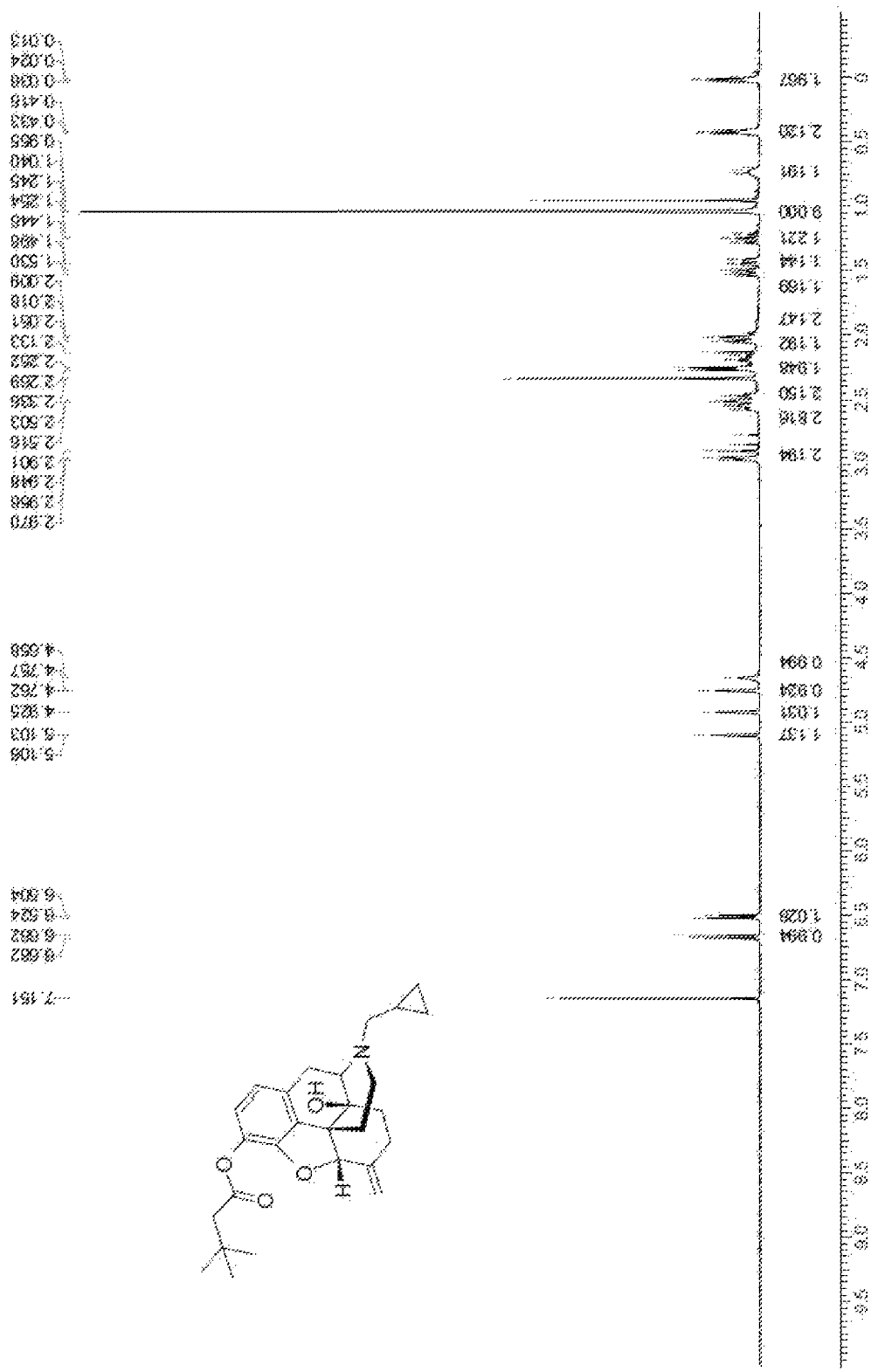
FIG. 38 provides the nuclear magnetic resonance spectrum of Example 38 (4aS,7aS,12bS)-3-(cyclopropylmethyl)-4a-hydroxy-7-methylene-2,3,4,4a,5,6,7,7a-octa-hydro-1H-4,12-methanobenzofuro[3,2-e]isoquinolin-9-yl 3,3-dimethylbutanoate.

The title compound was synthesized according to the general Scheme 1 for the synthesis of nalmefene prodrugs. 1.2 g; ¹H NMR (400 MHz, CDCl₃): see FIG. 38.

Example 39: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl 3-cyclopentylpropanoate

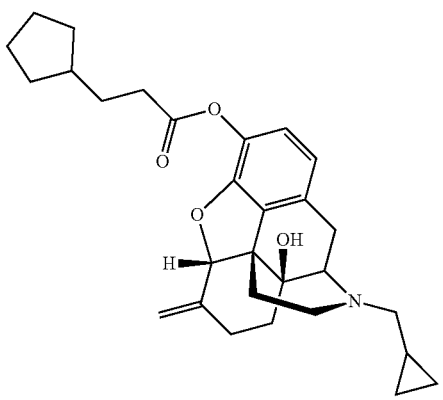

Figure 39:
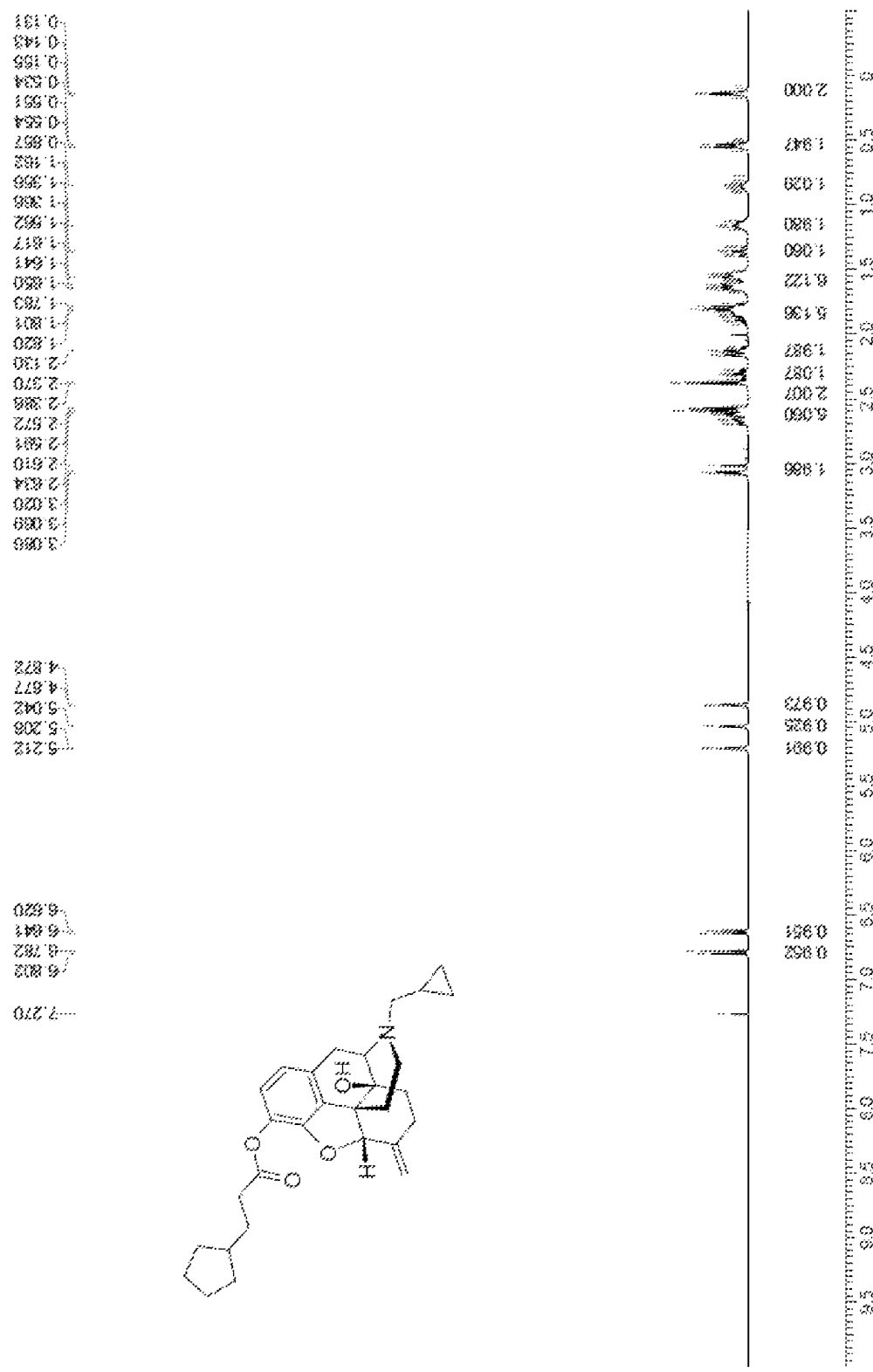
FIG. 39 provides the nuclear magnetic resonance spectrum of Example 39 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl 3-cyclopentylpropanoate.

The title compound was synthesized according to the general Scheme 1 for the synthesis of nalmefene prodrugs. 1.18 g; ¹H NMR (400 MHz, CDCl₃): see FIG. 39.

Example 40: Synthesis of (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tert-butylcarbamate

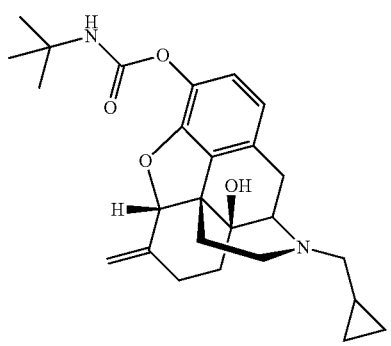

Figure 40:
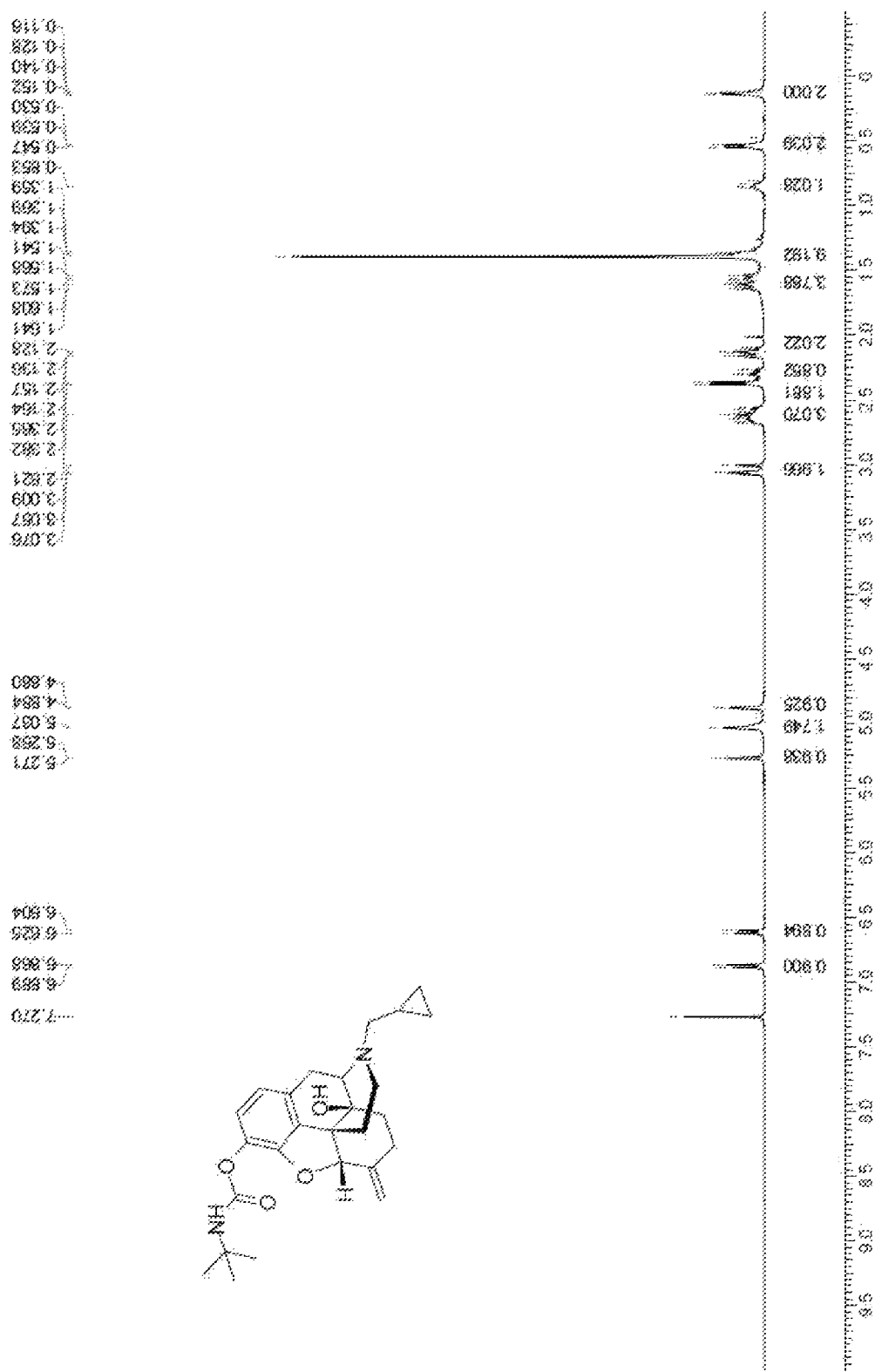
FIG. 40 provides the nuclear magnetic resonance spectrum of Example 40 (4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl tert-butylcarbamate.

The title compound was synthesized according to the general Scheme 1 for the synthesis of nalmefene prodrugs and was obtained as a solid. 3.0 g; ¹H NMR (400 MHz, CDCl₃): see FIG. 40.

Example 41: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl oleate

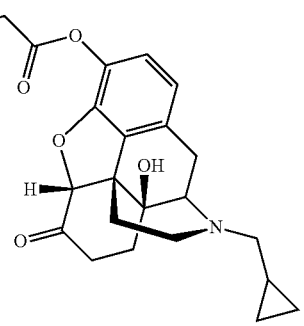

Figure 41:
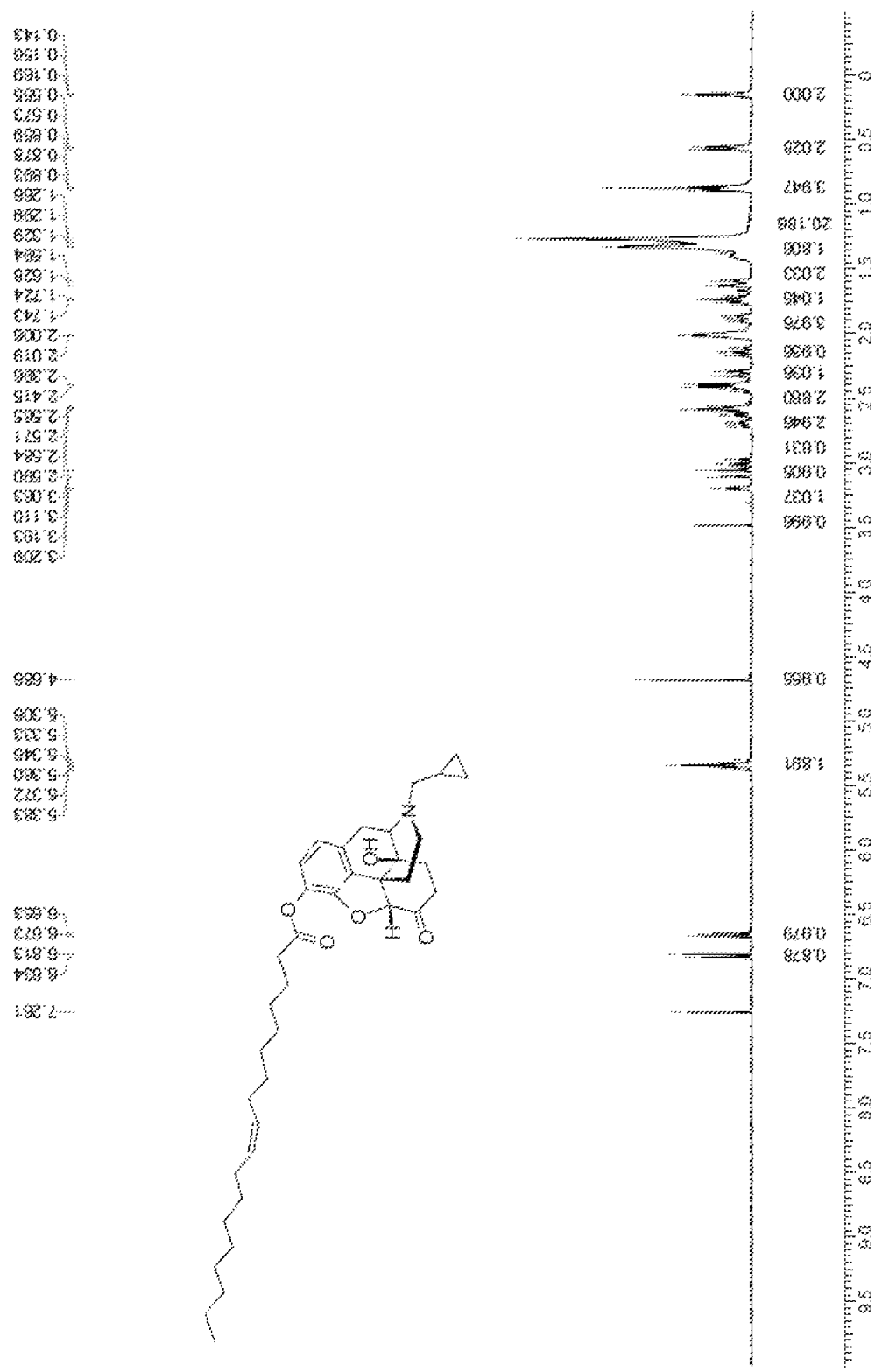
FIG. 41 provides the nuclear magnetic resonance spectrum of Example 41 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl oleate.

The title compound was synthesized according to the general Scheme 2 for the synthesis of naltrexone prodrugs. 1.5 g; ¹H NMR (400 MHz, CDCl₃): see FIG. 41.

Example 42: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3,3-dimethylbutanoate

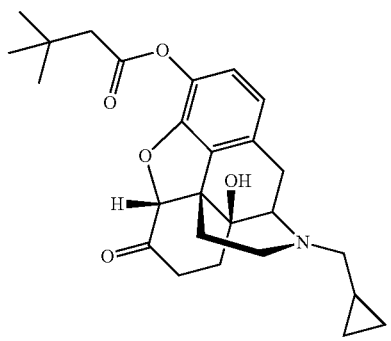

Figure 42:
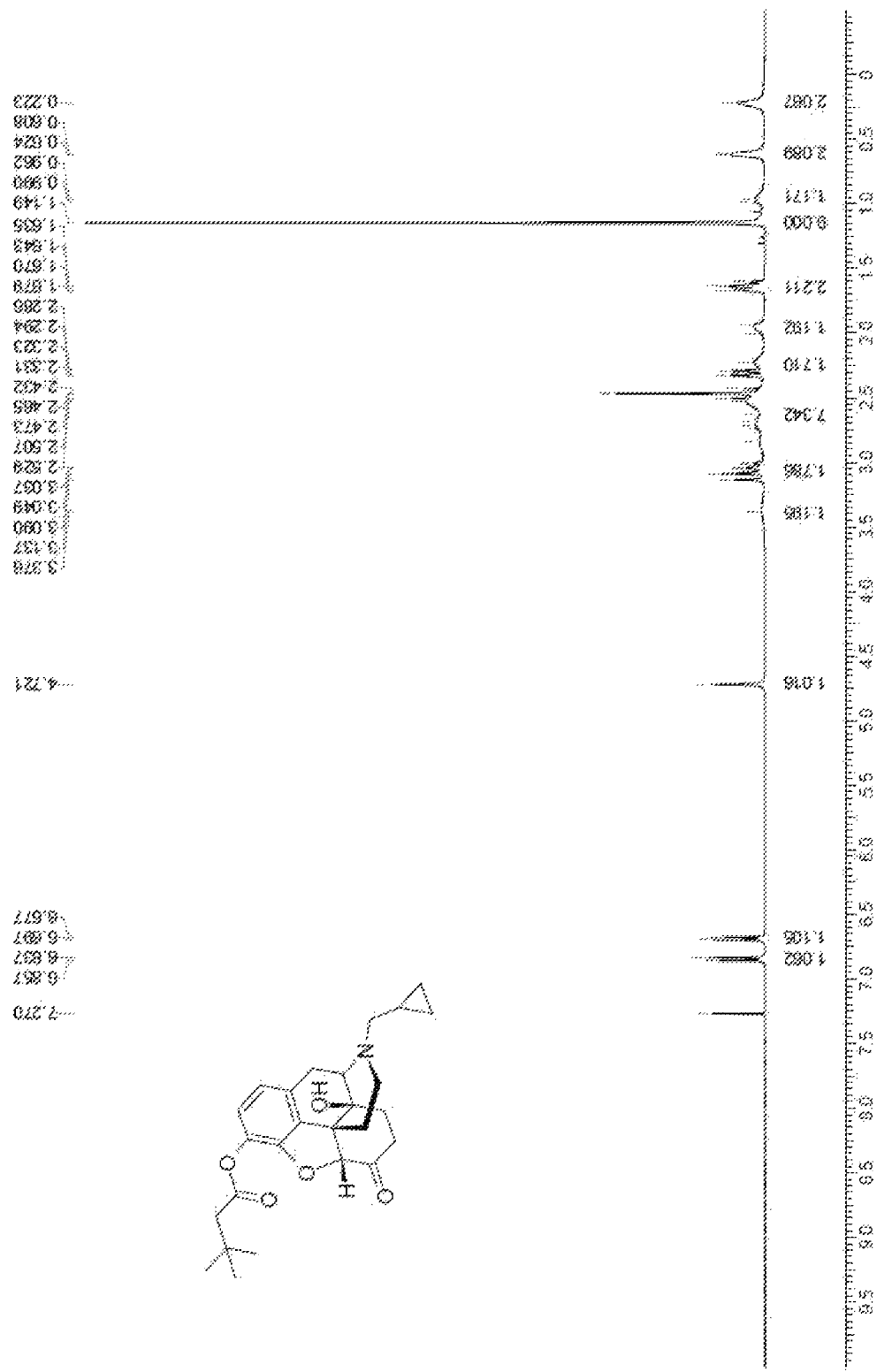
FIG. 42 provides the nuclear magnetic resonance spectrum of Example 42 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3,3-dimethylbutanoate.

The title compound was synthesized according to the general Scheme 2 for the synthesis of naltrexome prodrugs. 1.3 g; ¹H NMR (400 MHz, CDCl₃): see FIG. 42.

Example 43: Synthesis of (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3-cyclopentylpropanoate

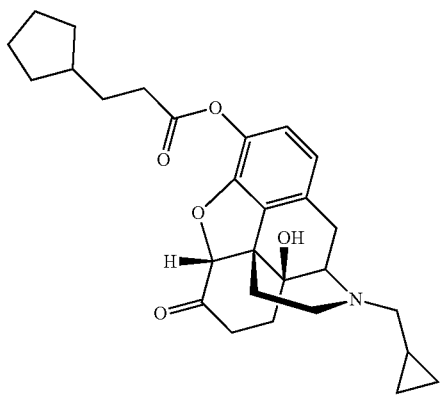

Figure 43:
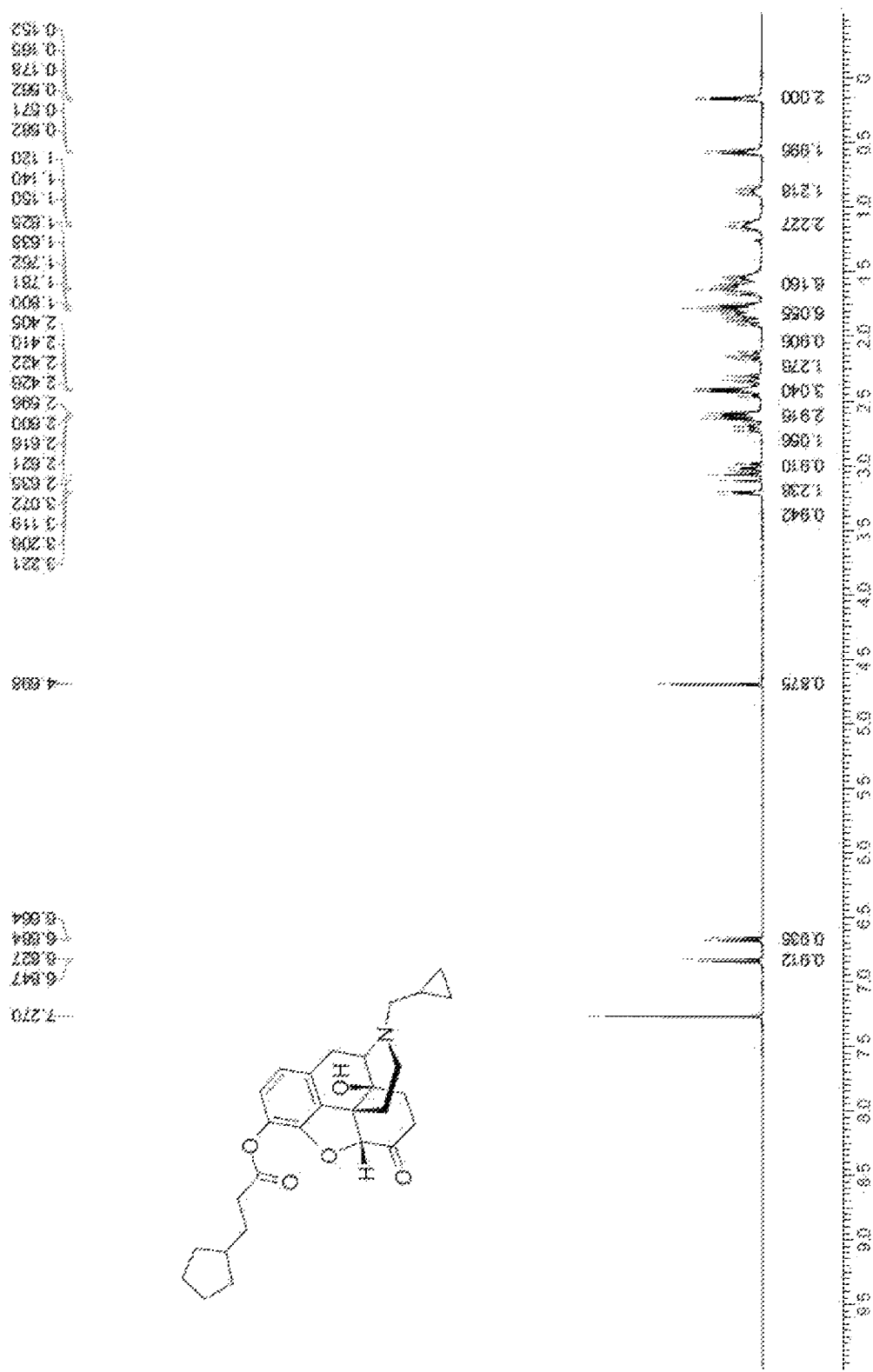
FIG. 43 provides the nuclear magnetic resonance spectrum of Example 43 (4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl 3-cyclopentylpropanoate.

The title compound was synthesized according to the general Scheme 2 for the synthesis of naltrexone prodrugs. 1.3 g; ¹H NMR (400 MHz, CDCl₃): see FIG. 43.

Example 44: Step 44A: Synthesis of Chloromethyl Dodecanoate

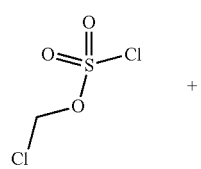

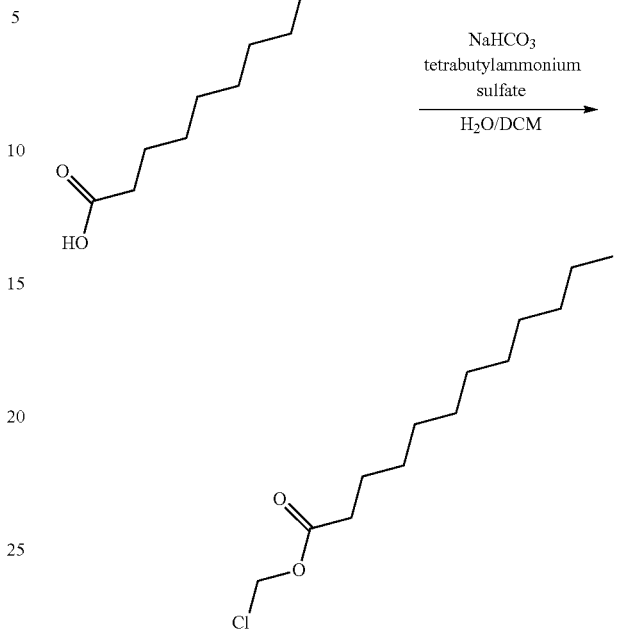

To a mixture of dodecanoic acid (20 g, 99.84 mmol, 1 eq) in DCM (60 mL) and H₂O (80 mL) was added NaHCO₃ (33.55 g, 399.37 mmol, 15.53 mL, 4 eq) and tetrabutylammonium sulfate (11.60 g, 9.98 mmol, 11.49 mL, 50% purity, 0.1 eq) in one portion at 25° C. under N2, then the mixture was cooled to 0° C. The reactant of chloro(chlorosulfonyloxy)methane (16.47 g, 99.84 mmol, 1 eq) in DCM (20 mL) were added to the mixture in one portion at 0° C. The mixture was heated to 25° C. and stirred for 18 hours. The reaction mixture was extracted with DCM 50 mL (25 mL*2). The combined organic layers were dried over Na₂SO₄, filtered and concentrated under reduced pressure to give a residue. The residue was purified by column chromatography (SiO₂, Petroleum ether/Ethyl acetate=1/0 to 80:1). Compound chloromethyl dodecanoate (10.8 g, 43.41 mmol, 43.48% yield) was obtained as a colorless oil.

Step 44B: Synthesis of Iodomethyl Dodecanoate

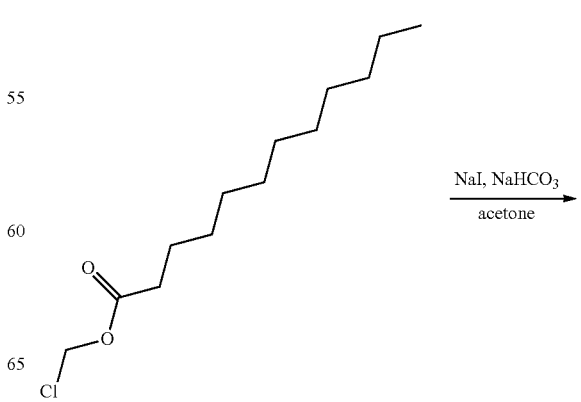

117
-continued

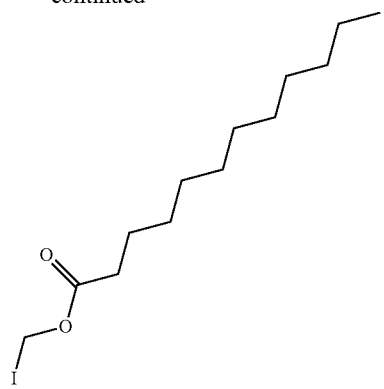

118
-continued

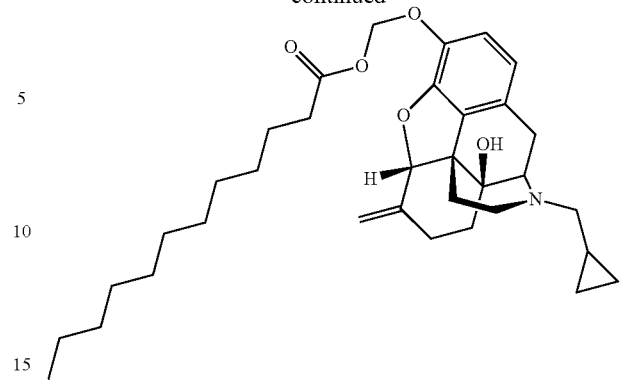

A mixture of chloromethyl dodecanoate (9 g, 36.18 mmol, 1 eq) in acetone (80 mL) was degassed and purged with N₂ for 3 times, and then NaHCO₃ (3.04 g, 36.18 mmol, 1.41 mL, 1 eq) and NaI (5.42 g, 36.18 mmol, 1 eq) was added to the mixture in dark, and the result mixture was stirred at 15° C. for 12 h under N₂ atmosphere in dark. The reaction mixture was filtered and concentrated under reduced pressure to remove solvent. The residue was diluted with H₂O O 50 mL and extracted with EtOAc 120 mL. The combined organic layers were washed with H₂O 100 mL (50 mL*2), dried, filtered and concentrated under reduced pressure to give a residue. Compound iodomethyl dodecanoate (9 g, crude) was obtained as a yellow liquid and used into the next step without further purification.

Figure 44:
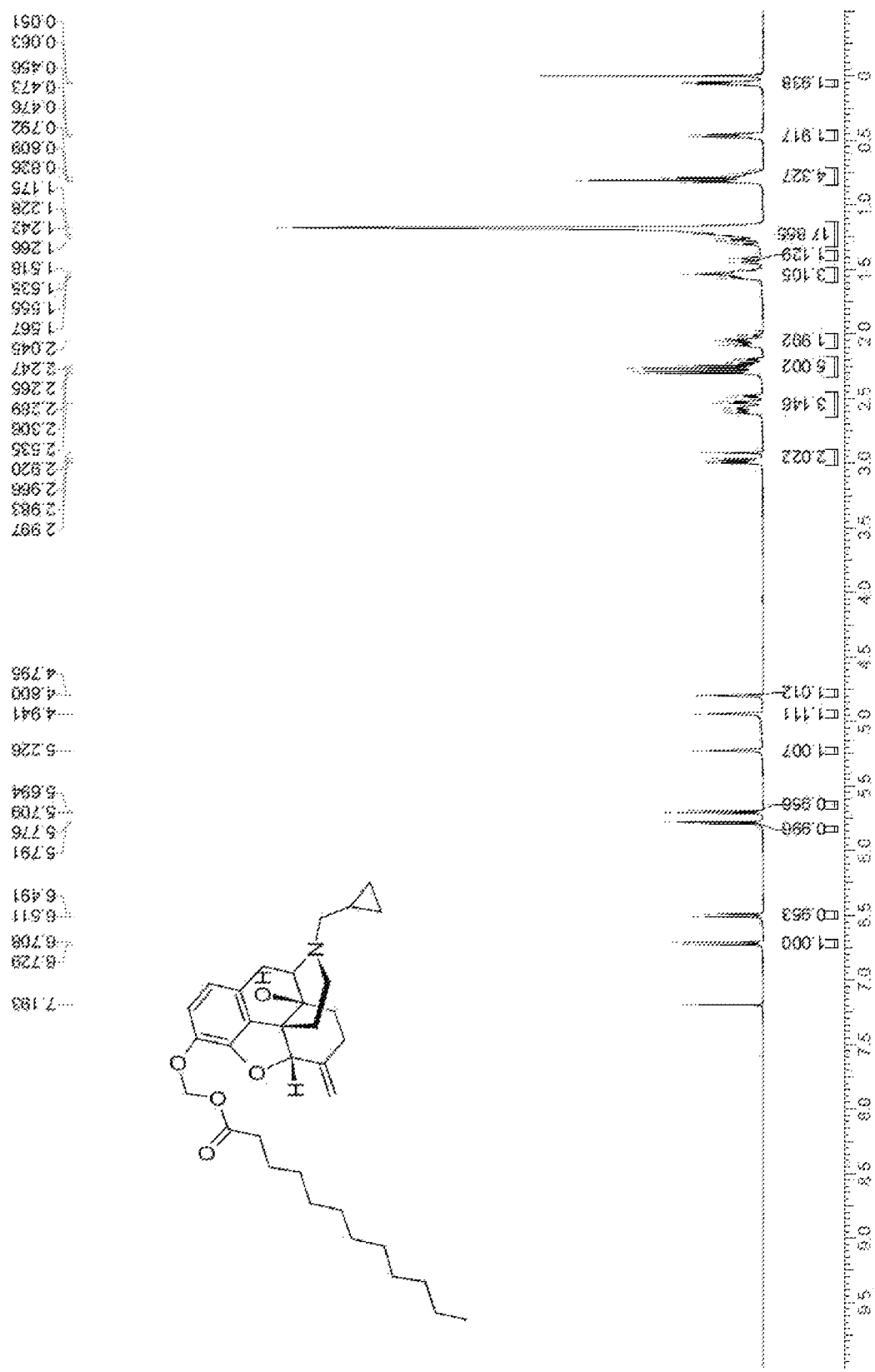
FIG. 44 provides the nuclear magnetic resonance spectrum of Example 44 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl dodecanoate.

Step 44C: Synthesis of ((((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl dodecanoate A mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (3.5 g, 10.31 mmol, 1 eq), K₂CO₃ (4.28 g, 30.93 mmol, 3 eq) in H₂O (40 mL) was stirred at 15° C. for 30 min and then tetrabutylammonium sulfate (5.99 g, 10.31 mmol, 5.93 mL, 1 eq) and DCM (20 mL) was added to the mixture and a solution of iodomethyl dodecanoate (8.42 g, 24.75 mmol, 2.4 eq) in DCM (20 mL) was added to the mixture and degassed and purged with N₂ for 3 times, and then the mixture was stirred at 15° C. for 11.5 h under N₂ atmosphere. The reaction mixture was diluted with H₂O 20 mL and extracted with DCM 20 mL. The combined organic layers were dried, filtered and concentrated under reduced pressure to give a residue. The residue was purified by column chromatography (SiO₂, Petroleum ether/Ethyl acetate=1:0 to 20:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl dodecanoate (1.51 g, 2.70 mmol, 26.14% yield) was obtained as a colorless oil. M+H⁺=552.5 (LCMS). ¹H NMR (400 MHz, CDCl₃): see FIG. 44.

Example 45: Step 45A Synthesis of Chloromethyl Tetradecanoate

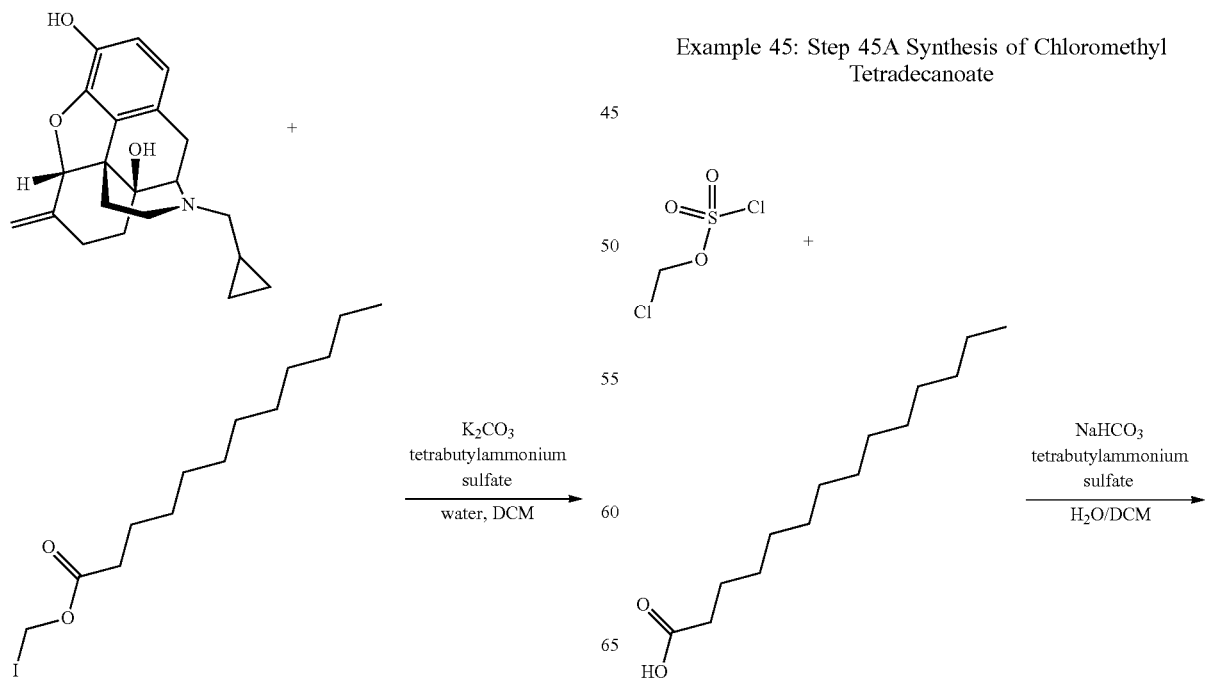

-continued

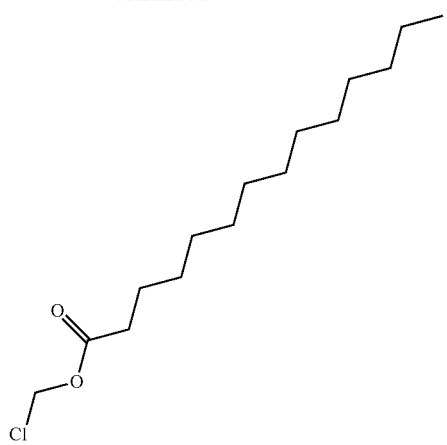

To a mixture of tetradecanoic acid (20 g, 87.58 mmol, 1 eq) in H₂O (80 mL) was added NaHCO₃ (29.43 g, 350.31 mmol, 13.62 mL, 4 eq) and tetrabutylammonium sulfate (10.18 g, 8.76 mmol, 10.08 mL, 50% solution, 0.1 eq) and DCM (60 mL) under N₂. The mixture was cooled to 0° C. The reactant chloro(chlorosulfonyloxy)methane (14.45 g, 87.58 mmol, 1 eq) in DCM (20 mL) was added to the mixture in one portion at 0° C. under N₂. The mixture was heated to 25° C. and stirred for 18 hours. The reaction mixture was extracted with DCM 50 mL (25 mL*2). The combined organic layers were dried over Na₂SO₄, filtered and concentrated under reduced pressure to give a residue. The residue was purified by column chromatography (SiO₂, Petroleum ether/Ethyl acetate=1/0 to 80:1). Compound chloromethyl tetradecanoate (15.5 g, 55.99 mmol, 63.93% yield) was obtained as a colorless oil.

Step 45B: Synthesis of Iodomethyl Tetradecanoate

-continued

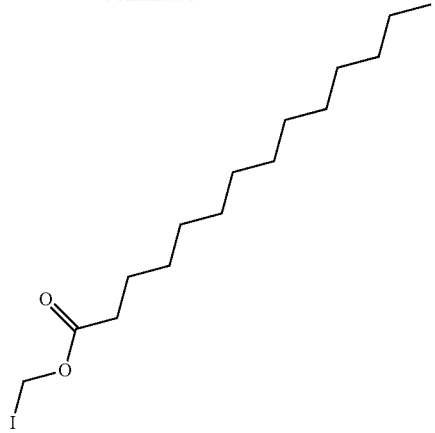

A mixture of chloromethyl tetradecanoate (8 g, 28.90 mmol, 1 eq) in acetone (70 mL) was degassed and purged with N₂ for 3 times, and then NaHCO₃ (2.43 g, 28.90 mmol, 1.12 mL, 1 eq) and NaI (4.33 g, 28.90 mmol, 1 eq) was added to the mixture in dark, the result mixture was stirred at 15° C. for 12 hr under N₂ atmosphere in dark. The reaction mixture was filtered and concentrated under reduced pressure to remove solvent. The residue was diluted with H₂O 50 mL and extracted with EtOAc 120 mL. The combined organic layers were washed with H₂O 100 mL (50 mL*2), dried over Na₂SO₄, filtered and concentrated under reduced pressure to give a residue. The crude product was used into the next step without further purification. Compound iodomethyl tetradecanoate (9 g, crude) was obtained as a yellow solid.

Step 45C: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecanoate

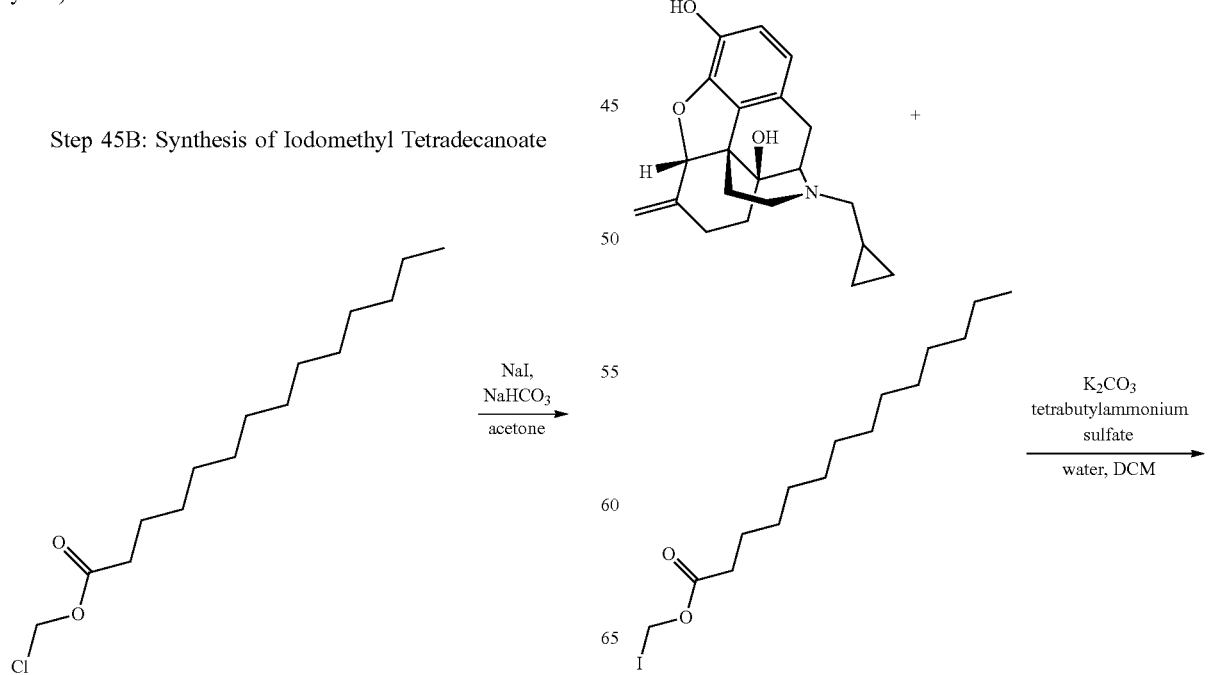

121

-continued

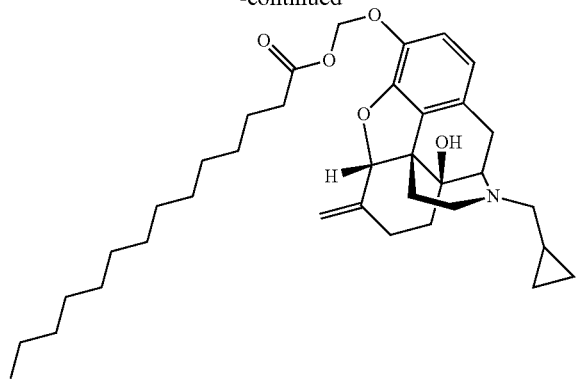

Figure 45:
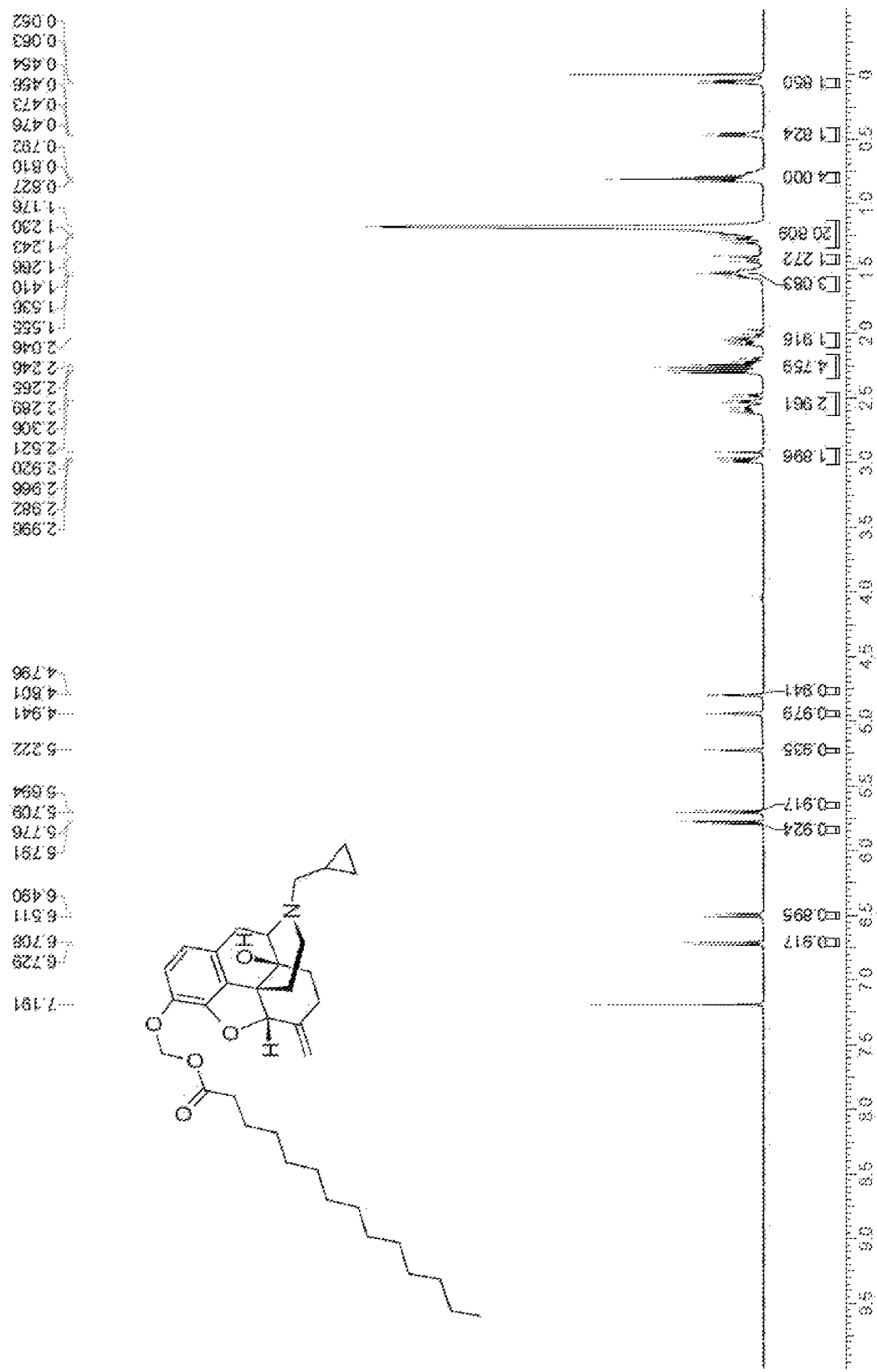
FIG. 45 provides the nuclear magnetic resonance spectrum of Example 45 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecanoate.

A mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (3.5 g, 9.31 mmol, 1 eq, HCl), $K_2CO_3$ (3.86 g, 27.93 mmol, 3 eq) in $H_2O$ (30 mL) was stirred at 15° C. for 30 min, and then tetrabutylammonium sulfate (5.41 g, 9.31 mmol, 5.36 mL, 1 eq) and DCM (15 mL) was added to the mixture and a solution of iodomethyl tetradecanoate (8.23 g, 22.35 mmol, 2.4 eq) in DCM (15 mL) was added to the mixture and degassed and purged with $N_2$ for 3 times, and then the mixture was stirred at 15° C. for 11.5 h under $N_2$ atmosphere. The reaction mixture was diluted with $H_2O$ 20 mL and extracted with DCM 20 mL. The combined organic layers were dried, filtered and concentrated under reduced pressure to give a residue. The residue was purified by column chromatography ($SiO_2$, Petroleum ether/Ethyl acetate=1:0 to 20:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl tetradecanoate (1.5 g, 2.54 mmol, 27.26% yield) was obtained as a colorless oil. M+H$^+$=580.5 (LCMS). $^1$H NMR (400 MHz, $CDCl_3$): see FIG. 45.

Example 46: Step 46A: Synthesis of Chloromethyl Hexadecanoate

122

-continued

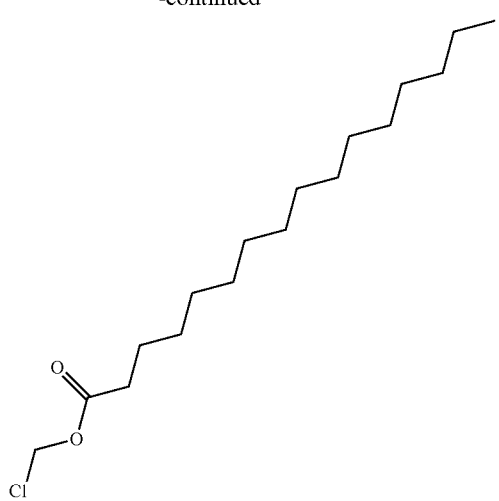

To a mixture of palmitic acid (20 g, 78.00 mmol, 23.47 mL, 1 eq) in DCM (60 mL) and $H_2O$ (80 mL) was added $NaHCO_3$ (26.21 g, 311.98 mmol, 12.13 mL, 4 eq) and tetrabutylammonium sulfate (9.06 g, 7.80 mmol, 8.97 mL, 50% purity, 0.1 eq) in one portion at 25° C. under $N_2$ and then the mixture was cooled to 0° C. The reactant of chloro(chlorosulfonyloxy)methane (12.87 g, 78.00 mmol, 1 eq) in DCM (20 mL) were added to the mixture in one portion at 0° C. The mixture was heated to 25° C. and stirred for 18 hours. The reaction mixture was extracted with DCM 50 mL (25 mL*2). The combined organic layers were dried over $Na_2SO_4$, filtered and concentrated under reduced pressure to give a residue. The residue was purified by column chromatography ($SiO_2$, Petroleum ether/Ethyl acetate=1/0 to 80:1). Compound chloromethyl hexadecanoate (17.6 g, 57.72 mmol, 74.01% yield) was obtained as a white solid.

Step 46B: Synthesis of Iodomethyl Hexadecanoate

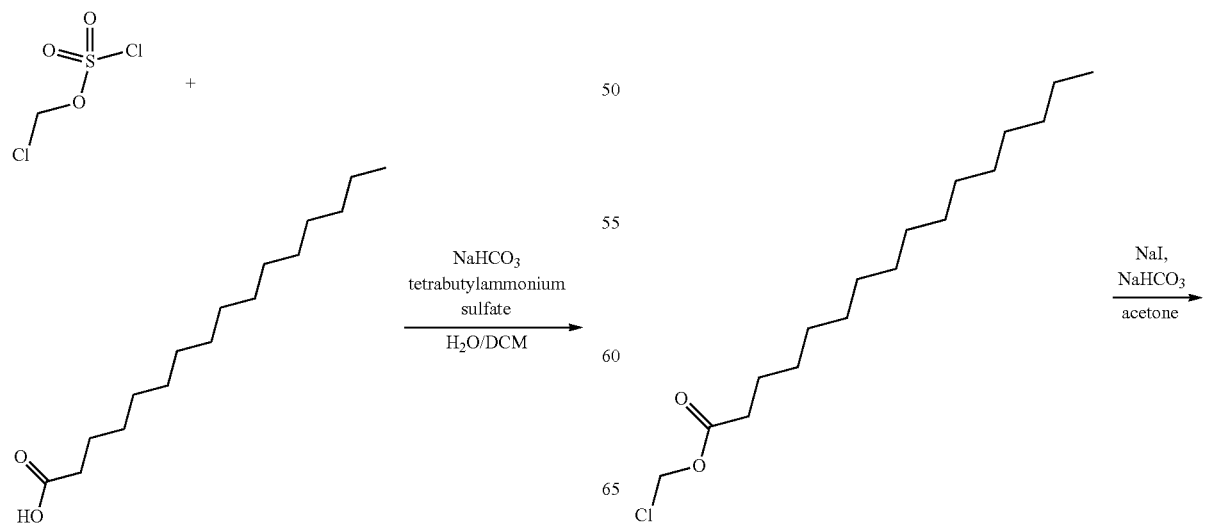

123
-continued

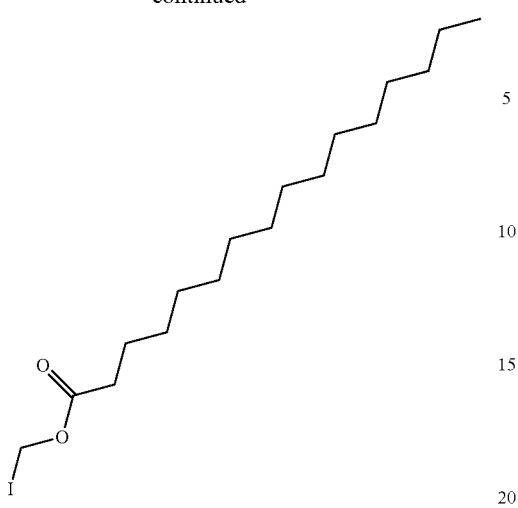

A mixture of chloromethyl hexadecanoate (3 g, 9.84 mmol, 1 eq) in acetone (30 mL) was degassed and purged with N₂ for 3 times at 15° C. in dark, and then the mixture was added NaHCO₃ (826.58 mg, 9.84 mmol, 382.68 uL, 1 eq) and NaI (1.47 g, 9.84 mmol, 1 eq) and stirred at 15° C. for 12 h under N₂ atmosphere in dark. The reaction mixture filtered and the filtrate was concentrated under reduced pressure to remove solvent. The residue was diluted with H₂O 20 mL and extracted with EtOAc 60 mL. The combined organic layers were washed with H₂O 40 mL (20 mL*2), dried, filtered and concentrated under reduced pressure to give a residue. Compound iodomethyl hexadecanoate (3.5 g, crude) was obtained as a yellow solid and used into the next step without further purification.

Step 46C: Synthesis of (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecanoate

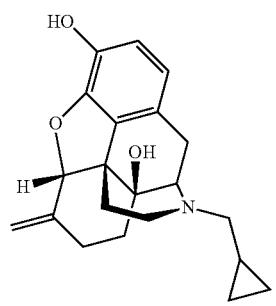

+

124
-continued

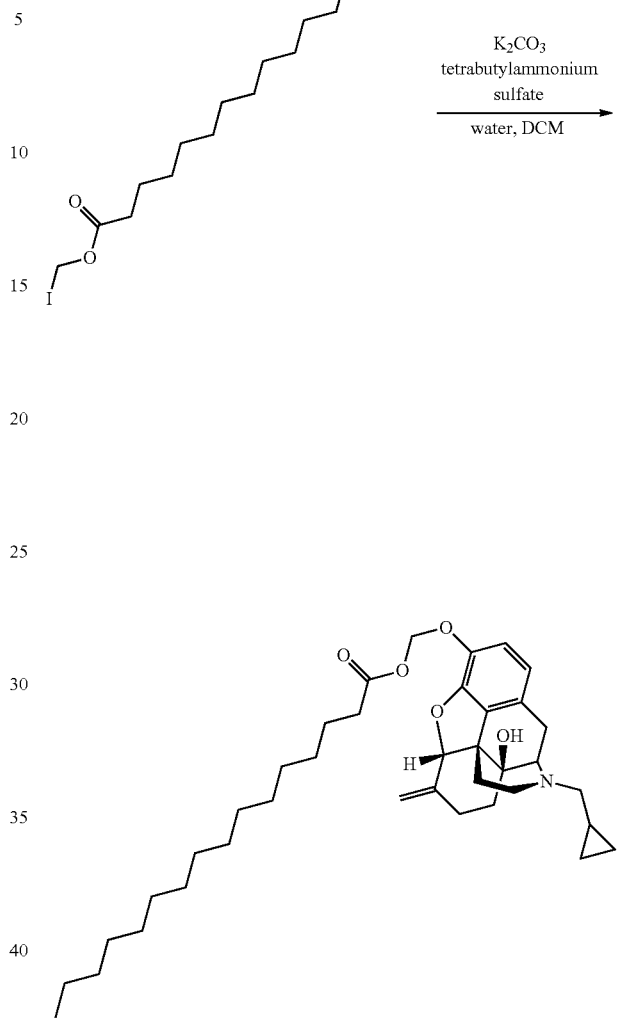

Figure 46:
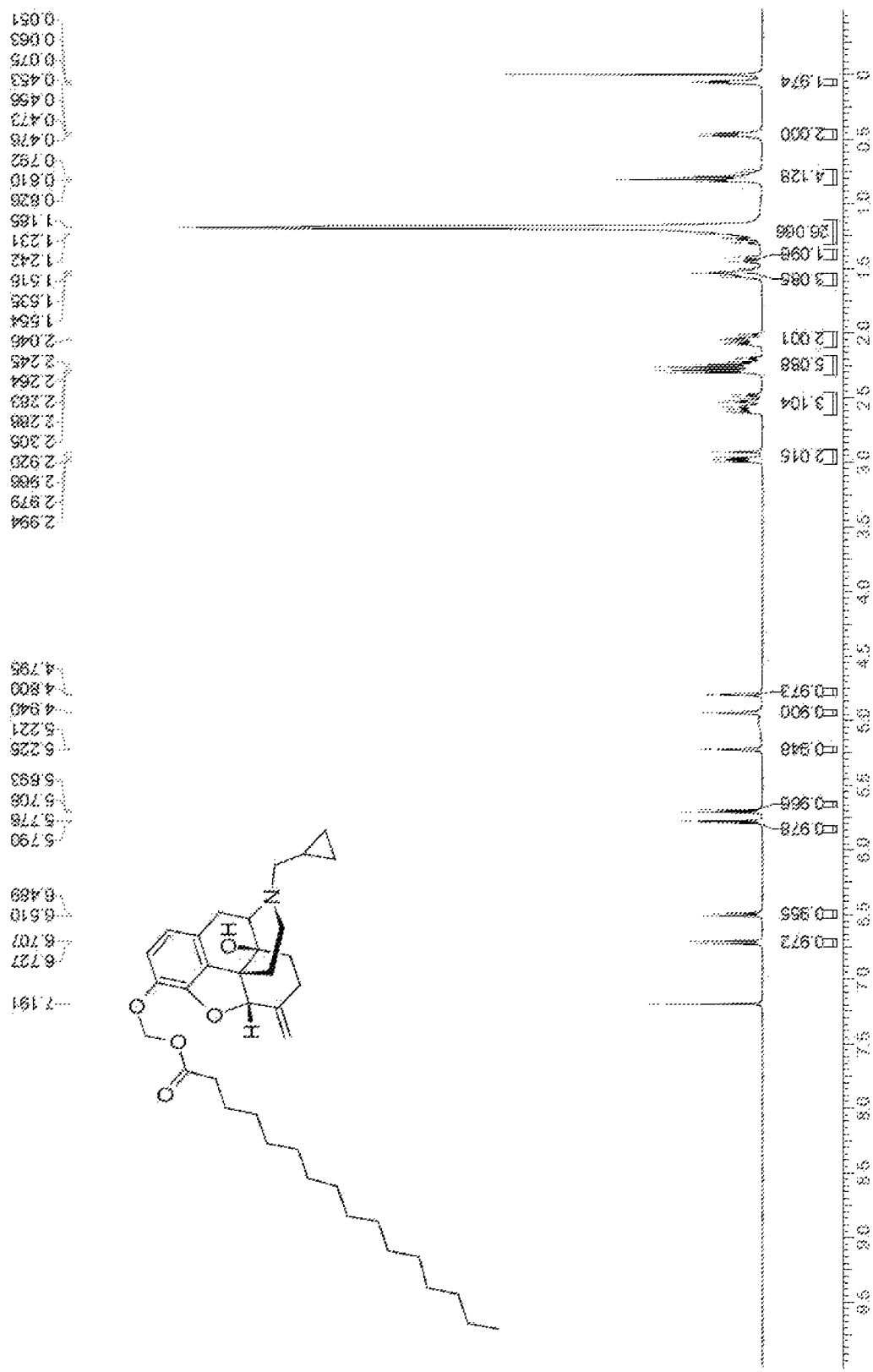
FIG. 46 provides the nuclear magnetic resonance spectrum of Example 46 (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl hexadecanoate.

A mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (1.8 g, 4.79 mmol, 1 eq, HCl), K2CO3 (1.99 g, 14.37 mmol, 3 eq) in H2O (15 mL) was stirred for 30 min, and tetrabutylammonium sulfate (2.78 g, 4.79 mmol, 2.75 mL, 1 eq) and DCM (7.5 mL) was added to the mixture, and a solution of iodomethyl hexadecanoate (4.56 g, 11.49 mmol, 2.4 eq) in DCM (7.5 mL) was added to the mixture and degassed and purged with N2 for 3 times, and then the mixture was stirred at 15° C. for 11.5 h under N2 atmosphere. The reaction mixture was diluted with H2O 10 mL and extracted with DCM 10 mL. The combined organic layers were dried, filtered and concentrated under reduced pressure to give a residue. The residue was purified by column chromatography (SiO2, Petroleum ether/Ethyl acetate=1:0 to 20:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl hexadecanoate (1.6 g, 24.35% yield) was obtained as a colorless oil. M+H+=608.6 (LCMS). 1H NMR (400 MHz, CDCl3): see FIG. 46.

Example 47: Synthesis of ((((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecyl carbonate

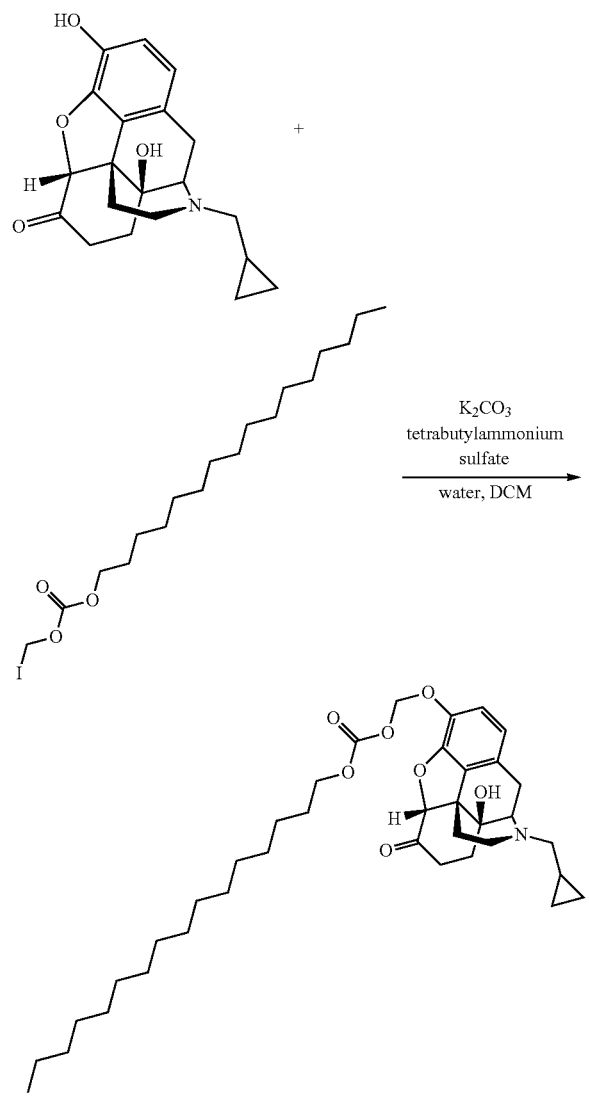

Figure 47:
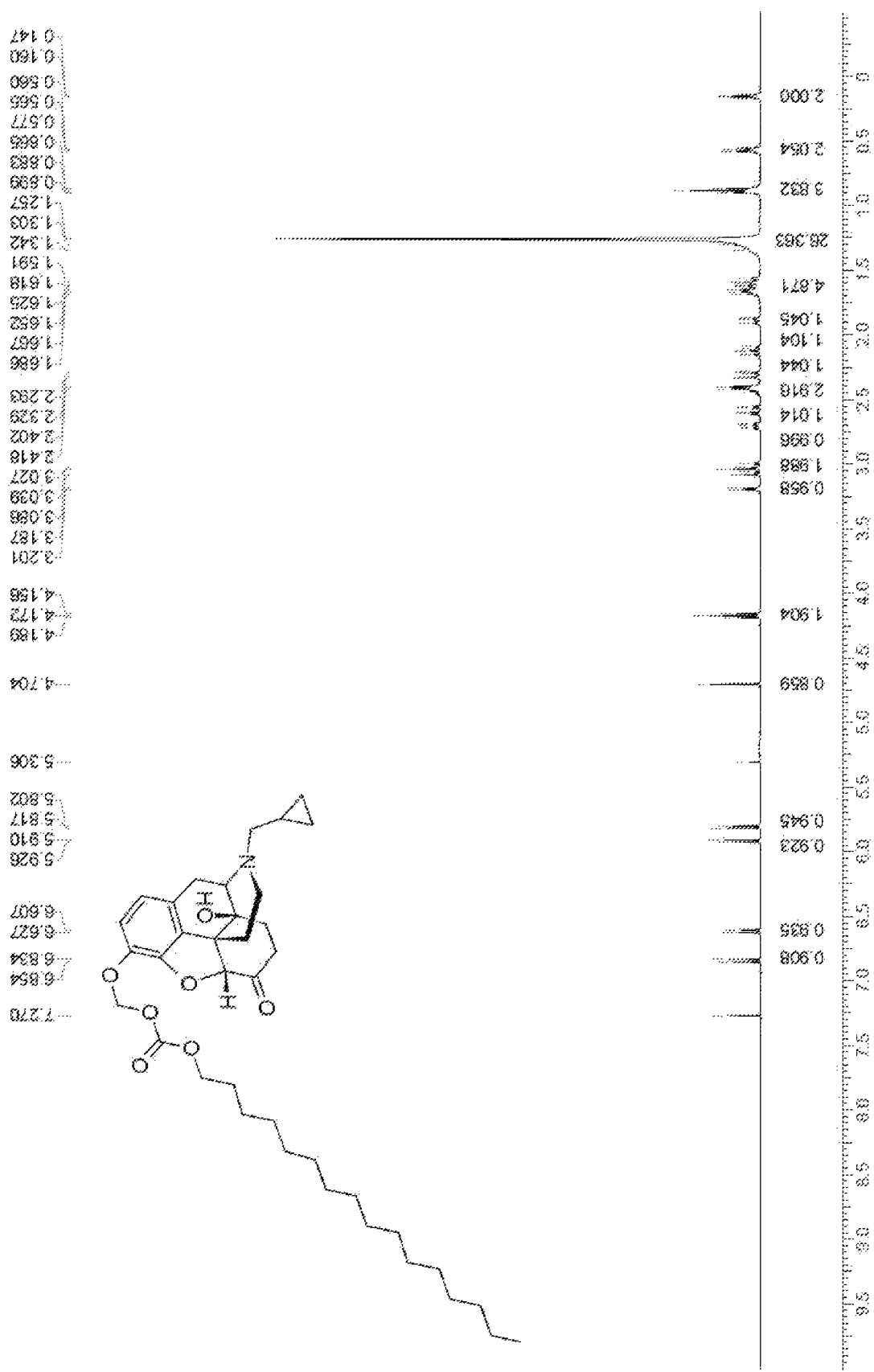
FIG. 47 provides the nuclear magnetic resonance spectrum of Example 47 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecyl carbonate.

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (5.45 g, 14.42 mmol, 1 eq, HCl) in H₂O (30 mL) was added K₂CO₃ (5.98 g, 43.27 mmol, 3 eq) in one portion at 25° C. under N₂. The mixture was stirred at 25° C. for 30 min. tetrabutylammonium sulfate (16.76 g, 14.42 mmol, 16.59 mL, 50% solution, 1 eq) and DCM (30 mL) were added to the mixture at 25° C. and the mixture was stirred for 10 min at 25° C. hexadecyl iodomethyl carbonate (14.76 g, 34.62 mmol, 2.4 eq) was added to the mixture in one portion at 25° C. and the mixture was stirred at 25° C. for 12 hr. The reaction mixture was extracted with DCM 30 mL (15 mL*2). The combined organic layers were dried over Na₂SO₄, filtered and concentrated under the reduced pressure to give a residue. The residue was purified by column chromatography (SiO₂, Petroleum ether/Ethyl acetate=1/0 to 5:1). Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl hexadecyl carbonate (4.68 g, 7.29 mmol, 50.56% yield) was obtained as a colorless oil. M+H$^+$=640.3 (LCMS). $^1$H NMR (400 MHz, CDCl₃): see FIG. 47.

Example 48: Synthesis of ((((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl dodecanoate

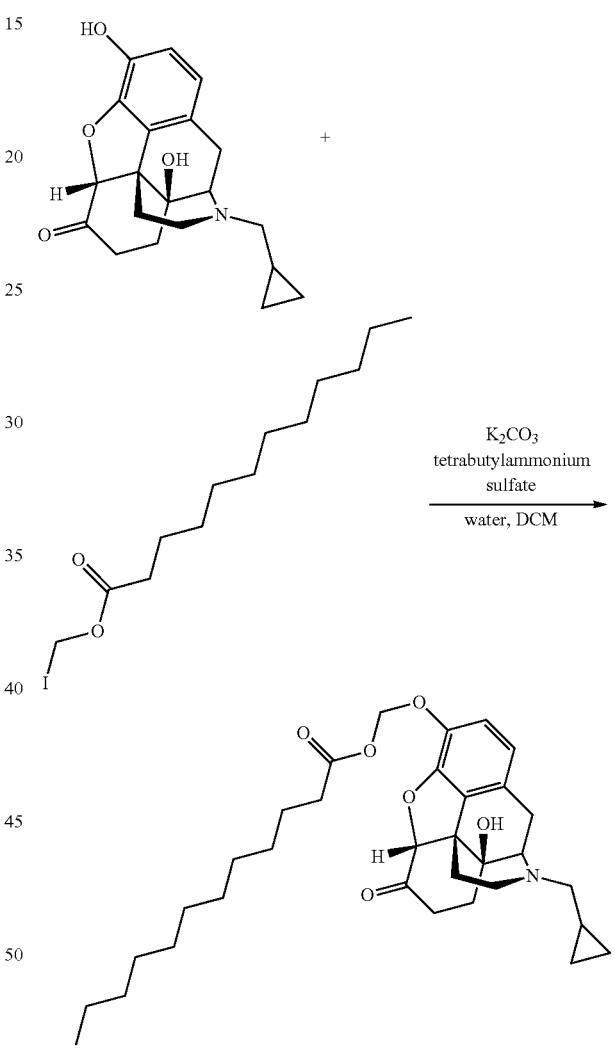

Figure 48:
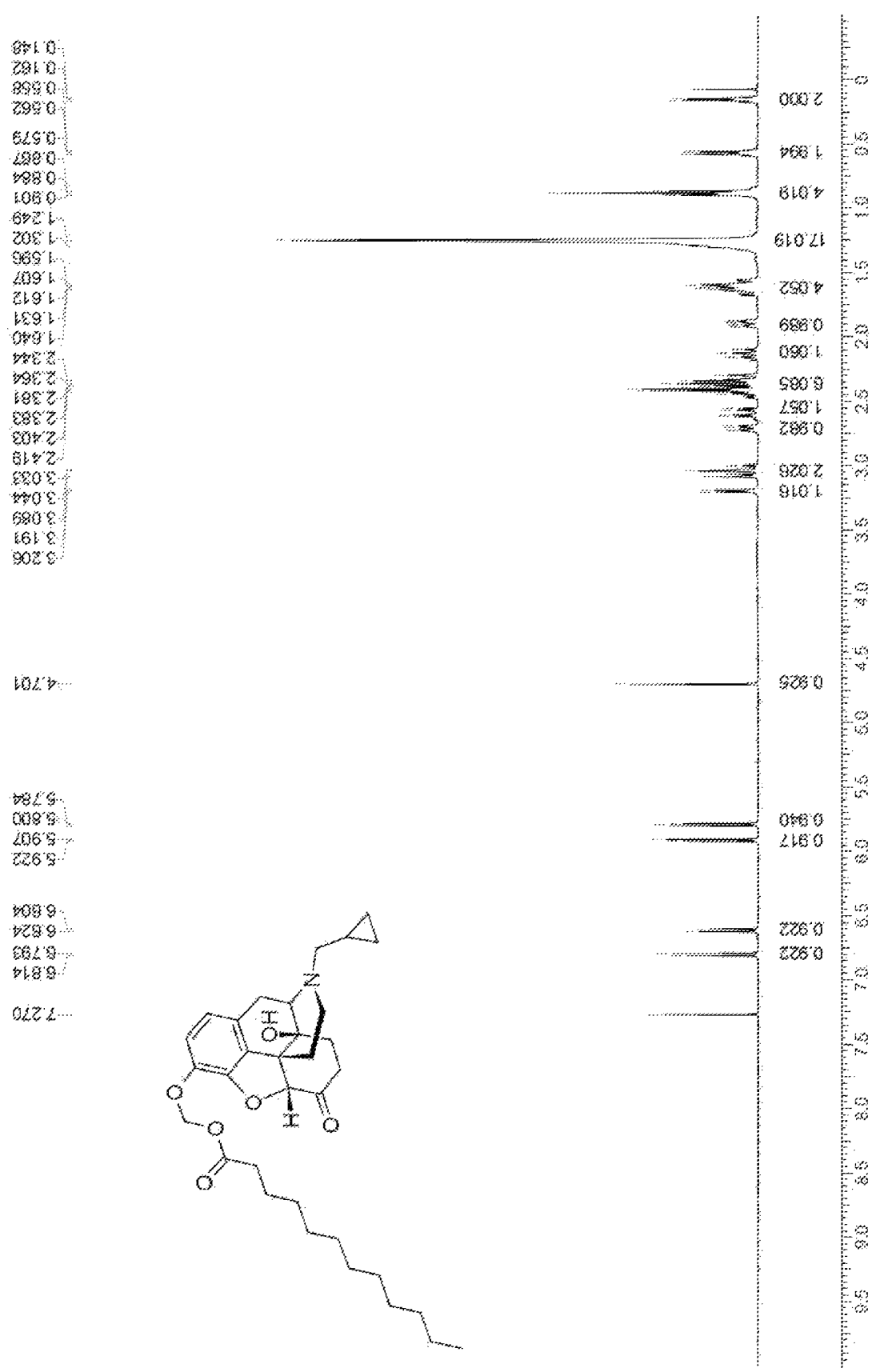
FIG. 48 provides the nuclear magnetic resonance spectrum of Example 48 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl dodecanoate.

A mixture of (3R,4aS,7aS,12bS)-3-(cyclopropylmethyl)-7-methylene-2,4,5,6,7a,13-hexahydro-1H-4,12-methanobenzofuro[3,2-e]isoquinoline-4a,9-diol (3.5 g, 10.31 mmol, 1 eq), K₂CO₃ (4.28 g, 30.93 mmol, 3 eq) in H₂O (40 mL) was stirred at 15° C. for 30 min and then tetrabutylammonium sulfate (5.99 g, 10.31 mmol, 5.93 mL, 1 eq) and DCM (20 mL) was added to the mixture and a solution of iodomethyl dodecanoate (8.42 g, 24.75 mmol, 2.4 eq) in DCM (20 mL) was added to the mixture and degassed and purged with N₂ for 3 times, and then the mixture was stirred at 15° C. for 11.5 h under N₂ atmosphere. The reaction mixture was diluted with H₂O 20 mL and extracted with DCM 20 mL. The combined organic layers were dried, filtered and concentrated under reduced pressure to give a residue. The residue was purified by column chromatography (SiO$_2$, Petroleum ether/Ethyl acetate=1:0 to 20:1). Compound [(3R,4aS,7aS,12bS)-3-(cyclopropylmethyl)-4a-hydroxy-7-methylene-2,4,5,6,7a,13-hexahydro-1H-4,12-methanobenzofuro[3,2-e]isoquinoline-9-yl]oxymethyl dodecanoate (1.51 g, 2.70 mmol, 26.14% yield) was obtained as a colorless oil. M+H$^+$=554.3 (LCMS). $^1$H NMR (400 MHz, CDCl$_3$): see FIG. 48.

Example 49: Synthesis of ((((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecanoate

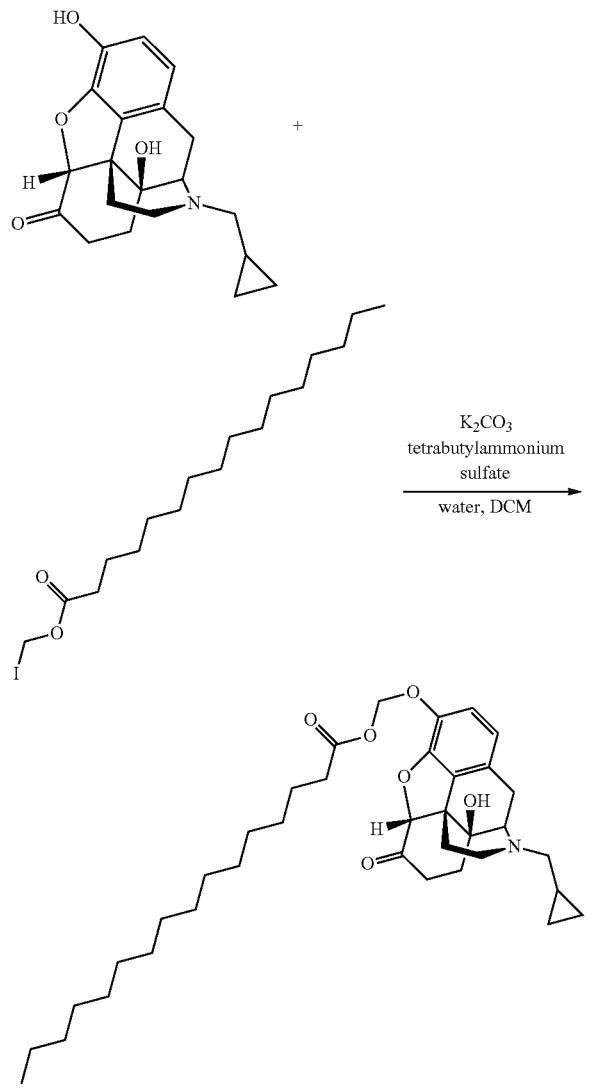

Figure 49:
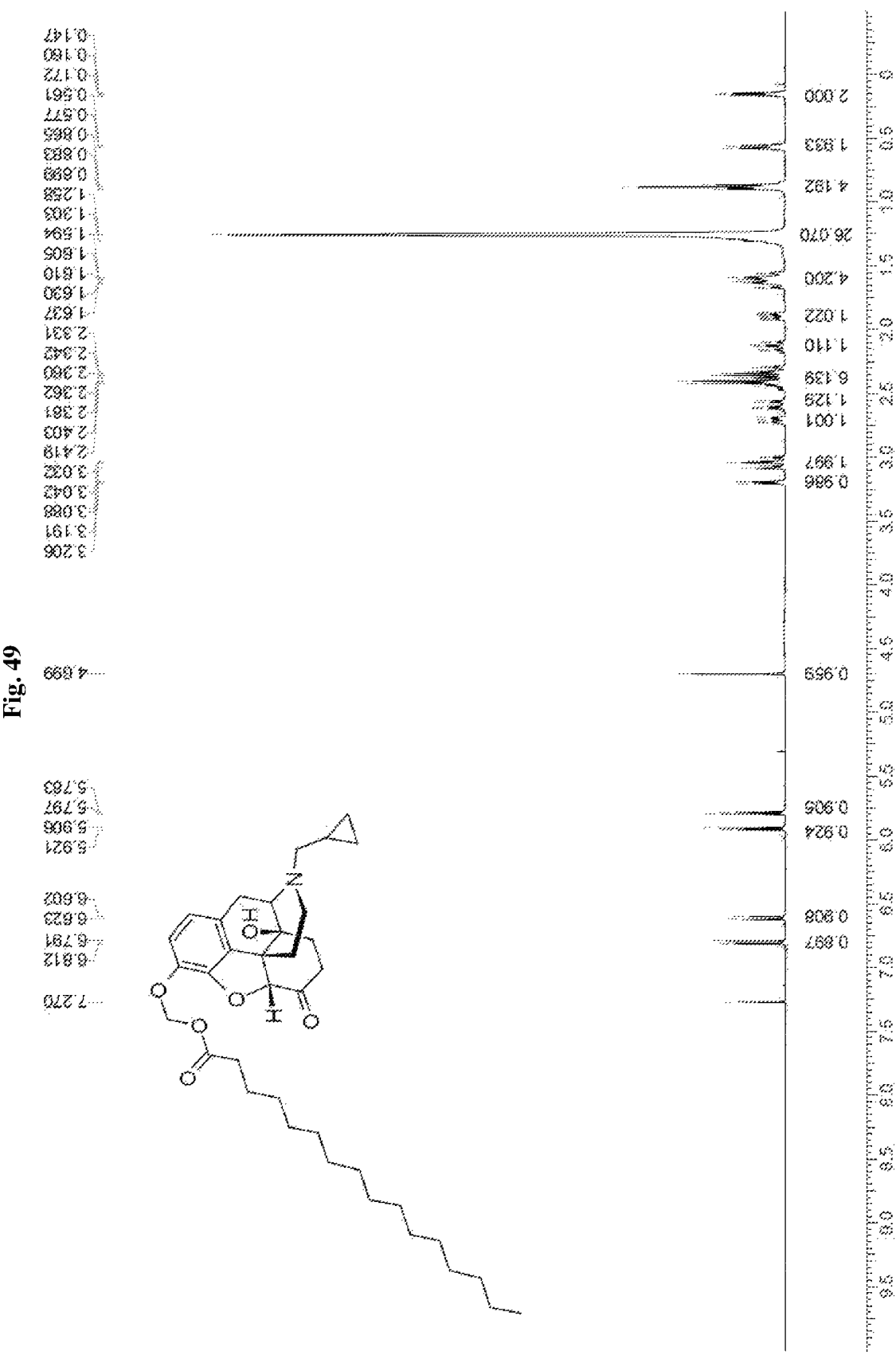
FIG. 49 provides the nuclear magnetic resonance spectrum of Example 49 (((4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl)oxy)methyl hexadecanoate.

To a mixture of (3R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one (5 g, 13.23 mmol, 1 eq, HCl) in H$_2$O (30 mL) was added K$_2$CO$_3$ (5.49 g, 39.70 mmol, 3 eq) in one portion at 25° C. under N$_2$. The mixture was stirred at 25° C. for 30 min. tetrabutylammonium sulfate (15.38 g, 13.23 mmol, 15.22 mL, 50% solution, 1 eq) and DCM (30 mL) were added to the mixture in one portion at 25° C. under N2. The mixture was stirred at 25° C. for 10 min. Iodomethyl hexadecanoate (12.59 g, 31.76 mmol, 2.4 eq) was added to the mixture in one portion at 25° C. under N$_2$. The mixture was stirred at 25° C. for 12 hr. The reaction mixture was extracted with DCM 30 mL (15 mL*2). The combined organic layers were dried over Na$_2$SO$_4$, filtered and concentrated under reduced pressure to give a residue. The residue was purified by column chromatography (SiO$_2$, Petroleum ether/Ethyl acetate=1/0 to 5:1). Compound [(3R,4aS,7aR,12bS)-3-(cyclopropylmethyl)-4a-hydroxy-7-oxo-2,4,5,6,7a,13-hexahydro-1H-4,12-methanobenzofuro[3,2-e]isoquinoline-9-yl]oxymethyl hexadecanoate (5.2 g, 6.14 mmol, 46.40% yield) was obtained as a light yellow oil. M+H$^+$=610.3 (LCMS). $^1$H NMR (400 MHz, CDCl$_3$): see FIG. 49.

Examples 50-61. Compounds 50-61 Listed in Table 2 can be Prepared According to General Scheme 1 for the Synthesis of Nalmefene Prodrugs or General Scheme 2 for the Synthesis of Naltrexone Prodrugs with Suitable Starting Materials II. Biological Evaluation Example 1: Plasma and Liver S9 Fraction Stability Assay Plasma stability determination of the test compounds in rat, dog, cynomolgus monkey and human plasma is performed using HPLC-MS. For rat, incubations are carried out in 96-well polypropylene plates in 5 aliquots of 70 µL each (one for each time point). Test compounds (10 µM, final solvent concentration 1%) are incubated at 37° C. Five time points are analyzed (0, 15, 120, 480 and 1440 min). For dog, monkey and human, test compounds (2 µM, final solvent concentration 1%) were also incubated at 37° C. and analyzed at five time points (0, 10, 30, 60 and 120 min). All incubations are performed in duplicates. The samples are analyzed by HPLC-MS. The percentage of parent compound remaining after incubation in plasma is determined. Nalmefene dodecanoate and nalmefene palmitate were previously reported (Gaekens et al, Journal of Controlled Release 232 (2016) 196-202). Results are provided in Table 4a-d.

TABLE 4a

Rat Plasma Stability

| Compound | % remaining at time point in minutes | | | | |
|---|---|---|---|---|---|
| | 0 min | 15 min | 120 min | 480 min | 1440 min |
| 36 | 100 | 74.4 | 66.3 | 39.8 | 19.1 |
| 6 | 100 | 31.3 | 7.6 | 4 | 1.6 |
| 53 | 100 | 46.85 | 19.6 | 7.3 | 1.9 |
| 11 | 100 | 0.7 | 0.3 | 0.2 | 0 |
| 54 | 100 | 98.8 | 62.4 | 45.6 | 19.4 |
| 14 | 100 | 94 | 112 | 107 | 120 |
| 15 | 100 | 72 | 69.3 | 52 | 35 |
| 17 | 100 | 0 | 0 | 0 | 0 |
| 18 | 100 | 0.6 | 0.3 | 0.1 | 0 |
| 19 | 100 | 70.1 | 71.5 | 43.8 | 33.3 |
| 55 | 100 | 77.3 | 47.2 | 27.1 | 15.6 |
| 23 | 100 | 0 | 0 | 0 | 0 |
| 10 | 100 | 0 | 0 | 0 | 0 |
| 21 | 100 | 73.5 | 68.3 | 59.8 | 40.9 |
| 50 | 100 | 114.5 | 102.7 | 83.3 | 73.9 |
| 51 | 100 | 107.4 | 105.3 | 88.2 | 92.7 |
| 8 | 100 | 44.2 | 34.3 | 15.3 | 5.2 |
| 57 | 100 | 10.5 | 3.2 | 1.2 | 0 |

TABLE 4a-continued

Rat Plasma Stability

| Compound | % remaining at time point in minutes | | | | |
|---|---|---|---|---|---|
| | 0 min | 15 min | 120 min | 480 min | 1440 min |
| 58 | 100 | 37 | 20 | 2.9 | 1.8 |
| 30 | 100 | 65.7 | 40.3 | 30.5 | 22.2 |
| 31 | 100 | 123.2 | 73.5 | 54.4 | 46.4 |
| 24 | 100 | 32 | 11.8 | 8.2 | 3 |
| 25 | 100 | 82.6 | 69.3 | 62.2 | 51.7 |
| 59 | 100 | 5.9 | 0.7 | 0.2 | 0 |
| 56 | 100 | 73.1 | 56.7 | 35.8 | 16.8 |
| Aripiprazole Lauroxil (plasma cleavage control) | 100 | 84 | 85.5 | 76.4 | 46 |
| Enalapril maleate salt (plasma cleavage control) | 100 | 44 | 2.9 | 8.2 | 4.8 |

TABLE 4b

Dog Plasma stability

| Compound | % remaining at time point in minutes | | | | |
|---|---|---|---|---|---|
| | 0 min | 15 min | 120 min | 480 min | 1440 min |
| 6 | 100 | 89.1 | 96.9 | 107.2 | 101.2 |
| 15 | 100 | 82.5 | 80.6 | 90.1 | 86.1 |
| 24 | 100 | 94.7 | 104.5 | 115.7 | 116.2 |
| Aripiprazole lauroxil | 100 | 103 | 81.3 | 78.6 | 74.3 |
| Paliperidone palmitate | 100 | 91.2 | 88.4 | 95.9 | 93.1 |

TABLE 4c

Monkey Plasma stability

| Compound | % remaining at time point in minutes | | | | |
|---|---|---|---|---|---|
| | 0 min | 15 min | 120 min | 480 min | 1440 min |
| 6 | 100 | 88.7 | 74.3 | 68.4 | 70.1 |
| 15 | 100 | 74.5 | 72.7 | 80.6 | 76.5 |
| 24 | 100 | 90.7 | 93.5 | 96.2 | 97.8 |
| Aripiprazole lauroxil | 100 | 95.2 | 94.5 | 75.5 | 83.2 |
| Paliperidone palmitate | 100 | 92 | 89.5 | 98.4 | 92.5 |

TABLE 4d

Human Plasma stability

| Compound | % remaining at time point in minutes | | | | |
|---|---|---|---|---|---|
| | 0 min | 15 min | 120 min | 480 min | 1440 min |
| 6 | 100 | 97.6 | 102 | 109.8 | 115.1 |
| 15 | 100 | 83.3 | 82.5 | 107.1 | 109.0 |
| 24 | 100 | 94 | 102.3 | 105.3 | 112.5 |
| Aripiprazole lauroxil | 100 | 99.7 | 80 | 73.2 | 75.5 |
| Paliperidone palmitate | 100 | 103.7 | 97.6 | 109.1 | 104.1 |

Liver S9 fraction stability determination of the test compounds in dog, cynomolgus monkey and human is performed using HPLC-MS. Test compound (2 µM, 0.1% DMSO, 1% Methanol final concentration) was assessed for stability in a 50 µl phosphate buffer containing 1.0 mg/ml S9 protein from each of the three species and 5 mM D-saccharic acid-1, 4-lactone. Samples were incubated at 37° C. for 60 minutes and the % compound remaining was assessed.

TABLE 4e

Liver S9 Fraction Stability

| Compound | % remaining at 60 minutes | | |
|---|---|---|---|
| | Dog | Monkey | Human |
| 6 | 17.1 | 0 | 5.3 |
| 15 | 80.9 | 76.7 | 59.8 |
| 24 | 3.6 | 3 | 3.5 |
| Aripiprazole lauroxil | 66.1 | 56.6 | 47.8 |
| Paliperidone palmitate | 56.4 | 57.4 | 47.8 |

Example 2: Opioid Receptor Binding Assay

Receptor binding assays were performed to assess the ability of compounds to inhibit binding to radiolabeled ligand. First, the IC50 values were determined for select compounds for all 3 opioid receptor subtypes (DOR, MOR and KOR) and compared these values to that of the parent molecule, Nalmefene. The general observation is that pro-drug derivatization greatly reduces the binding affinity to the opioid receptors, in some cases by several orders of magnitude.

Apparatus

Unifilter-96 GF/C filter plates, Perkin Elmer (Cat#6005174)

96 well conical polypropylene plates, Agilent (Cat#5042-385)

TopSeal-A sealing film, Perkin Elmer (Cat#6005250)

TopCount NXT HTS, (PerkinElmer)

MicroBeta$^2$ (PerkinElmer)

Cell harvest C961961, (Perkin Elmer)

Reagents

The stable cell lines were established and prepared cell membrane obtained using these cell lines.

$^3$H-diprenophrine (PerkinElmer, Cat: NET1121250UC, Lot: 2143599)

$^3$H-DAMGO (PerkinElmer, Cat: NET902250UC, Lot: 2139100)

$^3$H-DADLE (PerkinElmer, Cat: NET648250UC, Lot: 2060549)

Tris base (Sigma, Cat: T6066-1KG), prepare 1M stock and adjust pH to 7.4.

0.5M EDTA (Invitrogen, Cat: 15575-038)

1M MgCl$_2$ (Sigma, Cat: M1028-100 ml)

PEI (Poly ethyleneimine) (Sigma, Cat: P3143)

Microscint 20 cocktail (PerkinElmer, Cat: 6013329)

Naltrindole (Sigma, Cat; N115)

(±)trans-U-50488 (Sigma, Cat: D8040)

DAMGO (Sigma, Cat: E7384)

Assay Buffer

| Op-delta Assay Buffer | |
|---|---|
| | Final Concentration |
| Tris-HCl | 50 mM |
| MgCl2 | 10 mM |
| EDTA | 1 mM |

Adjust pH to 7.4, stored at 4° C.

| Op-kappa Assay Buffer | |
| --- | --- |
| | Final Concentration |
| Tris-HCl | 50 mM |

Adjust pH to 7.4, stored at 4° C.

| Op-mu Assay Buffer | |
| --- | --- |
| | Final Concentration |
| Tris-HCl | 50 mM |
| MgCl2 | 5 mM |

Adjust pH to 7.4, stored at 4° C.

Wash Buffer

| op-kappa, op-delta and op-mu Wash Buffer | |
| --- | --- |
| | Final Concentration |
| Tris-HCl | 50 mM |

Adjust pH to 7.4, stored at 4° C.

Methods

| Target | Membrane Concentration (ug/well) | Radio ligand | Radio ligand concentraton (nM) |
| --- | --- | --- | --- |
| DOR | 6.7 | [3H]-DADLE | 0.5 |
| MOR | 20 | [3H]DAMGO | 0.5 |
| KOR | 6.7 | [3H]Diprenorphine | 0.3 |

| Target | Compound starting conc. In source plate (mM) | Final Starting Conc. In assay plate (nM) | Ref: starting conc. In source plate (mM) | Ref: Final Starting Conc. In assay plate (nM) | NSB compound Conc. in assay plate |
| --- | --- | --- | --- | --- | --- |
| DOR | 2 | 10000 | 0.02 | 100 | naltrindole (1 µM) |
| MOR | 2 | 10000 | 0.2 | 1000 | naltrindole (1 µM) |
| KOR | 2 | 10000 | 0.2 | 1000 | trans-U-50488 (5 µM) |

3) Assay Procedure
1) Transfer 1 µl of specified concentration compound to assay plate according to the plate map for nonspecific binding. Transfer 1 µl of DMSO to assay plate according to plate map for total binding.
2) Follow the plate map. Dispense 99 µl of membrane stocks into the plate.
3) Add 100 µl of radio ligand.
4) Seal the plates. Incubate at RT for 1 hour.
5) Soak the Unifilter-96 GF/C filter plates with 50 µl of 0.3% PEI per well for at least 0.5 hour at room temperature.
6) When binding assays are completed, filter the reaction mixture through GF/C plates using Perkin Elmer Filtermate Harvester, and then wash each plate for 4 times with cold wash buffer.
7) Dry the filter plates for 1 hour at 50 degrees.
8) After drying, seal the bottom of the filter plate wells using Perkin Elmer Unifilter-96 backing seal tape. Add 50 µl of Perkin Elmer Microscint 20 cocktail. Seal top of filter plates with Perkin Elmer TopSeal-A sealing film.
9) Count $^3$H trapped on filter using Perkin Elmer MicroBeta2 Reader second day.
10) Analyze the data with GraphPad Prism 5. Calculate the "Inhibition [% Control]" using the equation: % Inh=(1-Background subtracted Assay value/Background subtracted HC value)*100.

Results

| | Reference |
| --- | --- |
| KOR | U-50488 |
| DOR | naltrindole |
| MOR | DAMGO |

TABLE 5a

| | DOR | | |
| --- | --- | --- | --- |
| Compound | IC50 (nM) | MaxDose (nM) | % Inh@MaxDose |
| 30 | 1854 | 10000 | 84.3 |
| 32 | >10000 | 10000 | 43.2 |
| 25 | 9540 | 10000 | 62 |
| 6 | 499.5 | 10000 | 70.9 |
| 23 | 106.7 | 10000 | 95.6 |
| 24 | 2121 | 10000 | 48 |
| 34 | >10000 | 10000 | 22.7 |
| 44 | 190.1 | 10000 | 79.1 |
| 45 | 68.4 | 10000 | 73.8 |
| 46 | 1360 | 10000 | 72.3 |
| nalmefene | 18.1 | 1000 | 94.5 |
| Naltrindole | 0.2 | 100 | 98.8 |

TABLE 5b

| | KOR | | |
| --- | --- | --- | --- |
| Compound | IC50 (nM) | MaxDose (nM) | % Inh@MaxDose |
| 30 | 88.7 | 10000 | 97.6 |
| 32 | 2116 | 10000 | 80.1 |
| 25 | 889.3 | 10000 | 76.9 |
| 6 | 51.1 | 10000 | 99.6 |
| 23 | 11.7 | 10000 | 101.6 |
| 24 | 37.5 | 10000 | 82.9 |
| 34 | 1767 | 10000 | 68.1 |
| 44 | 18.4 | 10000 | 99.2 |
| 45 | 5.5 | 10000 | 100.1 |
| 46 | 33.85 | 10000 | 101.8 |
| nalmefene | 2 | 1000 | 103 |
| U-50488 | 10.1 | 1000 | 101.6 |

TABLE 5c

| | MOR | | |
|---|---|---|---|
| Compound | IC50 (nM) | MaxDose (nM) | % Inh@MaxDose |
| 30 | 9 | 10000 | 82.5 |
| 32 | 17.4 | 10000 | 75.9 |
| 25 | 5 | 10000 | 87.3 |
| 6 | 14.9 | 10000 | 102.5 |
| 23 | 2.8 | 10000 | 98.7 |
| 34 | 12.55 | 10000 | 92.7 |
| 44 | 3.029 | 10000 | 83.1 |
| 45 | 2 | 10000 | 93.7 |
| 46 | 4.523 | 10000 | 102.3 |
| 24 | 22.4 | 10000 | 88.7 |
| nalmefene | 0.4 | 1000 | 103.5 |
| DAMGO | 1.4 | 1000 | 99.3 |

Example 3: Solubility Determination

A known amount of test substance (~40 mg) was weighed into the vial, 100 μL of oil was added and heated to 60° C. and then system was slurried to reach equilibrium. More oil was added until clear solution was obtained or the solubility was <50 mg/mL. Then the clear solution was placed at room temperature (25° C.) for 24 h to confirm whether there was solid precipitation. Extra oil was added into the vial once compound precipitated out and then the system was re-equilibrated at 1000 rpm at room temperature (25° C.). Final concentration was determined by HPLC method as described below in Table 6a and 6b.

TABLE 6a

| Reagent | | | |
|---|---|---|---|
| Name | Grade | Company | Lot No. |
| Purified Water | HPLC | WuXiAppTec | N/A |
| Cottonseed oil | N/A | SIGMA | 038K000G |
| Cottonseed oil | SUPER REFINED | CRODA | 1070292 |
| Sesame oil | HPLC | CRODA | 1115393 |
| Ethanol | HPLC | J. T. Baker | 155943 |
| ACN | HPLC | Merck | I0904530 735 |

TABLE 6b

| Instrument | | | |
|---|---|---|---|
| Name | Model | Company | Serial number |
| Water Purification Equipment | Milli-Q Direct 8 | MILLIPORE | PDS-PF-WPE-01 |
| Balance | Mettler-Toledo XPR10 | Mettler-Toledo | PDS-PF-BAL-08 |
| Stirrer | C-MAG MS 10 | IKA | PDS-PF-ST-01 |
| Balance | Mettler-Toledo MX5 | Mettler-Toledo | PDS-PF-BAL-03 |
| HPLC | Shimadzu 20AB | Shimadzu | PDS-PF-HPLC-12 |
| Thermomixer | YQH-0623 | Eppendorf | PDS-PF-TM-02 |

The HPLC method for Compounds 6, 12-20, and 36-43 is provided in Table 7.

TABLE 7

| HPLC Method 1 | | | |
|---|---|---|---|
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.0 ml/min | | |
| Inject volume | 10 μL | | |
| Analysis Time | 20 min | | |
| Column Temp. | 40° C. | | |
| Wavelength | 280 nm | | |
| Gradient | Time (min) | A % | B % |
| Program | 0 | 80 | 20 |
| | 9 | 10 | 90 |
| | 9.01 | 10 | 90 |
| | 14 | 80 | 20 |
| | 20 | 80 | 20 |
| | 20.01 | Stop | |

The HPLC method for Compounds 10, 21-23, 53, 55, 56, nalmefene, and naltrexone is provided in Table 8.

TABLE 8

| HPLC Method 2 | | | |
|---|---|---|---|
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.0 ml/min | | |
| Inject volume | 10 uL | | |
| Analysis Time | 13 min | | |
| Column Temp. | 40° C. | | |
| Wavelength | 284 nm | | |
| Gradient | Time (min) | A % | B % |
| Program | 0 | 95 | 5 |
| | 9 | 10 | 90 |
| | 11 | 10 | 90 |
| | 11.01 | 95 | 5 |
| | 13 | 95 | 5 |
| | 13.01 | Stop | |

The HPLC method for Compounds 3-5, 8, 24-25, 26-34, 44-51, 54, 55, 57, 59, and 60 is provided in Table 9.

TABLE 9

| HPLC Method 3 | | | |
|---|---|---|---|
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.0 ml/min | | |
| Inject volume | 10 μL | | |
| Analysis Time | 13 min | | |
| Column Temp. | 40° C. | | |
| Wavelength | 280 nm | | |
| Gradient | Time (min) | A % | B % |
| Program | 0 | 90 | 10 |
| | 4 | 35 | 65 |
| | 25 | 20 | 80 |
| | 27 | 10 | 90 |
| | 27.01 | 90 | 10 |
| | 30 | 90 | 10 |
| | 30.01 | Stop | |

TABLE 10

| Compound | Approximate Solubility(mg/mL) in Excipient | | | | Equilibrium solubility (mg/mL) | Heating Temp. | Obs. Temp. |
| --- | --- | --- | --- | --- | --- | --- | --- |
| | Castor oil | Cottonseed oil | Sesame oil | Ethanol | Water | (° C.) | (° C.) |
| 36 | >217 | >418.7 | >411.6 | 20-30 | 0.005 | 40 | 40 |
| 36 | N/A | >407 | >408 | N/A | N/A | 60 | 25 |
| 37 | >226 | >405.3 | >408.4 | 75-90 | 0.002 | 40 | 40 |
| 37 | N/A | 68.5-82 | 80-102 | N/A | N/A | 60 | 25 |
| 38 | >248 | >406.9 | 230-411 | 160-200 | 0.617 | 40 | 40 |
| 38 | N/A | N/A | N/A | N/A | 0.21 | 60 | 40 |
| 39 | >218 | 225-402.2 | >400.3 | 150-200 | 0.018 | 40 | 40 |
| 39 | N/A | 104-139 | 106-141 | N/A | N/A | 60 | 25 |
| 6 | N/A | >420.8 | >402.8 | 120-170 | 0.002 | 40 | 40 |
| 6 | N/A | >397 | >386 | N/A | N/A | 60 | 25 |
| 41 | N/A | >407 | >403 | >201 | 0.084 | 40 | 40 |
| 41 | N/A | <50 | <50 | N/A | N/A | 60 | 25 |
| 53 | N/A | >403.8 | >406.3 | >404 | 0.0143 | 60 | 40 |
| 53 | N/A | >408.5 | >401.9 | N/A | N/A | 60 | 25 |
| 42 | N/A | <51 | <52 | 78-93 | 0.245 | 40 | 40 |
| 42 | N/A | <26 | <25.8 | N/A | 0.068 | 60 | 40 |
| 43 | N/A | <50 | <50 | >257 | 0.05 | 40 | 40 |
| 43 | N/A | 140-210 | 133-199 | N/A | N/A | 60 | 40 |
| 43 (in water) | N/A | N/A | N/A | N/A | 0.048 | 40 | 40 |
| 11 | N/A | >407 | >407 | >218 | 0.0005 | 40 | 40 |
| 11 | N/A | <51 | <50 | N/A | N/A | 60 | 25 |
| 11 after slurry in Heptane | N/A | N/A | N/A | N/A | 0.0026 | N/A | N/A |
| 12 | N/A | 100-120 | 70-95 | 65-75 | 0.043 | 40 | 40 |
| 12 | N/A | >398.5 | >411.1 | N/A | N/A | 60 | 40 |
| 12 | N/A | <51 | <50 | N/A | N/A | 60 | 25 |
| 12 (in water) | N/A | N/A | N/A | N/A | 0.026 | 40 | 40 |
| 54 | N/A | <51 | <50 | N/A | N/A | 60 | 25 |
| 54 (in water) | N/A | N/A | N/A | N/A | <0.001 | 40 | 40 |
| 13 | N/A | >381 | >406 | >214 | 0.002 | 40 | 40 |
| 13 | N/A | <50 | 91-121 | N/A | N/A | 60 | 25 |
| 14 | N/A | <50 | <51 | 69-83 | 0.01 | 40 | 40 |
| 14 | N/A | <25 | <25 | N/A | N/A | 60 | 40 |
| 14 (in water) | N/A | N/A | N/A | N/A | 0.0056 | 40 | 40 |
| 14 after slurry in Heptane | N/A | N/A | N/A | N/A | <0.0005 | N/A | N/A |
| 14 after slurry in EtOAc | N/A | N/A | N/A | N/A | <0.0005 | N/A | N/A |
| 15 | N/A | <51 | <52 | <20 | <0.0002 | 40 | 40 |
| 15 | N/A | >401 | >404 | N/A | N/A | 60 | 40 |
| 15 | N/A | >402.6 | >396.5 | N/A | N/A | 60 | 25 |
| 15 | N/A | N/A | >403.94 | N/A | N/A | 60 | 25 |
| 16 | N/A | 57-67 | 68-81 | <25 | 0.2059 | 40 | 40 |
| 16 | N/A | 201-403 | 202-404 | N/A | 0.011 | 60 | 40 |
| 17 | N/A | >416 | >416 | >209 | 0.0008 | 40 | 40 |
| 17 | N/A | >408 | >487 | N/A | N/A | 60 | 25 |
| 18 | N/A | >403 | >403 | >209 | <0.0002 | 40 | 40 |
| 18 | N/A | >400 | >402 | N/A | N/A | 60 | 25 |
| 19 | N/A | 67-80 | 103-137 | 27-42 | 0.0468 | 40 | 40 |
| 20 | N/A | >414 | >406 | 157-197 | <0.0002 | 40 | 40 |
| 20 | N/A | 68-82 | 80-100 | N/A | N/A | 60 | 25 |
| 61 (Nalmefene) | N/A | <25.0 | <25.5 | 102-137 | 0.025 | 60 | 40 |
| 62 (Naltrexone) | N/A | <26.6 | <25.9 | 103-137 | 0.295 | 60 | 40 |
| 56 | N/A | 25-50 | 25-50 | <40.4 | 0.0679 | 60 | 40 |
| 56 | N/A | <50 | <50 | N/A | N/A | 60 | 25 |
| 55 | N/A | >400.1 | >394.8 | >401.1 | 0.0066 | 60 | 40 |
| 55 | N/A | <50 | <50 | N/A | N/A | 60 | 25 |
| 55 (after ETOAc slurry) | N/A | N/A | N/A | N/A | <0.0005 | N/A | N/A |
| 22 | N/A | >405.9 | >401.9 | >397.7 | 0.0314 | 60 | 40 |
| 22 | N/A | 67-80 | 67-80 | N/A | N/A | 60 | 25 |
| 23 | N/A | >411.8 | >420.7 | >419.3 | 0.0094 | 60 | 40 |
| 23 | N/A | >407.7 | >423.9 | N/A | N/A | 60 | 25 |
| 10 | N/A | >420.7 | >404.1 | >404.7 | 0.0006 | 60 | 40 |
| 10 | N/A | 100-134 | <51 | N/A | N/A | 60 | 25 |
| 21 | N/A | 101-134.8 | 101-134.5 | 50-100 | 0.0006 | 60 | 40 |
| 50 | N/A | <51 | <52 | N/A | N/A | 60 | 25 |
| 50 (in water) | N/A | N/A | N/A | N/A | <0.001 | 40 | 40 |
| 51 | N/A | <50 | <46 | N/A | N/A | 60 | 25 |
| 51 (in water) | N/A | N/A | N/A | N/A | <0.001 | 40 | 40 |
| 8* | N/A | <50 | <52 | N/A | N/A | 60 | 25 |
| 8 (in water)* | N/A | N/A | N/A | N/A | 0.57 | 40 | 40 |
| 56 NMF palmitate | N/A | 25-50 | 25-50 | <40.4 | 0.0066 | 60 | 40 |
| 56 NMF palmitate | N/A | <50 | <50 | N/A | N/A | 60 | 25 |
| 57 | N/A | >423.7 | >417.3 | N/A | N/A | 60 | 25 |
| 57 (in water) | N/A | N/A | N/A | N/A | <0.001 | 40 | 40 |
| 58 | N/A | 101.8-203.6 | 99.4-198.8 | N/A | N/A | 60 | 25 |
| 58 (in water) | N/A | N/A | N/A | N/A | 0.0014 | 40 | 40 |
| 59 NMF dodecanoate | N/A | >414 | >393.3 | N/A | N/A | 60 | 25 |

TABLE 10-continued

| | Solubility by volumetric flask method | | | | Equilibrium solubility (mg/mL) | Heating Temp. (° C.) | Obs. Temp. (° C.) |
|---|---|---|---|---|---|---|---|
| 59 NMF dodecanoate (in water) | N/A | N/A | N/A | N/A | <0.001 | 40 | 40 |
| 30 | N/A | 252.5-404.06 | 252.55-398.6 | N/A | N/A | 60 | 25 |
| 30 (in water) | N/A | N/A | N/A | N/A | <0.001 | 40 | 40 |
| 31 | N/A | >416.9 | >413.5 | N/A | N/A | 60 | 25 |
| 31 (in water) | N/A | N/A | N/A | N/A | <0.001 | 40 | 40 |
| 32 | N/A | >395.8 | >410 | N/A | N/A | 60 | 25 |
| 32 (in water) | N/A | N/A | N/A | N/A | 0.0328 | 40 | 40 |
| 33 | N/A | <50 | <51 | N/A | N/A | 60 | 25 |
| 33 (in water) | N/A | N/A | N/A | N/A | <0.001 | 40 | 40 |
| 28 | N/A | <50.2 | <50.6 | N/A | N/A | 60 | 25 |
| 28 (in water) | N/A | N/A | N/A | N/A | <0.001 | 40 | 40 |
| 24 | N/A | >403 | 338-368 | N/A | N/A | 60 | 25 |
| 24 (in water) | N/A | N/A | N/A | N/A | <0.001 | 40 | 40 |
| 25 | N/A | >414 | >404 | N/A | N/A | 60 | 25 |
| 25 (in water) | N/A | N/A | N/A | N/A | <0.001 | 40 | 40 |
| 34 | N/A | >404 | >405 | N/A | N/A | 60 | 25 |
| 34 (in water) | N/A | N/A | N/A | N/A | <0.001 | 40 | 40 |
| 44 | N/A | >407 | 208-231 | N/A | N/A | 60 | 25 |
| 44 (in water) | N/A | N/A | N/A | N/A | <0.001 | 40 | 40 |
| 45 | N/A | >402 | 267-288 | N/A | N/A | 60 | 25 |
| 45 (in water) | N/A | N/A | N/A | N/A | <0.001 | 40 | 40 |
| 46 | N/A | >395.5 | 202-269 | N/A | N/A | 60 | 25 |
| 46 (in water) | N/A | N/A | N/A | N/A | <0.001 | 40 | 40 |
| 29 | N/A | >410.2 | >416.5 | N/A | N/A | 60 | 25 |
| 29 (in water) | N/A | N/A | N/A | N/A | <0.001 | 40 | 40 |
| 27 | N/A | >394.7 | >399.2 | N/A | N/A | 60 | 25 |
| 27 (in water) | N/A | N/A | N/A | N/A | <0.001 | 40 | 40 |
| 47 | N/A | >405.5 | >404.9 | N/A | N/A | 60 | 25 |
| 47 (in water) | N/A | N/A | N/A | N/A | <0.001 | 40 | 40 |
| 48 | N/A | >410.5 | >404.8 | N/A | N/A | 60 | 25 |
| 48 (in water) | N/A | N/A | N/A | N/A | 0.003 | 40 | 40 |
| 26 | N/A | 204.3-239 | <354 | N/A | N/A | 60 | 25 |
| 26 (in water) | N/A | N/A | N/A | N/A | <0.001 | 40 | 40 |
| 49 | N/A | <50 | <51 | N/A | N/A | 60 | 25 |
| 49 (in water) | N/A | N/A | N/A | N/A | 0.028 | 40 | 40 |
| | Solubility by volumetric flask method | | | | Equilibrium solubility (mg/mL) | Heating Temp. (° C.) | Obs. Temp. (° C.) |
| 8** | N/A | N/A | >399.8 | N/A | N/A | 60 | 25 |
| 8 (in water)** | N/A | N/A | N/A | N/A | <0.001 | 40 | 40 |
| 3 | N/A | >399.12 | >400.7 | N/A | N/A | 60 | 25 |
| 3 (in water) | N/A | N/A | N/A | N/A | <0.001 | 40 | 40 |
| 4 | N/A | >395.3 | >400.4 | N/A | N/A | 60 | 25 |
| 4 (in water) | N/A | N/A | N/A | N/A | <0.001 | 40 | 40 |
| 5 | N/A | >401.8 | >400.6 | N/A | N/A | 60 | 25 |
| 5 (in water) | N/A | N/A | N/A | N/A | <0.001 | 40 | 40 |

*Data from compound 8 initial failed batch due to non-optimized synthesis
**Data from compound 8 second batch after successfully optimized synthesis

Example 4: Stability Determination of Drug Product

Compounds were resuspended in oil vehicles, stored at room temperature for the indicated time period and assessed by HPLC. Data is presented as absolute percentage loss normalized to 30 days. Nalmefene dodecanoate were previously reported (Gaekens et al, Journal of Controlled Release 232 (2016) 196-202).

TABLE 11

| Reagents | | | |
|---|---|---|---|
| Name | Grade | Company | Lot No. |
| Water | HPLC | WuXiAppTec | N/A |
| ACN | HPLC | Merck | I0911030735 |
| Cottonseed oil | N/A | SIGMA | 038K000G |
| Cottonseed oil | SUPER REFINED | CRODA | 1070292 |
| Sesame oil | N/A | ACROS | A0377665 |
| Sesame oil | HPLC | CRODA | 1115393 |
| TFA | HPLC | J & K | LN20M33 |
| THF | HPLC | MACRON | 1613729801 |

TABLE 12

| Instruments | | | |
|---|---|---|---|
| Name | Model | Company | Serial number |
| Water Purification Equipment | Milli-Q Direct 8 | MILLIPORE | PDS-PF-WPE-01 |
| Balance | Mettler-Toledo XP6 | Mettler-Toledo | PDS-PF-BAL-05 |
| HPLC | Shimadzu 20AB | Shimadzu | PDS-PF-HPLC-12 |

TABLE 13

HPLC Method

| | | | |
|---|---|---|---|
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.2 ml/min | | |
| Inject volume | 10 uL | | |
| Analysis Time | 30 min | | |
| Column Temp. | 40° C. | | |
| Wavelength | 280 nm | | |
| Diluent | THF | | |
| Gradient | Time (min) | A % | B % |
| Program | 0 | 90 | 10 |
| | 4 | 35 | 65 |
| | 25 | 20 | 80 |
| | 27 | 10 | 90 |
| | 27.01 | 90 | 10 |
| | 30 | 90 | 10 |
| | 30.01 | Stop | |

TABLE 14

| Compound | % Avg Purity Degradation in Cottonseed Oil (normalized 30 day) | % Avg Purity Degradation in Sesame Oil (normalized 30 day) |
|---|---|---|
| 29 | 0.13 | 0.32 |
| 27 | 0.13 | 0.32 |
| 32 | — | 0.13 |
| 24 | 0.43 | (0.01) |
| 25 | 0.28 | (0.11) |
| 31 | 1.15 | 0.08 |
| 6 | 1.48 | 0.31 |
| 15 | 0.86 | 0.10 |
| 17 | 1.05 | 0.26 |
| 18 | 1.25 | 0.71 |
| 23 | 0.35 | 0.09 |
| 5 | 0.40 | 0.28 |
| 59 | 4.60 | 0.51 |
| 34 | (0.11) | 0.02 |
| 44 | 0.36 | (0.08) |
| 45 | 0.31 | 0.09 |
| 46 | 0.04 | Not tested |
| 47 | 0.43 | Not tested |
| 48 | 0.60 | Not tested |
| 3 | 0.04 | 0.07 |

Example 4: Stability Determination of Drug Substance

Compounds were stored at room temperature for the indicated time period and assessed by HPLC. Data is presented as absolute percentage loss normalized to 30 days. Nalmefene dodecanoate were previously reported (Gaekens et al, Journal of Controlled Release 232 (2016) 196-202).

TABLE 15

Reagent

| Name | Grade | Company | Lot No. |
|---|---|---|---|
| Purified Water | HPLC | WuXiAppTec | N/A |
| ACN | HPLC | Merck | JA056730 |
| TFA | HPLC | J & K | LN20M33 |
| THF | HPLC | MACRON | 1613729801 |

TABLE 16

Instrument

| Name | Model | Company | Serial number |
|---|---|---|---|
| Water Purification Equipment | Milli-Q Direct 8 | MILLIPORE | PDS-PF-WPE-01 |
| Balance | Mettler-Toledo XPR10 | Mettler-Toledo | PDS-PF-BAL-08 |
| Balance | Mettler-Toledo MX5 | Mettler-Toledo | PDS-PF-BAL-03 |
| HPLC | Shimadzu 20AB | Shimadzu | PDS-PF-HPLC-12 |

TABLE 17

HPLC method for compounds 10, 11, 21, 36, and 53

| | | | |
|---|---|---|---|
| | HPLC Method 1 | | |
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.2 ml/min | | |
| Inject volume | 10 uL | | |
| Analysis Time | 32 min | | |
| Column Temp. | 40° C. | | |
| Diluent | ACN:H2O(3:1) | | |
| Wavelength | 280 nm | | |
| Gradient | Time (min) | A % | B % |
| Program | 0 | 90 | 10 |
| | 4 | 40 | 60 |
| | 25 | 5 | 95 |
| | 27 | 5 | 95 |
| | 27.01 | 90 | 10 |
| | 32 | 90 | 10 |
| | 32.01 | Stop | |

TABLE 18

HPLC method for compounds 14, 19 and 55

| | | | |
|---|---|---|---|
| | HPLC Method 2 | | |
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.2 ml/min | | |
| Inject volume | 10 uL | | |
| Analysis Time | 32 min | | |
| Column Temp. | 40° C. | | |
| Diluent | ACN:H2O(3:1) | | |
| Wavelength | 280 nm | | |
| Gradient | Time (min) | A % | B % |
| Program | 0 | 90 | 10 |
| | 4 | 35 | 65 |
| | 25 | 20 | 80 |
| | 27 | 10 | 90 |
| | 27.01 | 90 | 10 |
| | 30 | 90 | 10 |
| | 30 | Stop | |

TABLE 19

HPLC method for compounds 1, 3-9, 15, 17, 18, 23-27, 29, 31, 32, 34, 35, 44-48, 57, and 59

| HPLC Method 3 | | | |
|---|---|---|---|
| Instrument | Shimadzu 20AB HPLC | | |
| Column | Ascentis Express C18, 10 cm * 4.6 mm, 2.7 μm | | |
| Gradient | A = 0.1% TFA/H$_2$O, B = 100% ACN | | |
| Flow Rate | 1.2 ml/min | | |
| Inject volume | 10 uL | | |
| Analysis Time | 32 min | | |
| Column Temp. | 40° C. | | |
| Diluent | THF | | |
| Wavelength | 280 nm | | |
| Gradient Program | Time (min) | A % | B % |
| | 0 | 90 | 10 |
| | 4 | 35 | 65 |
| | 25 | 20 | 80 |
| | 27 | 10 | 90 |
| | 27.01 | 90 | 10 |
| | 30 | 90 | 10 |
| | 30 | Stop | |

TABLE 20

| Compound | Purity (initial) | Purity (after room temperature storage) | % Degradation | % Degradation Normalized to 30 days |
|---|---|---|---|---|
| 36 | 97.70% | 81.19% | 16.51% | 5.27% |
| 6 | 99.00% | 99.56% | −0.56% | −0.18% |
| 53 | 97.00% | 89.90% | 7.10% | 3.95% |
| 11 | 98.20% | 98.96% | −0.76% | −0.28% |
| 14 | 97.01% | 97.90% | −0.89% | −0.33% |
| 15 | 98.40% | 98.64% | −0.24% | −0.10% |
| 17 | 96.30% | 98.38% | −2.08% | −0.84% |
| 18 | 98.44% | 98.43% | 0.01% | 0.00% |
| 19 | 99.70% | 100.00% | −0.30% | −0.13% |
| 55 | 98.80% | 98.89% | −0.09% | −0.04% |
| 23 | 97.30% | 99.97% | −2.67% | −1.31% |
| 10 | 97.40% | 80.74% | 16.66% | 8.19% |
| 21 | 97.60% | 98.81% | −1.21% | −0.60% |
| 57 | 99.60% | 99.84% | −0.24% | −0.17% |
| 59 | 97.41% | 99.09% | −1.68% | −1.23% |
| 31 | 98.80% | 98.80% | 0.00% | 0.00% |
| 32 | 99.00% | 99.22% | −0.22% | −0.23% |
| 24 | 99.00% | 98.86% | 0.14% | 0.11% |
| 25 | 99.00% | 98.33% | 0.67% | 0.38% |
| 34 | 98.00% | 97.87% | 0.13% | 0.07% |
| 44 | 98.00% | 98.40% | −0.40% | −0.22% |
| 45 | 98.00% | 98.49% | −0.49% | −0.28% |
| 46 | 97.00% | 96.97% | 0.03% | 0.02% |
| 29 | 99.00% | 99.43% | −0.43% | −0.46% |
| 27 | 98.90% | 98.11% | 0.79% | 0.85% |
| 47 | 99.00% | 99.24% | −0.24% | −0.29% |
| 48 | 99.00% | 98.89% | 0.11% | 0.15% |
| 26 | 99.00% | 95.89% | 3.11% | 0.72% |
| 7 | 99.00% | 99.32% | −0.32% | −0.10% |
| 8 | 98.30% | 98.48% | −0.18% | −0.05% |
| 9 | 99.00% | 97.59% | 1.41% | 0.35% |
| 1 | 99.00% | 99.18% | −0.18% | −0.07% |
| 3 | 99.00% | 99.62% | −0.62% | −0.30% |
| 4 | 99.00% | 99.73% | −0.73% | −0.24% |
| 5 | 100.00% | 100.00% | 0.00% | 0.00% |
| 35 | 100.00% | 100.00% | 0.00% | 0.00% |

Example 5: Physical Characterization of Solid State Drug Substance

The analysis of the physical characteristics of drug substances that were in a solid state was conducted using polarized light microscopy (PLM), X-ray powder diffractometer (XRPD) assessment, Differential Scanning Calorimetry (DSC) and Thermal Gravimetric Analysis (TGA). For PLM, samples were dispersed in immersion oil and were observed using an ocular lens (10×) and objective lens (20×) under crossed polarizers. For XRPD, samples were run on a diffractometer using the following method: Tube—Cu: K-alpha ($\lambda$=1.54179 Å); Generator—Voltage 40 kV, Current 40 mA; Scan scope—3 to 40°; sample rotation speed—15 rpm; scanning rate—10 deg/min. For DSC, ~1 mg of sample was tested using a crimped aluminum pan and covered by a lid with a hole, heated from room temperature to 300° C. at a speed of 10° C./minute. For TGA, 2-5 mg of sample was placed in an open platinum pan and heated from room temperature to 300° C. at a rate of 10° C./minute. Nalmefene palmitate were previously reported (Gaekens et al, Journal of Controlled Release 232 (2016) 196-202).

TABLE 21

XRPD, TGA and DSC results

| Cpd # | X-ray Powder Diffraction | Thermal Gravimetric Analysis | Differential scanning calorimetry |
|---|---|---|---|
| 11 | Crystal Form with obvious birefringence | Weight loss of 0.30% at 120° C. following decomposition | Single endothermic peak at 56.71° C. which could be melting point. |
| 12 | Crystal Form with obvious birefringence | Weight loss of 0.19% at 120° C. following decomposition | Single endothermic peak at 51.94° C. which could be melting point. |
| 14 | Weak crystallinity of the compound | Weight loss of 1.649% at 120° C. following decomposition | Single endothermic peak at 124.66° C. which could be melting point. |
| 16 | Crystal Form with obvious birefringence | Weight loss of 0.403% at 120° C. following decomposition | Single endothermic peak at 59.04° C. which could be melting point. |
| 19 | Crystal Form with obvious birefringence | Weight loss of 0.1623% at 120° C. following decomposition | Single endothermic peak at 56.31° C. which could be melting point. |
| 56 | Crystal Form with obvious birefringence | Weight loss of 0.1815% at 120° C. following decomposition | Two endothermic peak at 48.95° C. and 59.75° C. |

TABLE 21-continued

XRPD, TGA and DSC results

| Cpd # | X-ray Powder Diffraction | Thermal Gravimetric Analysis | Differential scanning calorimetry |
|---|---|---|---|
| 55 | Crystal Form with obvious birefringence | Weight loss of 0.2597% at 120° C. following decomposition | Single endothermic peak at 48.24° C. which could be melting point. |
| 10 | Crystal Form with obvious birefringence | Weight loss of 0.3047% at 120° C. following decomposition | Single endothermic peak at 47.18° C. which could be melting point. |
| 40 | Crystal form with partial birefringence | Weight loss of 0.57% at 120° C. following decomposition | Two endothermic peak at 107.6° C. and 195.0° C. |
| 21 | Crystal Form with partial birefringence. | Weight loss of 1.133% at 120° C. following decomposition | Single endothermic peak at 70.84° C. which could be melting point. |
| 31 | Crystal Form with obvious birefringence | Weight loss of 0.7244% at 120° C. following decomposition | Single endothermic peak at 45.15° C. which could be melting point. |

Example 5: Polymorph Screening of Solid State Drug Substances

In order to identify stable polymorph forms of solid state drug substances, approximately 50 mg of compound (nalmefene or naltrexone equivalents) was weighed into vials. Next, 500 μL of the indicated solvents was added and the suspension was stirred at 700 rpm, 50° C. for 72 hours. For samples in suspension, solids were separated by centrifuge (10 minutes, 14000 rpm) and dried in vacuum oven at 30° C. overnight. For samples in solution, solids were generated by evaporation (stir bar removed and covered with aluminum foil with pinholes, then dried in vacuum oven at 30° C. overnight). Dried solids were characterized by XRPD, TGA and DSC. Results are presented in Table 23.

TABLE 23

| Compound # | Solvents | Target conc. (mg/ml) | Visual observation RT | Visual observation 50° C. | Dry method and appearance | XRPD results (Dried) | Comment |
|---|---|---|---|---|---|---|---|
| 11 | Heptane | 100 | Clear | Clear | Evaporation/white powder | Pattern B | Initial crystal form (pattern A) likely to be stable form; Pattern A generated by evaporation with MTBE, IPA, EtOAc and Acetone, Compound evaporated in heptane was different form |
|  | MTBE |  | Clear | Clear | Evaporation/white powder | Pattern A |  |
|  | Isopropanol |  | Slurry | Clear | Evaporation/white powder | Pattern A |  |
|  | EtOAc |  | Slurry | Clear | Evaporation/white powder | Pattern A |  |
|  | Acetone |  | Slurry | Clear | Evaporation/white powder | Pattern A |  |
| 14 | Heptane | 100 | Slurry | Slurry | Centrifugation/white powder | Pattern B | Initial crystal form (pattern A) appears unstable; Same crystal from generated by evaporation from MTBE, IPA, EtOAc and acetone and might be unstable. Form evaporated in heptane different form and likely more stable |
|  | MTBE |  | Clear | Clear | Evaporation/white powder | Pattern A |  |
|  | Isopropanol |  | Clear | Clear | Evaporation/white powder | Pattern A |  |
|  | EtOAc |  | Slurry | Clear | Evaporation/white powder | Pattern A |  |
|  | Acetone |  | Slimy | Clear | Evaporation/white powder | Pattern A |  |
| 16 | Heptane | 100 | Slurry | Slurry | Centrifugation/white powder | Pattern A | Initial crystal form (pattern A) is likely stable form. Same crystal form (pattern A) was generated by evaporation from MTBE, EtOAc and Acetone. Same crystal form (pattern A) generated by slurry in Heptane and IPA |
|  | MTBE |  | Clear | Clear | Evaporation/white powder | Pattern A |  |
|  | Isopropanol |  | Slurry | Slurry | Centrifugation/white powder | Pattern A |  |
|  | EtOAc |  | Slurry | Clear | Evaporation/white powder | Pattern A |  |
|  | Acetone |  | Slurry | Clear | Evaporation/white powder | Pattern A |  |
| 19 | Heptane | 100 | Slurry | Clear | Evaporation/white powder | Pattern A | Initial crystal form (pattern A) likely to be stable fomr. Same crystal form (pattern A) was generated by evaporation from Heptane, MTBE, IPA, EtOAc and Acetone |
|  | MTBE |  | Clear | Clear | Evaporation/white powder | Pattern A |  |
|  | Isopropanol |  | Slurry | Clear | Evaporation/white powder | Pattern A |  |
|  | EtOAc |  | Slurry | Clear | Evaporation/white powder | Pattern A |  |
|  | Acetone |  | Slurry | Clear | Evaporation/white powder | Pattern A |  |
| 55 | Heptane | 100 | Slurry | Clear | Evaporation/white powder | Pattern B | Cannot determine which crystal form is more stable. Same form (pattern B) was generated by evaporation from Heptane, MTBE, IPA, EtOAc and Acetone. |
|  | MTBE |  | Clear | Clear | Evaporation/white powder | Pattern B |  |
|  | Isopropanol |  | Slurry | Clear | Evaporation/white powder | Pattern B |  |
|  | EtOAc |  | Slurry | Clear | Evaporation/white powder | Pattern B |  |
|  | Acetone |  | Slurry | Clear | Evaporation/white powder | Pattern B |  |
| 10 | Heptane | 100 | Slurry | Slurry | Centrifugation/White wax | Pattern A | Initial crystal form (pattern A) is a stable form. Same form (pattern A) generated by evaporation from MTBE, IPA, EtOAc and Acetone. Pattern A also generated by slurry in heptane. |
|  | MTBE |  | Clear | Clear | Evaporation/White wax | Pattern A |  |
|  | Isopropanol |  | Slurry | Clear | Evaporation/White wax | Pattern A |  |
|  | EtOAc |  | Slurry | Clear | Evaporation/White wax | Pattern A |  |
|  | Acetone |  | Slurry | Clear | Evaporation/White wax | Pattern A |  |
| 21 | Heptane | 100 | Slurry | Clear | Evaporation/white powder | Pattern A | Initial crystal form (pattern A) is a stable form. Same crystal form (pattern A) was generated by |
|  | MTBE |  | Clear | Clear | Evaporation/white powder | Pattern A |  |
|  | Isopropanol |  | Slurry | Clear | Evaporation/white powder | Pattern A |  |

TABLE 23-continued

| Compound # | Solvents | Target conc. (mg/ml) | Visual observation RT | Visual observation 50° C. | Dry method and appearance | XRPD results (Dried) | Comment |
|---|---|---|---|---|---|---|---|
| | EtOAc | | Slurry | Clear | Evaporation/white powder | Pattern A | evaporation from Heptane, MTBE, |
| | Acetone | | Slurry | Clear | Evaporation/white powder | Pattern A | IPA, EtOAc and Acetone |
| 31 | Heptane | 100 | Slurry | Clear | Evaporation/white powder | Pattern A | Initial crystal form (pattern A) very |
| | MTBE | | Slurry | Clear | Evaporation/white powder | Pattern A | likely to be a stable form. Same |
| | Isopropanol | | Clear | Clear | Evaporation/white powder | Pattern A | crystal form (pattern A) was generated |
| | EtOAc | | Clear | Clear | Evaporation/white powder | Pattern A | by evaporation from MTBE, IPA, |
| | Acetone | | Slurry | Clear | Evaporation/white powder | Pattern A | EtOAc and acetone |
| 40 | Heptane | 100 | Slurry | Slurry | Centrifugation/white powder | Pattern A | Initial crystal form (pattern A) is a |
| | MTBE | | Clear | Clear | Evaporation/white powder | Amorphous | stable form. Same crystal form |
| | Isopropanol | | Slurry | Clear | Evaporation/oil | Amorphous | (pattern A) was generated by slurry in |
| | EtOAc | | Slurry | Clear | Evaporation/white powder | Pattern A | heptane and evaporation form EtOAc. |
| | Acetone | | Slurry | Clear | Evaporation/white powder | Amorphous | Compound became amorphous by evaporation from MTBE, IPA and acetone. |

III. Preparation of Pharmaceutical Dosage Forms

Example 1: Oral Capsule

The active ingredient is a compound of Table 1, or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil, cottonseed oil, castor oil or other pharmaceutically acceptable lipophilic excipient, preferably at a concentration of greater than 100 mg/mL. The resulting solution is administered by intramuscular injection.

Compounds were resuspended to 1 mL at the indicated concentrations (in mg/ml base equivalents) by mixing with magnetic stirring (1000 rpm) at 60° C. until a homogeneous clear solution was achieved, then cooled down to room temperature and stored protected from light. Appearance of oil formulations was observed and recorded at room temperature (25° C.) at initial, 2 hours, and 24 hours. Samples for "Assay" measurements were taken at initial, 2 hours and 24 hours post resuspension and subjected to HPLC analysis where actual concentration was based on a standard curve (Assay=Concentration(measured by HPLC)/Actual concentration(by weight)×100%). Purity was calculated at indicated time points based on the percentage of area under the curve of the main peak from the HPLC spectrogram. Syringability was assessed by drawing through a 21 Gauge needle. Some indicated samples were assessed for Appearance, Assay and Purity after 7 months in 40° C./75% Relative Humidity. Data are presented in Table 21.

TABLE 24

| Compound | Vehicle | Volume | Target Conc. (mg/ml) in Base eq. | Appearance Initial | Appearance 2 hours | Appearance 24 hours | Assay Initial | Assay 2 hours |
|---|---|---|---|---|---|---|---|---|
| 6 | Sesame oil + 10 uL Benzyl Alcohol | 1 mL | 200 | Light amber transparent oil | Light amber transparent oil | Light amber transparent oil | 102.26% | 102.32% |
| | Sesame oil + 10 uL Benzyl Alcohol | 1 mL | 300 | Light amber transparent oil | Light amber transparent oil | Light amber transparent oil | 99.82% | 99.66% |
| | Sesame oil + 10 uL Benzyl Alcohol | 1 mL | 400 | Light amber transparent oil | Light amber transparent oil | Light amber transparent oil | 98.06% | 97.94% |
| 15 | Sesame oil + 10 uL Benzyl Alcohol | 1 mL | 200 | Light amber transparent oil | Light amber transparent oil | Light amber transparent oil | 107.68% | 109.70% |
| | Sesame oil + 10 uL Benzyl Alcohol | 1 mL | 300 | Light amber transparent oil | Light amber transparent oil | Light amber transparent oil | 101.55% | 108.28% |
| | Sesame oil + 10 uL Benzyl Alcohol | 1 mL | 400 | Light amber transparent oil | Light amber transparent oil | Light amber transparent oil | 93.52% | 99.92% |

TABLE 24-continued

| 17 | Sesame oil + 10 uL Benzyl Alcohol | 1 mL | 200 | Light amber transparent oil | Light amber transparent oil | Light amber transparent oil | 98.80% | 98.66% |
|---|---|---|---|---|---|---|---|---|
| | Sesame oil + 10 uL Benzyl Alcohol | 1 mL | 300 | Light amber transparent oil | Light amber transparent oil | Light amber transparent oil | 105.43% | 105.79% |
| | Sesame oil + 10 uL Benzyl Alcohol | 1 mL | 400 | Light amber transparent oil | Light amber transparent oil | Light amber transparent oil | 98.51% | 98.82% |
| 18 | Sesame oil + 10 uL Benzyl Alcohol | 1 mL | 200 | Light amber transparent oil | Light amber transparent oil | Light amber transparent oil | 97.56% | 97.79% |
| | Sesame oil + 10 uL Benzyl Alcohol | 1 mL | 300 | Light amber transparent oil | Light amber transparent oil | Light amber transparent oil | 99.00% | 100.43% |
| | Sesame oil + 10 uL Benzyl Alcohol | 1 mL | 400 | Light amber transparent oil | Light amber transparent oil | Light amber transparent oil | 98.54% | 98.70% |
| 23 | Sesame oil + 10 uL Benzyl Alcohol | 1 mL | 200 | Light amber transparent oil | Light amber transparent oil | Light amber transparent oil | 97.22% | 97.54% |
| | Sesame oil + 10 uL Benzyl Alcohol | 1 mL | 300 | Light amber transparent oil | Light amber transparent oil | Light amber transparent oil | 100.34% | 100.25% |
| | Sesame oil + 10 uL Benzyl Alcohol | 1 mL | 400 | Light amber transparent oil | Light amber transparent oil | Light amber transparent oil | 97.54% | 97.92% |
| 57 | Sesame oil + 10 uL Benzyl Alcohol | 1 mL | 200 | Light amber transparent oil | Light amber transparent oil | Light amber transparent oil | 104.75% | 104.82% |
| | Sesame oil + 10 uL Benzyl Alcohol | 1 mL | 300 | Light amber transparent oil | Light amber transparent oil | Light amber transparent oil | 102.67% | 102.47% |
| | Sesame oil + 10 uL Benzyl Alcohol | 1 mL | 400 | Light amber transparent oil | Light amber transparent oil | Light amber transparent oil | 101.03% | 101.18% |
| 31 | Sesame oil + 10 uL Benzyl Alcohol | 1 mL | 200 | Light amber transparent oil | Light amber transparent oil | Light amber transparent oil | 101.90% | 100.35% |
| | Sesame oil + 10 uL Benzyl Alcohol | 1 mL | 300 | Light amber transparent oil | Light amber transparent oil | White wax | 105.84% | 95.68% |
| | Sesame oil + 10 uL Benzyl Alcohol | 1 mL | 400 | Light amber transparent oil | Light amber transparent oil | White wax | 99.16% | 95.81% |
| 32 | Sesame oil + 10 uL Benzyl Alcohol | 1 mL | 300 | Light amber transparent oil | Light amber transparent oil | Light amber transparent oil | 95.61% | 96.59% |
| | Sesame oil + 10 uL Benzyl Alcohol | 1 mL | 350 | Light amber transparent oil | Light amber transparent oil | White wax | 102.17% | 103.30% |
| | Sesame oil + 10 uL Benzyl Alcohol | 1 mL | 400 | Light amber transparent oil | Light amber transparent oil | White wax | 97.21% | 97.10% |
| 24 | Cottonsseed oil + 10 uL Benzyl Alcohol | 1 mL | 400 | Light clear yellow oil | Light clear yellow oil | Light clear yellow oil | 107.62% | 99.58% |
| 29 | Sesame oil + 10 uL Benzyl Alcohol | 1 mL | 400 | Light amber transparent oil | Light amber transparent oil | Light amber transparent oil | 103.07% | 104.83% |

TABLE 24-continued

| | | | | | | | | | | |
|---|---|---|---|---|---|---|---|---|---|---|
| 27 | Sesame oil + 10 uL Benzyl Alcohol | 1 mL | 400 | Light amber transparent oil | Light amber transparent oil | Light amber transparent oil | | 95.52% | 98.43% | |
| 47 | Sesame oil + 10 uL Benzyl Alcohol | 1 mL | 400 | Light amber transparent oil | Light amber transparent oil | Light amber transparent oil | | 102.41% | 101.60% | |

| Compound | Vehicle | Assay 24 hours | Purity Initial | Purity 2 hours | Purity 24 hours | Syringability (21G needle) Initial | Syringability (21G needle) 2 hours | Syringability (21G needle) 24 hours | Follow up observation at room temperature |
|---|---|---|---|---|---|---|---|---|---|
| 6 | Sesame oil + 10 uL Benzyl Alcohol | 99.30% | 99.48% | 99.46% | 99.37% | feasible | feasible | feasible | Remains in solution |
| | Sesame oil + 10 uL Benzyl Alcohol | 102.90% | 99.37% | 99.35% | 99.44% | feasible | feasible | feasible | |
| | Sesame oil + 10 uL Benzyl Alcohol | 98.43% | 99.37% | 99.39% | 99.37% | feasible | feasible | feasible | |
| 15 | Sesame oil + 10 uL Benzyl Alcohol | 109.70% | 96.38% | 96.44% | 96.34% | feasible | feasible | feasible | Remains in solution |
| | Sesame oil + 10 uL Benzyl Alcohol | 103.00% | 96.44% | 96.38% | 96.45% | feasible | feasible | feasible | |
| | Sesame oil + 10 uL Benzyl Alcohol | 94.15% | 96.42% | 96.28% | 96.41% | feasible | feasible | feasible | |
| 17 | Sesame oil + 10 uL Benzyl Alcohol | 98.29% | 98.61% | 98.64% | 98.61% | feasible | feasible | feasible | Remains in solution |
| | Sesame oil + 10 uL Benzyl Alcohol | 105.65% | 98.61% | 98.60% | 98.63% | feasible | feasible | feasible | |
| | Sesame oil + 10 uL Benzyl Alcohol | 97.58% | 98.63% | 98.60% | 98.59% | feasible | feasible | feasible | |
| 18 | Sesame oil + 10 uL Benzyl Alcohol | 97.85% | 99.15% | 99.05% | 99.07% | feasible | feasible | feasible | Remains in solution |
| | Sesame oil + 10 uL Benzyl Alcohol | 99.52% | 98.93% | 99.06% | 98.84% | feasible | feasible | feasible | |
| | Sesame oil + 10 uL Benzyl Alcohol | 98.77% | 99.17% | 99.13% | 99.14% | feasible | feasible | feasible | |
| 23 | Sesame oil + 10 uL Benzyl Alcohol | 97.10% | 99.50% | 99.48% | 99.47% | feasible | feasible | feasible | Remains in solution |
| | Sesame oil + 10 uL Benzyl Alcohol | 99.51% | 99.49% | 99.48% | 99.50% | feasible | feasible | feasible | |
| | Sesame oil + 10 uL Benzyl Alcohol | 95.81% | 99.51% | 99.48% | 99.49% | feasible | feasible | feasible | |
| 57 | Sesame oil + 10 uL Benzyl Alcohol | 104.02% | 99.55% | 99.49% | 99.54% | feasible | feasible | feasible | Insoluble: gross precipitant/ phase seperation |
| | Sesame | 100.66% | 99.69% | 99.67% | 99.65% | feasible | feasible | feasible | |

TABLE 24-continued

| # | Vehicle | | | | | | | | Notes |
|---|---|---|---|---|---|---|---|---|---|
| | oil + 10 uL Benzyl Alcohol | | | | | | | | after 23 days |
| | Sesame oil + 10 uL Benzyl Alcohol | 100.34% | 99.63% | 99.59% | 99.63% | feasible | feasible | feasible | |
| 31 | Sesame oil + 10 uL Benzyl Alcohol | N/A | 99.29% | 99.28% | N/A | feasible | feasible | feasible | Insoluble: gross precipitant/ phase seperation after 24 hr |
| | Sesame oil + 10 uL Benzyl Alcohol | N/A | 99.14% | 99.31% | N/A | feasible | feasible | N/A | |
| | Sesame oil + 10 uL Benzyl Alcohol | N/A | 99.23% | 99.25% | N/A | feasible | feasible | N/A | |
| 32 | Sesame oil + 10 uL Benzyl Alcohol | 95.42% | 98.78% | 98.63% | 98.78% | feasible | feasible | feasible | Insoluble: gross precipitant/ phase seperation after 24 hr |
| | Sesame oil + 10 uL Benzyl Alcohol | N/A | 98.79% | 98.76% | N/A | feasible | feasible | N/A | |
| | Sesame oil + 10 uL Benzyl Alcohol | N/A | 98.80% | 98.78% | N/A | feasible | feasible | N/A | |
| 24 | Cottonssed oil + 10 uL Benzyl Alcohol | 100.58% | 99.02% | 98.86% | 98.93% | feasible | feasible | feasible | Remains in solution |
| 29 | Sesame oil + 10 uL Benzyl Alcohol | 103.35% | 99.21% | 99.21% | 99.28% | feasible | feasible | feasible | Drug substance shown to be unstable in oil solution at 4 months 40 C./75% RH |
| 27 | Sesame oil + 10 uL Benzyl Alcohol | 96.46% | 99.33% | 99.30% | 99.09% | feasible | feasible | feasible | Insoluble: gross precipitant/ phase seperation after 90 days |
| 47 | Sesame oil + 10 uL Benzyl Alcohol | 101.72% | 99.37% | 99.31% | 99.26% | feasible | feasible | feasible | Insoluble: gross precipitant/ phase seperation after 24 hr |

TABLE 25A

| Compound # | Vehicle | Sample Volume | Target conc. (mg/ml) Nalmefene amount | Appearance Initial | Appearance 2 hours | Appearance 24 hours | 7 months in 40 C./75% RH |
|---|---|---|---|---|---|---|---|
| 25 | Sesame oil + 20 uL Benzyl Alcohol | 1 + 1 mL | 400 | Light amber transparent oil | Light amber transparent oil | Light amber transparent oil | Light hazy oil, possible immiscible particles. |
| 34 | Sesame oil + 20 uL Benzyl Alcohol | 1 + 1 mL | 400 | Light amber transparent oil | Light amber transparent oil | Light amber transparent oil | Yellow hazy oil, possible immiscible oil droplets. |
| 44 | J&K Cottonseed oil + 10 uL | 1 mL | 350 | Light clear yellow oil | Light clear yellow oil | Light clear yellow oil | |

TABLE 25A-continued

| | | | | | | | |
|---|---|---|---|---|---|---|---|
| 45 | Benzyl Alcohol J&K Cottonseed oil + 20 uL Benzyl Alcohol | 1 + 1 mL | 300 | Light yellow clear oil | Light yellow clear oil | Light yellow clear oil | Yellow hazy oil, possible small oil droplets |
| 46 | J&K Cottonseed oil + 20 uL Benzyl Alcohol | 1 + 1 mL | 300 | Light yellow hazy oil | Light yellow hazy oil | Light yellow hazy oil | Yellow hazy non-homogenous oil with obvious immiscible oil droplets |
| 48 | Sesame oil + 10 uL Benzyl Alcohol | 1 mL | 400 | Light hazy oil | Light hazy oil | Light hazy oil | |

| | | Assay | | | | | |
|---|---|---|---|---|---|---|---|
| Compound # | Vehicle | Initial | 2 hours | 24 hours | 7 months in 40 C./75% RH-1 | 7 months in 40 C./75% RH-2 | 7 months in 40 C./75% RH-3 |
| 25 | Sesame oil + 20 uL Benzyl Alcohol | 102.48% | 102.90% | 108.2.5% | 98.02% | 94.38% | 98.31% |
| 34 | Sesame oil + 20 uL Benzyl Alcohol | 101.77% | 102.07% | 101.11% | 102.01% | 99.07% | 97.99% |
| 44 | J&K Cottonseed oil + 10 uL Benzyl Alcohol | 101.41% | 102.44% | 102.32% | | | |
| 45 | J&K Cottonseed oil + 20 uL Benzyl Alcohol | 98.86% | 98.68% | 98.64% | 100.57% | 99.54% | 98.78% |
| 46 | J&K Cottonseed oil + 20 uL Benzyl Alcohol | 98.94% | 99.28% | 99.00% | 106.24% | 108.43% | 107.85% |
| 48 | Sesame oil + 10 uL Benzyl Alcohol | 97.50% | 96.63% | 96.39% | | | |

TABLE 25B

| | Purity | | | | | | Syringeability (21 Gauge needle) | | | Follow up | Follow-up observation at 7 months at 40 C./75% RH |
|---|---|---|---|---|---|---|---|---|---|---|---|
| Compound # | Initial | 2 hours | 24 hours | 7 months in 40 C./75% RH-1 | 7 months in 40 C./75% RH-2 | 7 months in 40 C./75% RH-3 | Initial | 2 hours | 24 hours | observation at room temp | |
| 25 | 98.36% | 98.64% | 98.57% | 97.07% | 97.13% | 97.07% | feasible | feasible | feasible | Remains in solution | No clearly visible particles on PLM microcopy |
| 34 | 98.59% | 98.58% | 98.50% | 99.35% | 99.44% | 99.46% | feasible | feasible | feasible | Remains in solution | No clearly visible particles on PLM microcopy |
| 44 | 98.68% | 98.41% | 98.73% | | | | feasible | feasible | feasible | Insoluble: grossly hazy with visible solid precipitate after 20 days | |

TABLE 25B-continued

| | | | | Purity | | | Syringeability (21 Gauge needle) | | | Follow up | Follow-up observation at 7 |
|---|---|---|---|---|---|---|---|---|---|---|---|
| Compound # | Initial | 2 hours | 24 hours | 7 months in 40 C./75% RH-1 | 7 months in 40 C./75% RH-2 | 7 months in 40 C./75% RH-3 | Initial | 2 hours | 24 hours | observation at room temp | months at 40 C./75% RH |
| 45 | 99.58% | 101.17% | 100.62% | 94.60% | 94.68% | 94.67% | feasible | feasible | feasible | Remains in solution | Possible small visible particles on PLM microscopy |
| 46 | 97.96% | 97.96% | 97.95% | 95.48% | 95.42% | 95.54% | feasible | feasible | feasible | Insoluble: grossly hazy with visible solid precipitate after 20 days | Obvious particles on on PLM microscopy |
| 48 | 98.97% | 98.80% | 98.53% | | | | feasible | feasible | feasible | Insoluble: grossly hazy with visible solid precipitate after 170 days. Crystalline particles on PLM microscopy. Drug substance changed from colorless oil to white wax within 4 weeks. | |

TABLE 26A

| | | | Target conc. (mg/ml) | Appearance | | | |
|---|---|---|---|---|---|---|---|
| Compound # | Vehicle | Sample Volume | Nalmefene amount | Initial | 24 hours | 3 months in 40 C./75% RH | 6 months in 40 C./75% RH |
| 6 | Sesame oil + 50 uL Benzyl Alcohol | 5 mL | 400 | Light amber transparent oil | Light amber transparent oil | Light amber transparent oil (at 25 C.) | Light amber transparent oil |
| 15 | Sesame oil + 50 uL Benzyl Alcohol | 5 mL | 400 | Light amber transparent oil | Light amber transparent oil | Light amber transparent oil | Light amber transparent oil |
| 17 | Sesame oil + 50 uL Benzyl Alcohol | 5 mL | 400 | Light amber transparent oil | Light amber transparent oil | Light amber transparent oil | Light amber transparent oil |
| 18 | Sesame oil + 50 uL Benzyl Alcohol | 5 mL | 400 | Light amber transparent oil | Light amber transparent oil | Light amber transparent oil | Light amber transparent oil |
| 9 | Sesame oil + 50 uL Benzyl Alcohol | 5 mL | 400 | Light amber transparent oil | Light amber transparent oil | Light amber transparent oil | Light amber transparent oil |
| 59 | Sesame oil + 10 uL Benzyl Alcohol | 5 mL | 86 | Light amber transparent oil | Light amber transparent oil | | |
| 24 | Cottonseed oil + 200 uL Benzyl Alcohol | 20 mL | 400 | Pale yellow oil | | | |
| 45 | Sesame oil + 1% Benzyl alcohol | 20 mL | 400 | clear oil | | | |
| | Sesame oil + 1% Benzyl alcohol | 1 mL | 400 | clear oil | | | |
| | Sesame oil + 1% Benzyl alcohol | 1 mL | 400 | clear oil | | | |
| | Sesame oil + 1% Benzyl alcohol | 1 mL | 400 | clear oil | | | |
| 34 | Sesame oil + 100 ul Benzyl Alcohol | 10 mL | 400 | Brown oil | | | |
| 7 | Sesame oil + 1% Benzyl alcohol | 5 + 1 + 1 + 1 mL | 400 | Almost clear solution | | | |
| 43 | Sesame oil + 1% Benzyl alcohol | 10 mL | 400 | Brown oil | | | |
| 9 | Sesame oil + 1% Benzyl alcohol | 5 ml 1 ml 1 ml 1 ml | 400 | Almost clear solution | | | |
| 1 | Sesame oil + 1% Benzyl alcohol | 5 + 1 + 1 mL | 400 | Slightly turbid oil | | | |
| 3 | Sesame oil + 1% Benzyl alcohol | 5 + 5 mL | 400 | Light amber transparent oil | Light amber transparent oil (6 hr) | | |
| 4 | Sesame oil + 1% Benzyl alcohol | 5 + 1 + 1 mL | 400 | Almost clear solution | | | |

TABLE 26A-continued

| Compound # | Vehicle | Sample Volume | Target conc. (mg/ml) Nalmefene amount | Appearance Initial | 24 hours | 3 months in 40 C./75% RH | 6 months in 40 C./75% RH |
|---|---|---|---|---|---|---|---|
| 5 | Sesame oil + 1% Benzyl alcohol | 1 + 1 + 1 mL | 400 | Light amber transparent oil | | | |
| 35 | Sesame oil + 1% Benzyl alcohol | 10 mL | 400 | Almost clear oil | | | |

TABLE 26B

| Compound # | Assay | | | | | | |
|---|---|---|---|---|---|---|---|
| | Initial-1 | Initial-2 | Initial-3 | 24 hr-1 | 24 hr-2 | 24 hr-3 | 3 months in 40 C./75% RH-1 |
| 6 | 103.19% | 106.47% | 104.72% | 100.81% | 100.60% | 101.40% | 102.15% (25 C.) |
| 15 | 99.37% | 98.69% | 101.17% | 97.06% | 101.32% | 99.43% | 97.75% |
| 17 | 98.84% | 99.62% | 99.49% | 98.02% | 98.22% | 98.07% | 101.42% |
| 18 | 93.67% | 98.55% | 96.11% | 95.75% | 95.77% | 93.03% | 102.46% |
| 9 | 102.27% | 100.89% | 101.56% | 99.70% | 97.28% | 90.59% | 101.74% |
| 59 | 102.52% | 102.59% | 102.71% | 103.05% | 102.47% | 102.90% | |
| 24 | 112.73% | 105.24% | 103.76% | | | | |
| 45 | 98.12% | 98.99% | 100.30% | | | | |
| | 100.05% | 101.02% | 99.92% | | | | |
| | 99.86% | 101.14% | 99.39% | | | | |
| | 99.91% | 99.03% | 99.99% | | | | |
| 34 | 96.78% | 97.68% | 98.16% | | | | |
| 7 | 99.73% | 100.16% | 101.37% | | | | |
| 43 | 99.27% | 99.39% | 97.86% | | | | |
| 9 | 99.23% | 99.79% | 99.83% | | | | |
| | 99.35% | 98.76% | 98.66% | | | | |
| | 98.93% | 100.93% | 103.17% | | | | |
| | 109.00% | 109.82% | 111.59% | | | | |
| 1 | 110.88% | 111.97% | 110.59% | | | | |
| 3 | N/A | N/A | N/A | 97.91% (6 days) | 97.55% (6 days) | 94.13% (6 days) | |
| 4 | 100.31% | 97.12% | 97.52% | | | | |
| 5 | 96.64% | 95.72% | 96.29% | | | | |
| 35 | 98.21% | 96.79% | 99.37% | | | | |

| Compound # | Assay | | | | |
|---|---|---|---|---|---|
| | 3 months in 40 C./75% RH-2 | 3 months in 40 C./75% RH-3 | 6 months in 40 C./75% RH-1 | 6 months in 40 C./75% RH-2 | 6 months in 40 C./75% RH-3 |
| 6 | 101.9% (25 C.) | 99.07% (25 C.) | 101.25% | 101.08% | 101.24% |
| 15 | 97.98% | 97.53% | 101.91% | 101.82% | 102.09% |
| 17 | 101.39% | 101.30% | 103.37% | 103.24% | 103.18% |
| 18 | 103.29% | 102.94% | 99.73% | 100.49% | 100.23% |
| 9 | 102.03% | 101.57% | 98.23% | 98.80% | 93.52% |
| 59 | | | | | |
| 24 | | | | | |
| 45 | | | | | |
| 34 | | | | | |
| 7 | | | | | |
| 43 | | | | | |
| 9 | | | | | |
| 1 | | | | | |
| 3 | | | | | |
| 4 | | | | | |
| 5 | | | | | |
| 35 | | | | | |

TABLE 26C

| Compound # | Purity | | | | | | | | | | | Syringeability (21 Gauge needle) | | | | Follow up observation at room temp |
|---|---|---|---|---|---|---|---|---|---|---|---|---|---|---|---|---|
| | Initial-1 | Initial-2 | Initial-3 | 24 hr-1 | 24 hr-2 | 24 hr-3 | 3 months in 40 C./75% RH-1 | 3 months in 40 C./75% RH-2 | 3 months in 40 C./75% RH-3 | 6 months in 40 C./75% RH-1 | 6 months in 40 C./75% RH-2 | 6 months in 40 C./75% RH-3 | Initial | 24 hours | 3 months | 6 months | |
| 6 | 99.48% | 99.46% | 99.37% | 99.36% | 99.35% | 99.44% | 99.29% (25 C.) | 99.81% (25 C.) | 98.75% (25 C.) | 98.88% | 98.86% | 98.89% | feasible | feasible | feasible | feasible | Remains in Solution |
| 15 | 96.87% | 97.19% | 96.88% | 96.80% | 96.39% | 96.84% | 96.86% | 96.57% | 96.70% | 96.20% | 96.18% | 96.21% | feasible | feasible | feasible | feasible | Remains in Solution |
| 17 | 98.49% | 98.70% | 98.78% | 98.45% | 98.65% | 98.82% | 98.52% (25 C.) | 98.29% (25 C.) | 98.92% (25 C.) | 98.74% | 98.75% | 98.70% | feasible | feasible | feasible | feasible | Remains in Solution |
| 18 | 99.32% | 99.09% | 98.97% | 99.00% | 99.14% | 99.07% | 98.38% | 98.39% | 98.39% | 98.94% | 98.54% | 98.71% | feasible | feasible | feasible | feasible | Remains in Solution |
| 9 | 99.38% | 99.36% | 99.49% | 99.33% | 99.56% | 99.44% | 99.44% | 99.17% | 99.49% | 99.56% | 99.53% | 99.23% | feasible | feasible | feasible | feasible | Remains in Solution |
| 59 | 99.00% | 98.88% | 98.94% | 99.03% | 98.87% | 98.91% | | | | | | | feasible | feasible | | | Remains in Solution |
| 24 | 99.63% | 99.62% | 99.64% | | | | | | | | | | feasible | | | | Remains in Solution |
| 45 | 99.73% 99.48% 99.86% 99.73% | 99.71% 99.38% 99.63% 99.57% | 99.68% 99.58% 99.68% 99.78% | | | | | | | | | | Feasible N/A N/A N/A | | | | |
| 34 | 95.93% | 95.84% | 95.91% | | | | | | | | | | feasible | | | | Purity of compound in Drug product was 95.9%. Was found to be 99% after synthesis. Precipitation at 55 days |
| 7 | 99.34% | 99.31% | 99.23% | | | | | | | | | | feasible | | | | Remains in Solution |
| 43 | 98.60% | 98.61% | 98.49% | | | | | | | | | | feasible | | | | Remains in Solution |
| 9 | 98.26% | 98.14% | 97.98% | | | | | | | | | | feasible | | | | Hazy homogenous appearance, possible solution ~24 hr Visible sold precipitant ~24 hr Visible sold precipitant ~24 hr Clearly |

TABLE 26C-continued

| | Purity | | | | | | | | | | | Syringeability (21 Gauge needle) | | | Follow up |
|---|---|---|---|---|---|---|---|---|---|---|---|---|---|---|---|
| Compound # | Initial-1 | Initial-2 | Initial-3 | 24 hr-1 | 24 hr-2 | 24 hr-3 | 3 months in 40 C./75% RH-1 | 3 months in 40 C./75% RH-2 | 3 months in 40 C./75% RH-3 | 6 months in 40 C./75% RH-1 | 6 months in 40 C./75% RH-2 | 6 months in 40 C./75% RH-3 | Initial | 24 hours | 3 months | 6 months | observation at room temp |
| 1 | 100.00% | 100.00% | 100.00% | | | | | | | | | | | | | | precipitated out of solution ~24 hr |
| 3 | N/A | N/A | N/A | 99.5% (6 days) | 99.54% (6 days) | 99.34% (6 days) | | | | | | | feasible | | | | Remains in Solution |
| 4 | 99.65% | 99.66% | 99.76% | | | | | | | | | | feasible | | | | Remains in Solution |
| 5 | 99.72% | 99.71% | 99.72% | | | | | | | | | | feasible | | | | Remains in Solution |
| 35 | 100.00% | 100.00% | 100.00% | | | | | | | | | | feasible | | | | Remains in Solution |

IV. Pharmacokinetic Evaluation

Example 1: Rat Pharmacokinetic Studies

Purpose

The purpose of this study is to determine the pharmacokinetics of test compounds in plasma, following intramuscular administration to male Sprague Dawley Rats (n=3, unless otherwise specified).

Acclimation/Quarantine

Animals are assessed as to their general health and acclimated for at least 3 days before being placed on study.

Animal Husbandry

Animals are housed during acclimation and individually housed during the study. The animal room environment was controlled (target conditions: temperature 18 to 26° C., relative humidity 30 to 70%, 12 hours artificial light and 12 hours dark). Temperature and relative humidity were monitored daily. Water was provided to the animals ad libitum.

Animal Body Weights and Clinical Observation

Body weights were determined before selection to the study and on the day of dose administration. Weight monitoring was done every week.

Detailed clinical observation including behavior and activity, reflection, respiration, skin and fur, facial feature, genitourinary system, and other gross lesions was performed on the dosing day and at each sample collection time point.

Dose Administration

The dose formulation of 400 mg base equivalents/ml in sesame oil+1% benzyl alcohol (unless otherwise specified) was administered by intramuscular injection. The dose volume was determined by the animals' body weight determined on the morning of dosing day.

Sample Collection

Each blood collection (about 0.2 mL per time point) was performed from jugular vein puncture of each animal into pre-chilled plastic microcentrifuge tubes containing 5 μL of 160 mg/mL sodium fluoride/potassium oxalate (NaF/KO=1/3) with 5% PMSF (100 mM in ethanol) as stabilizer and 4 μL of EDTA-K2 as anti-coagulant and placed on wet ice until centrifugation.

Plasma Processing

Each collected blood sample was centrifuged for 4 minutes at 4° C. and 10000 rpm for plasma collection. Plasma was collected and transferred into a pre-labeled PP tube in dry ice at each time point and precipitated immediately using ACN at a ratio of 1:4 (plasma:ACN). Centrifuged again (10 minutes, 12000 rpm) and obtain the supernatant. After terminal collection, all supernatant was stored at approximately −80° C. until bioanalysis.

Bioanalytical Method and Sample Analysis

LC-MS/MS methods for the quantitative determination of test compound in biological matrix were developed. A calibration curve with 8 non-zero calibration standards were applied for the method including LLOQ (0.05 ng/ml). The sample analysis was performed concurrently with a set of calibration standards and two sets of QC samples using the LC-MS/MS method.

Data Analysis

Plasma concentration versus time data was analyzed by non-compartmental approaches using the Phoenix WinNonlin 6.3 software program. $C_{max}$, $T_{max}$, $T_{1/2}$, $AUC_{(0-t)}$, $AUC_{(0-inf)}$, $MRT_{(0-t)}$, $MRT_{(0-inf)}$ and graphs of plasma concentration versus time profile were prepared.

The dose for nalmefene dodecanoate was determined by allometric scaling to rat from dog doses as previously reported (Gaekens et al, Journal of Controlled Release 232 (2016) 196-202). Terminal half life was determined for active metabolite of select compounds, and is used for estimating duration above minimally effective plasma concentration for the active metabolite.

TABLE 27

| Compound | Nominal Dose (mg/kg) | Vehicle | Half-life $t_{1/2}$ (hour) prodrug | Terminal Half-life $t_{1/2}$ (hour) nalmefene | $AUC_{0-inf}$ (ng · h/mL) prodrug | $AUC_{0-inf}$ (ng · h/mL) nalmefene |
|---|---|---|---|---|---|---|
| Nalmefene HCl-IR | 0.80 | saline | — | 0.87 | — | 66.0 |
| 59 | 17 | Sesame oil + 1% Benzyl Alcohol | 15.2 | 248 | 10.4 | 1026 |
| 6 | 80 | Sesame oil + 1% Benzyl Alcohol | 340 | 569 | 78.9 | 3576 |
| 6 | 123 | Sesame oil + 1% Benzyl Alcohol | 213 | 425 | 620 | 14704 |
| 6 | 165 | Sesame oil + 1% Benzyl Alcohol | 204 | 491 | 637 | 18876 |
| 15 | 80 | Sesame oil + 1% Benzyl Alcohol | 1553 | 639 | 679 | 3046 |
| 15 | 123 | Sesame oil + 1% Benzyl Alcohol | 884 | 993 | 2574 | 7232 |
| 15 | 165 | Sesame oil + 1% Benzyl Alcohol | 500 | 451 | 2789 | 14019 |
| 17 | 200 | Sesame oil + 1% Benzyl Alcohol | Prodrug not detected | 266 | Prodrug not detected | 16178 |
| 18 | 80 | Sesame oil + 1% Benzyl Alcohol | Prodrug not detected | 599 | Prodrug not detected | 8217 |
| 18 | 123 | Sesame oil + 1% Benzyl Alcohol | Prodrug not detected | 3409 | Prodrug not detected | 13658 |
| 18 | 200 | Sesame oil + 1% Benzyl Alcohol | Prodrug not detected | 847 | Prodrug not detected | 15104 |
| 23 (naltrexone metabolite) | 200 | Sesame oil + 1% Benzyl Alcohol | Prodrug not detected | Not assessed | Prodrug not detected | 27105 (naltrexone metabolite) |
| 24 | 80 | Cottonseed + 1% Benzyl Alcohol | 398 | 1093 | 147 | 5584 |

TABLE 27-continued

| Compound | Nominal Dose (mg/kg) | Vehicle | Half-life $t_{1/2}$ (hour) prodrug | Terminal Half-life $t_{1/2}$ (hour) nalmefene | $AUC_{0\text{-}inf}$ (ng · h/mL) prodrug | $AUC_{0\text{-}inf}$ (ng · h/mL) nalmefene |
|---|---|---|---|---|---|---|
| 24 | 123 | Cottonseed oil + 1% Benzyl Alcohol | 717 | 445 | 547 | 11283 |
| 24 | 165 | Cottonseed oil + 1% Benzyl Alcohol | 851 | 458 | 453 | 19031 |
| 29 | 165 | Sesame oil + 1% Benzyl Alcohol | 175 | 911 | 74.8 | 17313 (naltrexone metabolite) |

No adverse affect on body weight or clinical observations were noted in any rats across all studies.

Time vs nalmefene concentration data for nalmefene HCL in 1 mg/ml at 0.80 mg/kg is provided in Table 28a.

TABLE 28a

| Time (h) | Mean conc Nalmefene (ng/mL) |
|---|---|
| 1.00 | 29.4 |
| 2.00 | 2.09 |
| 4.00 | 0.212 |
| 8.00 | 0.0178 |
| 12 | ND* |
| 24.0 | ND |

*Not detected

Time vs nalmefene concentration data for compound 59 (nalmefene dodecanoate) in 86 mg/ml concentration at 17 mg/kg is provided in Table 28b.

TABLE 28b

| Time (h) | Mean conc Nalmefene (ng/mL) |
|---|---|
| 1.00 | 7.85 |
| 2.00 | 8.10 |
| 4.00 | 7.45 |
| 8.00 | 6.85 |
| 24.0 | 6.96 |
| 48.0 | 7.92 |
| 72.0 | 5.77 |
| 144 | 1.59 |
| 312 | 0.403 |
| 480 | 0.235 |
| 648 | 0.145 |

Time vs nalmefene concentration data for compound 6 at 80 mg/kg is provided in Table 29.

TABLE 29

| Time (h) | Mean conc Nalmefene (ng/mL) |
|---|---|
| 1.00 | 9.51 |
| 2.00 | 7.11 |
| 4.00 | 5.48 |
| 8.00 | 5.09 |
| 24.0 | 5.74 |
| 48.0 | 8.48 |
| 72.0 | 7.18 |
| 144 | 3.73 |
| 312 | 3.08 |
| 480 | 2.49 |
| 648 | 2.09 |
| 816 | 1.80 |
| 984 | 1.39 |
| 1152 | 1.14 |
| 1320 | 0.833 |
| 1488 | 0.413 |

Time vs nalmefene concentration data for compound 6 at 123 mg/kg is provided in Table 30.

TABLE 30

| Time (h) | Mean conc Nalmefene (ng/mL) |
|---|---|
| 0.250 | 43.8 |
| 1.00 | 36.3 |
| 2.00 | 24.0 |
| 4.00 | 16.7 |
| 8.00 | 12.1 |
| 24.0 | 11.0 |
| 48.0 | 14.2 |
| 72.0 | 10.7 |
| 144 | 9.17 |
| 312 | 13.6 |
| 480 | 10.6 |
| 648 | 11.1 |
| 816 | 8.8 |
| 984 | 6.5 |
| 1152 | 4.0 |
| 1320 | 3.2 |
| 1488 | 1.6 |
| 1656 | 1.7 |
| 1824 | 1.2 |
| 1992 | 0.9 |
| 2160 | 0.8 |
| 2328 | 0.8 |
| 2496 | 0.6 |
| 2664 | 0.5 |

Time vs nalmefene concentration data for compound 6 at 165 mg/kg is provided in Table 31.

TABLE 31

| Time (h) | Mean conc Nalmefene (ng/mL) |
|---|---|
| 0.250 | 50.4 |
| 1.00 | 48.0 |
| 2.00 | 29.2 |
| 4.00 | 19.3 |
| 8.00 | 13.9 |
| 24.0 | 12.3 |
| 48.0 | 14.4 |
| 72.0 | 12.4 |
| 144 | 10.7 |

Time vs nalmefene concentration data for compound 15 at 80 mg/kg is provided in Table 32.

TABLE 32

| Time (h) | Mean conc Nalmefene (ng/mL) |
|---|---|
| 1.00 | 7.07 |
| 2.00 | 4.21 |
| 4.00 | 2.10 |
| 8.00 | 1.42 |
| 24.0 | 1.98 |
| 48.0 | 2.39 |
| 72.0 | 3.25 |
| 144 | 2.32 |
| 312 | 2.18 |
| 480 | 3.03 |
| 648 | 2.15 |
| 816 | 0.944 |
| 984 | 0.714 |
| 1152 | 0.745 |
| 1320 | 0.663 |
| 1488 | 0.706 |
| 1656 | 0.697 |
| 1824 | 0.514 |
| 1992 | 0.322 |
| 2160 | 0.441 |

Time vs nalmefene concentration data for compound 15 at 123 mg/kg is provided in Table 33.

TABLE 33

| Time (h) | Mean conc Nalmefene (ng/mL) |
|---|---|
| 0.250 | 18.7 |
| 1.00 | 20.4 |
| 2.00 | 13.4 |
| 4.00 | 6.20 |
| 8.00 | 2.74 |
| 24.0 | 1.54 |
| 48.0 | 1.89 |
| 72.0 | 2.00 |
| 144 | 2.97 |
| 312 | 5.64 |
| 480 | 7.88 |
| 648 | 6.60 |
| 816 | 5.33 |
| 984 | 3.87 |
| 1152 | 2.41 |
| 1320 | 2.10 |
| 1488 | 2.33 |
| 1656 | 2.01 |
| 1824 | 1.93 |
| 1992 | 1.50 |
| 2160 | 1.25 |
| 2328 | 1.01 |
| 2496 | 1.18 |
| 2664 | 0.831 |

Time vs nalmefene concentration data for compound 15 at 165 mg/kg is provided in Table 34.

TABLE 34

| Time (h) | Mean conc Nalmefene (ng/mL) |
|---|---|
| 0.250 | 30.3 |
| 1.00 | 24.1 |
| 2.00 | 15.3 |
| 4.00 | 7.60 |
| 8.00 | 2.92 |
| 24.0 | 1.65 |
| 48.0 | 2.43 |
| 72.0 | 2.60 |
| 144 | 3.11 |
| 312 | 6.45 |
| 480 | 13.2 |
| 648 | 12.5 |
| 816 | 7.92 |
| 984 | 6.30 |
| 1152 | 5.30 |
| 1320 | 4.54 |
| 1488 | 3.62 |
| 1656 | 3.24 |
| 1824 | 3.38 |
| 1992 | 2.16 |
| 2160 | 1.62 |
| 2328 | 0.966 |
| 2496 | 0.831 |
| 2664 | 0.903 |

Time vs nalmefene concentration data for compound 17 at 200 mg/kg is provided in Table 35.

TABLE 35

| IM Time (h) | Mean conc Nalmefene (ng/mL) |
|---|---|
| 1.00 | 249 |
| 2.00 | 299 |
| 4.00 | 364 |
| 8.00 | 340 |
| 24.0 | 157 |
| 48.0 | 80.0 |
| 72.0 | 44.3 |
| 144 | 15.5 |
| 312 | 5.09 |
| 480 | 3.04 |
| 648 | 3.37 |
| 816 | 1.90 |
| 984 | 1.29 |
| 1152 | 0.737 |
| 1320 | 0.375 |
| 1488 | 0.309 |

Time vs nalmefene concentration data for compound 18 at 80 mg/kg is provided in Table 36.

---

TABLE 31-continued

| Time (h) | Mean conc Nalmefene (ng/mL) |
|---|---|
| 312 | 14.5 |
| 480 | 18.1 |
| 648 | 17.1 |
| 816 | 14.2 |
| 984 | 10.5 |
| 1152 | 6.2 |
| 1320 | 4.9 |
| 1488 | 2.8 |
| 1656 | 2.3 |
| 1824 | 1.8 |
| 1992 | 1.3 |
| 2160 | 1.3 |
| 2328 | 1.1 |
| 2496 | 0.9 |
| 2664 | 0.7 |

TABLE 36

| Time (h) | Mean conc Nalmefene (ng/mL) |
|---|---|
| 0.250 | 5.13 |
| 1.00 | 14.9 |
| 2.00 | 22.9 |
| 4.00 | 39.9 |
| 8.00 | 35.6 |
| 24.0 | 36.6 |
| 48.0 | 32.7 |
| 72.0 | 28.2 |
| 144 | 21.5 |
| 312 | 5.60 |
| 480 | 2.99 |
| 648 | 1.58 |
| 816 | 1.29 |
| 984 | 1.34 |
| 1152 | 0.99 |
| 1320 | 0.75 |
| 1488 | 0.505 |
| 1656 | 0.465 |
| 1824 | 0.412 |
| 1992 | 0.383 |

Time vs nalmefene concentration data for compound 18 at 123 mg/kg is provided in Table 37.

TABLE 37

| Time (h) | Mean conc Nalmefene (ng/mL) |
|---|---|
| 0.250 | 3.98 |
| 1.00 | 15.6 |
| 2.00 | 24.4 |
| 4.00 | 43.5 |
| 8.00 | 43.7 |
| 24.0 | 39.2 |
| 48.0 | 29.8 |
| 72.0 | 26.5 |
| 144 | 15.9 |
| 312 | 4.21 |
| 480 | 5.59 |
| 648 | 4.73 |
| 816 | 4.01 |
| 984 | 4.26 |
| 1152 | 3.14 |
| 1320 | 3.10 |
| 1488 | 2.44 |
| 1656 | 2.55 |
| 1824 | 2.55 |
| 1992 | 1.38 |
| 2160 | 2.52 |
| 2328 | 3.11 |
| 2496 | 1.92 |
| 2664 | 2.27 |

Time vs nalmefene concentration data for compound 18 at 200 mg/kg is provided in Table 38.

TABLE 38

| Time (h) | Mean conc Nalmefene (ng/mL) |
|---|---|
| 1.00 | 32.3 |
| 2.00 | 59.0 |
| 4.00 | 64.8 |
| 8.00 | 76.8 |
| 24.0 | 54.2 |
| 48.0 | 46.7 |
| 72.0 | 38.4 |
| 144 | 29.0 |
| 312 | 13.4 |
| 480 | 5.17 |
| 648 | 5.51 |

TABLE 38-continued

| Time (h) | Mean conc Nalmefene (ng/mL) |
|---|---|
| 816 | 3.54 |
| 984 | 2.90 |
| 1152 | 2.80 |
| 1320 | 2.05 |
| 1488 | 1.77 |
| 1656 | 1.40 |
| 1824 | 1.68 |
| 1992 | 1.18 |
| 2160 | 1.42 |
| 2328 | 1.43 |
| 2496 | 0.781 |
| 2664 | 1.18 |
| 2832 | 2.34 |

Time vs naltrexone concentration data for compound 23 at 200 mg/kg is provided in Table 39.

TABLE 39

| Time (h) | Mean conc Naltrexone (ng/mL) |
|---|---|
| 1.00 | 32.3 |
| 2.00 | 655 |
| 4.00 | 727 |
| 8.00 | 603 |
| 24.0 | 384 |
| 48.0 | 181 |
| 72.0 | 109 |

Time vs nalmefene concentration data for compound 24 at 80 mg/kg is provided in Table 40.

TABLE 40

| Time (h) | Mean conc Nalmefene (ng/mL) |
|---|---|
| 0.250 | 1.93 |
| 1.00 | 2.94 |
| 2.00 | 4.06 |
| 4.00 | 4.69 |
| 8.00 | 4.86 |
| 24.0 | 5.47 |
| 48.0 | 5.43 |
| 72.0 | 5.46 |
| 144 | 3.87 |
| 312 | 3.87 |
| 480 | 4.60 |
| 648 | 5.29 |
| 816 | 3.16 |
| 984 | 2.32 |
| 1152 | 2.14 |
| 1320 | 1.45 |
| 1488 | 1.25 |
| 1656 | 1.05 |
| 1824 | 1.14 |
| 1992 | 1.09 |
| 2160 | 0.971 |
| 2328 | 0.798 |
| 2496 | 0.788 |
| 2664 | 0.719 |

Time vs nalmefene concentration data for compound 24 at 123 mg/kg is provided in Table 41.

TABLE 41

| Time (h) | Mean conc Nalmefene (ng/mL) |
|---|---|
| 0.250 | 1.89 |
| 1.00 | 2.38 |
| 2.00 | 3.28 |
| 4.00 | 4.14 |
| 8.00 | 4.32 |
| 24.0 | 6.20 |
| 48.0 | 5.56 |
| 72.0 | 5.03 |
| 144 | 4.54 |
| 312 | 5.42 |
| 480 | 9.14 |
| 648 | 10.6 |
| 816 | 8.71 |
| 984 | 6.46 |
| 1152 | 6.57 |
| 1320 | 3.41 |
| 1488 | 2.64 |
| 1656 | 1.93 |
| 1824 | 1.29 |
| 1992 | 1.13 |
| 2160 | 0.821 |
| 2328 | 0.763 |
| 2496 | 0.457 |
| 2664 | 0.562 |

Time vs nalmefene concentration data for compound 24 at 165 mg/kg is provided in Table 42.

TABLE 42

| Time (h) | Mean conc Nalmefene (ng/mL) |
|---|---|
| 0.250 | 3.48 |
| 1.00 | 4.90 |
| 2.00 | 5.23 |
| 4.00 | 6.41 |
| 8.00 | 7.24 |
| 24.0 | 8.44 |
| 48.0 | 8.24 |
| 72.0 | 7.80 |
| 144 | 9.93 |
| 312 | 12.8 |
| 480 | 18.0 |
| 648 | 16.6 |
| 816 | 15.3 |
| 984 | 9.14 |
| 1152 | 5.62 |
| 1320 | 5.44 |
| 1488 | 3.62 |
| 1656 | 3.90 |
| 1824 | 2.69 |
| 1992 | 1.81 |
| 2160 | 1.28 |
| 2328 | 1.34 |
| 2496 | 0.886 |
| 2664 | 0.591 |

Time vs naltrexone concentration data for compound 29 at 165 mg/kg (at 400 mg/ml in sesame oil) is provided in Table 43a.

TABLE 43a

| Time (h) | Mean conc Naltrexone (ng/mL) |
|---|---|
| 0.250 | 13.8 |
| 1.00 | 30.4 |
| 2.00 | 39.6 |
| 4.00 | 53.2 |
| 8.00 | 53.1 |
| 24.0 | 46.2 |
| 48.0 | 34.3 |
| 72.0 | 30.4 |
| 144 | 39.6 |
| 312 | 28.4 |
| 480 | 13.1 |
| 648 | 6.00 |
| 816 | 4.56 |
| 984 | 3.88 |
| 1152 | 3.71 |
| 1320 | 2.71 |
| 1488 | 2.70 |
| 1656 | 2.45 |
| 1824 | 2.25 |
| 1992 | 1.92 |

Time vs naltrexone concentration data for compound 29 (at 300 mg/ml in cottonseed oil, n=2) at 165 mg/kg is provided in Table 43b.

TABLE 43b

| Time (h) | Mean conc Naltrexone (ng/mL) |
|---|---|
| 0.250 | 29.0 |
| 1.00 | 40.1 |
| 2.00 | 69.3 |
| 4.00 | 91.4 |
| 8.00 | 90.5 |
| 24.0 | 92.1 |
| 48.0 | 66.9 |
| 72.0 | 54.7 |

Example 2: Dog Pharmacokinetic Studies

Purpose

The purpose of this study is to determine the pharmacokinetics of test compounds in plasma, following deep intramuscular administration to Beagle dogs (n=3, unless otherwise specified).

Acclimation/Quarantine

Animals are assessed as to their general health and acclimated for at least 5 days before being placed on study.

Animal Husbandry

Animals are pair housed during acclimation and individually housed during the study. The room(s) will be controlled and monitored for relative humidity (targeted mean range 40% to 70%, and any excursion from this range for more than 3 hours will be documented as a deviation) and temperature (targeted mean range 18° to 26° C., and any excursion from this range will be documented as a deviation) with 10 to 20 air changes/hour. The room will be on a 12-hour light/dark cycle except when interruptions are necessitated by study activities. Animals will be fed twice daily. Stock dogs will be fed approximately 220 grams of Certified Dog Diet daily (Beijing Keao Xieli Feed Co., Ltd. Beijing, P. R. China). These amounts can be adjusted as necessary based on food consumption of the group or an individual body weight changes of the group or an individual and/or changes in the certified diet. Reverse osmosis (RO) water is available to all animals, ad libitum. RO water is analyzed every three months and every batch of feed is analyzed before using. Enrichment toys are provided.

Animal Body Weights and Clinical Observation

Body weights were determined before selection to the study and on the day of dose administration. Weight monitoring was done every week.

Detailed clinical observation including behavior and activity, reflection, respiration, skin and fur, facial feature, genitourinary system, and other gross lesions was performed on the dosing day and at each sample collection time point.

Dose Administration

The dose formulation (concentration–400 mg base equivalents/ml in sesame oil+1% benzyl alcohol, unless otherwise specified) was administered via deep intramuscularly (unless otherwise specified). The injection vehicle was also dosed via deep intramuscular route (unless otherwise specified) on contralateral site of each animal at study initiation. The animals were sedated with Propofol at 6 mg/kg via IV administration. Following sedation hair was carefully removed from around the injection site and the area gently cleaned. Care will be taken to avoid irritating skin during shaving and cleaning the injection site. Then dogs will be dosed with deep IM administration. At least 2.5 cm depth from the surface into the central aspect of the quadriceps or biceps femoris muscle, by angling the needle toward the femur. If the needle hits the femur, simply draws back slightly and then inject. The dose volume will be determined by the animals' body weight collected on the morning of dosing day. For repeated administration, the injection sites may be rotated to minimize tissue injury.

Sample Collection

Blood samples were collected from a peripheral vessel from restrained, non-sedated animals per sampling time point.

Approximately 0.8 mL blood will be collected at each time point. All blood samples will be transferred into pre-chilled plastic microcentrifuge tubes containing 20 μL of 160 mg/mL sodium fluoride/potassium oxalate (NaF/KO=1/3) with 5% PMSF (100 mM in ethanol) as stabilizer and 16 μL of EDTA-K2 (0.5M) as anti-coagulant and placed on wet ice until centrifugation.

Each collected blood will be in the wet-ice before centrifuge.

Plasma Processing

Each collected blood sample was centrifuged for 4 minutes at 4° C. and 10000 rpm for plasma collection. Plasma was collected and transferred into a pre-labeled PP tube in dry ice at each time point and precipitated immediately using ACN at a ratio of 1:4 (plasma:ACN). Centrifuged again (10 minutes, 12000 rpm) and obtain the supernatant.

After terminal collection, all supernatant was stored at approximately −80° C. F until bioanalysis.

Bioanalytical Method and Sample Analysis

LC-MS/MS methods for the quantitative determination of test compound in biological matrix were developed. A calibration curve with 8 non-zero calibration standards were applied for the method including LLOQ (0.05 ng/ml). The sample analysis was performed concurrently with a set of calibration standards and two sets of QC samples using the LC-MS/MS method.

Data Analysis

Plasma concentration versus time data was analyzed by non-compartmental approaches using the Phoenix WinNonlin 6.3 software program. $C_{max}$, $T_{max}$, $T_{1/2}$, $AUC_{(0-t)}$, $AUC_{(0-inf)}$, $MRT_{(0-t)}$, $MRT_{(0-inf)}$ and graphs of plasma concentration versus time profile were prepared.

TABLE 44

| Compound | Nominal IM Dose (mg/kg) | Vehicle | Half-life $t_{1/2}$ (hour) prodrug | Terminal Half-life $t_{1/2}$ (hour) nalmefene or naltrexone | $AUC_{0-inf}$ (ng · h/mL) prodrug | $AUC_{0-inf}$ (ng · h/mL) nalmefene or naltrexone | Status |
|---|---|---|---|---|---|---|---|
| 6 | 30 | Sesame oil + 1% Benzyl Alcohol | 95 | Data pending | 398 | 6100 | Ongoing |
|  | 48 (shallow) | Sesame oil + 1% Benzyl Alcohol | 135 | 277.9 | 1025 | 11464 | Complete |
|  | 48 (deep) | Sesame oil + 1% Benzyl Alcohol | 54 | 552.6 | 2186 | 10619 | Complete |
|  | 96 | Sesame oil + 1% Benzyl Alcohol | 88 | Data pending | 1290 | 17090 | Ongoing |
| 15 | 30 | Sesame oil + 1% Benzyl Alcohol | 134 | Data pending | 521 | 682 | Ongoing |
|  | 48 | Sesame oil + 1% Benzyl Alcohol | 518 | 4244.8 | 1144 | 15021 | Ongoing |
|  | 96 | Sesame oil + 1% Benzyl Alcohol | 162 | Data pending | 1353 | 3789 | Ongoing |
| 24 | 48 (shallow) | Cottonseed + 1% Benzyl Alcohol | 102 | 308.8 | 526 | 8500 | Complete |
|  | 48 (deep) | Cottonseed + 1% Benzyl Alcohol | 59.6 | 404.0 | 613 | 7226 | Complete |
| 45 | 30 | Cottonseed + 1% Benzyl Alcohol | 151 | Data pending | 100 | 13069 | Ongoing |
|  | 48 | Cottonseed + 1% Benzyl Alcohol | 171 | Data pending | 267 | 10973 | Ongoing |
|  | 96 | Cottonseed oil + 1% Benzyl Alcohol | None detected | Data pending | None detected | 10215 | Ongoing |
| 7 | 48 | Sesame oil + 1% Benzyl Alcohol | 201 | Data pending | 610 | 2145 | Ongoing |
| 8 | 48 | Sesame oil + 1% Benzyl Alcohol | 128 | Data pending | 264 | 8980 | Ongoing |
| 1 | 48 | Sesame oil + 1% Benzyl Alcohol | 261 | Data pending | 1040 | 3708 | Ongoing |
| 3 | 48 | Sesame oil + 1% Benzyl Alcohol | 63.1 | Data pending | 360 | 9084 | Complete |
| 4 | 48 | Sesame oil + 1% Benzyl Alcohol | 28 | Data pending | 829 | 6535 | Complete |

TABLE 44-continued

| Compound | Nominal IM Dose (mg/kg) | Vehicle | Half-life $t_{1/2}$ (hour) prodrug | Terminal Half-life $t_{1/2}$ (hour) nalmefene or naltrexone | $AUC_{0\text{-}inf}$ (ng · h/mL) prodrug | $AUC_{0\text{-}inf}$ (ng · h/mL) nalmefene or naltrexone | Status |
|---|---|---|---|---|---|---|---|
| 5 | 48 | Sesame oil + 1% Benzyl Alcohol | 70.9 | Data pending | 3869 | 8579 | Complete |
| 35 | 48 | Sesame oil + 1% Benzyl Alcohol | 70 | Data pending | None detected | None detected | Complete |

Time vs nalmefene concentration data for compound 6 at 30 mg/kg is provided in Table 45.

TABLE 45*

| Time (h) | Mean conc Nalmefene (ng/mL) |
|---|---|
| 0.25 | 8.07 |
| 1 | 11.50 |
| 2 | 7.75 |
| 4 | 4.33 |
| 8 | 3.41 |
| 24 | 10.14 |
| 48 | 10.82 |
| 72 | 12.15 |
| 168 | 10.20 |
| 336 | 5.24 |
| 504 | 2.86 |
| 672 | 3.73 |

*study is ongoing

Time vs nalmefene concentration data for compound 6 at 48 mg/kg (shallow IM injection) is provided in Table 46.

TABLE 46

| Time (h) | Mean conc Nalmefene (ng/mL) |
|---|---|
| 0.25 | 4.75 |
| 1 | 5.03 |
| 2 | 3.98 |
| 4 | 5.26 |
| 8 | 5.40 |
| 34 | 10.25 |
| 48 | 14.50 |
| 72 | 21.40 |
| 196 | 26.80 |
| 336 | 15.37 |
| 504 | 8.34 |
| 672 | 5.15 |
| 840 | 2.18 |
| 1008 | 1.82 |
| 1176 | 1.53 |
| 1344 | 1.07 |
| 1512 | 0.53 |

Time vs nalmefene concentration data for compound 6 at 48 mg/kg (deep IM injection; redosed in dogs from Table 46) is provided in Table 47a.

TABLE 47a*

| Time (h) | Mean conc Nalmefene (ng/mL) |
|---|---|
| 0.25 | 8.99 |
| 1 | 18.97 |
| 2 | 13.23 |
| 4 | 9.70 |
| 8 | 11.08 |
| 24 | 12.91 |
| 48 | 15.83 |
| 72 | 19.93 |
| 168 | 21.93 |
| 336 | 12.00 |
| 504 | 5.59 |
| 672 | 4.31 |
| 840 | 2.24 |
| 1008 | 2.07 |
| 1176 | 1.86 |
| 1344 | 1.26 |
| 1512 | 1.11 |
| 2424 | 0.37 |

Time vs nalmefene concentration data for compound 6 at 48 mg/kg (deep IM injection; single dose in naïve dogs n=2) is provided in Table 47b.

TABLE 47b*

| Time (h) | Mean conc Nalmefene (ng/mL) |
|---|---|
| 0.25 | 17.3 |
| 1 | 17.0 |
| 2 | 13.2 |
| 4 | 9.99 |
| 8 | 7.73 |
| 24 | 12.3 |
| 48 | 17.6 |
| 72 | 25.0 |
| 168 | 13.7 |
| 336 | 6.87 |
| 504 | 5.26 |
| 672 | 2.96 |

*study is ongoing

Time vs nalmefene concentration data for compound 6 at 96 mg/kg is provided in Table 48.

TABLE 48*

| Time (h) | Mean conc Nalmefene (ng/mL) |
|---|---|
| 0.25 | 13.59 |
| 1 | 24.17 |
| 2 | 14.11 |
| 4 | 12.56 |
| 8 | 6.84 |
| 24 | 17.80 |
| 48 | 22.13 |
| 72 | 33.97 |
| 168 | 41.9 |
| 336 | 22.2 |

TABLE 48*-continued

| Time (h) | Mean conc Nalmefene (ng/mL) |
|---|---|
| 504 | 13.3 |
| 672 | 7.18 |

*study is ongoing

Time vs nalmefene concentration data for compound 15 at 30 mg/kg is provided in Table 49.

TABLE 49*

| Time (h) | Mean conc Nalmefene (ng/mL) |
|---|---|
| 0.25 | 5.74 |
| 1 | 10.04 |
| 2 | 5.49 |
| 4 | 2.84 |
| 8 | 0.67 |
| 24 | 0.41 |
| 48 | 0.56 |
| 72 | 0.78 |
| 168 | 0.578 |
| 336 | 0.437 |
| 504 | 0.385 |
| 672 | 0.401 |

*study is ongoing

Time vs nalmefene concentration data for compound 15 at 48 mg/kg is provided in Table 50a.

TABLE 50a*

| Time (h) | Mean conc Nalmefene (ng/mL) |
|---|---|
| 0.25 | 6.74 |
| 1 | 15.67 |
| 2 | 10.28 |
| 4 | 4.23 |
| 8 | 1.19 |
| 24 | 1.65 |
| 48 | 1.95 |
| 72 | 3.14 |
| 168 | 2.92 |
| 336 | 3.94 |
| 504 | 2.71 |
| 672 | 1.96 |
| 840 | 1.90 |
| 1008 | 2.10 |
| 1176 | 1.70 |
| 1344 | 2.40 |
| 1512 | 2.44 |
| 2064 | 1.75 |
| 2232 | 1.58 |
| 2400 | 1.72 |
| 2568 | 1.46 |
| 2736 | 2.06 |
| 2904 | 2.19 |
| 3072 | 1.67 |
| 3240 | 1.32 |
| 3408 | 1.32 |

*study is ongoing

Time vs nalmefene concentration data for compound 15 at 48 mg/kg (repeat of study from Table 50a) is provided in Table 50b.

TABLE 50b*

| Time (h) | Mean conc Nalmefene (ng/mL) |
|---|---|
| 0.25 | 7.55 |
| 1 | 12.3 |
| 2 | 10.3 |
| 4 | 4.48 |
| 8 | 1.55 |
| 24 | 0.965 |
| 48 | 1.53 |
| 72 | 1.64 |
| 168 | 2.32 |
| 336 | 2.08 |
| 504 | 1.28 |
| 672 | 1.47 |

*study is ongoing

Time vs nalmefene concentration data for compound 15 at 96 mg/kg is provided in Table 51.

TABLE 51*

| Time (h) | Mean conc Nalmefene (ng/mL) |
|---|---|
| 0.25 | 18.63 |
| 1 | 24.13 |
| 2 | 16.83 |
| 4 | 9.81 |
| 8 | 2.84 |
| 24 | 2.38 |
| 48 | 2.65 |
| 72 | 2.98 |
| 168 | 3.61 |
| 336 | 4.06 |
| 504 | 3.03 |
| 672 | 2.32 |

*study is ongoing

Time vs nalmefene concentration data for compound 18 at 48 mg/kg is provided in Table 52.

TABLE 52

| Time (h) | Mean conc Nalmefene (ng/mL) |
|---|---|
| 0.25 | 3.49 |
| 1 | 5.44 |
| 2 | 5.18 |
| 4 | 6.62 |
| 8 | 9.77 |
| 24 | 14.40 |
| 48 | 14.24 |
| 72 | 16.13 |

Time vs nalmefene concentration data for compound 24 at 48 mg/kg (shallow IM injection) is provided in Table 53.

TABLE 53

| Time (h) | Mean conc Nalmefene (ng/mL) |
|---|---|
| 0.25 | 1.33 |
| 1 | 1.62 |
| 2 | 2.17 |
| 4 | 4.70 |
| 8 | 4.71 |
| 24 | 8.34 |
| 48 | 10.93 |
| 72 | 15.83 |
| 168 | 24.07 |
| 336 | 11.29 |
| 504 | 5.13 |

TABLE 53-continued

| Time (h) | Mean conc Nalmefene (ng/mL) |
|---|---|
| 672 | 2.42 |
| 840 | 1.59 |
| 1008 | 1.26 |
| 1176 | 0.86 |
| 1344 | 0.56 |
| 1512 | 0.50 |

Time vs nalmefene concentration data for compound 24 at 48 mg/kg (deep IM injection) is provided in Table 54.

TABLE 54

| Time (h) | Mean conc Nalmefene (ng/mL) |
|---|---|
| 0.25 | 1.64 |
| 1 | 2.03 |
| 2 | 2.11 |
| 4 | 2.23 |
| 8 | 3.47 |
| 24 | 5.82 |
| 48 | 11.60 |
| 72 | 15.90 |
| 168 | 14.63 |
| 336 | 9.96 |
| 504 | 5.85 |
| 672 | 2.47 |
| 840 | 1.99 |
| 1008 | 1.51 |
| 1176 | 1.07 |
| 1344 | 0.85 |
| 1512 | 0.54 |

Time vs nalmefene concentration data for compound 45 at 30 mg/kg is provided in Table 55.

TABLE 55*

| Time (h) | Mean conc Nalmefene (ng/mL) |
|---|---|
| 0.25 | 2.82 |
| 1 | 4.04 |
| 2 | 3.24 |
| 4 | 2.75 |
| 8 | 2.61 |
| 24 | 3.00 |
| 48 | 5.31 |
| 72 | 4.72 |
| 168 | 6.26 |
| 336 | 4.36 |
| 504 | 3.09 |
| 672 | 3.51 |

*study is ongoing

Time vs nalmefene concentration data for compound 45 at 48 mg/kg is provided in Table 56.

TABLE 56*

| Time (h) | Mean conc Nalmefene (ng/mL) |
|---|---|
| 0.25 | 1.22 |
| 1 | 2.23 |
| 2 | 1.77 |
| 4 | 1.75 |
| 8 | 1.95 |
| 24 | 3.05 |
| 48 | 10.00 |
| 72 | 10.05 |
| 168 | 18.87 |

TABLE 56*-continued

| Time (h) | Mean conc Nalmefene (ng/mL) |
|---|---|
| 336 | 14.83 |
| 504 | 7.43 |
| 672 | 3.24 |
| 840 | 4.06 |
| 1008 | 2.49 |
| 1176 | 2.17 |
| 1344 | 2.16 |
| 1512 | 2.18 |
| 1680 | 2.00 |
| 1848 | 1.39 |
| 2016 | 1.33 |
| 2184 | 1.06 |

*study is ongoing

Time vs nalmefene concentration data for compound 45 at 96 mg/kg is provided in Table 57.

TABLE 57*

| Time (h) | Mean conc Nalmefene (ng/mL) |
|---|---|
| 0.25 | 2.93 |
| 1 | 7.71 |
| 2 | 6.64 |
| 4 | 4.86 |
| 8 | 3.66 |
| 24 | 7.14 |
| 48 | 11.30 |
| 72 | 9.32 |
| 168 | 17.8 |
| 336 | 16.5 |
| 504 | 6.81 |
| 672 | 5.30 |

*study is ongoing

Time vs naltrexone concentration data for compound 7 at 24 mg/kg (n=2) is provided in Table 58.

TABLE 58*

| Time (h) | Mean conc Naltrexone (ng/mL) |
|---|---|
| 0.25 | 3.61 |
| 1 | 5.25 |
| 2 | 2.52 |
| 4 | 0.82 |
| 8 | 0.29 |
| 24 | 0.61 |
| 48 | 0.61 |
| 72 | 0.67 |
| 168 | 1.75 |
| 336 | 2.29 |
| 504 | 2.44 |
| 672 | 2.19 |

*study is ongoing

Time vs naltrexone concentration data for compound 7 at 48 mg/kg is provided in Table 59.

TABLE 59*

| Time (h) | Mean conc Naltrexone (ng/mL) |
|---|---|
| 0.25 | 18.23 |
| 1 | 18.13 |
| 2 | 9.67 |
| 4 | 3.35 |
| 8 | 1.33 |
| 24 | 1.43 |

TABLE 59*-continued

| Time (h) | Mean conc Naltrexone (ng/mL) |
|---|---|
| 48 | 2.30 |
| 72 | 2.41 |
| 168 | 1.85 |
| 336 | 1.09 |
| 504 | 1.35 |
| 672 | 1.27 |
| 840 | 1.95 |
| 1008 | 1.54 |
| 1176 | 1.02 |
| 1344 | 1.03 |
| 1512 | 1.06 |

*study is ongoing

Time vs naltrexone concentration data for compound 8 at 48 mg/kg is provided in Table 60.

TABLE 60*

| Time (h) | Mean conc Naltrexone (ng/mL) |
|---|---|
| 0.25 | 103.20 |
| 1 | 159.67 |
| 2 | 52.33 |
| 4 | 9.74 |
| 8 | 5.03 |
| 24 | 3.46 |
| 48 | 4.06 |
| 72 | 4.87 |
| 168 | 7.28 |
| 336 | 3.91 |
| 504 | 9.72 |
| 672 | 4.59 |
| 840 | 2.52 |
| 1008 | 2.70 |
| 1176 | 1.71 |
| 1344 | 1.63 |
| 1512 | 1.60 |

*study is ongoing

Time vs nalmefene concentration data for compound 1 at 48 mg/kg is provided in Table 61.

TABLE 61*

| Time (h) | Mean conc Nalmefene (ng/mL) |
|---|---|
| 0.25 | 1.90 |
| 1 | 4.24 |
| 2 | 2.26 |
| 4 | 0.92 |
| 8 | 0.57 |
| 24 | 0.87 |
| 48 | 1.41 |
| 72 | 1.84 |
| 168 | 2.57 |
| 336 | 1.78 |
| 504 | 1.49 |
| 672 | 1.21 |
| 840 | 1.64 |
| 1008 | 1.85 |
| 1176 | 1.58 |
| 1344 | 1.24 |
| 1512 | 1.19 |

*study is ongoing

Time vs nalmefene concentration data for compound 3 at 48 mg/kg is provided in Table 62.

TABLE 62

| Time (h) | Mean conc Nalmefene (ng/mL) |
|---|---|
| 0.25 | 2.54 |
| 1 | 4.48 |
| 2 | 5.37 |
| 4 | 9.26 |
| 8 | 13.37 |
| 24 | 25.43 |
| 48 | 37.57 |
| 72 | 62.60 |
| 168 | 27.77 |
| 336 | 4.50 |
| 504 | 0.97 |
| 672 | 0.34 |

Time vs naltrexone concentration data for compound 4 at 48 mg/kg is provided in Table 63.

TABLE 63

| Time (h) | Mean conc Naltrexone (ng/mL) |
|---|---|
| 0.25 | 21.90 |
| 1 | 38.67 |
| 2 | 41.17 |
| 4 | 74.47 |
| 8 | 78.07 |
| 24 | 53.23 |
| 48 | 52.93 |
| 72 | 70.03 |
| 168 | 3.76 |
| 336 | ND** |
| 504 | ND |
| 672 | ND |

**ND = none detected

Time vs naltrexone concentration data for compound 5 at 48 mg/kg (n=2) is provided in Table 64.

TABLE 64

| Time (h) | Mean conc Nalmefene (ng/mL) |
|---|---|
| 0.25 | 1.12 |
| 1 | 2.75 |
| 2 | 3.55 |
| 4 | 5.49 |
| 8 | 6.67 |
| 24 | 17.40 |
| 48 | 26.95 |
| 72 | 30.65 |
| 168 | 27.85 |
| 336 | 11.00 |
| 504 | 2.07 |
| 672 | 1.06 |

Time vs naltrexone concentration data for compound 35 at 48 mg/kg is provided in Table 65.

TABLE 65

| Time (h) | Mean conc Nalmefene (ng/mL) |
|---|---|
| 0.25 | 9.57 |
| 1 | 19.07 |
| 2 | 14.50 |
| 4 | 18.80 |
| 8 | 25.80 |
| 24 | 103.87 |
| 48 | 174.67 |
| 72 | 237.00 |

| time point | D1501 | | D1502 | | D1503 | |
|---|---|---|---|---|---|---|
| | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 39 | No obvious clinical observation | No obvious clinical observation | a few erythema on the inside of the left foreleg | regression of erythema and escharosis on the outside of the hindleg/ a few erythema on the inside of the right foreleg | No obvious clinical observation | No obvious clinical observation |
| Day 41 | No obvious clinical observation | No obvious clinical observation | a few erythema on the inside of the left foreleg | new slight rashes and escharosis on the outside of the right leg/a few erythema on the inside of the right foreleg | No obvious clinical observation | No obvious clinical observation |
| Day 42 | slight rashes on the left thigh and crus | slight rashes on the outside of right thigh/ slight rashes on the right crus | a few erythema on the inside of the left foreleg | new slight rashes and escharosis on the outside of the right leg/a few erythema on the inside of the right foreleg | No obvious clinical observation | No obvious clinical observation |
| Day 43 | slight rashes on the left thigh and crus | slight rashes on the outside of right thigh/ slight rashes on the right crus | a few erythema on the inside of the left foreleg | new slight rashes and escharosis on the outside of the right leg/a few erythema on the inside of the right foreleg | No obvious clinical observation | No obvious clinical observation |
| Day 46 | slight rashes and escharosis on the left thigh and crus | slight rashes and escharosis on the outside of right thigh/ slight rashes on the right crus | a few erythema on the inside of the left foreleg, fresh erythema on the outside of the thigh | a few erythema on the outside of the thigh | No obvious clinical observation | No obvious clinical observation |
| Day 48 | slight rashes and escharosis of slight rashes on the outside of left leg/slight rashes on the inside and outside of the crus | slight rashes and escharosis on the outside of right thigh/ slight rashes on the right crus | slight rashes on the inside of the left foreleg/slight rashes on the outside of the left leg | slight rashes and escharosis on the outside of the thigh/ slight rashes on the inside of foreleg | No obvious clinical observation | No obvious clinical observation |
| Day 49 | slight rashes and escharosis of slight rashes on the outside of left leg/slight rashes on the inside and outside of the crus | slight rashes and escharosis on the outside of right thigh/ slight rashes on the right crus | slight rashes on the inside of the left foreleg/slight rashes on the outside of the left leg | slight rashes and escharosis on the outside of the thigh/ slight rashes on the inside of foreleg | No obvious clinical observation | No obvious clinical observation |
| Day 53 | slight rashes and escharosis of slight rashes on the outside of left leg/slight rashes on the inside and outside of the crus | Recovery of rashes on the outside of the leg | No obvious clinical observation | slight rashes on the outside of the leg/ slight rashes on the inside of foreleg | No obvious clinical observation | No obvious clinical observation |
| Day 55 | escharosis of slight rashes on the outside | No obvious clinical observation | No obvious clinical observation | slight rashes on the outside of the leg/ | No obvious clinical observation | No obvious clinical observation |

-continued

| time point | D1501 L-vehicle | D1501 R-TA | D1502 L-vehicle | D1502 R-TA | D1503 L-vehicle | D1503 R-TA |
|---|---|---|---|---|---|---|
| | of left leg/several rashes on the outside of the crus | | | several rashes on the inside of foreleg | | |
| Day 56 | No obvious clinical observation | No obvious clinical observation | No obvious clinical observation | escharosis of rashes on the outside of the leg/no obvious clinical observation on the inside of foreleg | No obvious clinical observation | No obvious clinical observation |
| Day 60 | No obvious clinical observation | No obvious clinical observation | No obvious clinical observation | escharosis of rashes on the outside of the leg/no obvious clinical observation on the inside of foreleg | No obvious clinical observation | No obvious clinical observation |

| time point | D1001 R-TA | D1001 L-vehicle | D1002 R-TA | D1002 L-vehicle | D1003 R-TA | D1003 L-vehicle |
|---|---|---|---|---|---|---|
| 8 hr | No obvious clinical observation | NA | No obvious clinical observation | NA | No obvious clinical observation | NA |
| 72 hr | No obvious clinical observation | NA | No obvious clinical observation | NA | Slight swelling | NA |
| Day 5 | No obvious clinical observation | NA | Slight swelling | NA | Larger swelling | NA |
| Day 7 | No obvious clinical observation | NA | Slight swelling | NA | Larger swelling | NA |
| Day 8 | Slight swelling, induration | NA | Slight swelling, induration | NA | Larger swelling, induration | NA |
| Day 9 | The same with Day 8 | NA | The same with Day 8 | NA | The same with Day8 | NA |
| Day 12 | Not obvious swelling and induration, no inflammation, painless with touching | NA | Not obvious swelling and induration, no inflammation, painless with touching | NA | Obvious swelling and induration, no inflammation, painless with touching | NA |
| Day 16 | Same with Day 15 | No obvious clinical observation | Same with Day 15 | No obvious clinical observation | Same with Day 15 | No obvious clinical observation |
| Day 17 | More indurated than the vehicle site | No obvious clinical observation | More indurated than the vehicle site | No obvious clinical observation | More indurated than the vehicle site | No obvious clinical observation |
| Day 18 | The same with Day 17 | No obvious clinical observation | The same with Day 17 | No obvious clinical observation | The same with Day 17 | No obvious clinical observation |
| Day 21 | No obvious clinical observation | No obvious clinical observation | No obvious clinical observation | No obvious clinical observation | No obvious clinical observation | No obvious clinical observation |
| Day 22 | No obvious clinical observation | No obvious clinical observation | No obvious clinical observation | No obvious clinical observation | No obvious clinical observation | No obvious clinical observation |
| Day 30 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |
| Day 63 | No obvious clinical observation | No obvious clinical observation | No obvious clinical observation | No obvious clinical observation | No obvious clinical observation | No obvious clinical observation |

| time point | D1001 | | D1002 | | D1003 | |
|---|---|---|---|---|---|---|
| | L-TA | R-vehicle | L-TA | R-vehicle | L-TA | R-vehicle |
| 8 hr | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |
| Day 63 | No obvious clinical observation | No obvious clinical observation | No obvious clinical observation | No obvious clinical observation | No obvious clinical observation | No obvious clinical observation |
| Day 101 | No obvious clinical observation | No obvious clinical observation | No obvious clinical observation | No obvious clinical observation | No obvious clinical observation | No obvious clinical observation |

| time point | D1001 | | D1002 | |
|---|---|---|---|---|
| | L-vehicle | R-TA | L-vehicle | R-TA |
| Day 0 | No obvious clinical observation | No obvious clinical observation | vomit about 20 g chyme at 1 hr post dose | |
| Day 3 | No obvious clinical observation | No obvious clinical observation | No obvious clinical observation | No obvious clinical observation |
| Day 7 | No obvious clinical observation | No obvious clinical observation | No obvious clinical observation | No obvious clinical observation |
| Day 14 | No obvious clinical observation | No obvious clinical observation | No obvious clinical observation | No obvious clinical observation |
| Day 21 | No obvious clinical observation | No obvious clinical observation | No obvious clinical observation | No obvious clinical observation |
| Day 28 | No obvious clinical observation | No obvious clinical observation | No obvious clinical observation | No obvious clinical observation |
| Day 35 | No obvious clinical observation | No obvious clinical observation | No obvious clinical observation | No obvious clinical observation |
| Day 42 | No obvious clinical observation | No obvious clinical observation | No obvious clinical observation | No obvious clinical observation |

| time point | D1501 | | D1502 | | D1503 | |
|---|---|---|---|---|---|---|
| | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |

-continued

| time point | D1501 | | D1502 | | D1503 | |
|---|---|---|---|---|---|---|
| | L-vehicle | R-TA | L-vehicle | R-TA | L-vehicle | R-TA |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |

| time point | D1501 | | D1502 | | D1503 | |
|---|---|---|---|---|---|---|
| | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | large area of red spots on the outside and inside of the leg/the red spots of outside were in decrustation | large area of red spots on the outside and inside of the leg/ the red spots of outsidewere in decrustation | No obvious clinical observation | No obvious clinical observation |
| Day 18 | No obvious clinical observation | No obvious clinical observation | large area of red spots on the outside of the leg/the red spots of outside were in decrustation and escharosis | large area of red spots on the outside of the leg/the red spots of outside in decrustation and escharosis | No obvious clinical observation | No obvious clinical observation |
| Day 20 | No obvious clinical observation | No obvious clinical observation | regression of red spots on the outside of the leg and decrustation | regression of red spots on the outside of the leg escharosis/ scap 1.5 cm * 1.5 cm on the inside of right leg | No obvious clinical observation | No obvious clinical observation |
| Day 21 | No obvious clinical observation | No obvious clinical observation | decrustation on the outside of the left leg | escharosis on the outside of the leg/ scap 1.5 cm * 1.5 cm on the inside of right leg | No obvious clinical observation | No obvious clinical observation |
| Day 25 | No obvious clinical observation | No obvious clinical observation | decrustation on the outside of the left leg | decrustation on the outside of the right leg | No obvious clinical observation | No obvious clinical observation |
| Day 27 | No obvious clinical observation | No obvious clinical observation | escharosis and decrustation on the outside of the left leg/erythema on inside of the left leg | erythema, escharosis and decrustation on the outside of the right leg/erythema on the inside of the right leg | No obvious clinical observation | No obvious clinical observation |
| Day 28 | No obvious clinical observation | No obvious clinical observation | decrustation on the outside of the left leg | decrustation on the outside of the right leg | No obvious clinical observation | No obvious clinical observation |

-continued

| | D1501 | | D1502 | | D1503 | |
|---|---|---|---|---|---|---|
| time point | L-vehicle | R-TA | L-vehicle | R-TA | L-vehicle | R-TA |
| Day 32 | No obvious clinical observation | No obvious clinical observation | escharosis on the outside of the left leg/erythema on the inside of the left leg | escharosis on the outside of the right leg/erythema on the inside of the right leg | No obvious clinical observation | No obvious clinical observation |
| Day 34 | No obvious clinical observation | No obvious clinical observation | escharosis on the outside of the left leg/erythema on the inside of the left leg | escharosis and a few erythema on the outside of the right leg/erythema on the inside of the right leg | No obvious clinical observation | No obvious clinical observation |
| Day 35 | No obvious clinical observation | No obvious clinical observation | escharosis on the outside of the left leg/erythema on the inside of the left leg | escharosis and a few erythema on the outside of the right leg/erythema on the inside of the right leg | No obvious clinical observation | No obvious clinical observation |
| Day 39 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 41 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 42 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 43 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 46 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 49 | No obvious clinical observation | No obvious clinical observation | recovery for escharosis/several rashes and slight decrustation on the outside of the left leg/several rashes on the inside of the left leg | recovery for escharosis/several rashes and slight decrustation on the outside of the right leg/several rashes on the inside of the left leg | No obvious clinical observation | No obvious clinical observation |
| Day 53 | No obvious clinical observation | No obvious clinical observation | Recovery for rashes on the leg | Recovery for rashes on the leg | No obvious clinical observation | No obvious clinical observation |
| Day 56 | No obvious clinical observation | No obvious clinical observation | No obvious clinical observation | No obvious clinical observation | No obvious clinical observation | No obvious clinical observation |
| Day 59 | No obvious clinical observation | No obvious clinical observation | No obvious clinical observation | No obvious clinical observation | No obvious clinical observation | No obvious clinical observation |

| time point | D1501 | | D1502 | | D1503 | |
| --- | --- | --- | --- | --- | --- | --- |
| | L-TA | R-vehicle | L-TA | R-vehicle | L-TA | R-vehicle |
| before day 7 | No obvious clinical observation | No obvious clinical observation | No obvious clinical observation | No obvious clinical observation | No obvious clinical observation | No obvious clinical observation |
| day 7 | No obvious clinical observation | No obvious clinical observation | Swelling for the whole leg | No obvious clinical observation | No obvious clinical observation | No obvious clinical observation |
| day 8 | No obvious clinical observation | No obvious clinical observation | Swelling at upper leg/edema at lower leg | No obvious clinical observation | No obvious clinical observation | No obvious clinical observation |
| day 9 | No obvious clinical observation | No obvious clinical observation | Swelling at upper leg/edema at lower leg/skin rashes at groin | No obvious clinical observation | No obvious clinical observation | No obvious clinical observation |
| day 10 | No obvious clinical observation | No obvious clinical observation | Swelling at the upper leg/skin rashes at groin | No obvious clinical observation | No obvious clinical observation | No obvious clinical observation |
| day 11 | No obvious clinical observation | No obvious clinical observation | Swelling 9 * 7 cm at the upper leg/skin rashes at groin | No obvious clinical observation | No obvious clinical observation | No obvious clinical observation |
| day 12 | No obvious clinical observation | No obvious clinical observation | Swelling 9 * 7 cm at the upper leg/skin rashes at groin | No obvious clinical observation | No obvious clinical observation | No obvious clinical observation |
| day 13 | No obvious clinical observation | No obvious clinical observation | Slight swelling at upper leg/skin rashes at groin | No obvious clinical observation | No obvious clinical observation | No obvious clinical observation |
| day 14 | No obvious clinical observation | No obvious clinical observation | Slight swelling at upper leg/skin rashes at groin | No obvious clinical observation | No obvious clinical observation | No obvious clinical observation |
| day 15 | No obvious clinical observation | No obvious clinical observation | Slight swelling at upper leg/skin rashes at groin | No obvious clinical observation | No obvious clinical observation | No obvious clinical observation |
| day 16 | No obvious clinical observation | No obvious clinical observation | Slight swelling at upper leg/skin rashes at groin | No obvious clinical observation | No obvious clinical observation | No obvious clinical observation |
| day 17 | No obvious clinical observation | No obvious clinical observation | No obvious clinical observation | No obvious clinical observation | No obvious clinical observation | No obvious clinical observation |
| day 21 | No obvious clinical observation | No obvious clinical observation | No obvious clinical observation | No obvious clinical observation | No obvious clinical observation | No obvious clinical observation |
| day 28 | No obvious clinical observation | No obvious clinical observation | No obvious clinical observation | No obvious clinical observation | No obvious clinical observation | No obvious clinical observation |
| day 35 | No obvious clinical observation | No obvious clinical observation | No obvious clinical observation | No obvious clinical observation | No obvious clinical observation | No obvious clinical observation |
| day 42 | No obvious clinical observation | No obvious clinical observation | No obvious clinical observation | No obvious clinical observation | No obvious clinical observation | No obvious clinical observation |
| day 49 | No obvious clinical observation | No obvious clinical observation | No obvious clinical observation | No obvious clinical observation | No obvious clinical observation | No obvious clinical observation |
| day 56 | No obvious clinical observation | No obvious clinical observation | No obvious clinical observation | No obvious clinical observation | No obvious clinical observation | No obvious clinical observation |
| day 63 | No obvious clinical observation | No obvious clinical observation | No obvious clinical observation | No obvious clinical observation | No obvious clinical observation | No obvious clinical observation |
| day 86 | No obvious clinical observation | No obvious clinical observation | No obvious clinical observation | No obvious clinical observation | No obvious clinical observation | No obvious clinical observation |
| day 93 | No obvious clinical observation | No obvious clinical observation | No obvious clinical observation | No obvious clinical observation | No obvious clinical observation | No obvious clinical observation |
| day 100 | No obvious clinical observation | No obvious clinical observation | No obvious clinical observation | No obvious clinical observation | No obvious clinical observation | No obvious clinical observation |
| day 107 | No obvious clinical observation | No obvious clinical observation | No obvious clinical observation | No obvious clinical observation | No obvious clinical observation | No obvious clinical observation |
| Day 114 | No obvious clinical observation | No obvious clinical observation | No obvious clinical observation | No obvious clinical observation | No obvious clinical observation | No obvious clinical observation |
| Day 121 | No obvious clinical observation | No obvious clinical observation | No obvious clinical observation | No obvious clinical observation | No obvious clinical observation | No obvious clinical observation |
| Day 128 | No obvious clinical observation | No obvious clinical observation | No obvious clinical observation | No obvious clinical observation | No obvious clinical observation | No obvious clinical observation |
| Day 135 | No obvious clinical observation | No obvious clinical observation | No obvious clinical observation | No obvious clinical observation | No obvious clinical observation | No obvious clinical observation |
| Day 142 | No obvious clinical observation | No obvious clinical observation | No obvious clinical observation | No obvious clinical observation | No obvious clinical observation | No obvious clinical observation |
| Day 149 | No obvious clinical observation | No obvious clinical observation | No obvious clinical observation | No obvious clinical observation | No obvious clinical observation | No obvious clinical observation |

| | D1001 | | D1002 | | D1003 | |
|---|---|---|---|---|---|---|
| time point | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | several rashes on the outside of the right leg | several rashes on the outside of the left leg | several rashes on the outside of the right leg | several rash on the outside of the left leg | several rash on the outside of the right leg |
| Day 24 | a few rashes of the left leg | a few rashes on the outside of the right leg | lots of rashes on the outside of the left leg | escharosis of the rashes part on the outside of the right leg | a few rashes of the left leg | a few rashes and decrustation on the outside of the right leg |
| Day 26 | escharosis of the several rashes part on the outside of the left leg | Fading in rashes and escharosis on the outside of the right leg | lots of rashes on the outside of the left leg/escharosis of half rashes | lots of rashes on the outside of the right leg/escharosis of half rashes | several rashes on the outside of the left leg/escharosis of rashes part | several rashes and slight decrustation on the outside of the right leg |
| Day 28 | escharosis of the several rashes part on the outside of the left leg | Fading in rashes and escharosis on the outside of the right leg/new several rashes on the right crus | lots of rashes on the outside of the left leg/escharosis of half rashes | lots of rashes on the outside of the right leg/escharosis of half rashes | several rashes on the outside of the left leg/escharosis of rashes | several rashes and slight decrustation on the outside of the right leg |
| Day 31 | escharosis of the several rashes part on the outside of the left leg | Fading in rashes and escharosis on the outside of the right leg/new several rashes on the right crus | escharosis of the several rashes part on the outside of the left leg | escharosis and rashes on the outside of the leg | several rashes on the outside of the left leg/escharosis of rashes | several rashes and slight decrustation on the outside of the right leg |
| Day 33 | escharosis of the several rashes on the left leg | Fading in several rashes and escharosis on the outside of the right leg/new several rashes on the right crus | recovery for rashes on the outside of the left leg/only a few rash, escharosis and decrustation | recovery for rashes on the outside of the right leg/only a few rash, escharosis and decrustation | several rashes on the outside of the left leg/escharosis of rashes | several rashes and slight decrustation on the outside of leg |
| Day 35 | rashes subside on the leg | rashes subside on the outside of leg/several rashes on the right crus | recovery for rashes on the outside of the left leg/only a few rash, escharosis and decrustation | rashes subside on the leg | several rashes and escharosis on the outside of the left leg | several rashes and slight decrustation on the outside of leg |
| Day 38 | No obvious clinical observation | No obvious clinical observation | No obvious clinical observation | Fading in rashes on the leg | No obvious clinical observation | No obvious clinical observation |
| Day 40 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 45 | No obvious clinical observation | No obvious clinical observation | No obvious clinical observation | No obvious clinical observation | No obvious clinical observation | No obvious clinical observation |

| | D1501 | | D1502 | | D1503 | |
|---|---|---|---|---|---|---|
| time point | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | Swelling 8 * 4 cm |
| Day 14 | No obvious clinical observation | No obvious clinical observation | No obvious clinical observation | No obvious clinical observation | No obvious clinical observation | No obvious clinical observation |

-continued

| time point | D1501 L-vehicle | D1501 R-TA | D1502 L-vehicle | D1502 R-TA | D1503 L-vehicle | D1503 R-TA |
|---|---|---|---|---|---|---|
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | Slight rashes on the outside of the hindlimb | No obvious clinical observation | No obvious clinical observation | No obvious clinical observation | No obvious clinical observation |
| Day 38 | Slight rashes on the outside of the hindlimb | Slight rashes on the outside of the hindlimb | Slight rashes on the outside of the upper hindlimb | Slight rashes on the outside of the upper hindlimb | Slight rashes on the outside of the hindlimb, skin exuviating | Slight rashes on the outside of the hindlimb, skin exuviating |
| Day 40 | Slight rashes on the outside of the hindlimb | Slight rashes on the outside of the upper hindlimb were disappearing, new rashes appeared on the inside. | Slight rashes on the outside of the upper hindlimb were disappearing, new rashes appeared on the inside. | Slight rashes on the outside of the upper hindlimb | Slight rashes on the outside of the hindlimb, skin exuviating | Slight rashes on the outside of the hindlimb, skin exuviating |
| Day 42 | New rashes appeared on the iniside of the hindlimb | No obvious clinical observation | Slight rashes on the inside of the hindlimb | Slight rashes on the inside of the hindlimb | Slight rashes on the outside of the hindlimb | Slight rashes on the outside of the hindlimb |
| Day 45 | Slight rashes appeared on the inside of the hindlimb | New rashes appeared on the inside of the hindlimb | Slight rashes on the inside of the hindlimb | Slight rashes on the inside of the hindlimb | Slight rashes on the outside of the hindlimb, skin exuviating | Slight rashes on the outside of the hindlimb, some were scabbing |
| Day 47 | Slight rashes on the iniside of the hindlimb | Slight rashes on the iniside of the hindlimb | Slight rashes on the inside of the hindlimb | Slight rashes on the inside of the hindlimb | Slight rashes on the outside of the hindlimb, skin exuviating | Slight rashes on the outside of the hindlimb, some were scabbing |
| Day 49 | Slight rashes scabbing on the iniside of the hindlimb | Slight rashes scabbing on the iniside of the hindlimb | Slight rashes on the inside of the hindlimb | Slight rashes on the inside of the hindlimb | Slight rashes on the outside of the hindlimb, skin exuviating | Slight rashes on the outside of the hindlimb, some were scabbing |
| Day 52 | No obvious clinical observation | No obvious clinical observation | No obvious clinical observation | No obvious clinical observation | No obvious clinical observation | No obvious clinical observation |
| Day 54 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |

| time point | D1501 L-vehicle | D1501 R-TA | D1502 L-vehicle | D1502 R-TA | D1502 L-vehicle | D1502 R-TA |
|---|---|---|---|---|---|---|
| 8 hr | No obvious clinical observation | No obvious clinical observation | No obvious clinical observation | No obvious clinical observation | About 10 mL loose feces at 8 hr post dose | |
| 24 hr | No obvious clinical observation | Induration at the upper leg 18 * 10 cm/swelling at the inner upper leg 6 * 9 cm/BT: 39.1° C. | Red spots at the upper leg | Swelling 15 * 12 cm at the upper leg/swelling 8 * 11 at inner upper leg with redness and warmth/swelling and deep redness at the calf/BT: 40.1° C. | No obvious clinical observation | Induration 15 * 13 cm for the whole leg with redness and warmth/Induration at the inner upper leg 9 * 11 cm with redness and warmth/BT: 39.9° C. |
| 48 hr | swelling 3 * 6 cm | Induration at the upper leg 18 * 10 cm/swelling at the inner upper leg 8 * 9 cm/Red spots at the 1 'clock position/BT: 39.1° C. | Red spots at the upper leg | Swelling 15 * 12 cm at the upper leg/swelling 8 * 11 at inner upper leg with redness and warmth/swelling and black at the calf/BT: 40.0° C. | No obvious clinical observation | Induration 15 * 13 cm for the whole leg with redness and warmth/Induration at the inner upper leg 9 * 11 cm with redness and warmth/BT: 39.9° C. |
| 72 hr | swelling 3 * 6 cm | Induration at the upper leg 18 * 10 cm/swelling at the inner upper leg 8 * 9 cm/Red spots at the 1 'clock position/BT: 39.1° C./thin/inappetence | Red spots at the upper leg | Swelling 15 * 12 cm at the upper leg/swelling 8 * 11 at inner upper leg with redness and warmth/swelling and black at the calf/BT: 38.7° C./ulcerated scab 2 * 4 at inner upper leg/thin/inappetence | No obvious clinical observation | Induration 15 * 13 cm for the whole leg with redness and warmth/Induration at the inner upper leg 9 * 11 cm with redness and warmth/BT: 39.4° C./thin/inappetence |
| 96 hr | swelling 3 * 6 cm | lame/serious induration of the whole leg/edema at ankle/Red spots at the 1 'clock | slight swelling/red spots at the upper leg | lame/induration of the whole leg/edema at distal lower leg/induration and black at proximal lower | No obvious clinical observation | Induration for the whole leg with redness and warmth/BT: 39.4° C./thin/inappetence/weight |

-continued

| time point | D1501 | | D1502 | | D1502 | |
|---|---|---|---|---|---|---|
| | L-vehicle | R-TA | L-vehicle | R-TA | L-vehicle | R-TA |
| | | position/BT: 39.1° C./thin/inappetence/weight decreases from 6.71 kg to 6.0 kg/bloody stools | | leg/necrosis(black and muscle atrophy) 1.5 * 1.5 cm at upper leg and 6 * 2 cm at lower leg with red secreta/BT: 39.0° C./thin/inappetence/weight decreases from 7.76 kg to 6.86 kg/bloody stools | | decreases from 6.52 kg to 6.17 kg/bloody stools |
| 120 hr | swelling 3 * 6 cm | lame/serious induration of the whole leg/edema at ankle/Red spots at the 1 'clock position/BT: 39.8° C./thin/inappetence | slight swelling/red spots at the upper leg | lame/induration of the whole leg/edema at distal lower leg/induration and black at proximal lower leg/necrosis(black and muscle atrophy) 1.5 * 1.5 cm at upper leg and 6 * 2 cm at lower leg with red secreta/BT: 39.1° C./thin/inappetence | No obvious clinical observation | Induration for the whole leg with redness and warmth/BT: 39.5° C./thin |
| 144 hr | swelling 3 * 6 cm | lame/serious induration of the whole leg/edema at ankle/Red spots at the 1 'clock position/induration at the inner upper leg with deep color and warmth/BT: 39.3° C./thin/inappetence/6.18 kg | slight swelling/red spots at the upper leg | lame/induration of the whole leg/edema at distal lower leg/induration and black at proximal lower leg/necrosis(black and muscle atrophy) 1.5 * 1.5 cm at upper leg and 6 * 2 cm at lower leg with red secreta/BT: 39.2° C./thin/inappetence/6.92 kg | No obvious clinical observation | Induration for the whole leg with redness and warmth/BT: 39.5° C./thin/6.15 kg |
| 168 hr | swelling 3 * 6 cm | lame/serious induration of the whole leg/edema at ankle/Red spots at the 1 'clock position/induration at the inner upper leg with deep color and warmth/BT: 39.2° C./thin/inappetence/6.13 kg | slight swelling/red spots at the upper leg | lame/induration of the whole leg/edema at distal lower leg/induration and black at proximal lower leg/necrosis(black and muscle atrophy) 1.5 * 1.5 cm at upper leg and 6 * 2 cm at lower leg with red secreta/BT: 39.6° C./thin/inappetence/7.01 kg | No obvious clinical observation | Induration for the whole leg with redness and warmth/ulceration at upper leg with 0.5 * 0.5 cm/BT: 38.7° C./thin/5.93 kg |
| day 8 | swelling 3 * 6 cm/ | lame/serious induration of the whole leg/edema at ankle/ulteration with red and thick secreta at upper leg/induration at the inner upper leg with deep color and warmth/BT: 39.4° C./thin/inappetence/6.11 kg | slight swelling/red spots at the upper leg | lame/induration of the whole leg/edema at distal lower leg/induration and black at proximal lower leg/necrosis(black and muscle atrophy) 3 * 1.5 cm at upper leg and 6 * 4 cm at lower leg with red secreta and muscle exposure/BT: 39.5° C./thin/inappetence/6.76 kg | No obvious clinical observation | Induration for the whole leg with redness and warmth/ulceration at upper leg with 0.5 * 0.5 cm and redness and warmth/Induration at the front lower leg and fluctuation with red and thick liquid at the back lower legBT: 38.7° C./thin/5.98 kg |
| day 9 | swelling 3 * 6 cm/ | lame/serious induration of the whole leg/edema at ankle/3 parts of ulceration with yellow and thick secreta at upper leg/induration at the inner upper leg with deep color and warmth/BT: 38.7° C./thin/inappetence/6.09 kg | slight swelling/red spots at the upper leg | lame/induration of the whole leg/edema at distal lower leg/induration and black at proximal lower leg/necrosis(black and muscle atrophy) 3 * 1.5 cm at upper leg and 6 * 4 cm at lower leg with yellow secreta and muscle exposure/BT: 38.5° C./thin/inappetence/6.79 kg | No obvious clinical observation | Induration for the whole leg with redness and warmth/ulceration at upper leg with 0.5 * 0.5 cm and redness and warmth/Induration at the front lower leg and fluctuation with red and thick liquid at the back lower legBT: 38.8° C./thin/6.15 kg |
| day 10 | swelling 3 * 6 cm/ | lame/serious induration of the whole leg/edema at ankle/3 parts of ulceration with yellow and thick secreta at upper leg one part of ulceration with pink and thick secreta at inner upper leg/induration at the inner upper leg with deep color and warmth/BT: 38.3° C./thin/inappetence/6.05 kg | No obvious clinical observation | induration of the whole leg/edema at distal lower leg/induration and black at proximal lower leg/necrosis(black and muscle atrophy) 3 * 1.5 cm at upper leg and 6 * 4 cm at lower leg with yellow secreta and muscle exposure/BT: 38.8° C./thin/inappcetence/6.68 kg | No obvious clinical observation | Induration for the whole leg with redness and warmth/ulceration at upper leg with 0.5 * 0.5 cm and redness and warmth and becoming scab/Induration at the front lower leg and fluctuation with red and thick liquid at the back lower legBT: 38.7° C./thin/6.13 kg |

-continued

| time point | D1501 | | D1502 | | D1502 | |
|---|---|---|---|---|---|---|
| | L-vehicle | R-TA | L-vehicle | R-TA | L-vehicle | R-TA |
| day 11 | No obvious clinical observation | lame/serious induration of the whole leg/edema at ankle/3 parts of ulceration with yellow and thick secreta at upper leg one part of ulceration with pink and thick secreta at inner upper leg/induration at the inner upper leg with deep color and warmth/BT: 38.5° C./thin/inappetence/5.99 kg | No obvious clinical observation | induration of the whole leg/edema at distal lower leg/induration and black at proximal lower leg/necrosis(black and muscle atrophy) 3 * 1.5 cm at upper leg and 6 * 4 cm at lower leg with yellow secreta and muscle exposure/BT: 38.9° C./thin/inappetence/6.83 kg | No obvious clinical observation | Induration for the whole leg with redness and warmth/ulceration at upper leg with 0.5 * 0.5 cm and redness and warmth and becoming scab/Induration at the front lower leg and fluctuation with red and thick liquid at the back lower legBT: 38.7° C./thin/6.13 kg |
| day 12 | No obvious clinical observation | lame/serious induration of the whole leg/edema at ankle/3 parts of ulceration with yellow and thick secreta at upper leg one part of ulceration at inner upper leg/induration at the inner upper leg with deep color and warmth/thin/inappetence | No obvious clinical observation | induration of the whole leg/edema at distal lower leg/induration and black at proximal lower leg/necrosis(black and muscle atrophy) 3 * 1.5 cm at upper leg and 6 * 4 cm at lower leg with yellow secreta and muscle exposure/thin/inappetence/ | No obvious clinical observation | Induration for the whole leg with redness and warmth/ulceration at upper leg with 0.5 * 0.5 cm and redness and warmth and becoming scab/thin |
| day 13 | No obvious clinical observation | lame/swelling at the inner upper leg with purple color/edema at ankle/3 parts of ulceration with yellow and thick secreta at upper leg one part of ulceration with pink and thick secreta at inner upper leg/6.06 kg | No obvious clinical observation | induration of the whole leg/necrosis(black and muscle atrophy) 1.5 * 1.5 cm at upper leg and 5 * 1.5 cm at lower leg with muscle exposure/6.92 kg | No obvious clinical observation | Induration for the whole leg/ulceration at upper leg with scab/6.45 kg |
| day 14 | No obvious clinical observation | lame/swelling at the inner upper leg with purple color/edema at ankle//3 parts of ulceration with yellow and thick secreta at upper leg one part of ulceration with pink and thick secreta at inner upper leg/6.01 kg | No obvious clinical observation | induration of the whole leg/necrosis(black and muscle atrophy) 1.5 * 1.5 cm at upper leg and 5 * 1.5 cm at lower leg with muscle exposure/6.93 kg | No obvious clinical observation | Induration for the whole leg/ulceration at upper leg with scab/6.38 kg |
| day 15 | No obvious clinical observation | lame/swelling at the inner upper leg with purple color/edema at ankle/73 parts of ulceration with yellow and thick secreta at upper leg one part of ulceration with pink and thick secreta at inner upper leg | No obvious clinical observation | induration of the whole leg/necrosis(black and muscle atrophy) 1.5 * 1.5 cm at upper leg and 5 * 1.5 cm at lower leg with muscle exposure | No obvious clinical observation | Induration for the whole leg/ulceration at upper leg with scab |

| time point | D1001 L-vehicle | D1001 R-TA | D1002 L-vehicle | D1002 R-TA | D1003 L-vehicle | D1003 R-TA |
|---|---|---|---|---|---|---|
| 2 hr | No obvious clinical observation | Swelling | No obvious clinical observation | Swelling | No obvious clinical observation | Swelling |
| 8 hr | No obvious clinical observation | Larger swelling | No obvious clinical observation | Larger swelling | No obvious clinical observation | Larger swelling |
| 24 hr | No obvious clinical observation | Larger swelling | No obvious clinical observation | Larger swelling and a scab on the edge of the swelling part | No obvious clinical observation | Larger swelling |
| 48 hr | No obvious clinical observation | Larger swelling | No obvious clinical observation | Larger swelling and a scab on the edge of the swelling part | No obvious clinical observation | Larger swelling |
| 72 hr | No obvious clinical observation | Larger swelling | No obvious clinical observation | Larger swelling and a scab on the edge of the swelling part | No obvious clinical observation | Larger swelling |
| 96 hr | No obvious clinical observation | Larger swelling | No obvious clinical observation | Larger swelling and a scab on the edge of the swelling part | No obvious clinical observation | Larger swelling |
| 120 hr | No obvious clinical observation | Larger swelling with induration | No obvious clinical observation | Larger swelling with induration and a scab on the edge of the swelling part | No obvious clinical observation | Larger swelling with induration |
| 144 hr | 0.1 * 0.2 cm/few red site | Larger swelling with induration | 2 yellow scab with 0.8 * 0.5 cm of each, one was yellow with red edge | Larger swelling with induration and a scab on the edge of the swelling part | No obvious clinical observation | Larger swelling with induration |
| 178 hr | 4 yellow scabs with 0.1 * 0.2 cm each/superficial | induration/7 * 8 cm wide/ 5 * 8 cm wide/ 0.5-0.8 cm depth | 3 yellow scab with 0.2 * 0.2 cm each/superficial(one scab cover two red site) | induration/5 * 8 cm wide/0.5-0.8 cm depth; 0.3 * 0.3 cm/red scab | No obvious clinical observation | induration/5 * 5 cm wide/0.5-1 cm depth |
| 192 hr | 4 yellow scabs with 0.1 * 0.2 cm each/superficial. | induration/slight red/ 5 * 8 cm wide/ 0.5-0.8 cm depth | 2 yellow scabs with 0.2 * 0.2 each; 2 yellow scabs with 0.3 * 0.5 cm each | 0.3 * 0.1 cm/red scab induration/5 * 8 cm wide/0.5-0.8 cm depth; 0.3 * 0.3 cm/red scab; | No obvious clinical observation | induration/5 * 5 cm wide/0.5-1 cm depth |
| 216 hr | 4 yellow scabs with 0.1 * 0.2 cm each/superficial/ leasion shrinking | induration/slight red/ 4 * 8 cm wide/0.5-0.8 cm depth | Yellow scab/superficial/slight/ shrinking | 0.2 * 0.1 cm/red scab/shrinking; Induration/4 * 8 cm wide/0.5-0.8 cm depth; two discolorer shin became yellow scab/1 * 1 cm, 2 * 2 cm | No obvious clinical observation | Induration/5 * 8 cm wide/0.5-1 cm depth |
| 240 hr | 4 yellow scabs with 0.1 * 0.2 cm each/superficial/ leasion shrinking | induration/7 * 7 cm wide | Yellow scab/superficial/slight/ shrinking | 0.2 * 0.1 cm/red scab/shrinking; Induration/4 * 8 cm wide/; two discolorer shin became yellow scab/1 * 1 cm, 2 * 2 cm | No obvious clinical observation | Induration/5 * 7 cm wide |
| 264 hr | 4 yellow scabs with 0.1 * 0.1 cm/ each/superficial/ shrinking | Induration/7 * 7 cm wide/ | Yellow scab/superficial/slight/ shrinking | 0.1 * 0.1 cm/red scab/shrinking; Induration/7 * 7 cm wide/; two yellow scab/1 * 1 cm, 2 * 2 cm/superficial | No obvious clinical observation | Induration/9 * 3.5 cm wide/ |
| 288 hr | Yellow scab/superficial/ slight/shrinking to a red spot | Induration/7 * 7 cm wide/ | The yellow scab/disappeared, skin repairing; | Induration/7 * 8 cm/; two yellow scab/1 * 1 cm, 2 * 2 cm/superficial | no significant abnormal | Induration/9 * 5.5 cm wide/ |

| | D1001 | | D1002 | | D1003 | |
|---|---|---|---|---|---|---|
| time point | L-vehicle | R-TA | L-vehicle | R-TA | L-vehicle | R-TA |
| 312 hr | Yellow scab/superficial/slight/shrinking; 1 red rash/0.2 * 0.2 cm | Induration/slight red/ 10 * 6 cm(longest * shortest, short boot shape) wide/Skin 0.5-0.8 cm depth; Skin rashes at groin and oxter/moderate | skin repairing/the skin of scab site; New yellow scab/superficial/1.5 * 2 cm | Induration/slight red/10 * 6 cm wide/0.5-0.8 cm depth; 3 yellow scabs/moderate; Skin discolored/red/3 * 2 cm/with some little red spot; | No obvious clinical observation | Induration/9 * 5 cm wide/0.5-1.5 cm depth |
| 336 hr | No obvious clinical observation | Induration/slight red/ 10 * 6 cm(longest * shortest, short boot shape) wide/Skin rashes at groin | yellow scab/superficial/2 * 2 cm | Induration/10 * 6 cm wide; 5 yellow scabs(2 * 1 cm, 2 * 2 cm, 1 * 1 cm, 3 * 2 cm, 2 * 0.5 cm) on the right and one scab 2 * 2 on the left/moderate ulcer; | No obvious clinical observation | Induration/9 * 5 cm wide |
| 360 hr | No obvious clinical observation | Induration/slight red/ 10 * 6 cm(longest * shortest, short boot shape) wide/Skin rashes at groin and oxter | yellow scab/superficial/2 * 2 cm/ alopecia | Induration/10 * 6 cm wide; 5 yellow scabs(2 * 1 cm, 2 * 2 cm, 1 * 1 cm, 3 * 2 cm, 2 * 0.5 cm) on the right and one scab 2 * 2 on the left/alopecia | No obvious clinical observation | Induration/9 * 5 cm wide |
| 384 hr | No obvious clinical observation | Induration/slight red/ 9.5 * 6 cm(longest * shortest, short boot shape) wide/Skin rashes at groin and oxter/moderate | yellow scab/superficial/2 * 2 cm/ alopecia | Induration, the edge of the induration became soft/10 * 7 cm wide; 4 yellow scabs(1 * 1 cm, 2 * 2 cm, 3 * 2 cm, 2 * 0.5 cm) on the right and one scab 2 * 2 on the left/alopecia | No obvious clinical observation | Induration/9 * 5 cm wide |
| 408 hr | No obvious clinical observation | Induration/slight red/ 10 * 7 cm(longest * shortest, short boot shape) wide/Skin rashes at groin | yellow scab/superficial/2 * 2 cm/ alopecia | Induration, the edge of the induration became soft/10 * 7 cm wide; 4 yellow scabs(1 * 1 cm, 2 * 2 cm, 3 * 2 cm, 2 * 0.5 cm) on the right and one scab 2 * 2 on the left/alopecia | No obvious clinical observation | Induration/11 * 6 cm wide |
| 432 hr | No obvious clinical observation | Induration/slight red/ 10 * 6 cm(longest * shortest, short boot shape) wide/Skin rashes at groin and oxter | yellow scab/superficial/2 * 2 cm/ alopecia | Induration, the edge of the induration became soft/10 * 6 cm wide; 3 yellow scabs(1 * 1 cm, 3 * 2 cm, 2 * 0.5 cm) on the right and one scab 2 * 2 on the left/alopecia | No obvious clinical observation | Induration/10 * 5 cm wide |
| 456 hr | No obvious clinical observation | Induration/slight red/ 10 * 6 cm(longest * shortest, short boot shape) wide/Skin rashes at groin and oxter | yellow scab/superficial/2 * 2 cm/ alopecia | Induration, the edge of the induration became soft/11 * 7 cm wide(oval); 3 yellow scabs(1 * 1 cm, 3 * 2 cm, 2 * 0.5 cm) on the right and one scab 2 * 2 on the left/alopecia | No obvious clinical observation | Induration/9 * 6 cm wide(oval) |

-continued

| time point | D1001 L-vehicle | D1001 R-TA | D1002 L-vehicle | D1002 R-TA | D1003 L-vehicle | D1003 R-TA |
|---|---|---|---|---|---|---|
| 480 hr | No obvious clinical observation | Induration/slight red/ 10 * 7 cm(longest * shortest, short boot shape) wide/Skin rashes at groin | yellow scab/superficial/2 * 2 cm/ alopecia | Induration, the edge of the induration became soft/11 * 7 cm wide(oval); 3 yellow scabs(1 * 1 cm, 3 * 2 and 2 * 0.5 cm) on the right and one scab 2 * 2 on the left/two red bumps/alopecia | No obvious clinical observation | Induration/9 * 6 cm wide(oval) |
| 504 hr | No obvious clinical observation | Induration shrink/ 9 * 3 cm/some induration near the right knee, 0.2–0.5 deep/Skin rashes at groin | alopecia | Induration shrink, the edge of the induration became soft/9 * 6 cm wide; 2 yellow scabs(1 * 1 cm and 1.5 * 0.8 cm) on the right/two red bumps/alopecia | No obvious clinical observation | Induration shrink/7 * 3 cm wide |
| 528 hr | rashes at the vehicle injection area | Induration shrink/ 9 * 3 cm/some induration near the right knee, 0.2–0.5 deep/Skin rashes at groin and oxter | alopecia | Induration shrink, the edge of the induration became soft/8 * 6 cm wide; 1 yellow scab(0.8 * 0.7 cm) on the right/two red bumps/alopecia | No obvious clinical observation | Induration shrink/7 * 3 cm wide |
| 552 hr | rashes began to scab | Induration shrink/ 8 * 3 cm/some induration near the right knee, 0.2–0.5 deep/Skin rashes at groin and oxter/scabs 0.8 * 0.6 cm | alopecia | Induration shrink, the edge of the induration became soft/8 * 5 cm wide; 1 yellow scab(0.8 * 0.7 cm) on the right/two red bumps/alopecia | No obvious clinical observation | Induration shrink/7 * 3 cm wide |
| 576 hr | rashes began to scab | Induration shrink/ 7 * 3 cm/some induration near the right knee, 0.2–0.5 deep/Skin rashes at groin/ scabs 0.8 * 0.6 cm | alopecia | Induration shrink, the edge of the induration became soft/7 * 5 cm wide;/ two red bumps/alopecia | No obvious clinical observation | Induration shrink/6 * 3 cm wide |
| 600 hr | rashes began to scab | Induration shrink/ 7 * 3 cm/some induration near the right knee, 0.2–0.5 deep/Skin rashes at groin and oxter/scabs 0.8 * 0.6 cm | alopecia | Induration shrink, the edge of the induration became soft/7 * 5 cm wide;/two red bumps/alopecia | No obvious clinical observation | Induration shrink/6 * 3 cm wide |
| 624 hr | rashes began to scab | Induration shrink/ 7 * 3 cm/some induration near the right knee, 0.2–0.5 deep/Skin rashes at groin and oxter/scabs 0.8 * 0.6 cm | alopecia | Induration shrink, the edge of the induration became soft/7 * 5 cm wide;/two red bumps/alopecia | No obvious clinical observation | Induration shrink/6 * 3 cm wide |
| 648 hr | rashes began to scab | Induration shrink/ 7 * 3 cm/Skin rashes at groin and oxter | No obvious clinical observation | Induration shrink, the edge of the induration became soft/7 * 5 cm wide; | No obvious clinical observation | Induration shrink |
| 672 hr | rashes | Induration shrink/ 5.5 * 3 cm/Skin rashes at groin and oxter | rashes | Induration shrink, the edge of the induration became soft/7 * 4 cm wide; | No obvious clinical observation | Swelling/6.5 * 3 cm |
| 696 hr | rashes | Induration shrink/ 5 * 3 cm/Skin rashes at groin and oxter | rashes shrink | Induration shrink, the edge of the induration became soft/6.5 * 4 cm wide; | No obvious clinical observation | Swelling/5.5 * 3 cm |

-continued

| time point | D1001 | | D1002 | | D1003 | |
| --- | --- | --- | --- | --- | --- | --- |
| | L-vehicle | R-TA | L-vehicle | R-TA | L-vehicle | R-TA |
| 720 hr | rashes | Induration shrink/ 4.5 * 3 cm/Skin rashes at groin | No obvious clinical observation | Induration shrink, the edge of the induration became soft/5 * 4 cm wide | No obvious clinical observation | Swelling/5 * 3 cm |
| 744 hr | rashes | Induration shrink/ 4 * 3 cm/Skin rashes at groin and oxter | No obvious clinical observation | Induration shrink, the edge of the induration became soft/5 * 4 cm wide; | No obvious clinical observation | Swelling/5 * 3 cm/ induration at the middle of swelling |
| 768 hr | rashes | Induration shrink/ 4 * 3 cm/Skin rashes at groin and oxter | No obvious clinical observation | Induration shrink, the edge of the induration became soft/5 * 4 cm wide; some rushes were found at the stomach | No obvious clinical observation | Swelling/5 * 3 cm/ induration at the middle of swelling |
| 792 hr | rashes | Induration shrink/ 4 * 3 cm/Skin rashes at groin and oxter | No obvious clinical observation | Induration shrink, the edge of the induration became soft/5 * 4 cm wide; some rushes were found at the stomach | No obvious clinical observation | Swelling/5 * 3 cm/ induration at the middle of swelling |
| 816 hr | rashes | Induration shrink/ 4 * 3 cm/Skin rashes at groin and oxter | No obvious clinical observation | Induration shrink, the edge of the induration became soft/5 * 3 cm wide; some rushes were found at the stomach | No obvious clinical observation | Swelling/4 * 3 cm/ induration at the middle of swelling |
| 840 hr | rashes | Induration shrink/ 4 * 3 cm/Skin rashes at groin and oxter/BT: 38.5° C. | Swelling/red/warmth | swelling for whole leg/red/warmth/BT: 38.5° C. | No obvious clinical observation | Swelling/4 * 3 cm/ rushes at groin/BT: 38.4° C. |
| 864 hr | rashes | Induration shrink/ 4 * 3 cm/Skin rashes at groin and oxter/BT: 38.7° C. | Swelling/red/warmth | swelling 5 * 3 cm at upper leg and swelling for the whole calf/red/warmth/BT: 38.9° C. | No obvious clinical observation | Swelling/4 * 3 cm/ rushes at groin/BT: 38.8° C. |
| 888 hr | rashes | Induration shrink/ 4 * 3 cm/Skin rashes at groin and oxter/BT: 38.0° C. | Swelling/red/warmth | swelling 5 * 3 cm at upper leg and swelling for the whole calf/red/warmth/BT: 38.5° C. | No obvious clinical observation | Swelling/4 * 3 cm/ rushes at groin/BT: 38.6° C. |
| 912 hr | rashes | Induration shrink/ 3 * 2 cm/Skin rashes at groin and oxter/BT: 38.6° C. | Swelling/red/warmth | swelling 5 * 3 cm at upper leg and swelling for the whole calf/red/warmth/BT: 38.9° C. | No obvious clinical observation | Swelling/4 * 3 cm/ rushes at groin/BT: 38.6° C. |
| 936 hr | rashes | Induration shrink/ 3 * 2 cm/Skin rashes at groin and oxter/BT: 38.2° C. | red/warmth | swelling 3 * 2 cm at upper leg and swelling for the whole calf/red/warmth/BT: 38.9° C. | No obvious clinical observation | Swelling/3 * 2 cm/ rushes at groin/BT: 38.6° C. |
| 960 hr | rashes | Induration shrink/ 3 * 2 cm/Skin rashes at groin and oxter/BT: 38.5° C. | No obvious clinical observation | swelling 3 * 2 cm at upper leg/ BT: 39.0° C. | No obvious clinical observation | Swelling/3 * 2 cm/ rushes at groin/BT: 38.8° C. |
| 984 hr | rashes | Induration shrink/ 2 * 2 cm/Skin rashes at groin and oxter/BT: 38.3° C. | No obvious clinical observation | swelling 3 * 2 cm at upper leg/ BT: 39.2° C. | No obvious clinical observation | Swelling/3 * 2 cm/ rushes at groin/BT: 38.9° C. |
| 1008 hr | rashes | Induration shrink/ 2 * 2 cm/Skin rashes at groin and oxter/BT: 38.6° C. | No obvious clinical observation | swelling 3 * 2 cm at upper leg/ BT: 38.9° C. | No obvious clinical observation | Swelling/3 * 2 cm/ rushes at groin/BT: 38.6° C. |
| 1032 hr | rashes | Skin rashes at groin and oxter | No obvious clinical observation | swelling 3 * 2 cm at upper leg | No obvious clinical observation | Swelling/2 * 2 cm/ rushes at groin |

-continued

| time point | D1001 | | D1002 | | D1003 | |
| --- | --- | --- | --- | --- | --- | --- |
| | L-vehicle | R-TA | L-vehicle | R-TA | L-vehicle | R-TA |
| 1056 hr | rashes | Skin rashes at groin and oxter/BT: 38.3° C. | No obvious clinical observation | swelling 3 * 2 cm at upper leg/BT: 38.9° C. | No obvious clinical observation | Swelling/2 * 2 cm/ rushes at groin/BT: 38.6° C. |
| 1080 hr | rashes | Skin rashes at groin and oxter | No obvious clinical observation | swelling 3 * 2 cm at upper leg/BT: 38.8° C. | No obvious clinical observation | Swelling/2 * 2 cm/ rushes at groin/BT: 38.9° C. |
| 1104 hr | rashes | Skin rashes at groin and oxter/BT: 38.6° C. | No obvious clinical observation | swelling 2 * 2 cm at upper leg/BT: 38.9° C. | No obvious clinical observation | swelling shrinking/rashes subsiding/BT: 39.1° C. |
| 1128 hr | rashes subsiding | Skin rashes at groin and oxter | No obvious clinical observation | swelling 2 * 2 cm at upper leg/BT: 38.8° C. | No obvious clinical observation | swelling shrinking/rashes subsiding |
| 1152 hr | rashes subsiding | Skin rashes at groin and oxter | No obvious clinical observation | swelling 2 * 2 cm at upper leg | No obvious clinical observation | swelling shrinking/rashes subsiding |
| 1176 hr | rashes subsiding | Skin rashes at groin and oxter | No obvious clinical observation | swelling shrinking | No obvious clinical observation | swelling shrinking/rashes subsiding |
| 1200 hr | rashes subsiding | Skin rashes at groin and oxter/BT: 38.7° C. | No obvious clinical observation | swelling shrinking/BT: 38.8 | No obvious clinical observation | swelling shrinking/rashes subsiding/BT: 38.9° C. |
| 1224 hr | rashes subsiding | Skin rashes at groin and oxter/BT: 38.8 | No obvious clinical observation | swelling shrinking/BT: 39.0 | No obvious clinical observation | swelling shrinking/rashes subsiding |
| 1248 hr | No obvious clinical observation | Skin rashes at groin and oxter/BT: 38.9 | No obvious clinical observation | swelling shrinking/BT38.9 | No obvious clinical observation | swelling shrinking/rashes subsiding/BT: 39.2 |
| 1272 hr | No obvious clinical observation | Skin rashes at groin and oxter | No obvious clinical observation | No obvious clinical observation | No obvious clinical observation | swelling shrinking/rashes subsiding/BT: 38.8 |
| 1296 hr | No obvious clinical observation | Skin rashes at groin and oxter | No obvious clinical observation | No obvious clinical observation | No obvious clinical observation | No obvious clinical observation |
| 1512 hr | No obvious clinical observation | Skin rashes at groin and oxter | No obvious clinical observation | No obvious clinical observation | No obvious clinical observation | No obvious clinical observation |

|  | D1501 | | D1502 | | D1502 | |
|---|---|---|---|---|---|---|
| time point | L-vehicle | R-TA | L-vehicle | R-TA | L-vehicle | R-TA |
| 8 hr | No obvious clinical observation | No obvious clinical observation | No obvious clinical observation | No obvious clinical observation | No obvious clinical observation | No obvious clinical observation |
| 24 hr | No obvious clinical observation | No obvious clinical observation/BT: 38.8 | No obvious clinical observation | No obvious clinical observation | No obvious clinical observation | No obvious clinical observation |
| 48 hr | No obvious clinical observation | red spot near the saphenous vein of hind limb/BT: 38.6 | No obvious clinical observation | No obvious clinical observation | No obvious clinical observation | No obvious clinical observation |
| 72 hr | No obvious clinical observation | red spot near the saphenous vein of hind limb/BT: 38.8 | No obvious clinical observation | No obvious clinical observation | No obvious clinical observation | No obvious clinical observation |
| 96 hr | No obvious clinical observation | red spot near the saphenous vein of hind limb/BT: 39.2 | No obvious clinical observation | Swelling at the whole leg, induration 11 * 11 cm at the groin/red/BT: 38.3 | No obvious clinical observation | No obvious clinical observation |
| 120 hr | No obvious clinical observation | red spot near the saphenous vein of hind limb subsiding/BT: 39.2 | No obvious clinical observation | Swelling at the whole leg, induration 11 * 11 cm at the groin/red/BT: 38.7 | No obvious clinical observation | No obvious clinical observation |
| 144 hr | Red spot at the groin | Sweling 8 * 5 cm at inner upper leg with redness/swelling at calf/red spot near the saphenous vein of hind limb subsiding/BT: 39.6 | No obvious clinical observation | Swelling at the whole leg, induration 11 * 11 cm at the groin/red/BT: 38.3 | No obvious clinical observation | swelling at inner upper leg 8 * 8 cm/BT: 39.5 |
| 168 hr | Red spot at the groin | Sweling 8 * 5 cm at inner upper leg with redness/swelling at calf/red spot near the saphenous vein of hind limb subsiding/BT: 39.6 | No obvious clinical observation | Swelling at the whole leg, induration 11 * 11 cm at the groin/red/BT: 38.4 | Red spot at the groin | swelling at inner upper leg 8 * 8 cm/BT: 39.3 |
| 192 hr | Red spot at the groin | Sweling 8 * 5 cm at inner upper leg with redness/swelling at calf/BT: 39.0 | No obvious clinical observation | Swelling at the whole leg, induration 9 * 9 cm at the groin/red/BT: 38.5 | Red spot at the groin | swelling at inner upper leg 8 * 8 cm/BT: 38.0 |
| 216 hr | Red spot at the groin | swelling 8 * 5 cm/BT: 39.0 | No obvious clinical observation | Swelling at the whole leg, induration 9 * 9 cm at the groin/red/BT: 38.4 | Red spot at the groin | swelling at inner upper leg 8 * 8 cm/BT: 38.8 |
| 240 hr | Red spot at the groin | swelling 8 * 5 cm/BT: 39.0 | No obvious clinical observation | Swelling 9 * 9 cm at the back and inner upper leg/red/BT: 38.9 | Red spot at the groin | swelling at inner upper leg 8 * 8 cm/BT: 39.2 |
| 264 hr | Red spot at the groin | swelling 6 * 5 cm/BT: 38.9 | No obvious clinical observation | Swelling 9 * 9 cm at the back and inner upper leg/red/BT: 38.3 | Red spot at the groin | swelling at inner upper leg 8 * 8 cm/BT: 38.9 |
| 288 hr | Red spot at the groin | swelling 6 * 5 cm/BT: 38.9 | No obvious clinical observation | Swelling 9 * 9 cm at the back and inner upper leg/red/BT: 38.5 | Red spot at the groin subsiding | swelling at inner upper leg 8 * 8 cm/BT: 38.8 |
| day 13 | Red spot at the groin | swelling 6 * 5 cm | No obvious clinical observation | Swelling 9 * 9 cm at the back and inner upper leg | No obvious clinical observation | swelling at inner upper leg 8 * 8 cm |
| day 14 | Red spot at the groin | swelling 3 * 4 cm | No obvious clinical observation | Swelling 9 * 8 cm at the back and inner upper leg | No obvious clinical observation | swelling at inner upper leg 8 * 7 cm |

-continued

| time point | D1501 | | D1502 | | D1502 | |
| --- | --- | --- | --- | --- | --- | --- |
| | L-vehicle | R-TA | L-vehicle | R-TA | L-vehicle | R-TA |
| day 15 | Red spot at the groin | swelling 3 * 4 cm | No obvious clinical observation | Swelling 8 * 8 cm at the back and inner upper leg | No obvious clinical observation | swelling at inner upper leg 8 * 7 cm |
| day 16 | Red spot at the groin | No obvious clinical observation | No obvious clinical observation | Swelling 6 * 6 cm at the back and inner upper leg | No obvious clinical observation | swelling at inner upper leg 6 * 6 cm |
| day 17 | Red spot at the groin | No obvious clinical observation | No obvious clinical observation | Swelling 6 * 5 cm at the back and inner upper leg | No obvious clinical observation | swelling at inner upper leg 4 * 5 cm |
| day 18 | Red spot at the groin | No obvious clinical observation | No obvious clinical observation | Swelling 6 * 5 cm at the back and inner upper leg | No obvious clinical observation | swelling at inner upper leg 4 * 5 cm |
| day 19 | Red spot at the groin | No obvious clinical observation | No obvious clinical observation | Swelling 5 * 5 cm at the back and inner upper leg | No obvious clinical observation | swelling at inner upper leg 4 * 5 cm |
| day 20 | Red spot at the groin | No obvious clinical observation | No obvious clinical observation | Swelling 5 * 5 cm at the back and inner upper leg | No obvious clinical observation | swelling at inner upper leg 4 * 5 cm |
| day 21 | Red spot at the groin | No obvious clinical observation | No obvious clinical observation | Swelling 4 * 4 cm at the back and inner upper leg | No obvious clinical observation | swelling at inner upper leg 3 * 3 cm |
| day 22 | Red spot at the groin | No obvious clinical observation | No obvious clinical observation | Swelling 4 * 4 cm at the back and inner upper leg | No obvious clinical observation | swelling at inner upper leg 2 * 2 cm |
| day 23 | Red spot at the groin | No obvious clinical observation | No obvious clinical observation | Swelling 4 * 4 cm at the back and inner upper leg | No obvious clinical observation | No obvious clinical observation |
| day 24 | Red spot at the groin | No obvious clinical observation | No obvious clinical observation | Swelling 4 * 3 cm at the back and inner upper leg | No obvious clinical observation | No obvious clinical observation |
| day 25 | Red spot at the groin | No obvious clinical observation | No obvious clinical observation | Swelling 4 * 3 cm at the back and inner upper leg | No obvious clinical observation | No obvious clinical observation |
| day 28 | Red spot at the groin | No obvious clinical observation | No obvious clinical observation | Swelling 3 * 3 cm at the back and inner upper leg | No obvious clinical observation | No obvious clinical observation |
| day 35 | No obvious clinical observation | No obvious clinical observation | No obvious clinical observation | No obvious clinical observation | No obvious clinical observation | No obvious clinical observation |
| day 42 | No obvious clinical observation | No obvious clinical observation | No obvious clinical observation | No obvious clinical observation | No obvious clinical observation | No obvious clinical observation |
| day 49 | No obvious clinical observation | No obvious clinical observation | No obvious clinical observation | No obvious clinical observation | No obvious clinical observation | No obvious clinical observation |
| day 56 | No obvious clinical observation | No obvious clinical observation | No obvious clinical observation | No obvious clinical observation | No obvious clinical observation | No obvious clinical observation |
| day 63 | No obvious clinical observation | No obvious clinical observation | No obvious clinical observation | No obvious clinical observation | No obvious clinical observation | No obvious clinical observation |

| time point | D1501 | | D1502 | | D1503 | |
| --- | --- | --- | --- | --- | --- | --- |
| | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |

-continued

| time point | D1501 L-vehicle | D1501 R-TA | D1502 L-vehicle | D1502 R-TA | D1503 L-vehicle | D1503 R-TA |
|---|---|---|---|---|---|---|
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | several rashes on the outside and inside of left leg/several rashes on the left crus | several rashes on the outside and inside of right thigh |
| Day 43 | No obvious clinical observation | No obvious clinical observation | No obvious clinical observation | No obvious clinical observation | several rashes on the outside and inside of left leg/several rashes on the left crus | several rashes on the outside and inside of right thigh |
| Day 46 | No obvious clinical observation | No obvious clinical observation | No obvious clinical observation | No obvious clinical observation | several rashes on the outside and inside of left leg/several rashes on the left crus/fresh rashes on the upper thigh | several rashes on the outside and inside of right thigh/fresh rashes on the upper thigh |
| Day 48 | No obvious clinical observation | No obvious clinical observation | No obvious clinical observation | No obvious clinical observation | several rashes on the outside of left leg/escharosis of several rashes on the left crus/several rashes on the thighs | several rashes on the outside of right thigh/several rashes on the thighs/escharosis of several rashes on the inside of the leg |
| Day 49 | several rashes on the outside and inside of left leg/several rashes on the thighs | No obvious clinical observation | No obvious clinical observation | No obvious clinical observation | several rashes on the outside and inside of left leg/several rashes on the thighs | several rashes on the outside and inside of right thigh |
| Day 53 | No obvious clinical observation | No obvious clinical observation | No obvious clinical observation | No obvious clinical observation | recovery for rashes on the leg | recovery for rashes on the leg |
| Day 55 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |

| time point | D1501 L-TA | D1501 R-vehicle | D1502 L-TA | D1502 R-vehicle | D1503 L-TA | D1503 R-vehicle |
|---|---|---|---|---|---|---|
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | No obvious clinical observation | No obvious clinical observation |
| Day 63 | No obvious clinical observation | No obvious clinical observation | No obvious clinical observation | No obvious clinical observation | No obvious clinical observation | No obvious clinical observation |
| Day 70 | No obvious clinical observation | No obvious clinical observation | No obvious clinical observation | No obvious clinical observation | Slight rashes on the outside of the hindlimb | Slight rashes on the outside of the hindlimb. |
| Day 73 | No obvious clinical observation | No obvious clinical observation | No obvious clinical observation | No obvious clinical observation | Recovery for rashes, skin exuviating | Recovery for rashes, skin exuviating |
| Day 75 | Slight rashes appeared on the outside of hindlimb. | Slight rashes appeared on the outside of hindlimb. | No obvious clinical observation | No obvious clinical observation | Recovery for rashes, slight skin exuviating | Recovery for rashes, slight skin exuviating |
| Day 77 | Slight rashes appeared on the outside of hindlimb. | Slight rashes appeared on the outside of hindlimb. | New rashes appeared on the inside of the hindlimb. | New rashes appeared on the inside of the hindlimb. | New rashes appeared on both outside and inside of the hindlimb. | New rashes appeared on both outside and inside of the hindlimb. |
| Day 80 | Slight rashes appeared on the outside of hindlimb. | Slight rashes appeared on the outside of hindlimb. | Slight rashes on the inside of the hindlimb, and new rashes appeared on the outside. | Slight rashes on the inside of the hindlimb, and new rashes appeared on the outside. | Recovery for the rashes on the outside and inside of the hindlimb. | Slight rashes on the inside of the hindlimb, and recovery for the rashes on the inside |
| Day 82 | a few rash on the outside of left leg | No obvious clinical observation | a few rash on the outside of leg | a few rash on the outside of leg | rashes disappeared on the inside and outside of leg | recovery for the rashes on the outside leg/ several rashes on the inside of leg |
| Day 84 | rashes disappeared on the outside of left leg | No obvious clinical observation | escharosis of rashes on the outside of leg | rashes disappeared on the outside of leg | rashes disappeared on the inside and outside of leg | recovery for the rashes on the outside leg/ several rashes on the inside of leg |

-continued

| time point | D1501 | | D1502 | | D1503 | |
|---|---|---|---|---|---|---|
| | L-TA | R-vehicle | L-TA | R-vehicle | L-TA | R-vehicle |
| Day 87 | No obvious clinical observation | No obvious clinical observation | No obvious clinical observation | No obvious clinical observation | No obvious clinical observation | slight rashes on the inside of leg |
| Day 89 | No obvious clinical observation | No obvious clinical observation | No obvious clinical observation | No obvious clinical observation | No obvious clinical observation | slight rashes on the inside of leg |
| Day 91 | No obvious clinical observation | No obvious clinical observation | No obvious clinical observation | No obvious clinical observation | No obvious clinical observation | No obvious clinical observation |

| time point | D1501 | | D1502 | | D1503 | |
|---|---|---|---|---|---|---|
| | L-vehicle | R-TA | L-vehicle | R-TA | L-vehicle | R-TA |
| Day 0 | No obvious clinical observation | No obvious clinical observation | No obvious clinical observation | No obvious clinical observation | No obvious clinical observation | No obvious clinical observation |
| Day 1 | No obvious clinical observation | No obvious clinical observation | No obvious clinical observation | No obvious clinical observation | Liquid feces about 20 mL | |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 4 | No obvious clinical observation | No obvious clinical observation | No obvious clinical observation | No obvious clinical observation | No obvious clinical observation | No obvious clinical observation |
| Day 5 | No obvious clinical observation | No obvious clinical observation | No obvious clinical observation | No obvious clinical observation | No obvious clinical observation | No obvious clinical observation |
| Day 6 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | Rashes on the outside of the hindlimb | Rashes and exuviate on the outside of the hindlimb | No obvious clinical observation | No obvious clinical observation |
| Day 38 | Slight rashes on the inside and outside of the hindlimb | Slight rashes on the outside of the hindlimb | Much rashes on the outside of the hindlimb, skin exuviating | Much rashes on the outside of the hindlimb, skin exuviating | No obvious clinical observation | No obvious clinical observation |
| Day 40 | Slight rashes on the inside and outside of the hindlimb | Slight rashes on the outside of the hindlimb | Much rashes on the outside of the hindlimb, skin exuviating | Much rashes on the outside of the hindlimb, skin exuviating | No obvious clinical observation | No obvious clinical observation |
| Day 42 | Slight rashes on the inside | Slight rashes on the inside | Slight rashes on the outside of | Much rashes on | No obvious clinical | No obvious clinical |

-continued

| time point | D1501 | | D1502 | | D1503 | |
|---|---|---|---|---|---|---|
| | L-vehicle | R-TA | L-vehicle | R-TA | L-vehicle | R-TA |
| | and outside of the hindlimb | and outside of the hindlimb | the hindlimb, skin exuviating | the outside of the hindlimb, skin exuviating | observation | observation |
| Day 45 | Slight rashes on the inside and outside of the hindlimb | Slight rashes on the inside and outside of the hindlimb | Slight rashes on the outside of the hindlimb, skin exuviating | Much rashes on the outside of the hindlimb, skin exuviating | No obvious clinical observation | No obvious clinical observation |
| Day 47 | Rashes scabbing on the outside of the hindlimb/ Slight rashes on the inside of the hindlimb | Rashes scabbing on the outside of the hindlimb/ Slight rashes on the inside of the hindlimb | Slight rashes on the outside of the hindlimb, skin exuviating | Much rashes on the outside of the hindlimb, skin exuviating | No obvious clinical observation | No obvious clinical observation |
| Day 49 | rashes disappeared on the inside and outside of the leg | rashes disappeared on the inside and outside of the leg | Slight rashes on the outside of the hindlimb, skin exuviating | slight rashes on the outside of the hindlimb, skin exuviating | No obvious clinical observation | No obvious clinical observation |
| Day 52 | No obvious clinical observation | rashes disappeared on the inside and outside of the leg | Slight rashes on the outside of the hindlimb, skin exuviating | slight rashes on the outside of the hindlimb, skin exuviating | No obvious clinical observation | No obvious clinical observation |
| Day 54 | No obvious clinical observation | No obvious clinical observation | rashes disappeared on the outside of the hindlimb | rashes disappeared on the outside of the hindlimb | No obvious clinical observation | No obvious clinical observation |
| Day 56 | No obvious clinical observation | No obvious clinical observation | No obvious clinical observation | rashes disappeared on the outside of the hindlimb | No obvious clinical observation | No obvious clinical observation |
| Day 59 | No obvious clinical observation | No obvious clinical observation | No obvious clinical observation | No obvious clinical observation | No obvious clinical observation | No obvious clinical observation |

| time point | D1001 | | D1002 | |
|---|---|---|---|---|
| | L-vehicle | R-TA | L-vehicle | R-TA |
| Day 0 | No obvious clinical observation | No obvious clinical observation | No obvious clinical observation | No obvious clinical observation |
| Day 1 | No obvious clinical observation | No obvious clinical observation | No obvious clinical observation | No obvious clinical observation |
| Day 2 | No obvious clinical observation | No obvious clinical observation | No obvious clinical observation | No obvious clinical observation |
| Day 3 | No obvious clinical observation | No obvious clinical observation | No obvious clinical observation | No obvious clinical observation |
| Day 4 | No obvious clinical observation | No obvious clinical observation | No obvious clinical observation | No obvious clinical observation |
| Day 5 | No obvious clinical observation | No obvious clinical observation | No obvious clinical observation | No obvious clinical observation |

-continued

| time point | D1001 | | D1002 | |
|---|---|---|---|---|
| | L-vehicle | R-TA | L-vehicle | R-TA |
| Day 6 | No obvious clinical observation | No obvious clinical observation | No obvious clinical observation | No obvious clinical observation |
| Day 7 | No obvious clinical observation | No obvious clinical observation | No obvious clinical observation | No obvious clinical observation |
| Day 14 | No obvious clinical observation | No obvious clinical observation | No obvious clinical observation | No obvious clinical observation |
| Day 21 | No obvious clinical observation | No obvious clinical observation | No obvious clinical observation | No obvious clinical observation |
| Day 28 | Left hind leg lateral small red rash, inside a small amount of red rash | The right hind leg a few red rash, molting, inside a small amount of red rash | No obvious clinical observation | No obvious clinical observation |
| Day 30 | Left hind leg lateral small red rash, inside a small amount of red rash | Right leg lateral have small red rash, peeling | No obvious clinical observation | No obvious clinical observation |
| Day 32 | Left hind leg lateral small red rash, inside a lot of red rash | ; Right leg lateral small red rash, inside a lot of red rash | No obvious clinical observation | No obvious clinical observation |
| Day 35 | Left hind leg lateral small red rash, inside a lot of red rash | ; Right leg lateral small red rash, inside a lot of red rash | No obvious clinical observation | No obvious clinical observation |
| Day 37 | a small amount of exuviate on the outside of leg/a lagre amount of rashes on the inside of leg | exuviate on the outside of leg/a lagre amount of rashes on the inside of leg | No obvious clinical observation | No obvious clinical observation |
| Day 39 | a small amount of exuviate on the outside of leg/a lagre amount of rashes on the inside of leg | exuviate on the outside of leg/a lagre amount of rashes on the inside of leg | No obvious clinical observation | No obvious clinical observation |
| Day 42 | a lagre amount of rashes on the inside of leg | a large amount of rashes on the inside of leg | No obvious clinical observation | No obvious clinical observation |
| Day 44 | a small amount of rashes on the inside of leg | a small amount of rashes on the inside of leg | No obvious clinical observation | No obvious clinical observation |
| Day 46 | a small amount of rashes on the inside of leg | a small amount of rashes on the inside of leg | No obvious clinical observation | No obvious clinical observation |
| Day 49 | a small amount of rashes on the inside of leg | a small amount of rashes on the inside of leg, Red rash subsided | No obvious clinical observation | No obvious clinical observation |

| time point | D1501 | | D1502 | | D1503 | |
|---|---|---|---|---|---|---|
| | L-vehicle | R-TA | L-vehicle | R-TA | L-vehicle | R-TA |
| 8 hr | No obvious clinical observation | No obvious clinical observation | No obvious clinical observation | No obvious clinical observation | No obvious clinical observation | No obvious clinical observation |
| 24 hr | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |

-continued

| time point | D1501 | | D1502 | | D1503 | |
|---|---|---|---|---|---|---|
| | L-vehicle | R-TA | L-vehicle | R-TA | L-vehicle | R-TA |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |
| Day 56 | No obvious clinical observation | No obvious clinical observation | No obvious clinical observation | No obvious clinical observation | several rashes on the left leg | several rashes on the right leg |
| Day 58 | No obvious clinical observation | No obvious clinical observation | No obvious clinical observation | No obvious clinical observation | several rashes on the left leg | several rashes on the right leg |
| Day 61 | No obvious clinical observation | No obvious clinical observation | No obvious clinical observation | No obvious clinical observation | several rashes on the left leg | several rashes on the right leg |
| Day 63 | No obvious clinical observation | No obvious clinical observation | No obvious clinical observation | No obvious clinical observation | escharosis of several rashes on the outside of left leg/ several rashes on the inside of left leg | several rashes on the outside of right leg |
| Day 65 | No obvious clinical observation | No obvious clinical observation | No obvious clinical observation | No obvious clinical observation | escharosis of rashes on the outside of left leg/ rashes subside on the inside of left leg | recovery for rashes on the inside of right leg |
| Day 68 | No obvious clinical observation | No obvious clinical observation | No obvious clinical observation | No obvious clinical observation | No obvious clinical observation | No obvious clinical observation |
| Day 70 | No obvious clinical observation | No obvious clinical observation | No obvious clinical observation | No obvious clinical observation | No obvious clinical observation | No obvious clinical observation |
| Day 72 | No obvious clinical observation | No obvious clinical observation | No obvious clinical observation | No obvious clinical observation | No obvious clinical observation | No obvious clinical observation |

| time point | D1501 | | D1502 | | D1503 | |
|---|---|---|---|---|---|---|
| | L-vehicle (Sesameoil + 1% Benzyl Alcohol) | R-TA | L-vehicle (Cottonseed + 1% Benzyl Alcohol) | R-TA | L-vehicle (Sesameoil + 1% Benzyl Alcohol) | R-TA |
| 8 hr | No obvious clinical observation | No obvious clinical observation | No obvious clinical observation | No obvious clinical observation | No obvious clinical observation | No obvious clinical observation |
| 24 hr | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |

| time point | D1501 L-vehicle (Sesameoil + 1% Benzyl Alcohol) | D1501 R-TA | D1502 L-vehicle (Cottonseed + 1% Benzyl Alcohol) | D1502 R-TA | D1503 L-vehicle (Sesameoil + 1% Benzyl Alcohol) | D1503 R-TA |
|---|---|---|---|---|---|---|
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | Swelling 6 * 6.5 cm | No obvious clinical observation | No obvious clinical observation | No obvious clinical observation | No obvious clinical observation |
| Day 28 | No obvious clinical observation | Swelling 5 * 3.5 cm | No obvious clinical observation | No obvious clinical observation | No obvious clinical observation | No obvious clinical observation |
| Day 35 | No obvious clinical observation | Swelling 5 * 3 cm | No obvious clinical observation | No obvious clinical observation | No obvious clinical observation | No obvious clinical observation |
| Day 37 | Several rashes on the inside and outside of the left hindlimb. | Several rashes on the outside of the right hindlimb. Swelling 5 * 3 cm. | No obvious clinical observation | No obvious clinical observation | No obvious clinical observation | No obvious clinical observation |
| Day 40 | Several rashes on the inside and outside of the left hindlimb, more on the inside. | Several rashes on the inside and outside of the right hindlimb, more on the inside. | No obvious clinical observation | No obvious clinical observation | No obvious clinical observation | No obvious clinical observation |
| Day 42 | Several rashes on the inside and outside of the left hindlimb, more on the inside | Several rashes on the inside and outside of the right hindlimb, more on the inside | Several rashes on the outside of the left hindlimb | Several rashes on the outside of the right hindlimb | No obvious clinical observation | No obvious clinical observation |
| Day 44 | Several rashes on the inside of the left hindlimb | Several rashes on the inside and outside of the right hindlimb, more on the inside | Several rashes on the outside of the left hindlimb | Several rashes on the outside of the right hindlimb | No obvious clinical observation | One rash on the outside of the right hindlimb |
| Day 47 | Rashes on the inside of the left hindlimb were scabbing | Rashes on the outside of the hindlimb were disappearing, rashes on the inside were scabbing | Rashes on the outside of the hindlimb were disappearing | Rashes on the outside of the hindlimb were disappearing | No obvious clinical observation | Rashes on the outside of the hindlimb were disappearing |
| Day 49 | Slight rashes appeared on the outside of the hindlimb, rashes on the inside were scabbing | Slight rashes appeared on the outside of the hindlimb, rashes on the inside were scabbing | Slight rashes appeared on the outside of the hindlimb | Slight rashes appeared on the outside of the hindlimb | No obvious clinical observation | No obvious clinical observation |
| Day 51 | Slight rashes on the outside of the hindlimb, some new rashes appeared on the inside | Slight rashes on the outside of the hindlimb, rashes on the inside were scabbing | Slight rashes on the outside of the hindlimb | Slight rashes on the outside of the hindlimb, rashes and exuviate appeared on the groin | No obvious clinical observation | No obvious clinical observation |

-continued

| time point | D1501 | | D1502 | | D1503 | |
|---|---|---|---|---|---|---|
| | L-vehicle (Sesameoil + 1% Benzyl Alcohol) | R-TA | L-vehicle (Cottonseed + 1% Benzyl Alcohol) | R-TA | L-vehicle (Sesameoil + 1% Benzyl Alcohol) | R-TA |
| Day 54 | Slight rashes on the outside of the hindlimb | Recovery for the rashes | Recovery for the rashes | Slight rashes on the outside of the hindlimb, rashes and exuviate appeared on the groin, some new rashes appeared on the inside | No obvious clinical observation | No obvious clinical observation |
| Day 56 | Slight rashes and skin exuviating on the outside of the hindlimb, some new rashes appeared on the inside. | New rashes appeared on the outside of the hindlimb. | Slight rashes on the outside of the hindlimb | Slight rashes appeared on both inside and outside of the hindlimb, rashes and skin exuviating on the groin. | No obvious clinical observation | No obvious clinical observation |
| Day 58 | Slight rashes and skin exuviating on the outside of the hindlimb, slight rashes on the inside | Slight rashes on the outside of the hindlimb | Slight rashes on the outside of the hindlimb | Slight rashes on both inside and outside of the hindlimb, rashes and skin exuviating on the groin | No obvious clinical observation | No obvious clinical observation |
| Day 61 | Slight rashes on the inside of the hindlimb | Recovery for the rashes on the outside of the hindlimb | Slight rashes on the outside of the hindlimb, skin exuviating | Slight rashes on both inside and outside of the hindlimb, skin exuviating on the outside, rashes and skin exuviating on the groin | No obvious clinical observation | No obvious clinical observation |
| Day 63 | Recovery for the rashes on the outside of the hindlimb/ rashes on the inside of the hindlimb | Recovery for the rashes on the outside of the hindlimb | Slight rashes on the outside of the hindlimb, skin exuviating | Slight rashes on both inside and outside of the hindlimb, skin exuviating on the outside, rashes and skin exuviating on the groin | No obvious clinical observation | No obvious clinical observation |
| Day 65 | Recovery for the rashes on the outside of the hindlimb/ escharosis of rashes on the inside of the hindlimb | Recovery for the rashes on the outside of the hindlimb | Slight rashes on the outside of the hindlimb, skin exuviating | Slight rashes on both inside and outside of the hindlimb, skin exuviating on the outside, rashes and skin exuviating on the groin | No obvious clinical observation | No obvious clinical observation |

-continued

| time point | D1501 L-vehicle (Sesameoil + 1% Benzyl Alcohol) | D1501 R-TA | D1502 L-vehicle (Cottonseed + 1% Benzyl Alcohol) | D1502 R-TA | D1503 L-vehicle (Sesameoil + 1% Benzyl Alcohol) | D1503 R-TA |
|---|---|---|---|---|---|---|
| Day 68 | rashes scabbing on the inside of the hindlimb | No obvious clinical observation | Slight rashes on the outside of the hindlimb, skin exuviating | Slight rashes on both inside and outside of the hindlimb, skin exuviating on the outside, rashes and skin exuviating on the groin | No obvious clinical observation | No obvious clinical observation |
| Day 70 | rashes scabbing on the inside of the hindlimb | No obvious clinical observation | No obvious clinical observation | rashes and skin exuviating on the groin | No obvious clinical observation | No obvious clinical observation |
| Day 72 | rashes scabbing on the inside of the hindlimb | No obvious clinical observation | No obvious clinical observation | rashes and skin exuviating on the inside of the hindlimb and groin | No obvious clinical observation | No obvious clinical observation |
| Day 75 | rashes disappeared on the inside of the hindlimb | No obvious clinical observation | No obvious clinical observation | slight rashes and skin exuviating on the inside of the hindlimb and groin | No obvious clinical observation | No obvious clinical observation |

| time point | D1501 L-vehicle | D1501 R-TA | D1502 L-vehicle | D1502 R-TA | D1503 L-vehicle | D1503 R-TA |
|---|---|---|---|---|---|---|
| 8 hr | No obvious clinical observation | No obvious clinical observation | No obvious clinical observation | No obvious clinical observation | No obvious clinical observation | No obvious clinical observation |
| 24 hr | No obvious clinical observation | No obvious clinical observation | No obvious clinical observation | No obvious clinical observation | No obvious clinical observation | No obvious clinical observation |
| Day 2 | No obvious clinical observation | No obvious clinical observation | No obvious clinical observation | No obvious clinical observation | No obvious clinical observation | No obvious clinical observation |
| Day 3 | No obvious clinical observation | No obvious clinical observation | No obvious clinical observation | No obvious clinical observation | No obvious clinical observation | No obvious clinical observation |
| Day 7 | No obvious clinical observation | No obvious clinical observation | No obvious clinical observation | No obvious clinical observation | No obvious clinical observation | No obvious clinical observation |
| Day 14 | No obvious clinical observation | No obvious clinical observation | No obvious clinical observation | No obvious clinical observation | No obvious clinical observation | No obvious clinical observation |
| Day 21 | No obvious clinical observation | No obvious clinical observation | No obvious clinical observation | No obvious clinical observation | No obvious clinical observation | No obvious clinical observation |
| Day 28 | No obvious clinical observation | No obvious clinical observation | No obvious clinical observation | No obvious clinical observation | No obvious clinical observation | No obvious clinical observation |
| Day 35 | No obvious clinical observation | No obvious clinical observation | No obvious clinical observation | No obvious clinical observation | No obvious clinical observation | No obvious clinical observation |
| Day 42 | No obvious clinical observation | No obvious clinical observation | No obvious clinical observation | No obvious clinical observation | No obvious clinical observation | No obvious clinical observation |
| Day 49 | No obvious clinical observation | No obvious clinical observation | No obvious clinical observation | No obvious clinical observation | No obvious clinical observation | No obvious clinical observation |

-continued

| time point | D1501 | | D1502 | | D1503 | |
|---|---|---|---|---|---|---|
| | L-vehicle | R-TA | L-vehicle | R-TA | L-vehicle | R-TA |
| Day 56 | No obvious clinical observation | No obvious clinical observation | No obvious clinical observation | No obvious clinical observation | several rashes on the left leg | No obvious clinical observation |
| Day 58 | No obvious clinical observation | No obvious clinical observation | No obvious clinical observation | No obvious clinical observation | several rashes on the outside of left leg | No obvious clinical observation |
| Day 61 | No obvious clinical observation | No obvious clinical observation | No obvious clinical observation | No obvious clinical observation | several rashes and escharosis on the outside of left leg | No obvious clinical observation |
| Day 63 | No obvious clinical observation | No obvious clinical observation | No obvious clinical observation | No obvious clinical observation | escharosis of rashes on the outside of left leg | No obvious clinical observation |
| Day 65 | No obvious clinical observation | No obvious clinical observation | No obvious clinical observation | No obvious clinical observation | recovery for rashes on the outside of left leg | No obvious clinical observation |
| Day 68 | No obvious clinical observation | No obvious clinical observation | No obvious clinical observation | No obvious clinical observation | No obvious clinical observation | No obvious clinical observation |
| Day 70 | No obvious clinical observation | No obvious clinical observation | No obvious clinical observation | No obvious clinical observation | No obvious clinical observation | No obvious clinical observation |
| Day 72 | No obvious clinical observation | No obvious clinical observation | No obvious clinical observation | No obvious clinical observation | No obvious clinical observation | No obvious clinical observation |

| time point | D1001 | | D1002 | | D1003 | |
|---|---|---|---|---|---|---|
| | L-vehicle | R-TA | L-vehicle | R-TA | L-vehicle | R-TA |
| 8 hr | No obvious clinical observation | No obvious clinical observation | No obvious clinical observation | Swelling 4 * 3.5 | No obvious clinical observation | Swelling 4 * 3 |
| Day 1 | spotted slight red skin | swelling/4 * 4.5 cm/BT: 39.2° C./2 * 2 cm red spot at the edge of shaving area | No obvious clinical observation | Induration/7 * 5 cm/obvious bulge/BT: 39.1° C. | spotted slight red skin | Induration/8 * 5.5 cm/obvious bulge/red skin/higher temperature than left injection side/BT: 39.6° C. |
| Day 2 | swelling/5 * 6 cm/spotted slight red skin | Induration/8 * 11 * 1 cm/1 * 1 red spot near the injection site/3 * 3 red spot with yellow discharge at edge of shaving area/BT: 38.9° C. | Swelling/3 * 3 cm | Induration/7 * 7 * 1.5 cm/obvious bulge/BT: 39.3° C. | Swelling/3 * 3 cm/spotted slight red skin | Induration/8 * 5.5 * 1 cm/obvious bulge/red skin/higher temperature than left injection side/BT: 39.7° C. |
| Day 3 | swelling/5 * 6 cm/spotted slight red skin | Induration/8 * 11 * 1 cm/3 * 3 red spot with yellow discharge at edge of shaving area/BT: 39.1° C. | Swelling/3 * 3 cm/spotted slight red skin | Induration/9 * 11 * 1.5 cm/obvious bulge/BT: 39.3° C. | Swelling/3 * 3 cm/spotted slight red skin | Induration/7 * 11 * 1 cm/obvious bulge/red skin/higher temperature than left injection side/BT: 39.2° C. |
| Day 4 | swelling/5 * 6 cm/spotted slight red skin | Induration/10 * 11 * 1 cm/3 * 3 red spot with yellow discharge at edge of shaving area/BT: 38.5° C. | Swelling/3 * 4 cm/spotted slight red skin | Induration/9 * 11 * 1.5 cm/obvious bulge/BT: 38.5° C. | Swelling/3 * 3 cm/spotted slight red skin | Induration/8 * 12 * 1.5 cm/obvious bulge/red skin/higher temperature than left injection side/another induration 4 cm to the injection site/BT: 38.7° C. |
| Day 5 | swelling/5 * 6 cm/spotted | Induration for the whole | Swelling/2.5 * 3.5 cm/spotted | Induration/9 * 10 * 2 cm/obvious | Swelling/2 * 3.5 cm/spotted | Induration for the whole upper |

-continued

| time point | D1001 L-vehicle | D1001 R-TA | D1002 L-vehicle | D1002 R-TA | D1003 L-vehicle | D1003 R-TA |
|---|---|---|---|---|---|---|
| | slight red skin | upper leg/edema for the whole calf/tenderness, fluctuance, warmth/1.5 * 2 red spot with yellow discharge at edge of shaving area/BT: 38.6° C. | slight red skin | bulge/slight warmth/BT: 38.7° C. | slight red skin | leg/slight swelling for the whole calf/another induration and obverious bulge 4 cm to the injection site/3 * 3 cm red spot behind the upper leg with slight swelling/BT: 39.0° C. |
| Day 6 | swelling/5 * 6 cm/spotted slight red skin/swelling for whole calf | Induration for the whole upper leg with slight red/edema for the whole calf/tenderness, fluctuance, warmth/1.5 * 2 red spot with yellow discharge at edge of shaving area/BT: 38.4° C. | Swelling/2 * 2 cm/spotted slight red skin | Induration/9 * 10 * 2 cm/obvious bulge/slight warmth/BT: 38.8° C. | Swelling/2 * 3.5 cm/spotted slight red skin | Induration for the whole upper leg/slight swelling for the whole calf/another induration and obverious bulge 4 cm to the injection site/3 * 3 cm red spot behind the upper leg with slight swelling/BT: 39.2° C. |
| Day 7 | swelling/4 * 4 cm/spotted slight red skin/swelling for whole calf | Induration for the whole upper leg with slight red/swelling for the whole calf/red/warmth/1 * 1 red spot with yellow discharge at edge of shaving area/BT: 38.4° C. | Swelling/2 * 2 cm/spotted slight red skin | Induration/9 * 10 * 2 cm/obvious bulge/slight warmth/BT: 38.6° C. | Swelling/2 * 3.5 cm/spotted slight red skin | Induration for the whole upper leg/slight swelling for the whole calf/another induration and obverious bulge 4 cm to the injection site/3 * 3 cm red spot behind the upper leg with slight swelling/BT: 39.5° C. |
| Day 8 | swelling/4 * 4 cm/spotted slight red skin/swelling for whole calf | Induration for the whole upper leg with slight red/swelling for the whole calf/red/warmth/1 * 1 red spot with yellow discharge at edge of shaving area/BT: 38.7° C. | Swelling/2 * 2 cm/spotted slight red skin | Induration/9 * 10 * 2 cm/obvious bulge/slight warmth/BT: 38.7° C. | Swelling/2 * 3.5 cm/spotted slight red skin | Induration for the whole upper leg/slight swelling for the whole calf/another induration and obverious bulge 4 cm to the injection site/3 * 3 cm red spot behind the upper leg with slight swelling/BT: 39.4° C. |
| Day 9 | swelling/4 * 4 cm/spotted slight red skin/swelling for whole calf | Induration 11.5 * 9 cm at the upper leg with slight red and warmth/slight swelling for the whole calf/BT: 38.7° C. | Swelling shrinking | Induration/9 * 10 * 2.5 cm/obvious bulge/4 scabs at 5 o'clock 2 cm near the induration and one fell off/sight red/swelling at the whole calf/BT: 38.3° C. | Swelling/2 * 3.5 cm/spotted slight red skin | Induration/10 * 9 * 1.5 cm at the injection site/slight swelling for the whole calf/another induration and obverious bulge 4 cm to the injection site/upper leg with slight swelling/BT: 38.8° C. |
| Day 10 | swelling/4 * 4 cm/spotted slight red skin/swelling | Induration 11 * 9 cm at the upper leg with slight red and | Swelling shrinking | Induration/9 * 10 * 2.5 cm/obvious bulge/4 scabs at 5 o'clock 2 cm | Swelling/2 * 3.5 cm/spotted slight red skin | Induration/10 * 9 * 1.5 cm at the injection site/slight swelling for the whole calf/another |

-continued

| | D1001 | | D1002 | | D1003 | |
|---|---|---|---|---|---|---|
| time point | L-vehicle | R-TA | L-vehicle | R-TA | L-vehicle | R-TA |
| | for whole calf | warmth/slight swelling for the whole calf/BT: 38.4° C. | | near the induration and two scabs fell off/sight red/swelling at the whole calf/BT: 38.3° C. | | induration and obverious bulge 4 cm to the injection site/upper leg with slight swelling/BT: 38.9° C. |
| Day 11 | swelling/4 * 4 cm/spotted slight red skin/ swelling for whole calf | Induration 9 * 6 cm at the upper leg with slight red and warmth/slight swelling for the whole calf/BT: 38.8° C. | Swelling shrinking | Induration/9 * 10 * cm/3 yellow scabs at 5 o'clock 2 cm near the induration and two scabs fell off/sight red/BT: 38.9° C. | Swelling | Induration and warmth/10 * 9 * 1.5 cm at the injection site/another induration and obverious bulge 4 cm to the injection site/upper leg with slight swelling/BT: 39.4° C. |
| Day 12 | swelling/4 * 4 cm | Induration 9 * 6 cm at the upper leg with slight red and warmth/BT: 38.0° C. | Swelling shrinking | Induration/9 * 10 cm/3 yellow scabs at 5 o'clock 2 cm near the induration and two scabs fell off/sight red/BT: 38.5° C. | Swelling | Induration and warmth/10 * 9 * 1.5 cm at the injection site/another induration and obverious bulge 4 cm to the injection site/3 * 3 cm red spot behind the upper leg with slight swelling/BT: 39.3° C. |
| Day 13 | swelling/4 * 4 cm | Induration 9 * 5 cm at the upper leg with slight red and warmth/BT: 38.4° C. | Swelling shrinking | Induration/9 * 10 cm/slight red/warmth/BT: 38.8° C. | Swelling | Induration and warmth/10 * 9 cm at the injection site/another induration and obverious bulge 4 cm to the injection site/3 * 3 cm red spot behind the upper leg with slight swelling/BT: 39.9° C. |
| Day 14 | swelling/4 * 4 cm | Induration 9 * 5 cm at the dosing site | No obvious clinical observation | Induration/8 * 8 cm/slight red/warmth/BT: 38.3° C. | No obvious clinical observation | Induration and warmth/8 * 9 cm at the injection site/another induration and obverious bulge 4 cm to the injection site/upper leg with slight swelling/BT: 39.6° C. |
| Day 15 | swelling/4 * 4 cm | Induration shrinking 9 * 5 cm at the dosing site/ BT: 37.8° C. | No obvious clinical observation | Induration/8 * 8 cm/slight red/warmth/BT: 37.8° C. | No obvious clinical observation | Induration and warmth/8 * 9 cm at the injection site/another induration and obverious bulge 4 cm to the injection site/upper leg with slight swelling/BT: 39.4° C. |
| Day 16 | swelling/4 * 4 cm | Induration shrinking 9 * 5 cm at the dosing site | No obvious clinical observation | Induration/8 * 8 cm/slight red/warmth | No obvious clinical observation | Induration and warmth/8 * 9 cm at the injection site/slight swelling for the whole calf/another induration and obverious bulge 4 cm to the injection site/upper leg with slight swelling/BT: 39.6° C. |
| Day 17 | swelling/4 * 4 cm | Induration shrinking 9 * 5 cm at the | No obvious clinical observation | Induration/8 * 8 cm/BT: 38.7° C. | No obvious clinical observation | Induration and warmth/8 * 9 cm at the injection site/ |

-continued

| | D1001 | | D1002 | | D1003 | |
|---|---|---|---|---|---|---|
| time point | L-vehicle | R-TA | L-vehicle | R-TA | L-vehicle | R-TA |
| | | dosing site/ BT: 38.3° C. | | | | upper leg with slight swelling/BT: 39.5° C. |
| Day 18 | Swelling shrinking | Induration shrinking 9 * 5 cm at the dosing site/ BT: 38.4° C. | No obvious clinical observation | Induration/8 * 8 cm/BT: 38.8° C. | No obvious clinical observation | Induration and warmth/8 * 9 cm at the injection site/ upper leg with slight swelling/BT: 39.5° C. |
| Day 19 | Swelling shrinking | Induration shrinking 9 * 5 cm at the dosing site/ BT: 38.3° C. | No obvious clinical observation | Induration/8 * 8 cm/BT: 38.7° C. | No obvious clinical observation | Induration and warmth/8 * 9 cm at the injection site/ upper leg with slight swelling/BT: 39.4° C. |
| Day 20 | Swelling shrinking | Induration shrinking 9 * 5 cm at the dosing site/ BT: 37.9° C. | No obvious clinical observation | Induration/8 * 8 cm/BT: 38.6° C. | No obvious clinical observation | Induration and warmth/8 * 9 cm at the injection site/ upper leg with slight swelling/BT: 39.6° C. |
| Day 21 | Swelling shrinking | Induration shrinking 9 * 5 cm at the dosing site/ BT: 38.6° C. | No obvious clinical observation | Induration shrinking/8 * 8 cm/ warmth/BT: 38.5° C. | No obvious clinical observation | Induration and warmth/8 * 9 cm at the injection site/ upper leg with slight swelling/BT: 39.3° C. |
| Day 22 | Swelling shrinking | Induration shrinking 8 * 5 cm at the dosing site/ BT: 38.8° C. | No obvious clinical observation | Induration shrinking/8 * 8 cm/ warmth/BT: 39.3° C. | No obvious clinical observation | Induration and warmth/8 * 9 cm at the injection site/ upper leg with slight swelling/BT: 39.9° C. |
| Day 23 | Swelling shrinking | Induration shrinking 8 * 5 cm at the dosing site/ BT: 38.3° C. | No obvious clinical observation | Induration shrinking/8 * 8 cm/ warmth/BT: 38.8° C. | No obvious clinical observation | Induration and warmth/8 * 9 cm at the injection site/ upper leg with slight swelling/BT: 39.6° C. |
| Day 24 | No obvious clinical observation | Swelling 6 * 3 cm at the dosing site/ BT: 38.5° C. | No obvious clinical observation | Swelling shrinking/6 * 8 cm/ warmth/BT: 39.1° C. | No obvious clinical observation | Swelling and warmth/6 * 6 cm at the injection site/ BT: 39.5° C. |
| Day 25 | No obvious clinical observation | Swelling 6 * 3 cm at the dosing site/ BT: 38.4° C. | No obvious clinical observation | Swelling shrinking/6 * 8 cm/ warmth/BT: 38.6° C. | No obvious clinical observation | Swelling and warmth/6 * 6 cm at the injection site/ BT: 39.8° C. |
| Day 26 | No obvious clinical observation | Swelling 5 * 3 cm at the dosing site/ BT: 38.2° C. | No obvious clinical observation | Swelling shrinking/6 * 8 cm/ BT: 38.6° C. | No obvious clinical observation | Swelling 6 * 6 cm at the injection site/ BT: 39.3° C. |
| Day 27 | No obvious clinical observation | Swelling 5 * 3 cm at the dosing site/ BT: 38.4° C. | No obvious clinical observation | Swelling shrinking/6 * 6 cm/ BT: 38.6° C. | No obvious clinical observation | Swelling 5 * 6 cm at the injection site/ BT: 38.9° C. |
| Day 28 | No obvious clinical observation | No obvious clinical observation | No obvious clinical observation | Swelling shrinking/3 * 5 cm | No obvious clinical observation | Swelling3 * 5 cm at the injection site |
| Day 29 | No obvious clinical observation | No obvious clinical observation | No obvious clinical observation | Swelling shrinking/3 * 5 cm | No obvious clinical observation | Swelling3 * 3 cm at the injection site |
| Day 30 | No obvious clinical observation | No obvious clinical observation | No obvious clinical observation | Swelling shrinking/3 * 3 cm | No obvious clinical observation | Swelling3 * 3 cm at the injection site |
| Day 31 | No obvious clinical observation | No obvious clinical observation | No obvious clinical observation | Swelling shrinking/3 * 3 cm | No obvious clinical observation | No obvious clinical observation |
| Day 32 | No obvious clinical observation | No obvious clinical observation | No obvious clinical observation | Swelling shrinking/3 * 3 cm | No obvious clinical observation | No obvious clinical observation |

| time point | D1501 | | D1502 | | D1503 | |
|---|---|---|---|---|---|---|
| | L-vehicle | R-TA | L-vehicle | R-TA | L-vehicle | R-TA |
| 8 hr | No obvious clinical observation | No obvious clinical observation | No obvious clinical observation | No obvious clinical observation | No obvious clinical observation | No obvious clinical observation |
| Day 1 | Slight swelling | Induration for the whole leg/warmth/lame | No obvious clinical observation | Swelling at the upper leg 6 * 7 cm | No obvious clinical observation | Induration for the whole leg |
| Day 2 | Slight swelling | Induration for the whole leg/warmth/lame | No obvious clinical observation | Swelling at the upper leg 6 * 7 cm, induration at the inner upper leg 7 * 7 cm/warmth | No obvious clinical observation | Induration for the whole leg/warms |
| Day 3 | Slight swelling | Induration for the whole leg/warmth/lame | No obvious clinical observation | Swelling at the upper leg 6 * 7 cm, induration at the inner upper leg 7 * 7 cm/warmth | No obvious clinical observation | Induration for the whole leg/warms |
| Day 5 | Slight swelling | Induration for the upper leg/warmth | No obvious clinical observation | Swelling at the upper leg 6 * 7 cm, induration at the inner upper leg 7 * 7 cm/warmth/scap 1 * 0.5 cm at the right of vulva | No obvious clinical observation | Induration for the whole leg/warms |
| Day 7 | Slight swelling | Induration for the upper leg/warmth | No obvious clinical observation | Swelling at the upper leg 3 * 4 cm, induration at the inner upper leg 7 * 7 cm/warmth/scap 1 * 0.5 cm at the right of vulva | No obvious clinical observation | Induration for the whole leg/warms |
| Day 10 | No obvious clinical observation | Induration for the upper leg | No obvious clinical observation | Induration at the upper leg/Scap at the vulva fell off | No obvious clinical observation | Induration for the whole leg/warms |
| Day 12 | No obvious clinical observation | Induration for the upper leg | No obvious clinical observation | Induration at the upper leg 7 * 4 cm/Scap at the vulva fell off | No obvious clinical observation | Induration at the upper leg 9 * 7 cm |
| Day 17 | No obvious clinical observation | Induration for the upper leg | No obvious clinical observation | Induration at the upper leg 7 * 4 cm | No obvious clinical observation | Induration at the upper leg 9 * 6 cm |
| Day 19 | No obvious clinical observation | Induration at the upper leg 8 * 5 cm | No obvious clinical observation | Induration at the upper leg 7 * 4 cm | No obvious clinical observation | Induration at the upper leg 7 * 4.5 cm |
| Day 21 | No obvious clinical observation | Induration at the upper leg 8 * 4 cm | No obvious clinical observation | Induration at the upper leg 4 * 4 cm | No obvious clinical observation | No obvious clinical observation |
| Day 24 | No obvious clinical observation | Induration at the upper leg 7.5 * 4 cm | No obvious clinical observation | Induration at the upper leg 3.5 * 4 cm | No obvious clinical observation | No obvious clinical observation |
| Day 26 | No obvious clinical observation | Induration at the upper leg 6 * 4 cm | No obvious clinical observation | No obvious clinical observation | No obvious clinical observation | No obvious clinical observation |
| Day 28 | No obvious clinical observation | Induration at the upper leg 6 * 4 cm | No obvious clinical observation | No obvious clinical observation | No obvious clinical observation | No obvious clinical observation |
| Day 31 | No obvious clinical observation | Induration at the upper leg 6 * 4 cm | No obvious clinical observation | No obvious clinical observation | No obvious clinical observation | No obvious clinical observation |
| Day 33 | No obvious clinical observation | Induration at the upper leg | No obvious clinical observation | No obvious clinical observation | No obvious clinical observation | No obvious clinical observation |

| time point | D1001 | | D1002 | |
|---|---|---|---|---|
| | L-vehicle | R-TA | L-vehicle | R-TA |
| 72 hr | No obvious clinical observation | Swelling 2 * 2.5 cm | Swelling 2 * 3 cm | Induration 6.5 cm * 4.5 cm |
| 96 hr | No obvious clinical observation | Swelling 3 * 3 cm | Swelling 4.5 * 2.5 cm | Induration 6 cm * 8 cm with slight red color |
| 120 hr | No obvious clinical observation | Swelling 3 * 3 cm | Swelling 4.5 * 2.5 cm | Induration 6 cm * 8 cm with slight red color |
| 144 hr | No obvious clinical observation | Swelling 3.5 * 3 cm | Swelling 4.5 * 2.5 cm | Induration 6 cm * 8 cm |
| 168 hr | No obvious clinical observation | Induration 4 * 3 cm | Swelling 4.5 * 2.5 cm | Induration 6 cm * 8 cm |
| 192 hr | No obvious clinical observation | Induration 4 * 3 cm | Swelling 4.5 * 2.5 cm | Induration 6 cm * 8 cm |
| 216 hr | No obvious clinical observation | Induration 4 * 3 cm | Swelling 4.5 * 2.5 cm | Induration 6 cm * 8 cm |
| 240 hr | No obvious clinical observation | Swelling 2 * 3 cm/a swellen with pus at groin | Swelling 3.5 * 2 cm | Induration 7 cm * 8 cm |
| 264 hr | No obvious clinical observation | No obvious clinical observation/BT: 38.6° C. | Swelling 2 * 2 cm | Induration 7 cm * 8 cm/warmth/BT: 39.5° C. |
| 288 hr | No obvious clinical observation | No obvious clinical observation/BT: 38.6° C. | Swelling 2 * 2 cm | Induration 6 cm * 8 cm/BT: 39.5° C. |
| 312 hr | No obvious clinical observation | No obvious clinical observation/BT: 38.0° C. | Swelling 2 * 2 cm | Induration shrinking/6 cm * 8 cm/BT: 38.5° C. |
| 336 hr | No obvious clinical observation | No obvious clinical observation/BT: 38.4° C. | Slight swelling 2 * 2 cm | Induration shrinking 3 cm * 4 cm/BT: 38.7° C. |
| 360 hr | No obvious clinical observation | No obvious clinical observation/BT: 38.1° C. | No obvious clinical observation | Induration shrinking 3 cm * 4 cm/BT: 39.1° C. |
| 384 hr | No obvious clinical observation | No obvious clinical observation/BT: 38.7° C. | No obvious clinical observation | Induration shrinking 3 cm * 4 cm/BT: 39.3° C. |
| 408 hr | No obvious clinical observation | No obvious clinical observation | No obvious clinical observation | Induration shrinking 3 cm * 4 cm/BT: 39.4° C. |
| 432 hr | No obvious clinical observation | No obvious clinical observation/BT: 38.0° C. | No obvious clinical observation | Swelling 3 cm * 3 cm/BT: 38.9° C. |
| 456 hr | No obvious clinical observation | No obvious clinical observation | No obvious clinical observation | Swelling 3 cm * 3 cm/BT: 38.9° C. |
| 480 hr | No obvious clinical observation | No obvious clinical observation/BT: 38.0° C. | No obvious clinical observation | Swelling 3 cm * 3 cm/BT: 39.2° C. |
| 504 hr | No obvious clinical observation | No obvious clinical observation | No obvious clinical observation | Swelling 3 cm * 3 cm/BT: 38.7° C. |
| 528 hr | No obvious clinical observation | No obvious clinical observation/BT38.2° C. | No obvious clinical observation | Swelling 3 cm * 3 cm/BT: 37.9° C. |
| 552 hr | No obvious clinical observation | No obvious clinical observation/BT: 38.4° C. | No obvious clinical observation | Swelling 3 cm * 3 cm/BT: 39.2° C. |
| 576 hr | No obvious clinical observation | No obvious clinical observation/BT: 38.4° C. | No obvious clinical observation | Swelling 3 cm * 3 cm/BT: 39.0° C. |
| 600 hr | No obvious clinical observation | No obvious clinical observation/BT: 38.3° C. | No obvious clinical observation | Swelling 3 cm * 3 cm/BT: 38.6° C. |
| 624 hr | No obvious clinical observation | No obvious clinical observation/BT: 38.6° C. | No obvious clinical observation | Swelling 3 cm * 3 cm/BT: 38.9° C. |
| 648 hr | No obvious clinical observation | No obvious clinical observation/BT: 38.3° C. | No obvious clinical observation | Swelling 3 cm * 3 cm/BT: 38.5° C. |
| 672 hr | No obvious clinical observation | No obvious clinical observation/BT: 38.3° C. | No obvious clinical observation | Swelling 3 cm * 3 cm/BT: 39.3° C. |
| 696 hr | No obvious clinical observation | No obvious clinical observation | No obvious clinical observation | No obvious clinical observation |
| 720 hr | No obvious clinical observation | No obvious clinical observation | No obvious clinical observation | No obvious clinical observation |

| time point | D1501 | | D1502 | | D1502 | |
|---|---|---|---|---|---|---|
| | L-vehicle | R-TA | L-vehicle | R-TA | L-vehicle | R-TA |
| 8 hr | No obvious clinical observation | No obvious clinical observation | No obvious clinical observation | No obvious clinical observation | No obvious clinical observation | No obvious clinical observation |
| 24 hr | Swelling 4 * 4 cm | Red spots at groin | Swelling 3 * 4 cm | No obvious clinical observation | Slight swelling | Slight swelling/red spot near the saphenous vein of hind limb |
| 48 hr | Swelling 4 * 4 cm | Red spots at groin | Swelling 3 * 4 cm | No obvious clinical observation | Slight swelling | Slight swelling/red spot near the saphenous vein of hind limb |
| 72 hr | Swelling 4 * 4 cm | Swelling for the whole leg; obvious swelling at upper leg with area of | Swelling 3 * 4 cm | Swelling in the whole leg; obvious swelling at | Swelling 5 * 5 cm | Swelling in the whole leg; obvious swelling at upper leg with area of |

-continued

| time point | D1501 | | D1502 | | D1502 | |
|---|---|---|---|---|---|---|
| | L-vehicle | R-TA | L-vehicle | R-TA | L-vehicle | R-TA |
| | | 10 * 11 cm/Red spots at groin/BT: 39.1° C. | | inner upper leg with volume of 15 * 13 * 3 cm and red/BT: 39.6° C. | | 8 * 12 cm/red at the inner upper leg/BT: 39.3° C. |
| 96 hr | Swelling 4 * 4 cm | Swelling for the whole leg; obvious swelling at upper leg with area of 10 * 11 cm/Red spots at groin/BT: 39.0° C. | Swelling 3 * 4 cm | Swelling in the whole leg; obvious swelling at inner upper leg with volume of 15 * 13 * 3 cm and red/BT: 38.9° C. | Swelling 5 * 5 cm | Swelling in the whole leg; obvious swelling at upper leg with area of 8 * 12 cm/ induration and red at the inner upper leg/BT: 39.3° C. |
| 120 hr | Swelling 4 * 4 cm | Swelling for the whole leg; obvious swelling at upper leg with area of 10 * 11 cm/Red spots at groin/BT: 39.1° C. | Swelling 3 * 4 cm | Swelling in the whole leg; obvious swelling at inner upper leg with volume of 15 * 13 * 3 cm and red/BT: 39.6° C. | Swelling 5 * 5 cm | Swelling in the whole leg; obvious swelling at upper leg with area of 8 * 12 cm/ induration and red at the inner upper leg/red spot at calf/ BT: 39.4° C. |
| 144 hr | Swelling 4 * 4 cm | Obvious swelling at upper leg with area of 10 * 11 cm/induration 5 * 4 cm at the back of upper leg with redness/induration 9 * 7 cm at inner side of upper leg with redness/Red spots at groin/BT: 38.7° C. | Swelling 3 * 4 cm | Induration in the whole leg; obvious swelling at inner upper leg with volume of 15 * 13 * 3 cm and redness/BT: 38.9° C. | Swelling 5 * 5 cm | Swelling in the whole leg; obvious swelling at upper leg with area of 8 * 12 cm/ induration and red at the inner upper leg/red spot at calf/ BT: 39.0° C. |
| 168 hr | Swelling 4 * 4 cm | Obvious swelling at upper leg with area of 10 * 11 cm/induration 5 * 4 cm at the back of upper leg with redness/induration 9 * 7 cm at inner side of upper leg with redness/Red spots at groin/BT: 38.9° C. | Swelling 3 * 4 cm | Induration in the whole leg; obvious swelling at inner upper leg with volume of 15 * 13 * 3 cm and redness/BT: 39.9° C. | Swelling 5 * 5 cm | Swelling in the whole leg; obvious swelling at upper leg with area of 8 * 12 cm/ induration at the back of upper leg with redness/induration 8 * 6 cm at the inner upper leg/red spot at calf/BT: 39.3° C. |
| 192 hr | Swelling 4 * 4 cm | Obvious swelling at upper leg with area of 10 * 11 cm/induration 5 * 4 cm at the back of upper leg with redness/induration 9 * 7 cm at inner side of upper leg with redness/Red spots at groin/BT: 38.2° C. | Swelling 3 * 4 cm | Induration in the whole leg; obvious induration at inner upper leg with 15 * 13 cm/ BT: 38.7° C. | Swelling 5 * 5 cm/red spots | Obvious swelling at upper leg with area of 8 * 12 cm/ induration at the back of upper leg with redness/induration 8 * 6 cm at the inner upper leg/red spot at calf/BT: 39.2° C. |
| 216 hr | Swelling 4 * 4 cm | Obvious swelling at upper leg with area of 10 * 11 cm/induration 5 * 4 cm at the back of upper leg with redness/induration 9 * 7 cm at inner side of upper leg with redness/Red spots at groin/BT: 38.6° C. | Swelling 3 * 4 cm | Obvious induration at inner upper leg with 13 * 9 cm/ BT: 39.2° C. | Swelling 4 * 4 cm/red spots | induration at the back and inner upper leg with 7 * 12 cm/red spot at calf/BT: 39.2° C. |
| 240 hr | Swelling shrinking | induration 5 * 4 cm at the back of upper leg with | Swelling 3 * 4 cm | Obvious induration at inner upper leg | Swelling 4 * 4 cm/red spots | induration at the back and inner upper leg with |

| time point | D1501 L-vehicle | D1501 R-TA | D1502 L-vehicle | D1502 R-TA | D1502 L-vehicle | D1502 R-TA |
|---|---|---|---|---|---|---|
| | | redness/induration 9 * 7 cm at inner side of upper leg with redness/Red spots at groin/BT: 38.2° C. | | with 13 * 9 cm/ BT: 38.6° C. | | 7 * 12 cm/red spot at calf/BT: 38.9° C. |
| 264 hr | Swelling shrinking | induration 3 * 4 cm at the back of upper leg with redness/induration 6 * 5 cm at inner side of upper leg with redness/Red spots at groin/BT: 38.0° C. | Swelling 3 * 3 cm | Obvious induration at inner upper leg with 10 * 9 cm/ BT: 38.4° C. | Swelling 2 * 2 cm/red spots | induration at the back and inner upper leg with 6 * 6 cm/BT: 38.7° C. |
| 288 hr | No obvious clinical observation | induration 3 * 4 cm at the back of upper leg with redness/induration 6 * 5 cm at inner side of upper leg with redness/Red spots at groin/BT: 38.4° C. | Swelling 3 * 3 cm | Obvious induration at inner upper leg with 9 * 9 cm/ BT: 38.6° C. | red spots | induration at the back and inner upper leg with 6 * 6 cm/BT: 38.7° C. |
| day 13 | No obvious clinical observation | induration 3 * 4 cm at the back of upper leg with redness/Red spots at groin | No obvious clinical observation | Obvious induration at inner upper leg with 7 * 7 cm | No obvious clinical observation | induration at the back and inner upper leg with 6 * 6 cm |
| day 14 | No obvious clinical observation | induration 3 * 4 cm at the back of upper leg with redness/Red spots at groin | No obvious clinical observation | Obvious induration at inner upper leg with 7 * 6 cm | No obvious clinical observation | induration at the back and inner upper leg with 6 * 6 cm |
| day 15 | No obvious clinical observation | induration 3 * 4 cm at the back of upper leg with redness/Red spots at groin | No obvious clinical observation | Obvious induration at inner upper leg with 7 * 7 cm | No obvious clinical observation | induration at the back and inner upper leg with 6 * 6 cm |
| day 16 | No obvious clinical observation | induration 3 * 4 cm at the back of upper leg with redness/Red spots at groin | No obvious clinical observation | Obvious induration at inner upper leg with 6 * 6 cm | No obvious clinical observation | induration at the back and inner upper leg with 6 * 6 cm |
| day 17 | No obvious clinical observation | induration 3 * 2 cm at the back of upper leg with redness/Red spots at groin | No obvious clinical observation | Obvious induration at inner upper leg with 6 * 6 cm | No obvious clinical observation | induration at the back and inner upper leg with 4 * 6 cm |
| day 18 | No obvious clinical observation | induration 3 * 2 cm at the back of upper leg with redness/Red spots at groin | No obvious clinical observation | Obvious induration at inner upper leg with 5 * 5 cm | No obvious clinical observation | induration at the back and inner upper leg with 4 * 3 cm |
| day 19 | No obvious clinical observation | redness/Red spots at groin | No obvious clinical observation | Obvious induration at inner upper leg with 4 * 5 cm | No obvious clinical observation | induration at the back and inner upper leg with 2 * 3 cm |
| day 20 | No obvious clinical observation | redness/Red spots at groin | No obvious clinical observation | Obvious induration at inner upper leg with 4 * 4 cm | No obvious clinical observation | Not obvious induration |

We claim:

1. A compound, or pharmaceutically acceptable salt thereof, wherein the compound is (((4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl)oxy)methyl tetradecanoate.

2. A pharmaceutical composition comprising a compound of claim 1, or a pharmaceutically acceptable salt thereof, and at least one pharmaceutically acceptable excipient.

3. The pharmaceutical composition of claim 2, wherein the pharmaceutically acceptable excipient is cottonseed oil.

4. The pharmaceutical composition of claim 2, wherein the pharmaceutically acceptable excipient is sesame oil.

* * * * *